US009630958B2

United States Patent
Dugar et al.

(10) Patent No.: US 9,630,958 B2
(45) Date of Patent: Apr. 25, 2017

(54) TRIAZINE COMPOUNDS

(71) Applicant: Sphaera Pharma Pte. Ltd., Singapore (SG)

(72) Inventors: Sundeep Dugar, IMT Manesar (IN); Dinesh Mahajan, IMT Manesar (IN); Frank Hollinger Peter, IMT Manesar (IN); Amit Sharma, IMT Manesar (IN); Vinayak Tripathi, IMT Manesar (IN); Bilash Kuila, IMT Manesar (IN)

(73) Assignee: SPHAERA PHARMA PTE. LTD., Singapore (SG)

( * ) Notice: Subject to any disclaimer, the term of this patent is extended or adjusted under 35 U.S.C. 154(b) by 0 days.

(21) Appl. No.: 14/416,140

(22) PCT Filed: Jul. 23, 2013

(86) PCT No.: PCT/IN2013/000458
§ 371 (c)(1),
(2) Date: Jan. 21, 2015

(87) PCT Pub. No.: WO2014/016849
PCT Pub. Date: Jan. 30, 2014

(65) Prior Publication Data
US 2015/0197515 A1    Jul. 16, 2015

(30) Foreign Application Priority Data
Jul. 23, 2012 (IN) .......................... 2283/DEL/2012

(51) Int. Cl.
| | |
|---|---|
| *C07D 413/14* | (2006.01) |
| *C07D 401/04* | (2006.01) |
| *C07D 403/04* | (2006.01) |
| *A61K 31/53* | (2006.01) |
| *A61K 31/5377* | (2006.01) |
| *A61K 31/4427* | (2006.01) |
| *A61P 35/00* | (2006.01) |
| *C07D 417/14* | (2006.01) |
| *C07D 401/14* | (2006.01) |
| *C07D 413/04* | (2006.01) |
| *C07D 417/04* | (2006.01) |
| *C07D 471/04* | (2006.01) |
| *C07D 491/08* | (2006.01) |
| *C07D 498/08* | (2006.01) |

(52) U.S. Cl.
CPC ......... *C07D 417/14* (2013.01); *C07D 401/04* (2013.01); *C07D 401/14* (2013.01); *C07D 403/04* (2013.01); *C07D 413/04* (2013.01); *C07D 413/14* (2013.01); *C07D 417/04* (2013.01); *C07D 471/04* (2013.01); *C07D 491/08* (2013.01); *C07D 498/08* (2013.01)

(58) Field of Classification Search
CPC .. C07D 471/04; C07D 471/14; C07D 403/04; C07D 403/14; C07D 401/04; C07D 401/14; A61K 31/53; A61K 31/5377; A61K 31/4427
USPC ................................. 544/209, 216; 514/245
See application file for complete search history.

(56) References Cited

U.S. PATENT DOCUMENTS

| | | |
|---|---|---|
| 2004/0132730 A1 | 7/2004 | Axon et al. |
| 2009/0291079 A1 | 11/2009 | Venkatesan et al. |
| 2011/0275762 A1 | 11/2011 | Cmiljanovic et al. |
| 2013/0303516 A1* | 11/2013 | Dugar .................. C07D 413/04 514/210.18 |

FOREIGN PATENT DOCUMENTS

WO    WO-2012/101654 A2    8/2012

OTHER PUBLICATIONS

Dugar US 20130303516, CA 157: 295197,2012; CAPLUS Abstract provided.*
Klempner et al.Cancer Discov. Dec. 2013;3(12):1345-54.*
Massacesi et al. Ann. N.Y. Acad. Sci. 1280 (2013) 19-23.*
Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p4.*
Dermer et al., Bio/Technology, 1994, 12:320.*
International Search Report dated Apr. 8, 2014 for International Patent Application No. PCT/IN2013/000458.

* cited by examiner

*Primary Examiner* — Venkataraman Balasubramanian
(74) *Attorney, Agent, or Firm* — Foley & Lardner LLP

(57) ABSTRACT

The present invention relates to novel triazine compounds of formula (1). The present invention also discloses compounds of formula I along with other pharmaceutical acceptable excipients and use of the compounds to modulate the PI3K/mTOR pathway.

5 Claims, No Drawings

TRIAZINE COMPOUNDS

FIELD OF THE INVENTION

The present invention relates to novel triazine compounds that may be useful as kinase inhibitors. More particularly, the present invention relates to substituted triazine derivatives, methods for their preparation, pharmaceutical compositions containing these compounds and uses of these compounds in the treatment of PI3K/mTOR pathway related disorders.

BACKGROUND OF THE INVENTION

PI3K/mTOR pathway is an intracellular signaling pathway that regulates cell growth, cell proliferation, cell motility, cell survival, protein synthesis, and transcription. The deregulation of the PI3K/mTOR is one of the major causes of cancer such as breast cancer and non-small-cell lung cancer. PI3K/mTOR is one of the three major signaling pathways that have been identified as important in cancer. PI3K/mTOR signaling pathway plays an important role in cancer stem cell self-renewal and resistance to chemotherapy or radiotherapy and hence dictates the success or failure of cancer chemotherapy. Hence, this pathway is considered important in determining the progression and/or cure for cancer.

The mammalian target of rapamycin (mTOR) is a key signaling molecule downstream in PI3K signaling pathway. mTOR also known as a mechanistic target of rapamycin or FK506 binding protein 12-rapamycin associated protein 1 (FRAP1) is a protein which in humans is encoded by the FRAP1 gene. mTOR is a serine/threonine protein kinase that regulates cell growth, cell proliferation, cell motility, cell survival, protein synthesis, and transcription. mTOR integrates the input from upstream pathways, including insulin, growth factors (such as IGF-1 and IGF-2), and amino acids. mTOR also senses cellular nutrient and energy levels and redox status. The mammalian target of rapamycin (mTOR) has emerged as a critical effector in cell-signaling pathways commonly deregulated in human cancers. This has led to the prediction that mTOR inhibitors may be useful in oncology. The dysregulation of the mTOR pathway has been found to be a contributing factor of a variety of cancer. Hence inhibitors of PI3K/mTOR pathways are believed to have a role in cancer inhibition.

Therefore, there is a need for the molecules that have mTOR enzyme selectively or in combination with other enzymes which inhibit the PI3K/mTOR pathway such as PI3K.

OBJECT OF THE INVENTION

An object of the invention is to provide compounds that inhibit mTOR enzyme selectively or in combination with other enzymes which inhibit the PI3K/mTOR pathway such as PI3K.

BRIEF DESCRIPTION OF THE INVENTION

The present invention also relates a composition comprising the compounds of formula (1)

A. COMPOUNDS OF THE PRESENT INVENTION

The present invention relates to novel triazine compounds of formula (1):

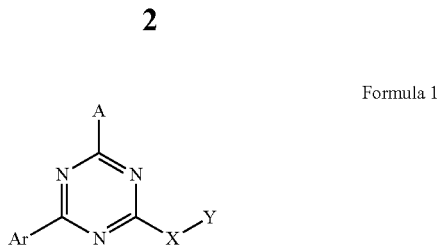

Formula 1 wherein:

A is preferably selected from:

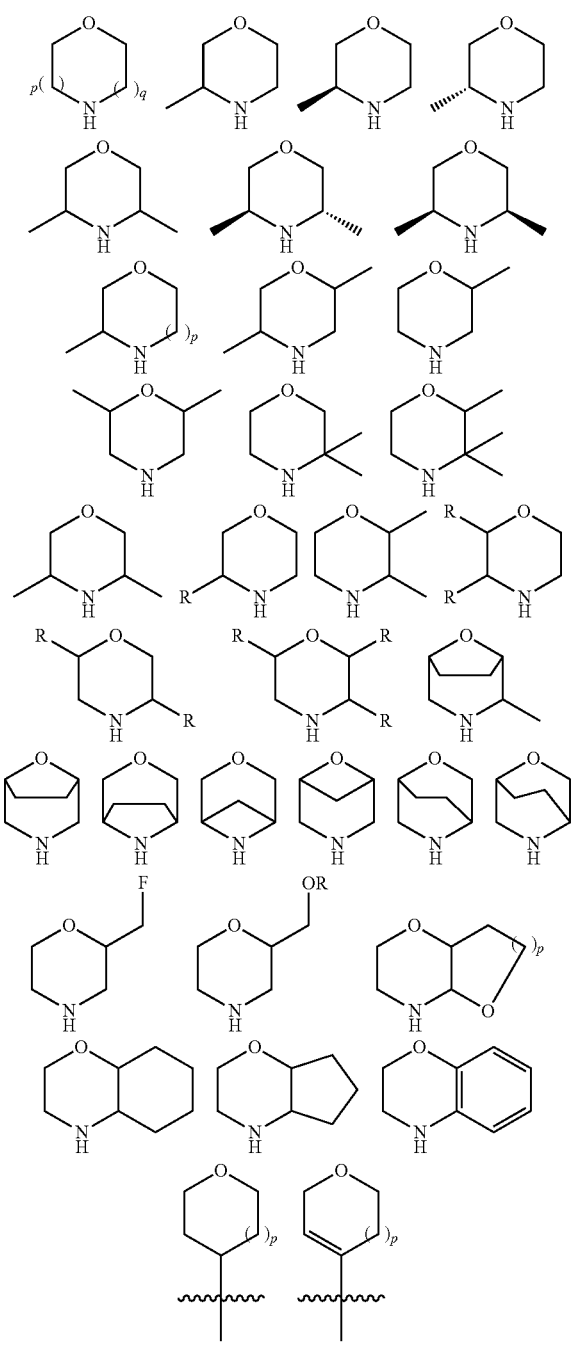

and all stereoisomers or isomers or enantiomers of above,

Ar is preferably selected from:
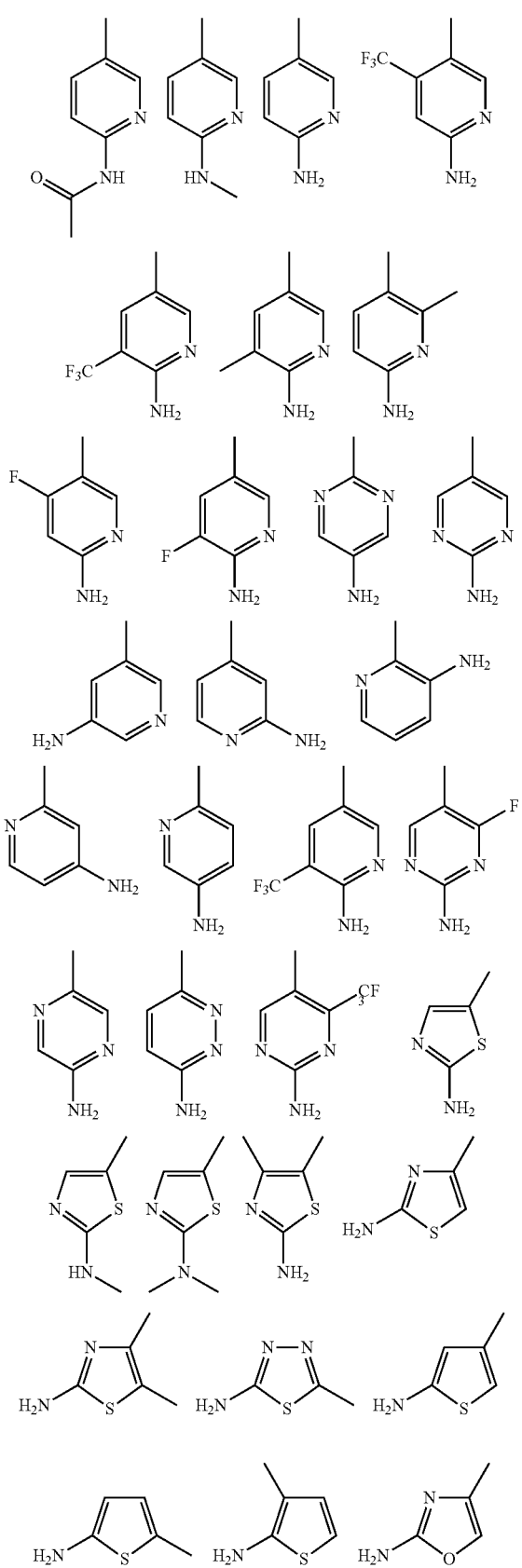
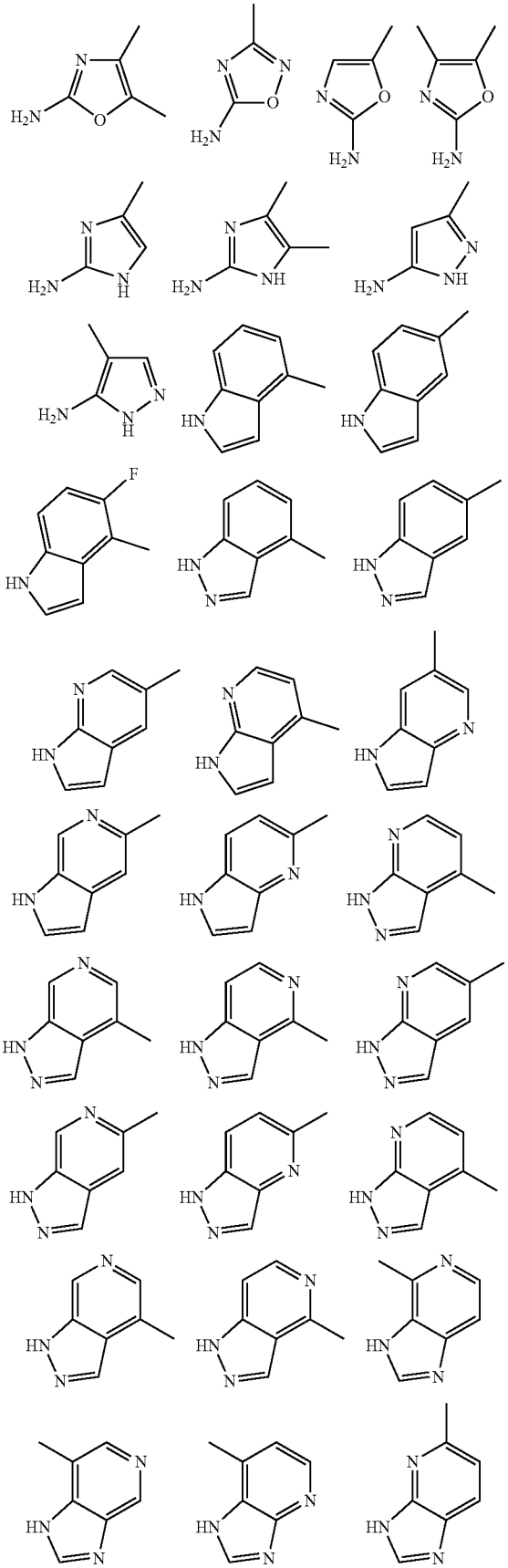

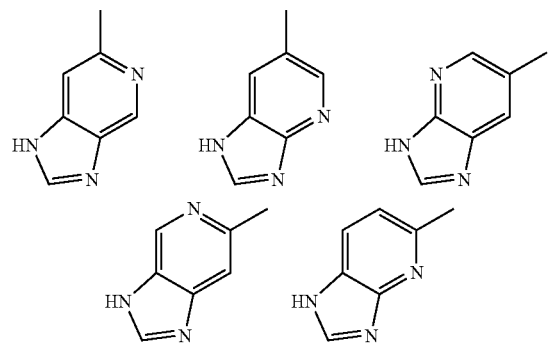
X is preferably O or N or C
Y is preferably selected from:
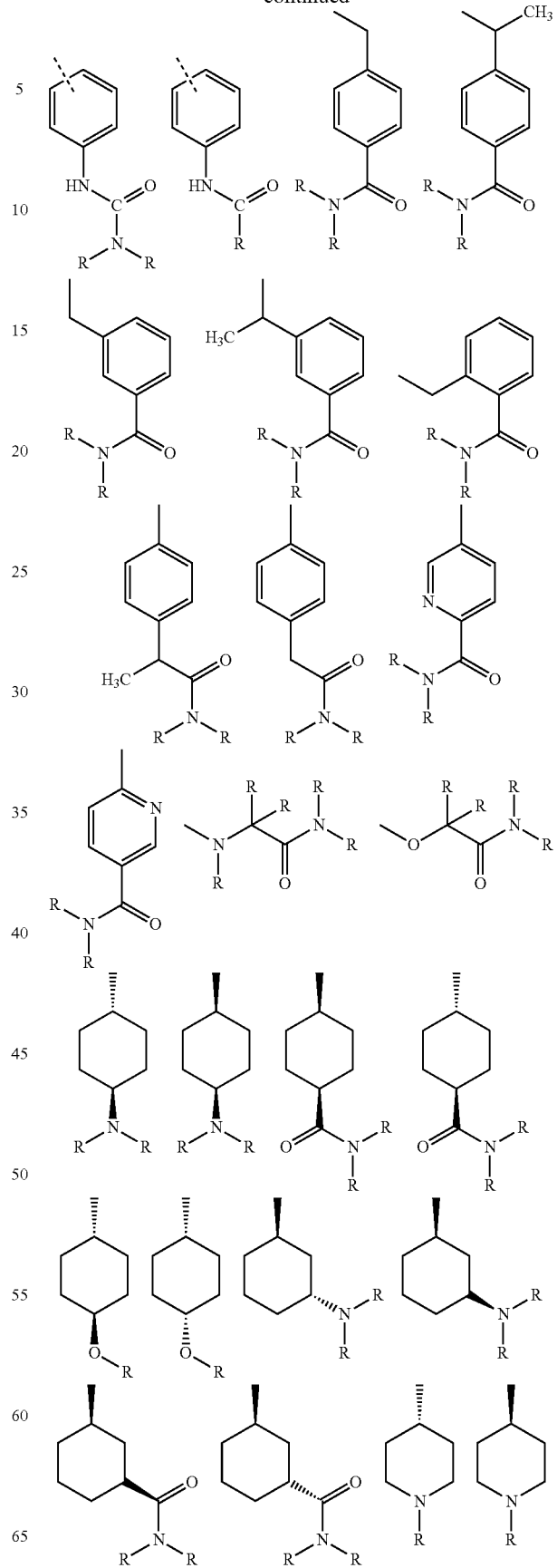

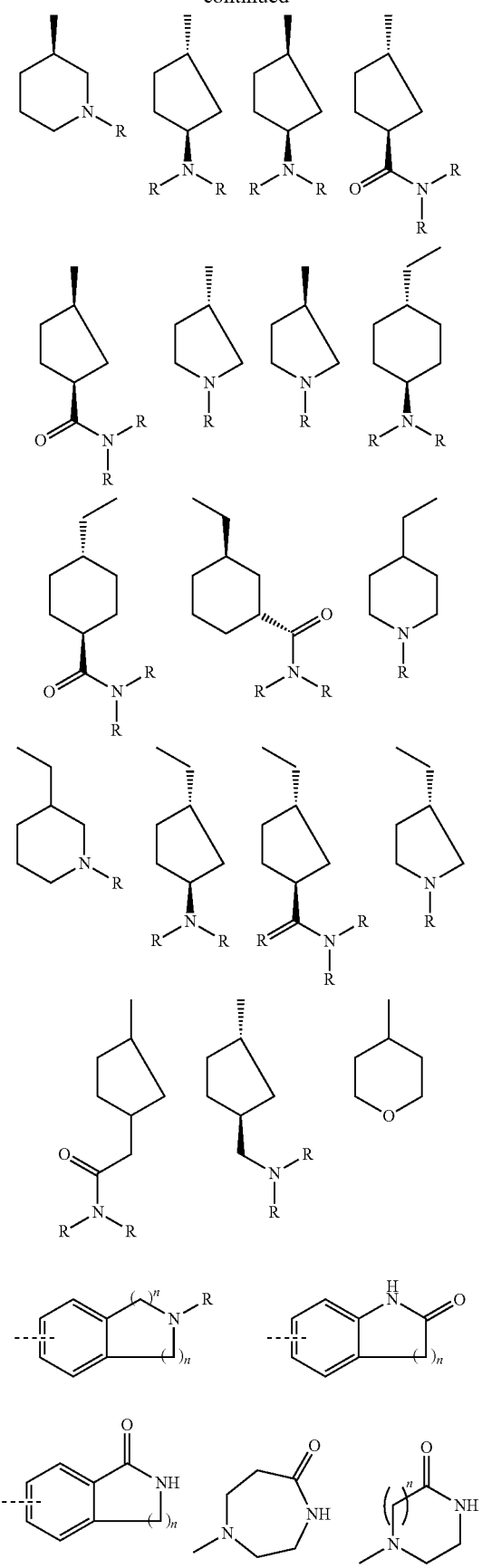

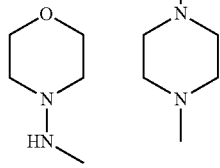

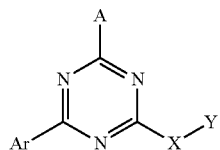

where, R may be independently selected from the group consisting of: H, F, Cl, Br, I, $OR^X$, $NO_2$, CN, $N(R^X)_2$, $COOR^X$, $CON(R^X)_2$, $N(R^X)CON(R^X)_2$, $N(R^X)COR^X$, $N(R^X)SO_2N(R^X)_2$, $SO_2N(R^X)_2$, $SO_2R^X$, $SOR^X$, $SR^X$, $N(R^X)SO_2R^X$; optionally substituted straight or branched chain $C_1$-$C_6$ alkyl, alkylene, alkenyl, alkenylene, alkenylene, fluoroalkyl, alkynyl, heteroalkyl; optionally substituted monocyclic or bicyclic or fused $C_3$-$C_8$ cycloalkyl, cycloalkenyl, heterocycloalkyl, heterocycloalkenyl; optionally substituted aryl, heteroaryl, arylalkyl; $(CH_2)_mCO_2R^X$; $(CH_2)_mCO_2N(R^X)_2$; optionally substituted $C_2$-$C_{12}$ alkenyloxy, alkynyloxy, heteroalkyloxy; optionally substituted $C_3$-$C_8$ cycloalkyloxy, cycloalkenyloxy, heterocycloalkyloxy, heterocycloalkenyloxy; optionally substituted $C_1$-$C_8$ alkylamino;

$R^X$ may be H, alkyl, alkene or alkylene or cycloalkyl or aryl m and n are an integer from 1 to 4 p and q=1, 2 or 3

The present invention also discloses compounds of formula I along with other pharmaceutical acceptable excipients and use of the compounds to modulate the PI3K/mTOR pathway.

DETAILED DESCRIPTION OF THE INVENTION

Accordingly, the present invention provides compound of formula I that inhibit mTOR and in addition may also exhibit PI3K inhibition.

The present invention relates to novel triazine compounds of formula (1):

Formula 1

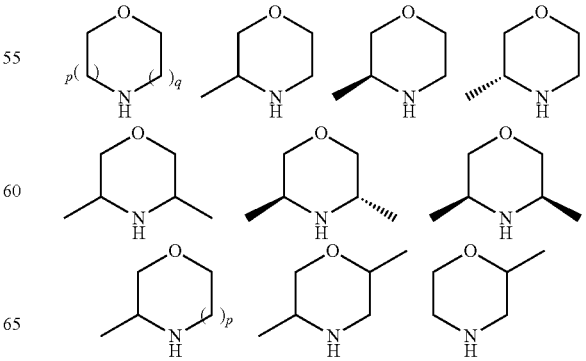

wherein:

A is preferably selected from:

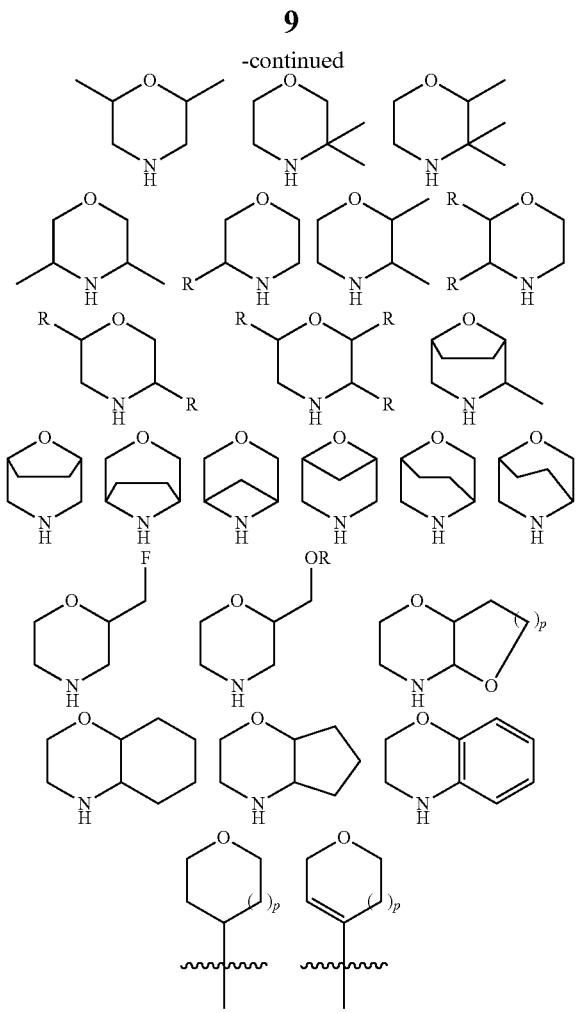
and all stereoisomers or isomers or enantiomers of above, Ar is preferably selected from:
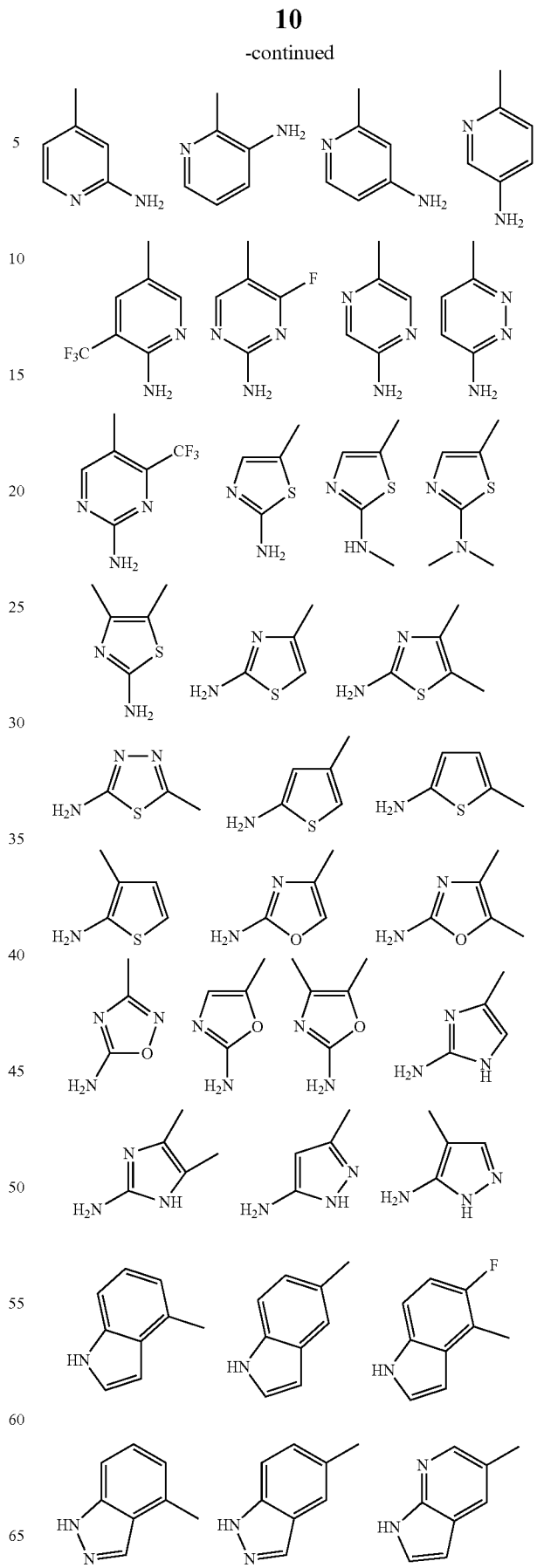

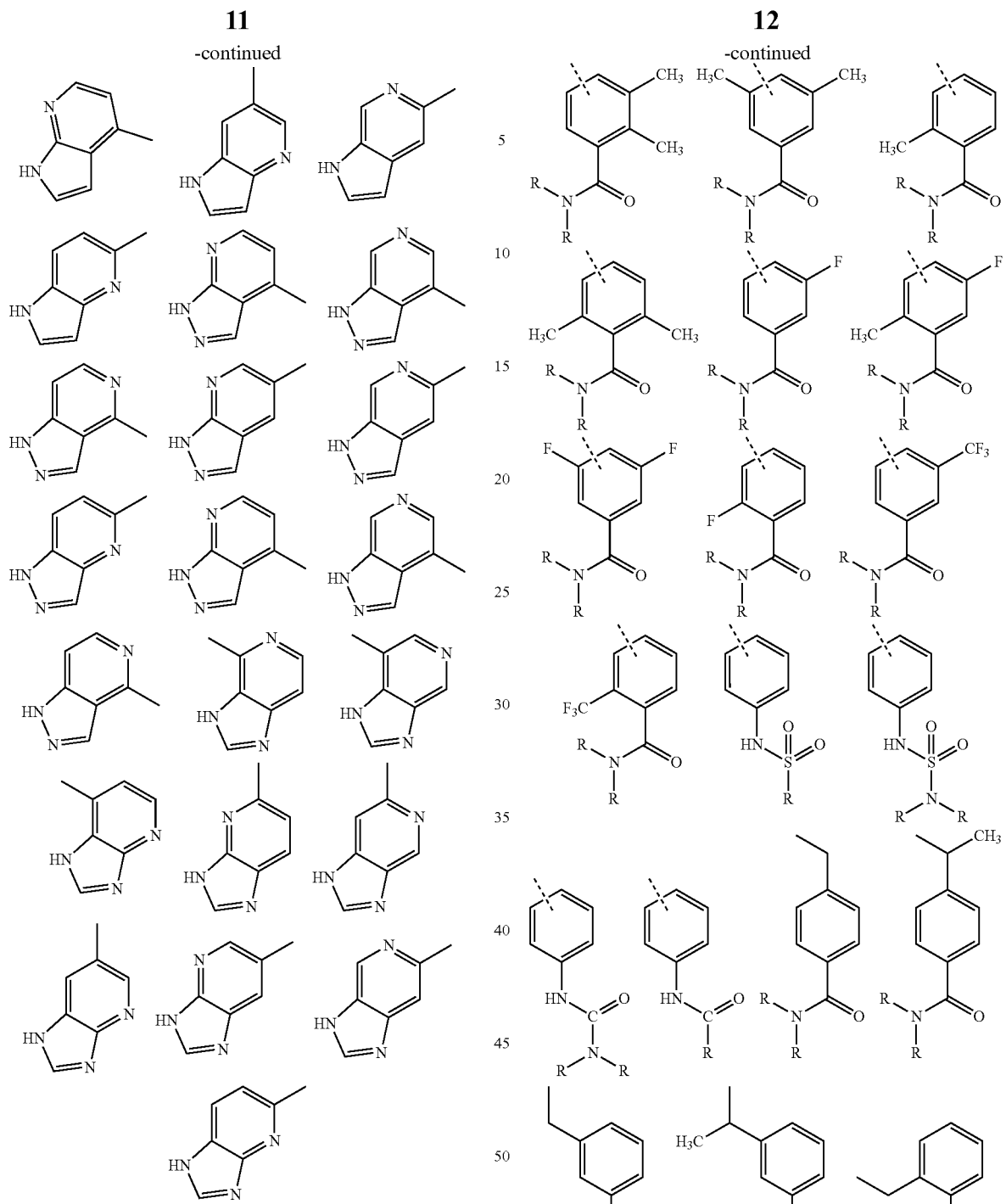
X is preferably O or N or C
Y is preferably selected from:
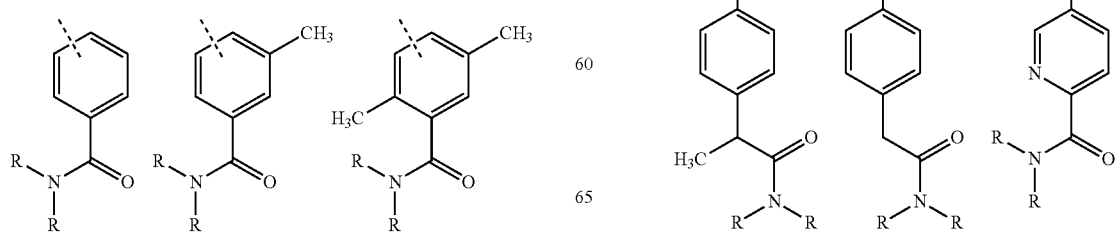

-continued

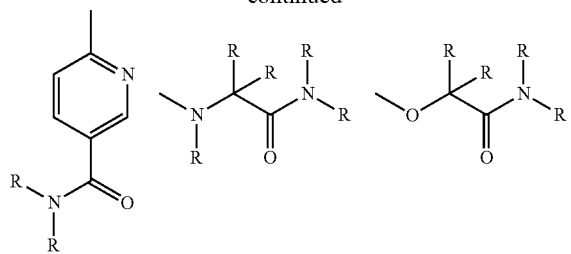
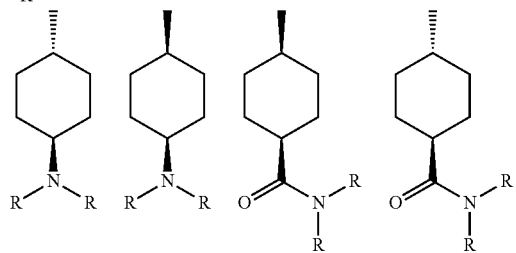
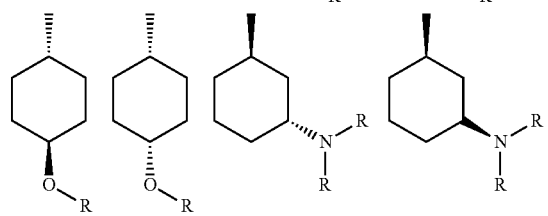
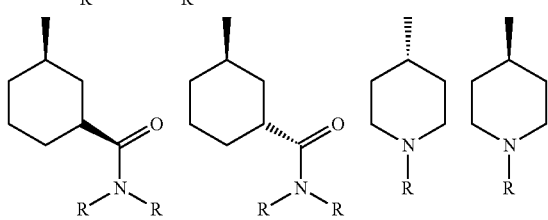
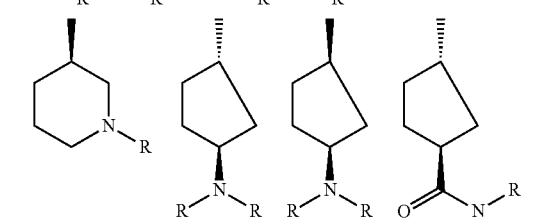
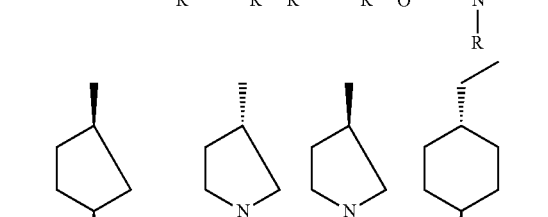
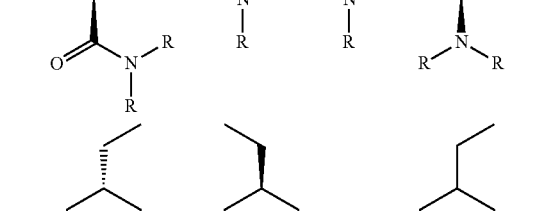
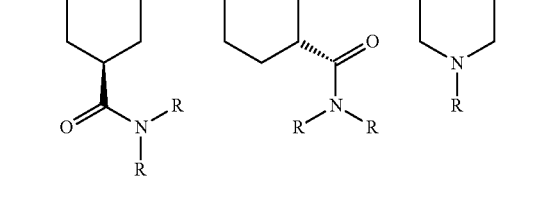

-continued

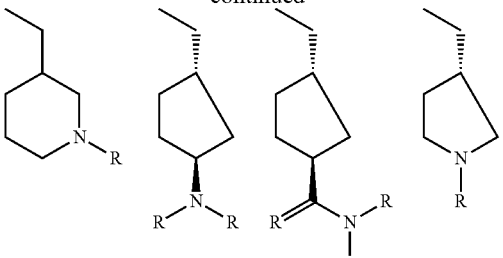
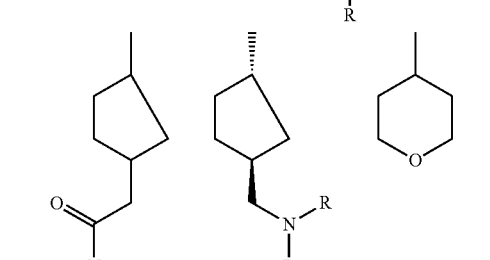
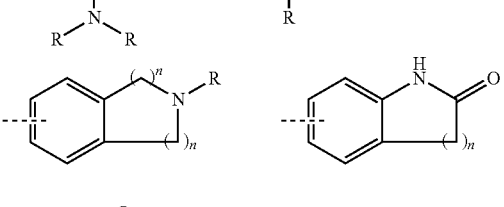
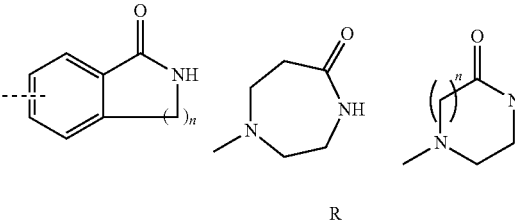
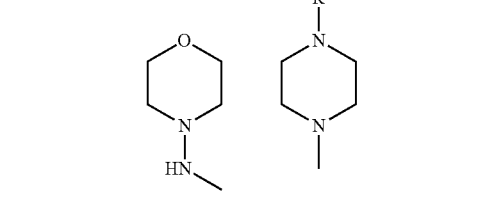
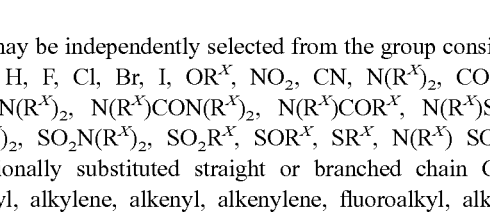
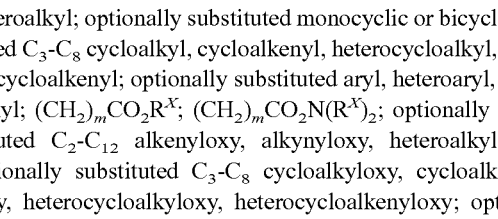
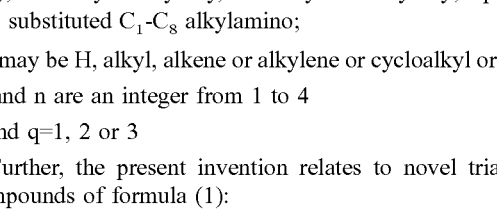

R may be independently selected from the group consisting of: H, F, Cl, Br, I, $OR^X$, $NO_2$, CN, $N(R^X)_2$, $COOR^X$, $CON(R^X)_2$, $N(R^X)CON(R^X)_2$, $N(R^X)COR^X$, $N(R^X)SO_2N(R^X)_2$, $SO_2N(R^X)_2$, $SO_2R^X$, $SOR^X$, $SR^X$, $N(R^X)$ $SO_2R^X$; optionally substituted straight or branched chain $C_1$-$C_6$ alkyl, alkylene, alkenyl, alkenylene, fluoroalkyl, alkynyl, heteroalkyl; optionally substituted monocyclic or bicyclic or fused $C_3$-$C_8$ cycloalkyl, cycloalkenyl, heterocycloalkyl, heterocycloalkenyl; optionally substituted aryl, heteroaryl, arylalkyl; $(CH_2)_m CO_2 R^X$; $(CH_2)_m CO_2 N(R^X)_2$; optionally substituted $C_2$-$C_{12}$ alkenyloxy, alkynyloxy, heteroalkyloxy; optionally substituted $C_3$-$C_8$ cycloalkyloxy, cycloalkenyloxy, heterocycloalkyloxy, heterocycloalkenyloxy; optionally substituted $C_1$-$C_8$ alkylamino;

$R^X$ may be H, alkyl, alkene or alkylene or cycloalkyl or aryl m and n are an integer from 1 to 4 p and q=1, 2 or 3

Further, the present invention relates to novel triazine compounds of formula (1):

Formula 1
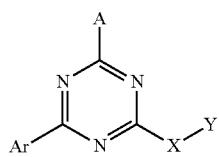
A is preferably selected from:
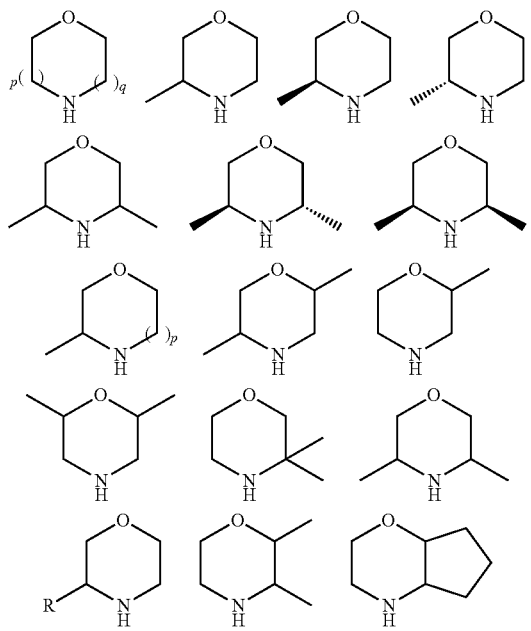
and all stereoisomers or isomers or enantiomers of above,
Ar is preferably selected from:
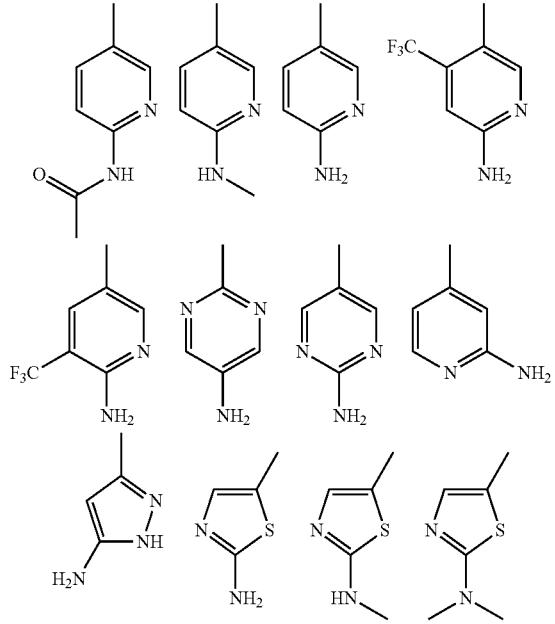
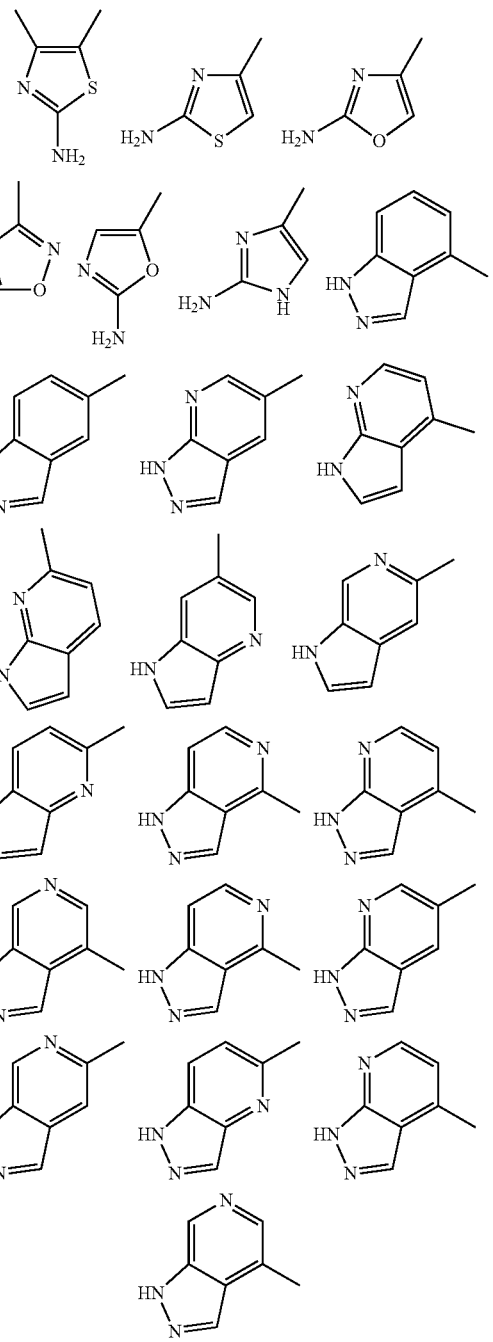
X is preferably O
Y is preferably selected from:
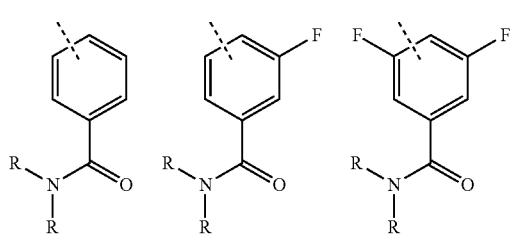

-continued

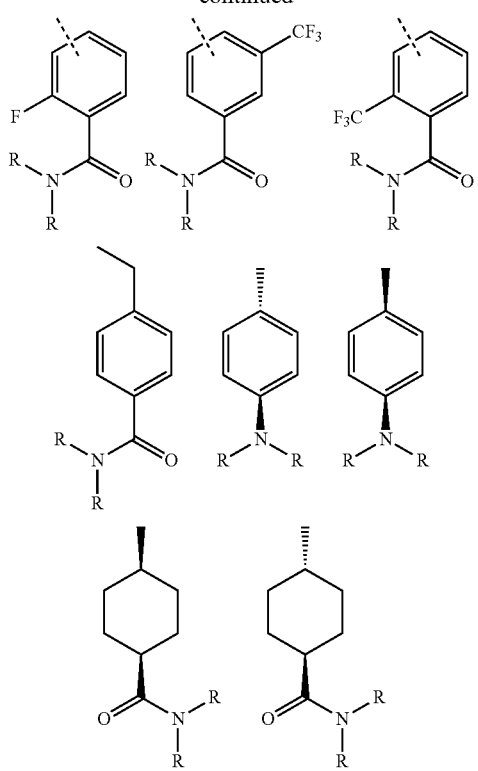

where, R may be independently selected from the group consisting of: H, F, Cl, Br, I, $OR^X$, $NO_2$, CN, $N(R^X)_2$, $COOR^X$, $CON(R^X)_2$, $N(R^X)CON(R^X)_2$, $N(R^X)COR^X$, $N(R^X)SO_2N(R^X)_2$, $SO_2N(R^X)_2$, $SO_2R^X$, $SOR^X$, $SR^X$, $N(R^X)SO_2R^X$; optionally substituted straight or branched chain $C_1$-$C_6$ alkyl, alkylene, alkenyl, alkenylene, fluoroalkyl, alkynyl, heteroalkyl; optionally substituted monocyclic or bicyclic or fused $C_3$-$C_8$ cycloalkyl, cycloalkenyl, heterocycloalkyl, heterocycloalkenyl; optionally substituted aryl, heteroaryl, arylalkyl; $(CH_2)_mCO_2R^X$; $(CH_2)_mCO_2N(R^X)_2$; optionally substituted $C_2$-$C_{12}$ alkenyloxy, alkynyloxy, heteroalkyloxy; optionally substituted $C_3$-$C_8$ cycloalkyloxy, cycloalkenyloxy, heterocycloalkyloxy, heterocycloalkenyloxy; optionally substituted $C_1$-$C_8$ alkylamino;

$R^X$ may be H, alkyl, alkene or alkylene or cycloalkyl or aryl m and n are an integer from 1 to 4 p and q=1, 2 or 3

Further, the present invention relates to novel triazine compounds of formula (1):

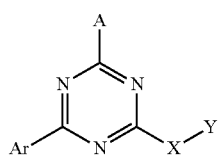

Formula 1 wherein:

A is preferably selected from:

and all stereoisomers or isomers or enantiomers of above,

Ar is preferably selected from:

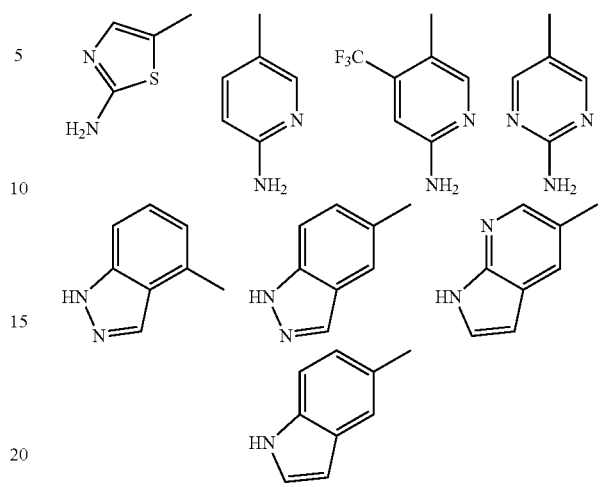

X is preferably O

Y is preferably selected from:

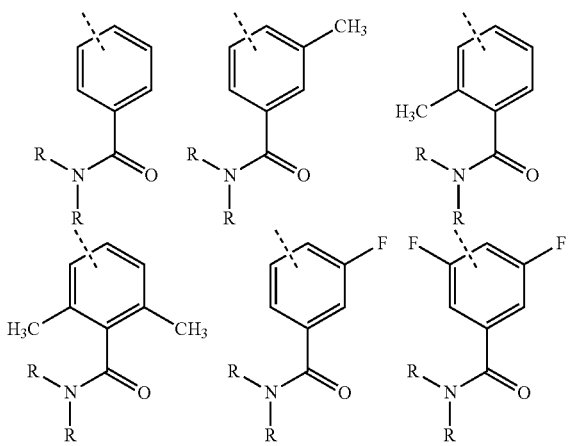

where,

R may be independently selected from the group consisting of: H, F, Cl, Br, I, $OR^X$, $NO_2$, CN, $N(R^X)_2$, $COOR^X$, $CON(R^X)_2$, $N(R^X)CON(R^X)_2$, $N(R^X)COR^X$, $N(R^X)SO_2N(R^X)_2$, $SO_2N(R^X)_2$, $SO_2R^X$, $SOR^X$, $SR^X$, $N(R^X)SO_2R^X$; optionally substituted straight or branched chain $C_1$-$C_6$ alkyl, alkylene, alkenyl, alkenylene, fluoroalkyl, alkynyl, heteroalkyl; optionally substituted monocyclic or bicyclic or fused $C_3$-$C_8$ cycloalkyl, cycloalkenyl, heterocycloalkyl, heterocycloalkenyl; optionally substituted aryl, heteroaryl, arylalkyl; $(CH_2)_mCO_2R^X$; $(CH_2)CO_2N(R^X)_2$; optionally substituted $C_2$-$C_{12}$ alkenyloxy, alkynyloxy, heteroalkyloxy; optionally substituted $C_3$-$C_8$ cycloalkyloxy, cycloalkenyloxy, heterocycloalkyloxy, heterocycloalkenyloxy; optionally substituted $C_1$-$C_8$ alkylamino;

$R^X$ may be H, alkyl, alkene or alkylene or cycloalkyl or aryl m and n are an integer from 1 to 4 p and q=1, 2 or 3

The present invention includes novel triazine compounds represented by Formula (I) as claimed in claim 1, their isomer, salt and solvate thereof; wherein:

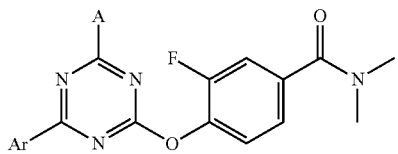

Formula 2 wherein:
A is preferably selected from:

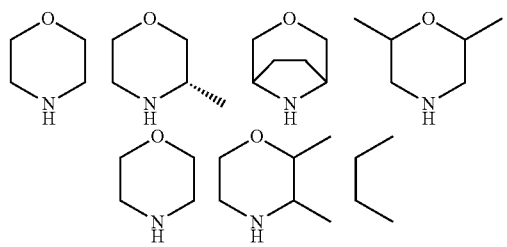

And all stereoisomers or isomers or enantiomers of above,
Ar is preferably selected from:

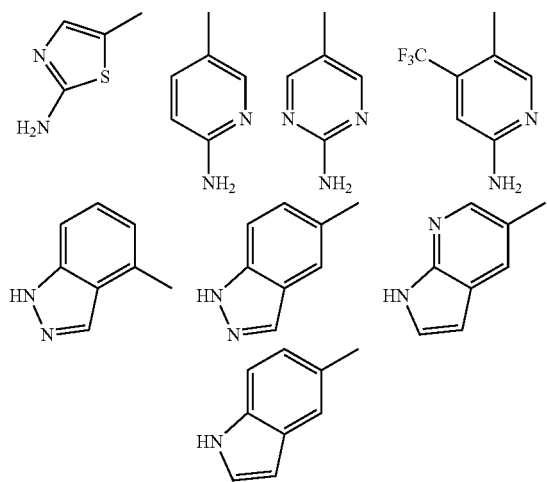

The term "alkyl" refers to a linear or branched saturated monovalent hydrocarbon, wherein the alkylene may optionally be substituted as described herein. The term "alkyl" also encompasses both linear and branched alkyl, unless otherwise specified. In certain embodiments, the alkyl is a linear saturated monovalent hydrocarbon that has the specified number of carbon atoms, or branched saturated monovalent hydrocarbon of specified number of carbon atoms. As used herein, linear $C_1$-$C_6$ and branched $C_3$-$C_6$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_1$-$C_6$ alkyl refers to a linear saturated monovalent hydrocarbon of 1 to 6 carbon atoms or a branched saturated monovalent hydrocarbon of 3 to 6 carbon atoms.

The term "alkylene" refers to a linear or branched saturated divalent hydrocarbon, wherein the alkylene may optionally be substituted as described herein. The term "alkylene" encompasses both linear and branched alkylene, unless otherwise specified. In certain embodiments, the alkylene is a linear saturated divalent hydrocarbon that has the specified number of carbon atoms, or branched saturated divalent hydrocarbon of the specified number of carbon atoms. As used herein, linear $C_1$-$C_6$ and branched $C_3$-$C_6$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_1$-$C_6$ alkylene refers to a linear saturated divalent hydrocarbon of 1 to 6 carbon atoms or a branched saturated divalent hydrocarbon of 3 to 6 carbon atoms.

The term "alkenyl" refers to a linear or branched monovalent hydrocarbon, which contains one or more, in one embodiment, one to five, carbon-carbon double bonds. The alkenyl may be optionally substituted as described herein. The term "alkenyl" also embraces compounds having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_2$-$C_6$ alkenyl refers to a linear unsaturated monovalent hydrocarbon of 2 to 6 carbon atoms or a branched unsaturated monovalent hydrocarbon of 3 to 6 carbon atoms. In certain embodiments, the alkenyl is a linear monovalent hydrocarbon that has the specified number of carbon atoms, or a branched monovalent hydrocarbon that has the specified number of carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon, which contains one or more, in one embodiment, one to five, carbon-carbon double bonds. The alkenylene may be optionally substituted as described herein. Similarly, the term "alkenylene" also embraces compounds having "cis" and "trans" configurations, or alternatively, "E" and "Z" configurations. As used herein, the term "alkenylene" encompasses both linear and branched alkenylene, unless otherwise specified. For example, $C_2$-$C_6$ alkenylene refers to a linear unsaturated divalent hydrocarbon of 2 to 6 carbon atoms or a branched unsaturated divalent hydrocarbon of 3 to 6 carbon atoms. In certain embodiments, the alkenylene is a linear divalent hydrocarbon that has the specified number of carbon atoms, or a branched divalent hydrocarbon that has the specified number of carbon atoms. Examples of alkenylene groups include, but are not limited to ethenylene, allylene, propenylene, butenylene, and 4-methylbutenylene.

The term "alkynyl" refers to a linear or branched monovalent hydrocarbon, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon that has the specified number of carbon atoms, or a branched monovalent hydrocarbon that has the specified number of carbon atoms. Examples of alkynyl groups include, but are not limited to, ethynyl (—C≡CH) and propargyl

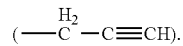

For example, $C_2$-$C_6$ alkynyl refers to a linear unsaturated monovalent hydrocarbon of 2 to 6 carbon atoms or a branched unsaturated monovalent hydrocarbon of 3 to 6 carbon atoms.

The term "alkynylene" refers to a linear or branched divalent hydrocarbon, which contains one or more, in one embodiment, one to five, carbon-carbon triple bonds. The alkynylene may be optionally substituted as described herein. The term "alkynylene" also encompasses both linear and branched alkynylene, unless otherwise specified. In certain embodiments, the alkynylene is a linear divalent hydrocarbon that has the specified number of carbon atoms, or a branched divalent hydrocarbon that has the specified number of carbon atoms. Examples of alkynylene groups include, but are not limited to, ethynylene (—C≡C—) and propargylene (—CH$_2$C≡C—). For example, $C_2$-$C_6$ alkynylene refers to a linear unsaturated divalent hydrocarbon of 2 to 6 carbon atoms or a branched unsaturated divalent hydrocarbon of 3 to 6 carbon atoms.

The term "cycloalkyl" refers to a cyclic saturated bridged and/or non-bridged monovalent hydrocarbon, which may be optionally substituted as described herein. In certain embodiments, the cycloalkyl has from 3 to 20 ($C_3$-$C_{20}$), from 3 to 15 ($C_3$-$C_{15}$), from 3 to 10 ($C_3$-$C_{10}$), or from 3 to 7 ($C_3$-$C_7$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkylene" refers to a cyclic saturated bridged and/or nonbridged divalent hydrocarbon, which may be optionally substituted as described herein. In certain embodiments, the cycloalkylene has from 3 to 20 ($C_3$-$C_{20}$), from 3 to 15 ($C_3$-$C_{15}$), from 3 to 10 ($C_3$-$C_{10}$), or from 3 to 7 ($C_3$-$C_7$) carbon atoms. Examples of cycloalkylene groups include, but are not limited to, cyclopropylene, cyclobutylene, cyclopentylene, cyclohexylene, cycloheptylene, decalinylene, and adamantylene.

The term "aryl" refers to a monocyclic aromatic group and/or multicyclic monovalent aromatic group that contain at least one aromatic hydrocarbon ring. In certain embodiments, the aryl has from 6 to 20 ($C_6$-$C_{20}$), from 6 to 15 ($C_6$-$C_{15}$), or from 6 to 10 ($C_6$-$C_{10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "arylene" refers to a monocyclic and/or multicyclic divalent aromatic group that contains at least one aromatic hydrocarbon ring. In certain embodiments, the arylene has from 6 to 20 ($C_6$-$C_{20}$), from 6 to 15 ($C_6$-$C_{15}$), or from 6 to 10 ($C_6$-$C_{10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). In certain embodiments, arylene may also be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group may contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heteroarylene" refers to a divalent aromatic group and/or multicyclic aromatic group that contain at least one aromatic ring, wherein at least one aromatic ring contains one or more heteroatoms independently selected from O, S, and N. Each ring of a heteroarylene group may contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzothiophenylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroaryl groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroaryl may also be optionally substituted as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic compounds include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, p-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heterocyclylene" refers to a divalent non-aromatic ring system and/or multicyclic ring system that contain at least one non-aromatic ring, wherein one or more of the non-aromatic ring atoms are heteroatoms independently selected from O, S, or N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may include a fused or bridged ring system, and in which the nitrogen or sulfur atoms may be optionally oxidized, and some nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, p-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted as described herein.

The term "halogen", "halide" or "halo" refers to fluorine, chlorine, bromine, and iodine.

The term "optionally substituted" is intended to mean that a group, such as an alkyl, alkylene, alkenyl, alkenylene, alkynyl, alkynylene, alkoxy, alkylamino, dialkylamino, carboxamido, cycloalkyl, cycloalkylene, aryl, arylene, heteroaryl, heteroarylene, heterocyclyl, or heterocyclylene, may be substituted with one or more substituents independently selected from, e.g., (a) $C_1$-$C_6$ alkyl, $C_2$-$C_6$ alkenyl, $C_2$-$C_6$ alkynyl, $C_3$-$C_7$ cycloalkyl, $C_6$-$C_{14}$ aryl, $C_7$-$C_{15}$ aralkyl, heteroaryl, and heterocyclyl, each optionally substituted with one or more substituents; and (b) halo, cyano (—CN), nitro (—$NO_2$), —C(O)$R_3$, —C(O)O$R_3$, —C(O)NR$_b$RC, —C(NR$_3$)NR)RC, —O$R_3$, —OC(O)$R_3$, —OC(O)OR$_3$, —OC(O)NR$_b$RC, —OC(=NR$_3$)NR)RC, —OS(O)$R_3$, —OS(O)$_2$R$_3$, —OS(O)NR$_b$RC, —OS(O)$_2$NR$_b$Rc, —NR$_b$Rc, —NR$_3$C(O)R$_d$, —NR$_3$C(O)OR$_d$, —NR$_3$C(O)NR$_b$RC, —NR$_3$C(=NR$_d$)NR$_b$RC, —NR$_3$S(O)R$_d$, —NR$_3$S(O)$_2$R$_d$, —NR$_3$S(O)NR$_b$RC, —NR$_3$S(O)NR$_b$Rc, —SR$_3$, —S(O)R$_3$, —S(O)$_2$R$_3$, —S(O)NR$_b$RC, and —S(O)$_2$NR$_b$RC, wherein each $R_3$, $R_b$, $R_e$, and $R_d$ is independently (i) hydrogen; (ii) $C_1$-$C_6$ alkyl, $C_2$-$C_6$ alkenyl, $C_2$-$C_6$ alkynyl, $C_3$-$C_7$ cycloalkyl, $C_6$-$C_{14}$ aryl, $C_7$-$C_{15}$ aralkyl, heteroaryl, or heterocyclyl, each optionally substituted with one or more substituents; or (iii) $R_b$ and $R_e$ together with the N atom to which they are attached form heteroaryl or heterocyclyl, optionally substituted with one or more, in one embodiment, one, two, three, or four, substituents. As used herein, all groups that may be substituted are "optionally substituted," unless otherwise specified.

The present invention provides compound represented by formula I that inhibits mTOR alone or in combination with PI3K.

The present invention provides compounds represented by formula I that inhibit mTOR and in addition may also exhibit PI3K inhibition.

A few exemplary compounds of the present invention are presented at Table 1:

TABLE 1

Certain exemplified compound of the present invention

| Chemical Number | Chemical Structure | Chemical Name |
|---|---|---|
| 10001 | 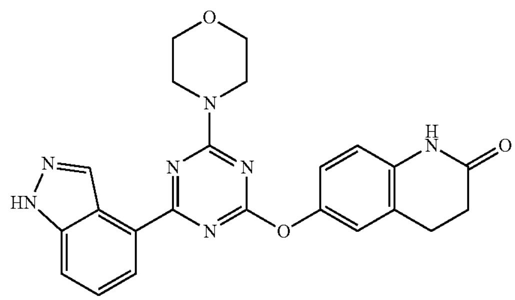 [SMILES: O=C1CCc2cc(Oc3nc(-c4cccc5[nH]ncc45)nc(N4CCOCC4)n3)ccc2N1] | 6-(4-(1H-indazol-4-yl)-6-morpholino-1,3,5-triazin-2-yloxy)-3,4-dihydroquinolin-2(1H)-one |
| 10002 | 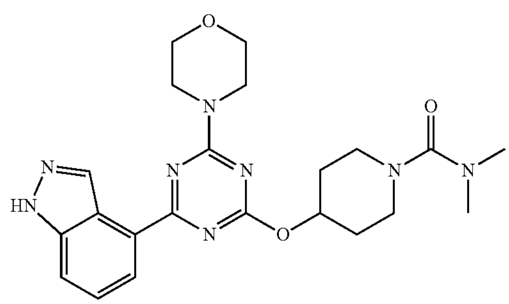 [SMILES: CN(C)C(=O)N1CCC(Oc2nc(-c3cccc4[nH]ncc34)nc(N3CCOCC3)n2)CC1] | 4-(4-(1H-indazol-4-yl)-6-morpholino-1,3,5-triazin-2-yloxy)-N,N-dimethylpiperidine-1-carboxamide |
| 10003 | 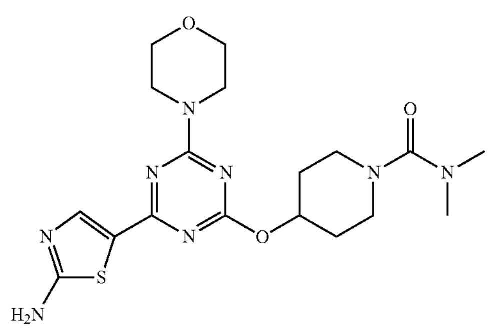 [SMILES: CN(C)C(=O)N1CCC(Oc2nc(-c3cnc(N)s3)nc(N3CCOCC3)n2)CC1] | 4-(4-(2-aminothiazol-5-yl)-6-morpholino-1,3,5-triazin-2-yloxy)-N,N-dimethylpiperidine-1-carboxamide |
| 10004 | 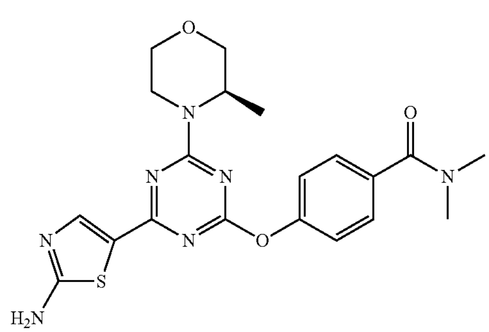 [SMILES: C[C@@H]1COCCN1c1nc(Oc2ccc(C(=O)N(C)C)cc2)nc(-c2cnc(N)s2)n1] | (R)-4-(4-(2-aminothiazol-5-yl)-6-(3-methylmorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10005 | 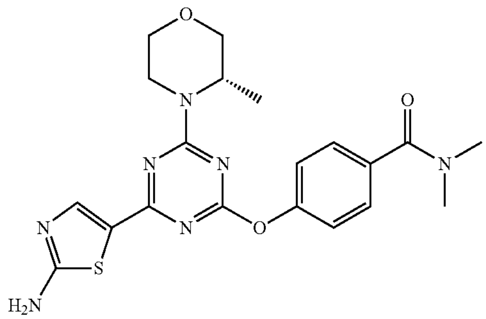 [SMILES: C[C@H]1COCCN1c1nc(Oc2ccc(C(=O)N(C)C)cc2)nc(-c2cnc(N)s2)n1] | (S)-4-(4-(2-aminothiazol-5-yl)-6-(3-methylmorpholino)-1,3,5-triazin-2-yloxy)-N,N-dimethylbenzamide |
| 10006 | 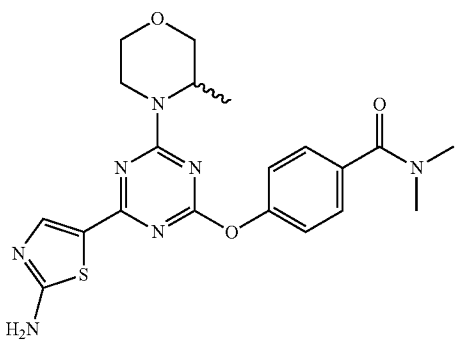 [SMILES: CC1COCCN1c1nc(Oc2ccc(C(=O)N(C)C)cc2)nc(-c2cnc(N)s2)n1] | 4-(4-(2-aminothiazol-5-yl)-6-(3-methylmorpholino)-1,3,5-triazin-2-yloxy)-N,N-dimethylbenzamide |
| 10007 | 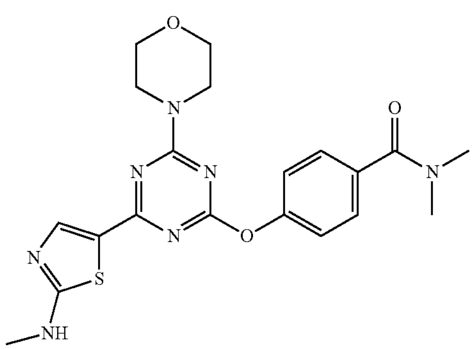 | N,N-dimethyl-4-(4-(2-(methylamino)thiazol-5-yl)-6-morpholino-1,3,5-triazin-2-yloxy)benzamide |
| 10008 | 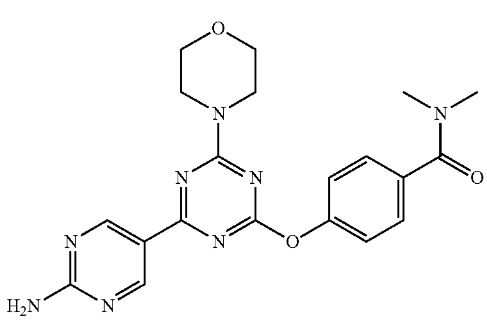 [SMILES: CN(C)C(=O)c1ccc(Oc2nc(-c3cnc(N)nc3)nc(N3CCOCC3)n2)cc1] | 4-(4-(2-aminopyrimidin-5-yl)-6-morpholino-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10009 | 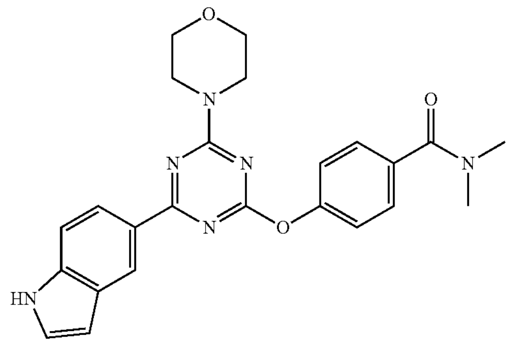 [SMILES: CN(C)C(=O)c1ccc(Oc2nc(-c3ccc4[nH]ccc4c3)nc(N3CCOCC3)n2)cc1] | 4-(4-(1H-indol-5-yl)-6-morpholino-1,3,5-triazin-2-yloxy)-N,N-dimethylbenzamide |
| 10010 | 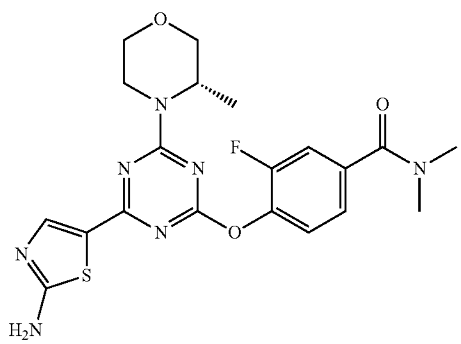 [SMILES: C[C@H]1COCCN1c1nc(Oc2ccc(C(=O)N(C)C)cc2F)nc(-c2cnc(N)s2)n1] | (S)-4-(4-(2-aminothiazol-5-yl)-6-(3-methylmorpholino)-1,3,5-triazin-2-yloxy)-3-fluoro-N,N-dimethylbenzamide |
| 10011 | 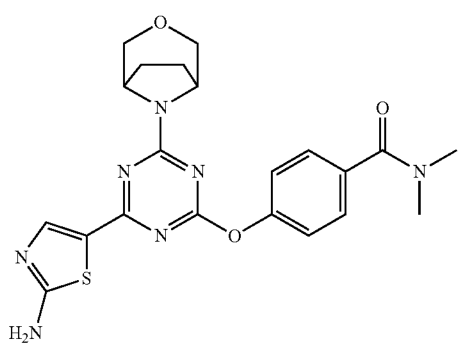 [SMILES: CN(C)C(=O)c1ccc(Oc2nc(-c3cnc(N)s3)nc(N3C4CCC3COC4)n2)cc1] | 4-(4-(2-aminothiazol-5-yl)-6-((1R,5S)-3-oxa-8-azabicyclo[3.2.1]octan-8-yl)-1,3,5-triazin-2-yloxy)-N,N-dimethylbenzamide |
| 10012 | 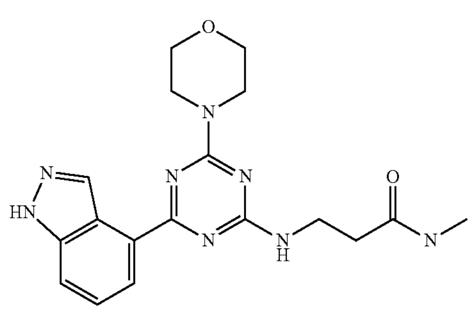 [SMILES: CNC(=O)CCNc1nc(-c2cccc3[nH]ncc23)nc(N2CCOCC2)n1] | 3-(4-(1H-indazol-4-yl)-6-morpholino-1,3,5-triazin-2-ylamino)-N,N-dimethylpropanamide |

TABLE 1-continued

Certain exemplified compound of the present invention

| Chemical Number | Chemical Structure | Chemical Name |
|---|---|---|
| 10013 | 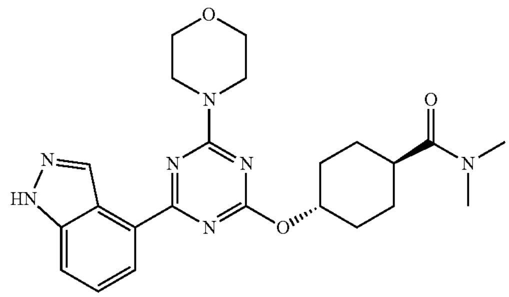 [SMILES: CN(C)C(=O)[C@H]1CC[C@H](Oc2nc(-c3cccc4[nH]ncc34)nc(N3CCOCC3)n2)CC1] | (1r,4r)-4-(4-(1H-indazol-4-yl)-6-morpholino-1,3,5-triazin-2-yloxy)-N,N-dimethylcyclohexanecarboxamide |
| 10014 | 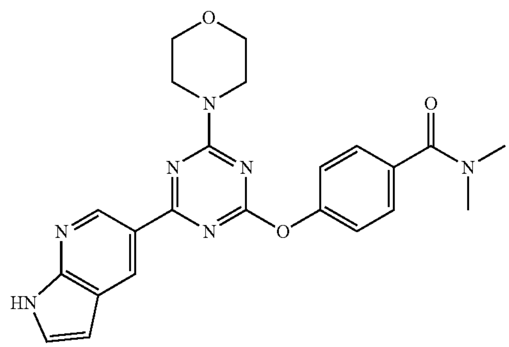 [SMILES: CN(C)C(=O)c1ccc(Oc2nc(-c3cnc4[nH]ccc4c3)nc(N3CCOCC3)n2)cc1] | N,N-dimethyl-4-(4-morpholino-6-(1H-pyrrolo[2,3-b]pyridin-5-yl)-1,3,5-triazin-2-yloxy)benzamide |
| 10015 | 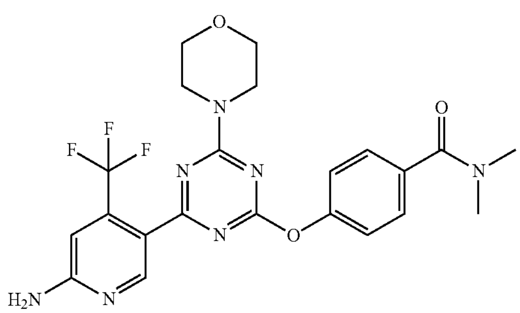 [SMILES: CN(C)C(=O)c1ccc(Oc2nc(-c3cnc(N)cc3C(F)(F)F)nc(N3CCOCC3)n2)cc1] | 4-(4-(6-amino-4-(trifluoromethyl)pyridin-3-yl)-6-morpholino-1,3,5-triazin-2-yloxy)-N,N-dimethylbenzamide |
| 10016 | 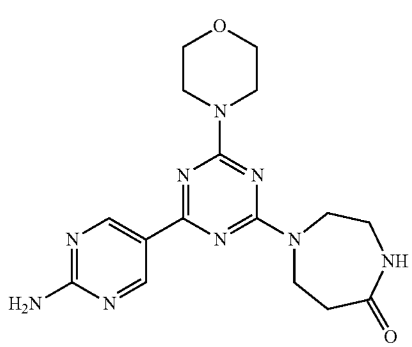 [SMILES: Nc1ncc(-c2nc(N3CCOCC3)nc(N3CCNC(=O)CC3)n2)cn1] | 1-(4-(2-aminopyrimidin-5-yl)-6-morpholino-1,3,5-triazin-2-yl)-1,4-diazepan-5-one |

TABLE 1-continued

Certain exemplified compound of the present invention

| Chemical Number | Chemical Structure | Chemical Name |
|---|---|---|
| 10017 | 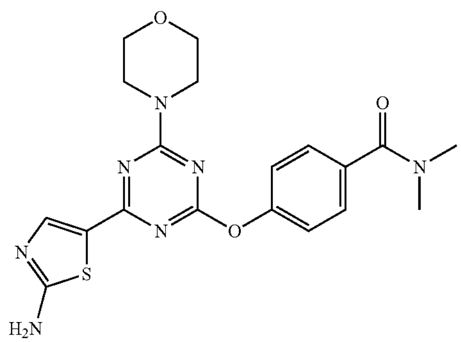 [SMILES: CN(C)C(=O)c1ccc(Oc2nc(-c3cnc(N)s3)nc(N3CCOCC3)n2)cc1] | 4-(4-(2-aminothiazol-5-yl)-6-morpholino-1,3,5-triazin-2-yloxy)-N,N-dimethylbenzamide |
| 10018 | 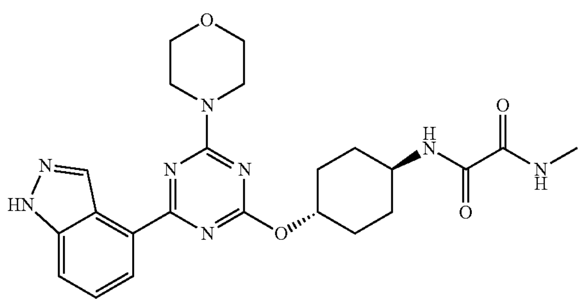 [SMILES: CNC(=O)C(=O)N[C@H]1CC[C@H](Oc2nc(-c3cccc4[nH]ncc34)nc(N3CCOCC3)n2)CC1] | N1-((1r,4r)-4-(4-(1H-indazol-4-yl)-6-morpholino-1,3,5-triazin-2-yloxy)cyclohexyl)-N2-methyloxalamide |
| 10019 | 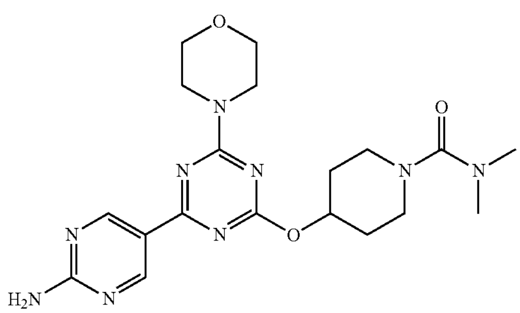 [SMILES: CN(C)C(=O)N1CCC(Oc2nc(-c3cnc(N)nc3)nc(N3CCOCC3)n2)CC1] | 4-(4-(2-aminopyrimidin-5-yl)-6-morpholino-1,3,5-triazin-2-yloxy)-N,N-dimethylpiperidine-1-carboxamide |
| 10020 | 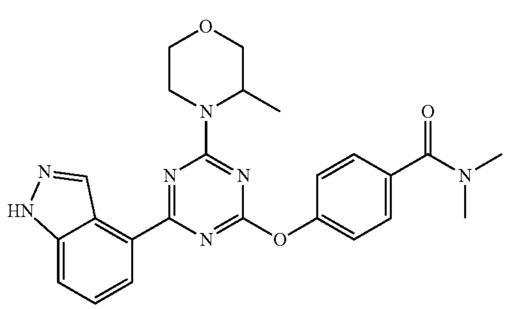 [SMILES: CC1COCCN1c1nc(Oc2ccc(C(=O)N(C)C)cc2)nc(-c2cccc3[nH]ncc23)n1] | 4-(4-(1H-indazol-4-yl)-6-(3-methylmorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10021 | 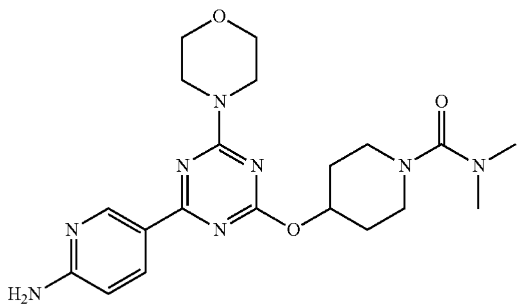 [SMILES: CN(C)C(=O)N1CCC(Oc2nc(-c3ccc(N)nc3)nc(N3CCOCC3)n2)CC1] | 4-(4-(6-aminopyridin-3-yl)-6-morpholino-1,3,5-triazin-2-yloxy)-N,N-dimethylpiperidine-1-carboxamide |
| 10022 | 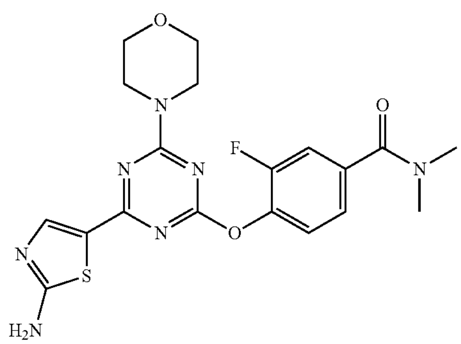 [SMILES: CN(C)C(=O)c1ccc(Oc2nc(-c3cnc(N)s3)nc(N3CCOCC3)n2)c(F)c1] | 4-(4-(2-aminothiazol-5-yl)-6-morpholino-1,3,5-triazin-2-yloxy)-3-fluoro-N,N-dimethylbenzamide |
| 10023 | 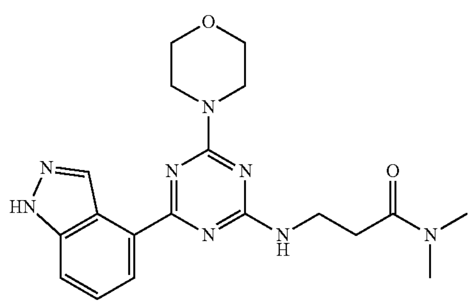 [SMILES: CN(C)C(=O)CCNc1nc(-c2cccc3[nH]ncc23)nc(N2CCOCC2)n1] | 3-(4-(1H-indazol-4-yl)-6-morpholino-1,3,5-triazin-2-ylamino)-N,N-dimethylpropanamide |
| 10024 | 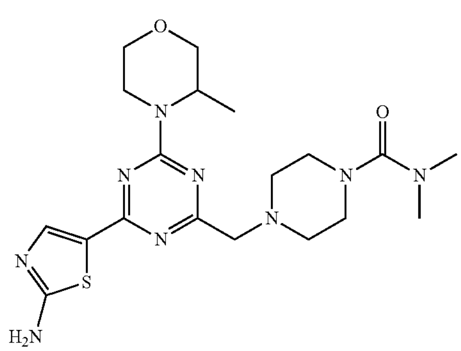 [SMILES: CC1COCCN1c1nc(CN2CCN(C(=O)N(C)C)CC2)nc(-c2cnc(N)s2)n1] | 4-((4-(2-aminothiazol-5-yl)-6-(3-methylmorpholino)-1,3,5-triazin-2-yl)methyl)-N,N-dimethylpiperazine-1-carboxamide |

TABLE 1-continued

Certain exemplified compound of the present invention

| Chemical Number | Chemical Structure | Chemical Name |
|---|---|---|
| 10025 | 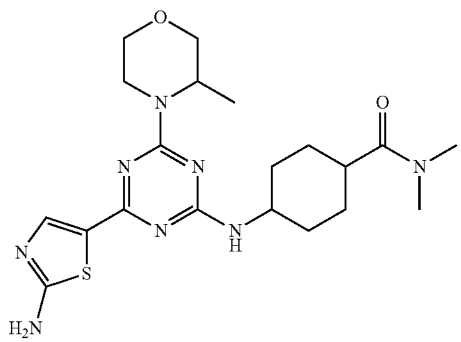 [SMILES: CC1COCCN1c1nc(NC2CCC(C(=O)N(C)C)CC2)nc(-c2cnc(N)s2)n1] | 4-(4-(2-aminothiazol-5-yl)-6-(3-methylmorpholino)-1,3,5-triazin-2-ylamino)-N,N-dimethylcyclohexanecarboxamide |
| 10026 | 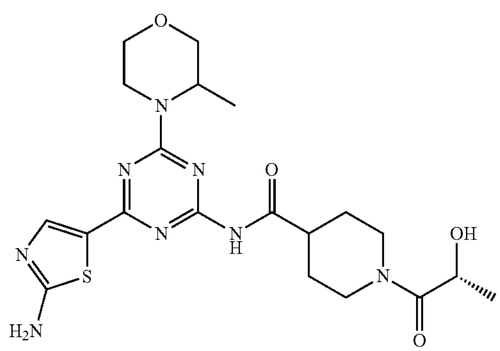 [SMILES: CC1COCCN1c1nc(NC(=O)C2CCN(C(=O)[C@@H](C)O)CC2)nc(-c2cnc(N)s2)n1] | N-(4-(2-aminothiazol-5-yl)-6-(3-methylmorpholino)-1,3,5-triazin-2-yl)-1-((R)-2-hydroxypropanoyl)piperidine-4-carboxamide |
| 10027 | 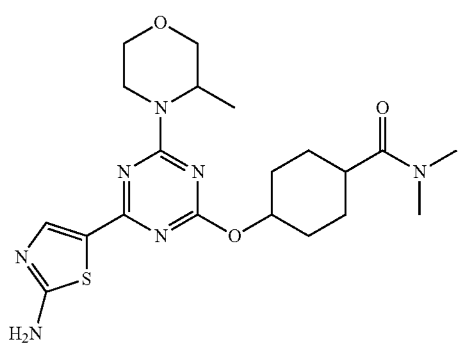 [SMILES: CC1COCCN1c1nc(OC2CCC(C(=O)N(C)C)CC2)nc(-c2cnc(N)s2)n1] | 4-(4-(2-aminothiazol-5-yl)-6-(3-methylmorpholino)-1,3,5-triazin-2-yloxy)-N,N-dimethylcyclohexanecarboxamide |
| 10028 | 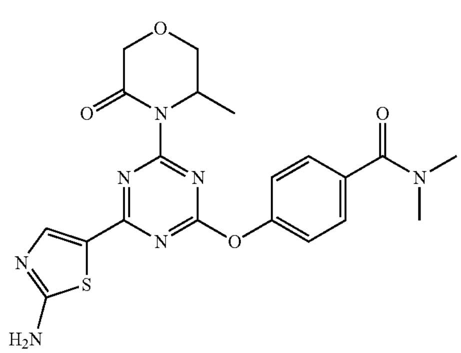 [SMILES: CC1COCC(=O)N1c1nc(Oc2ccc(C(=O)N(C)C)cc2)nc(-c2cnc(N)s2)n1] | 4-(4-(2-aminothiazol-5-yl)-6-(3-methyl-5-oxomorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10029 | 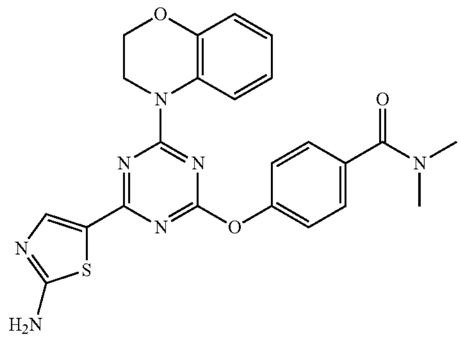 [SMILES: CN(C)C(=O)c1ccc(Oc2nc(-c3cnc(N)s3)nc(N3CCOc4ccccc43)n2)cc1] | 4-(4-(2-aminothiazol-5-yl)-6-(2H-benzo[b][1,4]oxazin-4(3H)-yl)-1,3,5-triazin-2-yloxy)-N,N-dimethylbenzamide |
| 10030 | 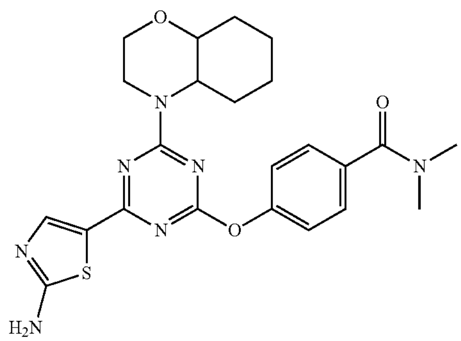 [SMILES: CN(C)C(=O)c1ccc(Oc2nc(-c3cnc(N)s3)nc(N3CCOC4CCCCC43)n2)cc1] | 4-(4-(2-aminothiazol-5-yl)-6-(2H-benzo[b][1,4]oxazin-4(3H,4aH,5H,6H,7H,8H,8aH)-yl)-1,3,5-triazin-2-yloxy)-N,N-dimethylbenzamide |
| 10031 | 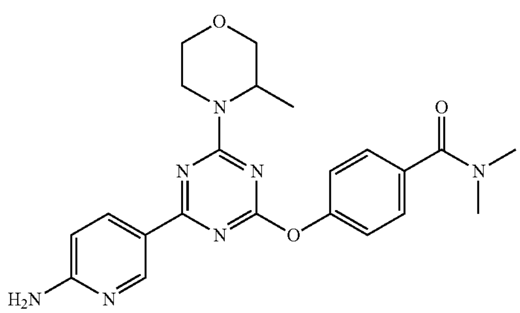 [SMILES: CC1COCCN1c1nc(Oc2ccc(C(=O)N(C)C)cc2)nc(-c2ccc(N)nc2)n1] | 4-(4-(6-aminopyridin-3-yl)-6-(3-methylmorpholino)-1,3,5-triazin-2-yloxy)-N,N-dimethylbenzamide |
| 10032 | 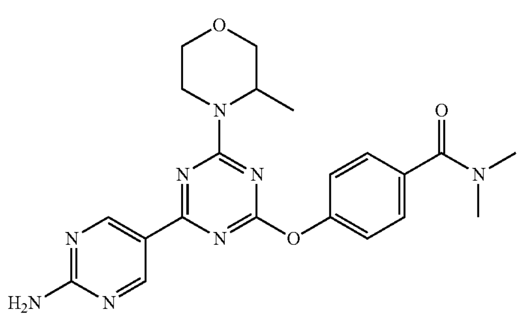 [SMILES: CC1COCCN1c1nc(Oc2ccc(C(=O)N(C)C)cc2)nc(-c2cnc(N)nc2)n1] | 4-(4-(2-aminopyrimidin-5-yl)-6-(3-methylmorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10033 | 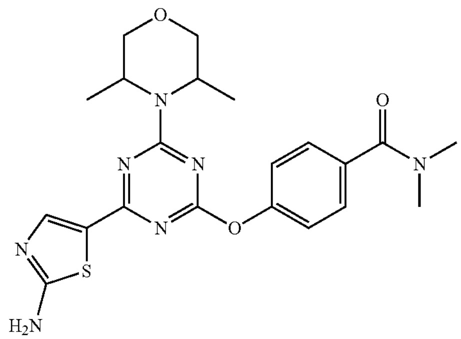 [SMILES: CC1COCC(C)N1c1nc(Oc2ccc(C(=O)N(C)C)cc2)nc(-c2cnc(N)s2)n1] | 4-(4-(2-aminothiazol-5-yl)-6-(3,5-dimethylmorpholino)-1,3,5-triazin-2-yloxy)-N,N-dimethylbenzamide |
| 10034 | 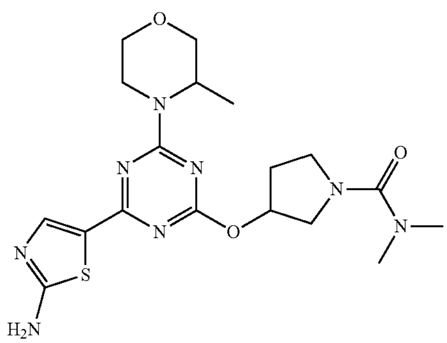 [SMILES: CC1COCCN1c1nc(OC2CCN(C(=O)N(C)C)C2)nc(-c2cnc(N)s2)n1] | 3-(4-(2-aminothiazol-5-yl)-6-(3-methylmorpholino)-1,3,5-triazin-2-yloxy)-N,N-dimethylpyrrolidine-1-carboxamide |
| 10035 | 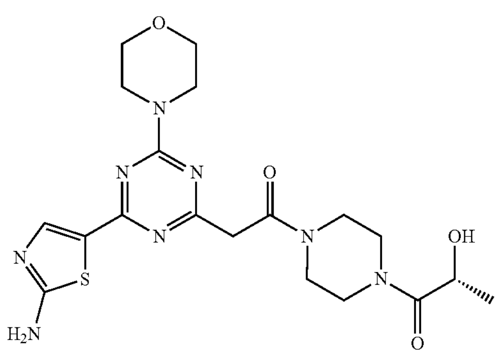 [SMILES: C[C@@H](O)C(=O)N1CCN(C(=O)Cc2nc(-c3cnc(N)s3)nc(N3CCOCC3)n2)CC1] | (R)-1-(4-(2-(4-(2-aminothiazol-5-yl)-6-morpholino-1,3,5-triazin-2-yl)acetyl)piperazin-1-yl)-2-hydroxypropan-1-one |
| 10036 | 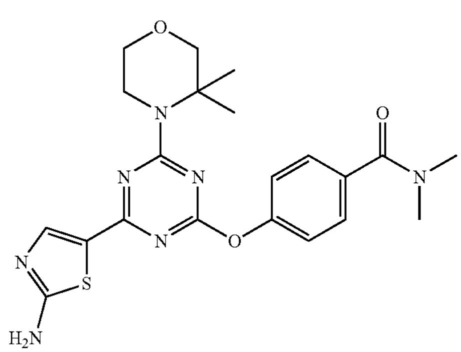 [SMILES: CN(C)C(=O)c1ccc(Oc2nc(-c3cnc(N)s3)nc(N3CCOCC3(C)C)n2)cc1] | 4-(4-(2-aminothiazol-5-yl)-6-(3,3-dimethylmorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10037 | 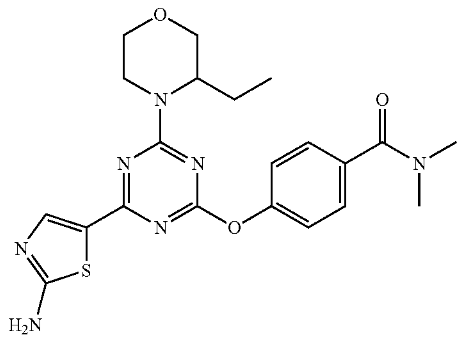 [SMILES: CCC1COCCN1c1nc(Oc2ccc(C(=O)N(C)C)cc2)nc(-c2cnc(N)s2)n1] | 4-(4-(2-aminothiazol-5-yl)-6-(3-ethylmorpholino)-1,3,5-triazin-2-yloxy)-N,N-dimethylbenzamide |
| 10038 | 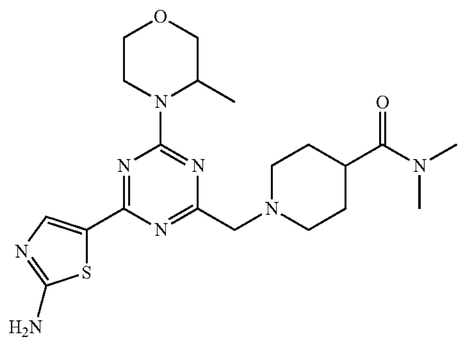 [SMILES: CC1COCCN1c1nc(CN2CCC(C(=O)N(C)C)CC2)nc(-c2cnc(N)s2)n1] | 1-((4-(2-aminothiazol-5-yl)-6-(3-methylmorpholino)-1,3,5-triazin-2-yl)methyl)-N,N-dimethylpiperidine-4-carboxamide |
| 10039 | 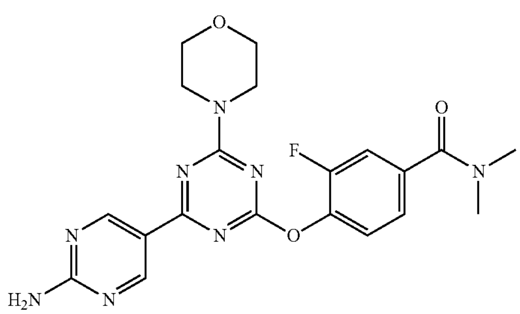 | 4-((4-(2-Aminopyrimidin-5-yl)-6-morpholino,1,3,5-triazin-2-yl)oxy)-3-fluoro-N,N-dimethylbenzamide |
| 10040 | 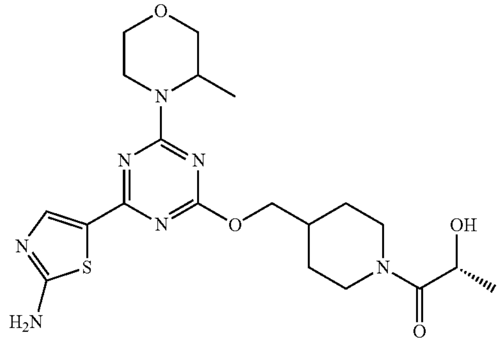 [SMILES: CC1COCCN1c1nc(OCC2CCN(C(=O)[C@@H](C)O)CC2)nc(-c2cnc(N)s2)n1] | (2R)-1-(4-((4-((4-(2-aminothiazol-5-yl)-6-(3-methylmorpholino)-1,3,5-triazin-2-yloxy)methyl)piperidin-1-yl)-2-hydroxypropan-1-one |

TABLE 1-continued

Certain exemplified compound of the present invention

| Chemical Number | Chemical Structure | Chemical Name |
|---|---|---|
| 10041 | 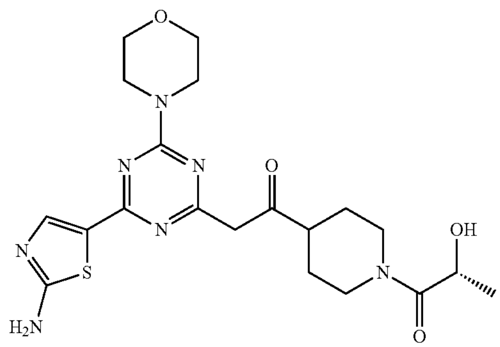 [SMILES: C[C@@H](O)C(=O)N1CCC(C(=O)Cc2nc(-c3cnc(N)s3)nc(N3CCOCC3)n2)CC1] | (R)-1-(4-(2-(4-(2-aminothiazol-5-yl)-6-morpholino-1,3,5-triazin-2-yl)acetyl)piperidin-1-yl)-2-hydroxypropan-1-one |
| 10042 | 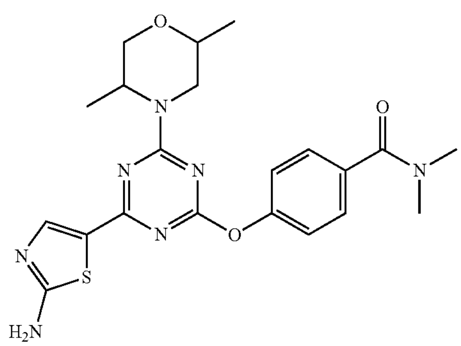 [SMILES: CC1CN(c2nc(Oc3ccc(C(=O)N(C)C)cc3)nc(-c3cnc(N)s3)n2)C(C)CO1] | 4-(4-(2-aminothiazol-5-yl)-6-(2,5-dimethylmorpholino)-1,3,5-triazin-2-yloxy)-N,N-dimethylbenzamide |
| 10043 | 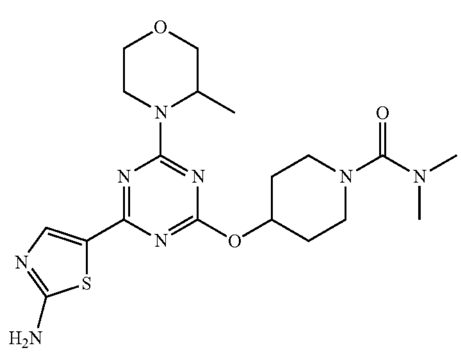 | 4-(4-(2-aminothiazol-5-yl)-6-(3-methylmorpholino)-1,3,5-triazin-2-yloxy)-N,N-dimethylpiperidine-1-carboxamide |
| 10044 | 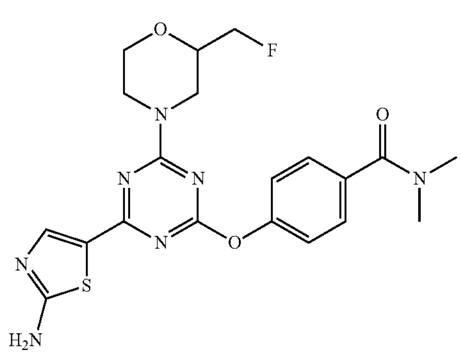 [SMILES: CN(C)C(=O)c1ccc(Oc2nc(-c3cnc(N)s3)nc(N3CCOC(CF)C3)n2)cc1] | 4-(4-(2-aminothiazol-5-yl)-6-(2-(fluoromethyl)morpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10045 | 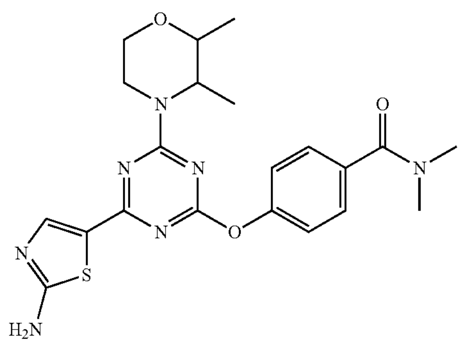 [SMILES: CC1OCCN(c2nc(Oc3ccc(C(=O)N(C)C)cc3)nc(-c3cnc(N)s3)n2)C1C] | 4-(4-(2-aminothiazol-5-yl)-6-(2,3-dimethylmorpholino)-1,3,5-triazin-2-yloxy)-N,N-dimethylbenzamide |
| 10046 | 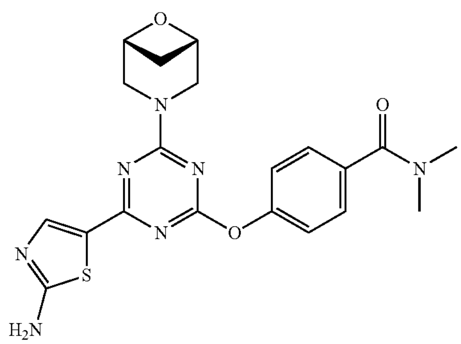 [SMILES: CN(C)C(=O)c1ccc(Oc2nc(-c3cnc(N)s3)nc(N3C[C@H]4C[C@@H](C3)O4)n2)cc1] | 4-(4-(2-aminothiazol-5-yl)-6-((1R,5S)-6-oxa-3-azabicyclo[3.1.1]heptan-3-yl)-1,3,5-triazin-2-yloxy)-N,N-dimethylbenzamide |
| 10047 | 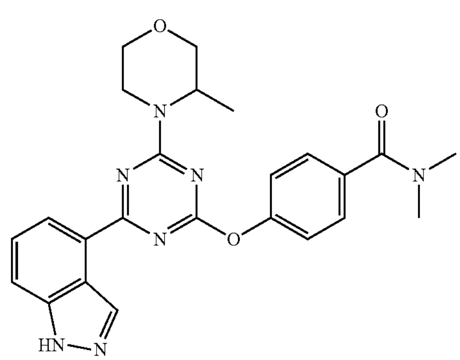 [SMILES: CC1COCCN1c1nc(Oc2ccc(C(=O)N(C)C)cc2)nc(-c2cccc3[nH]ncc23)n1] | 4-(4-(1H-indazol-4-yl)-6-(3-methylmorpholino)-1,3,5-triazin-2-yloxy)-N,N-dimethylbenzamide |
| 10048 | 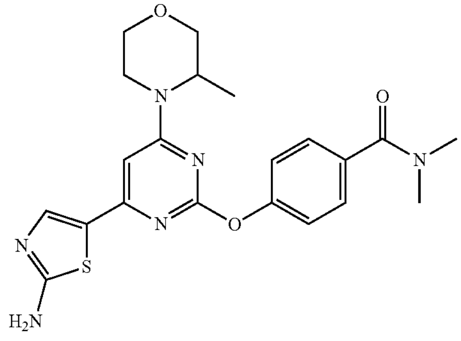 [SMILES: CC1COCCN1c1cc(-c2cnc(N)s2)nc(Oc2ccc(C(=O)N(C)C)cc2)n1] | 4-(4-(2-aminothiazol-5-yl)-6-(3-methylmorpholino)pyrimidin-2-yloxy)-N,N-dimethylbenzamide |

TABLE 1-continued

Certain exemplified compound of the present invention

| Chemical Number | Chemical Structure | Chemical Name |
|---|---|---|
| 10049 | 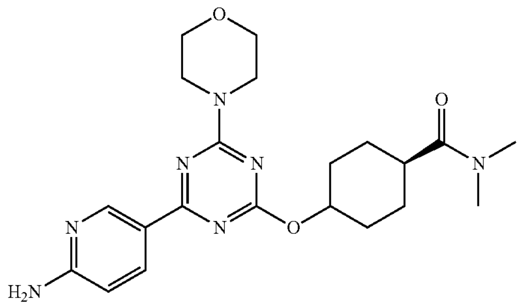 | (1r,4r)-4-(4-(6-aminopyridin-3-yl)-6-morpholino-1,3,5-triazin-2-yloxy)-N,N-dimethylcyclohexanecarboxamide |
| 10050 | 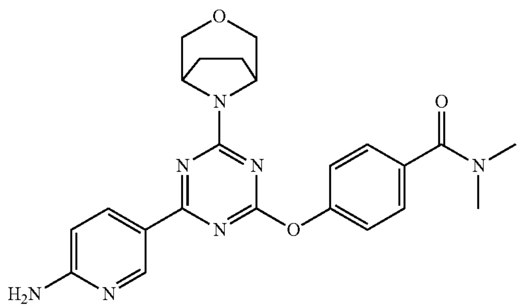 [SMILES: CN(C)C(=O)c1ccc(Oc2nc(-c3ccc(N)nc3)nc(N3C4CCC3COC4)n2)cc1] | 4-(4-(6-aminopyridin-3-yl)-6-((1R,5S)-3-oxa-8-azabicyclo[3.2.1]octan-8-yl)-1,3,5-triazin-2-yloxy)-N,N-dimethylbenzamide |
| 10051 | 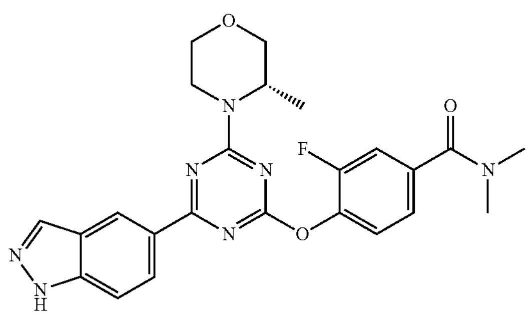 [SMILES: C[C@H]1COCCN1c1nc(Oc2ccc(C(=O)N(C)C)cc2F)nc(-c2ccc3[nH]ncc3c2)n1] | (S)-4-((4-(1H-indazol-5-yl)-6-(3-methylmorpholino)-1,3,5-triazin-2-yl)oxy)-3-fluoro-N,N-dimethylbenzamide |
| 10052 | 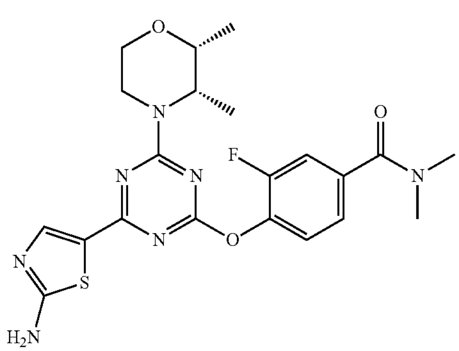 [SMILES: C[C@H]1OCCN(c2nc(Oc3ccc(C(=O)N(C)C)cc3F)nc(-c3cnc(N)s3)n2)[C@H]1C] | 4-((4-(2-Aminothiazol-5-yl)-6-((2R,3S)-2,3-dimethylmorpholino)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10053 | 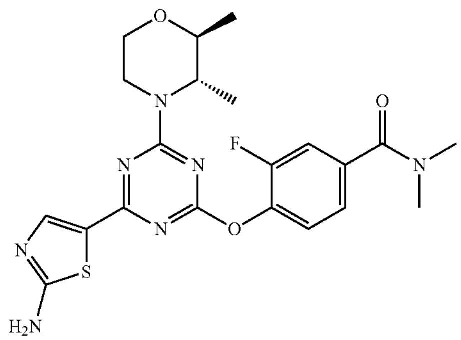 [SMILES: C[C@@H]1OCCN(c2nc(Oc3ccc(C(=O)N(C)C)cc3F)nc(-c3cnc(N)s3)n2)[C@H]1C] | 4-((4-(2-Aminothiazol-5-yl)-6-((2S,3S)-2,3-dimethylmorpholino)-1,3,5-triazin-2-yl)oxy)-3-fluoro-N,N-dimethylbenzamide |
| 10054 | 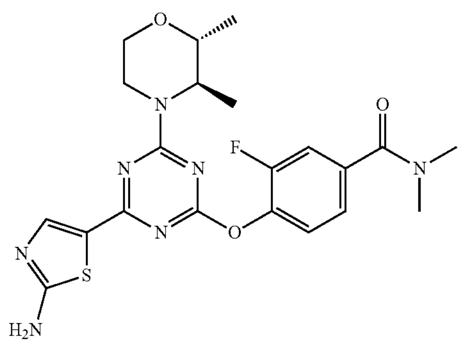 [SMILES: C[C@@H]1[C@@H](C)OCCN1c1nc(Oc2ccc(C(=O)N(C)C)cc2F)nc(-c2cnc(N)s2)n1] | 4-((4-(2-Aminothiazol-5-yl)-6-((2R,3R)-2,3-dimethylmorpholino)-1,3,5-triazin-2-yl)oxy)-3-fluoro-N,N-dimethylbenzamide |
| 10055 | 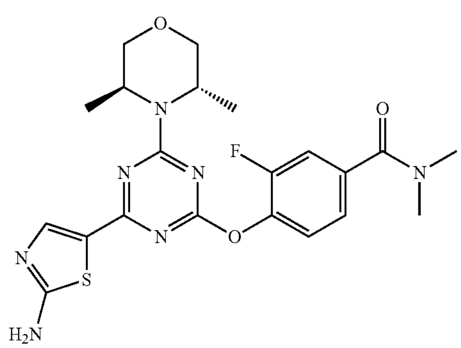 [SMILES: C[C@H]1COC[C@H](C)N1c1nc(Oc2ccc(C(=O)N(C)C)cc2F)nc(-c2cnc(N)s2)n1] | 4-((4-(2-Aminothiazol-5-yl)-6-((3S,5S)-3,5-dimethylmorpholino)-1,3,5-triazin-2-yl)oxy)-3-fluoro-N,N-dimethylbenzamide |
| 10056 | 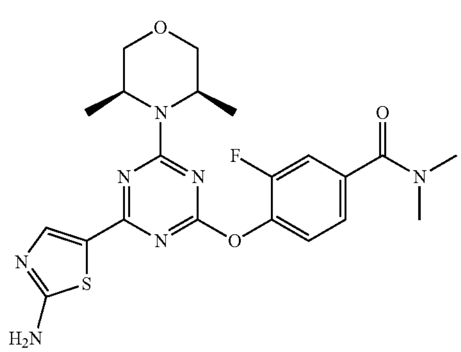 [SMILES: C[C@@H]1COC[C@H](C)N1c1nc(Oc2ccc(C(=O)N(C)C)cc2F)nc(-c2cnc(N)s2)n1] | 4-((4-(2-Aminothiazol-5-yl)-6-((3R,5S)-3,5-dimethylmorpholino)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10057 | 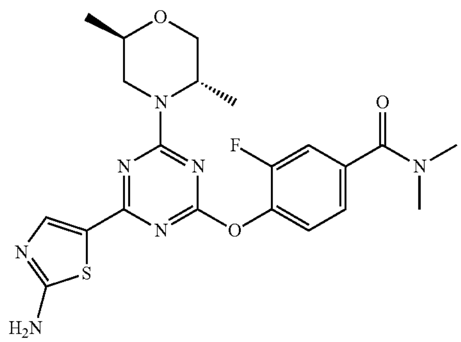 [SMILES: C[C@@H]1CN(c2nc(Oc3ccc(C(=O)N(C)C)cc3F)nc(-c3cnc(N)s3)n2)[C@@H](C)CO1] | 4-((4-(2-Aminothiazol-5-yl)-6-((2R,5S)-2,5-dimethylmorpholino)-1,3,5-triazin-2-yl)oxy)-3-fluoro-N,N-dimethylbenzamide |
| 10058 | 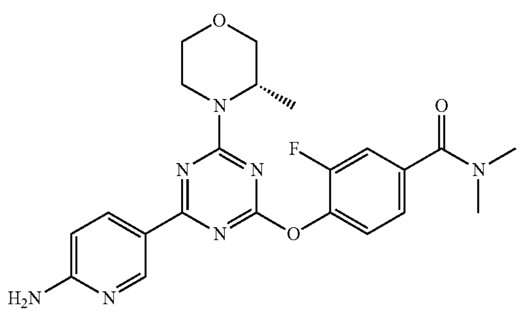 | (S)-4-((4-(6-Aminopyridin-3-yl)-6-(3-methylmorpholino)-1,3,5-triazin-2-yl)oxy)-3-fluoro-N,N-dimethylbenzamide |
| 10059 | 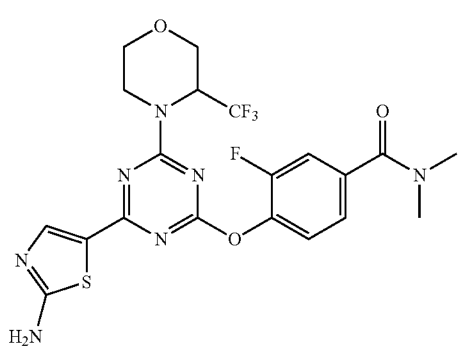 [SMILES: CN(C)C(=O)c1ccc(Oc2nc(-c3cnc(N)s3)nc(N3CCOCC3C(F)(F)F)n2)c(F)c1] | 4-((4-(2-Aminothiazol-5-yl)-6-(3-(trifluoromethyl)morpholino)-1,3,5-triazin-2-yl)oxy)-3-fluoro-N,N-dimethylbenzamide |
| 10060 | 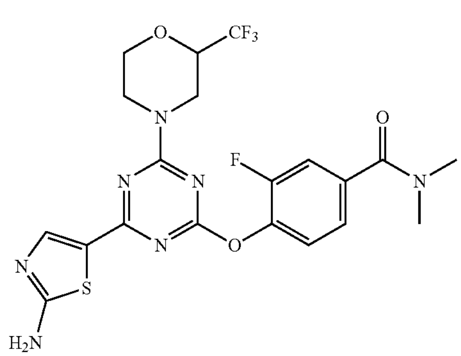 [SMILES: CN(C)C(=O)c1ccc(Oc2nc(-c3cnc(N)s3)nc(N3CCOC(C(F)(F)F)C3)n2)c(F)c1] | 4-((4-(2-Aminothiazol-5-yl)-6-(2-(trifluoromethyl)morpholino)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10061 | 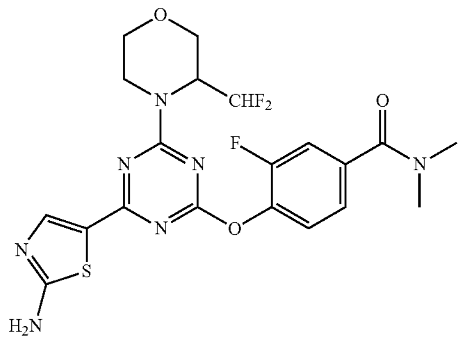 [SMILES: CN(C)C(=O)c1ccc(Oc2nc(-c3cnc(N)s3)nc(N3CCOCC3C(F)F)n2)c(F)c1] | 4-((4-(2-Aminothiazol-5-yl)-6-(3-(difluoromethyl)morpholino)-1,3,5-triazin-2-yl)oxy)-3-fluoro-N,N-dimethylbenzamide |
| 10062 | 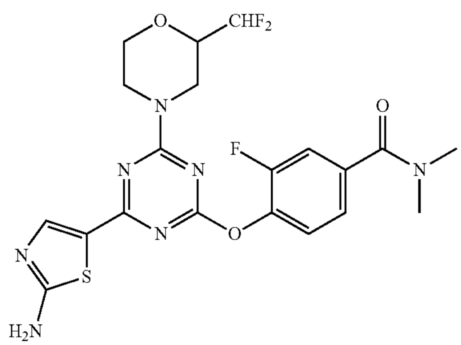 | 4-((4-(2-Aminothiazol-5-yl)-6-(2-(difluoromethyl)morpholino)-1,3,5-triazin-2-yl)oxy)-3-fluoro-N,N-dimethylbenzamide |
| 10063 | 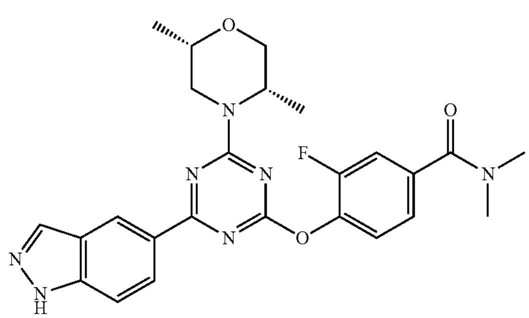 [SMILES: C[C@H]1CN(c2nc(Oc3ccc(C(=O)N(C)C)cc3F)nc(-c3ccc4[nH]ncc4c3)n2)[C@@H](C)CO1] | 4-((4-((2S,3S)-2,5-dimethylmorpholino)-6-(1H-indazol-5-yl)-1,3,5-triazin-2-yl)oxy)-3-fluoro-N,N-dimethylbenzamide |
| 10064 | 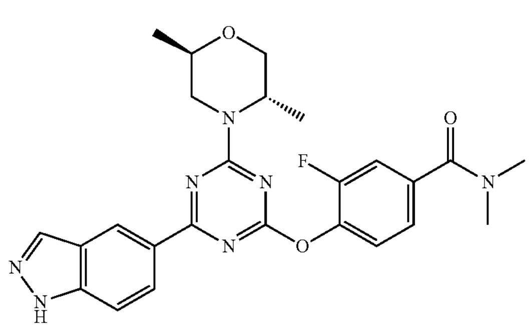 [SMILES: C[C@@H]1CN(c2nc(Oc3ccc(C(=O)N(C)C)cc3F)nc(-c3ccc4[nH]ncc4c3)n2)[C@@H](C)CO1] | 4-((4-((2R,3S)-2,5-dimethylmorpholino)-6-(1H-indazol-5-yl)-1,3,5-triazin-2-yl)oxy)3-fluoro-N,N-dimethylbenzamide |

TABLE 1-continued

Certain exemplified compound of the present invention

| Chemical Number | Chemical Structure | Chemical Name |
|---|---|---|
| 10065 | 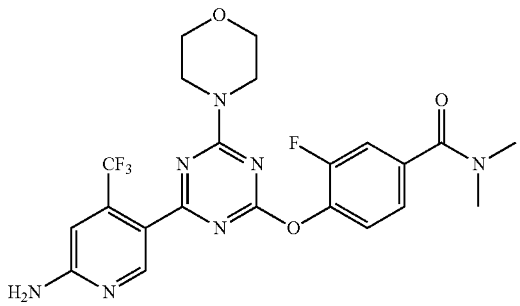 [SMILES: CN(C)C(=O)c1ccc(Oc2nc(-c3cnc(N)cc3C(F)(F)F)nc(N3CCOCC3)n2)c(F)c1] | 4-((4-(6-Amino-4-(trifluoromethyl)pyridine-3-yl)-6-morpholino-1,3,5-triazin-2-yl)oxy)-3-fluoro-N,N-dimethylbenzamide |
| 10066 | 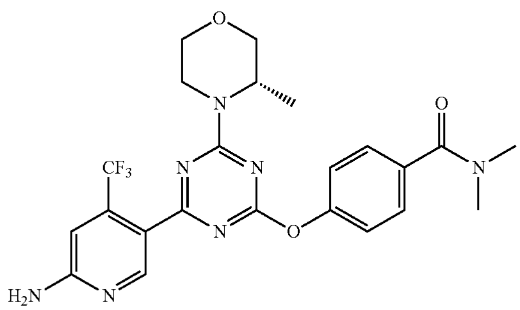 [SMILES: C[C@H]1COCCN1c1nc(Oc2ccc(C(=O)N(C)C)cc2)nc(-c2cnc(N)cc2C(F)(F)F)n1] | (S)-4-((4-(6-Amino-4-(trifluoromethyl)pyridine-3-yl)-6-(3-methylmorpholino)-1,3,5-triazin-2-yl)oxy)-N,N-dimethylbenzamide |
| 10067 | 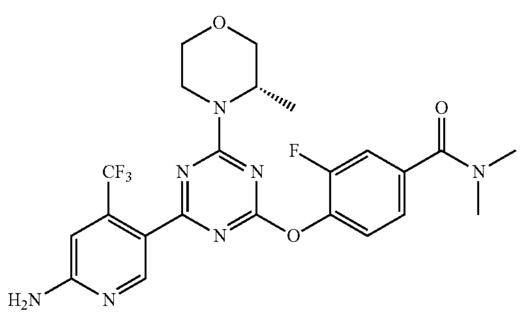 [SMILES: C[C@H]1COCCN1c1nc(Oc2ccc(C(=O)N(C)C)cc2F)nc(-c2cnc(N)cc2C(F)(F)F)n1] | (S)-4-((4-(6-Amino-4-(trifluoromethyl)pyridine-3-yl)-6-(3-methylmorpholino)-1,3,5-triazin-2-yl)oxy)-3-fluoro-N,N-dimethylbenzamide |
| 10068 | 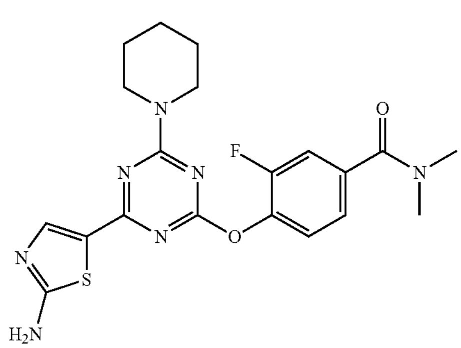 [SMILES: CN(C)C(=O)c1ccc(Oc2nc(-c3cnc(N)s3)nc(N3CCCCC3)n2)c(F)c1] | 4-((4-(2-Aminothiazol-5-yl)-6-(piperidin-1-yl)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
| --- | --- | --- |
| 10069 | 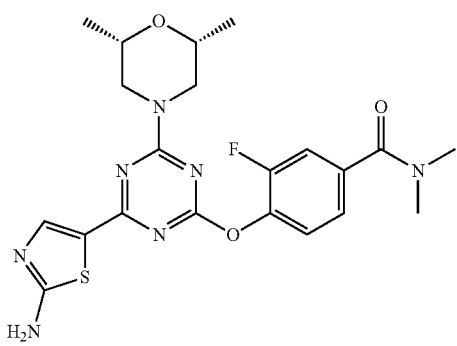 [SMILES: C[C@@H]1CN(c2nc(Oc3ccc(C(=O)N(C)C)cc3F)nc(-c3cnc(N)s3)n2)C[C@H](C)O1] | 4((4-(2-Aminothiazol-5-yl)-6-((2R,6S)-2,6-dimethylmorpholino-1,3,5-triazin-2-yl)-3-fluoro-N,N-dimethylbenzamide |
| 10070 | 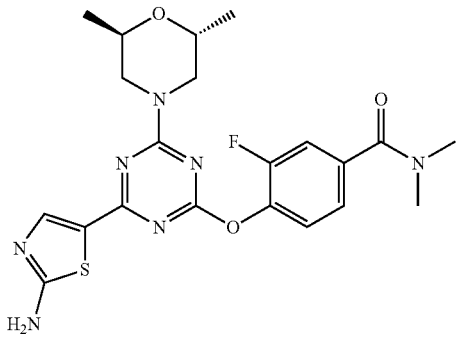 [SMILES: C[C@@H]1CN(c2nc(Oc3ccc(C(=O)N(C)C)cc3F)nc(-c3cnc(N)s3)n2)C[C@@H](C)O1] | 4-((4-2-Aminothiazol-5-yl)-6-((2R,6R)-2,6-dimethylmorpholino)-1,3,5-triazin-2-yl)oxy-3-fluoro-N,N-dimethylbenzamide |
| 10071 | 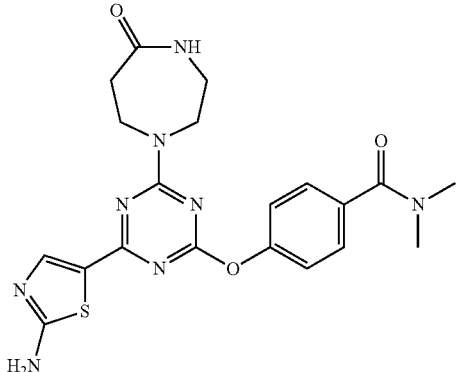 [SMILES: CN(C)C(=O)c1ccc(Oc2nc(-c3cnc(N)s3)nc(N3CCNC(=O)CC3)n2)cc1] | 4-((4-(2-Aminothiazol-5-yl)-6-(5-oxo-1,4-diazepan-1-yl)-1,3,5-triazin-2-yl)oxy)-N,N-dimethylbenzamide |
| 10072 | 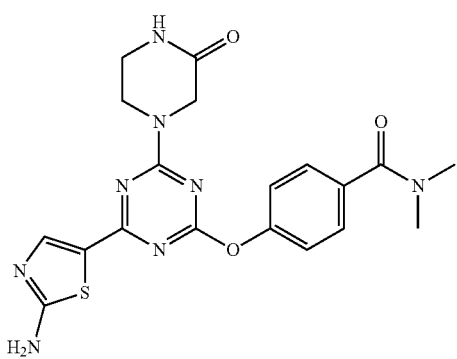 [SMILES: CN(C)C(=O)c1ccc(Oc2nc(-c3cnc(N)s3)nc(N3CCNC(=O)C3)n2)cc1] | 4-((4-(2-Aminothiazol-5-yl)-6-(3-oxopiperazin-1-yl)-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10073 | 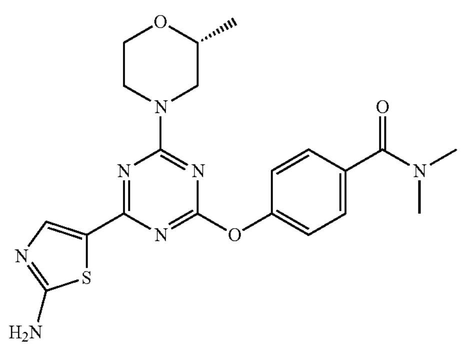 [SMILES: C[C@@H]1CN(c2nc(Oc3ccc(C(=O)N(C)C)cc3)nc(-c3cnc(N)s3)n2)CCO1] | (R)-4-((4-(2-Aminothiazol-5-yl)-6-(2-methylmorpholino)-1,3,5-triazin-2-yl)oxy)-N,N-dimethylbenzamide |
| 10074 | 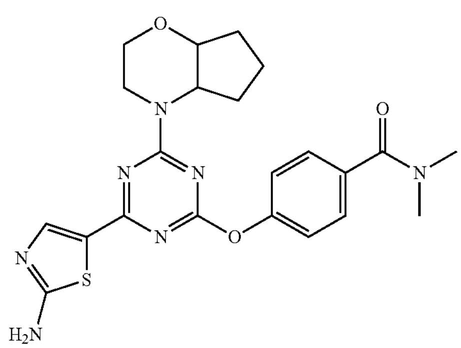 [SMILES: CN(C)C(=O)c1ccc(Oc2nc(-c3cnc(N)s3)nc(N3CCOC4CCCC43)n2)cc1] | 4-((4-(2-Aminothiazol-5-yl)-6-(hexahydrocyclopenta[b][1,4]oxazin-4-(4aH)-yl)-1,3,5-triazin-2-yl)oxy)-N,N-dimethylbenzamide |
| 10075 | 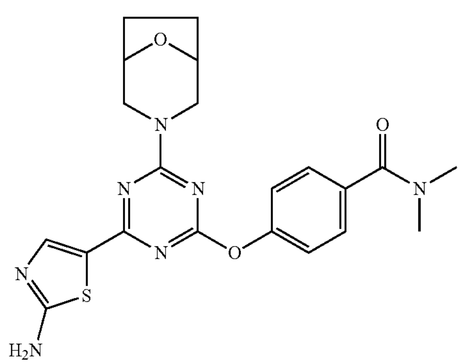 [SMILES: CN(C)C(=O)c1ccc(Oc2nc(-c3cnc(N)s3)nc(N3CC4CCC(C3)O4)n2)cc1] | 4-((4-(2-Aminothiazol-5-yl)-6-(8-oxa-3-azabicyclo[3.2.1]octan-3-yl)-1,3,5-triazin-2-yl)oxy)-N,N-dimethylbenzamide |
| 10076 | 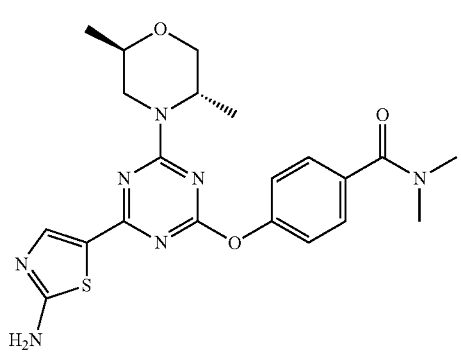 [SMILES: C[C@@H]1CN(c2nc(Oc3ccc(C(=O)N(C)C)cc3)nc(-c3cnc(N)s3)n2)[C@@H](C)CO1] | 4-((4-(2-Aminothiazol-5-yl)-6-((2R,5S)-2,5-dimethylmorpholino)-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10077 | 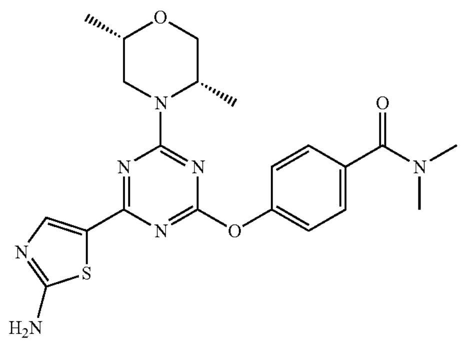 [SMILES: C[C@H]1CN(c2nc(Oc3ccc(C(=O)N(C)C)cc3)nc(-c3cnc(N)s3)n2)[C@@H](C)CO1] | 4-((4-(2-Aminothiazol-5-yl)-6-((2S,5S)-2,5-dimethylmorpholino)-1,3,5-triazin-2-yl)oxy)-N,N-dimethylbenzamide |
| 10078 | 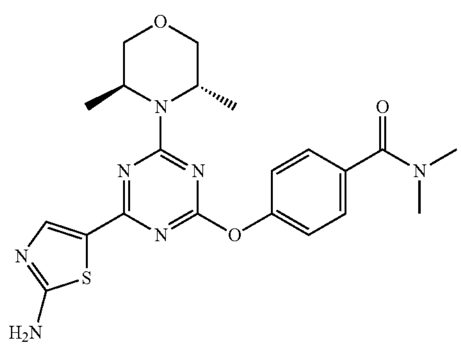 [SMILES: C[C@H]1COC[C@H](C)N1c1nc(Oc2ccc(C(=O)N(C)C)cc2)nc(-c2cnc(N)s2)n1] | 4-((4-(2-Aminothiazol-5-yl)-6-((3S,5S)-3,5-dimethylmorpholino)-1,3,5-triazin-2-yl)oxy)-N,N-dimethybenzamide |
| 10079 | 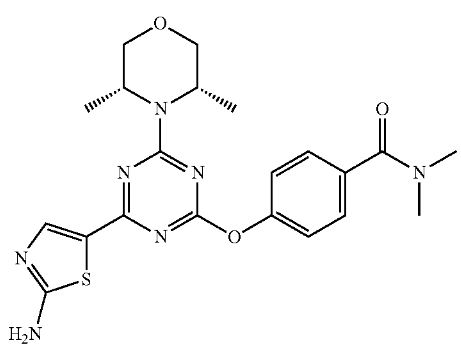 [SMILES: C[C@@H]1COC[C@H](C)N1c1nc(Oc2ccc(C(=O)N(C)C)cc2)nc(-c2cnc(N)s2)n1] | 4-((4-(2-Aminothiazol-5-yl)-6-((3S,5R)-3,5-dimethylmorpholino)-1,3,5-triazin-2-yl)oxy)-N,N-dimethybenzamide |
| 10080 | 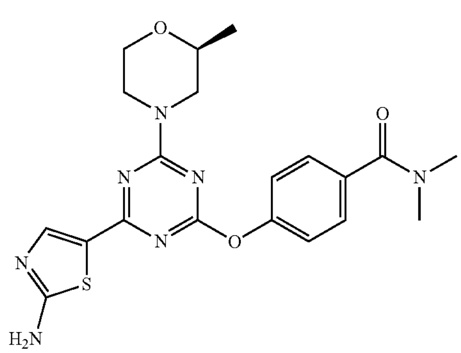 [SMILES: C[C@H]1CN(c2nc(Oc3ccc(C(=O)N(C)C)cc3)nc(-c3cnc(N)s3)n2)CCO1] | (S)-4-((4-(2-Aminothiazol-5-yl)-6-(2-methylmorpholino)-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10081 | 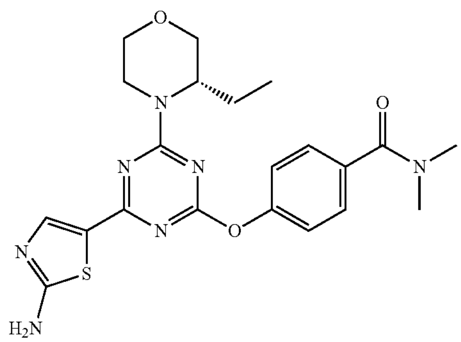 [SMILES: CC[C@H]1COCCN1c1nc(Oc2ccc(C(=O)N(C)C)cc2)nc(-c2cnc(N)s2)n1] | (S)-4-((4-(2-Aminothiazol-5-yl)-6-(3-ethylmorpholino)-1,3,5-triazin-2-yl)oxy)-N,N-dimethylbenzamide |
| 10082 | 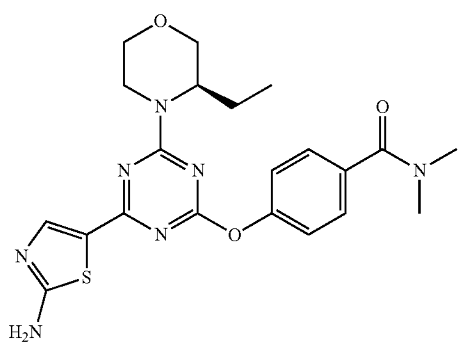 [SMILES: CC[C@@H]1COCCN1c1nc(Oc2ccc(C(=O)N(C)C)cc2)nc(-c2cnc(N)s2)n1] | (R)-4-((4-(2-Aminothiazol-5-yl)-6-(3-ethylmorpholino)-1,3,5-triazin-2-yl)oxy)-N,N-dimethylbenzamide |
| 10083 | 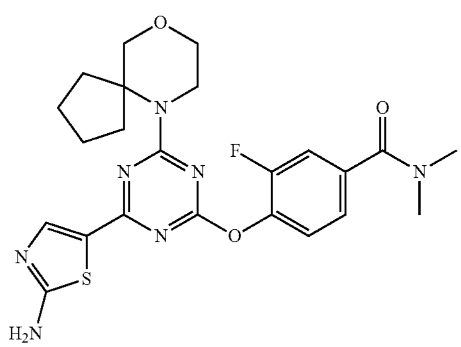 [SMILES: CN(C)C(=O)c1ccc(Oc2nc(-c3cnc(N)s3)nc(N3CCOCC34CCCC4)n2)c(F)c1] | 4-((4-(2-Aminothiazol-5-yl)-6-(9-oxa-6-azaspiro[4.5]decan-6-yl)-1,3,5-triazin-2-yl)oxy)-3-fluoro-N,N-dimethylbenzamide |
| 10084 | 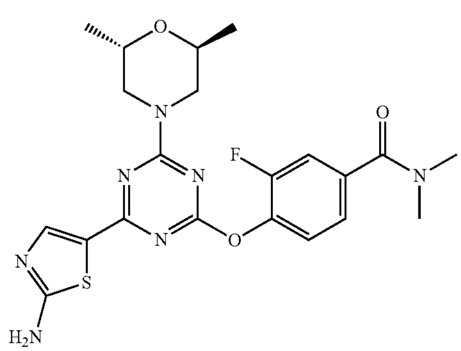 [SMILES: C[C@H]1CN(c2nc(Oc3ccc(C(=O)N(C)C)cc3F)nc(-c3cnc(N)s3)n2)C[C@H](C)O1] | 4-((4-2-Aminothiazol-5-yl)-6-((2S,6S)-2,6-dimethylmorpholino)-1,3,5-triazin-2-yl)oxy-3-fluoro-N,N-dimethylbenzamide |

TABLE 1-continued

Certain exemplified compound of the present invention

| Chemical Number | Chemical Structure | Chemical Name |
|---|---|---|
| 10085 | 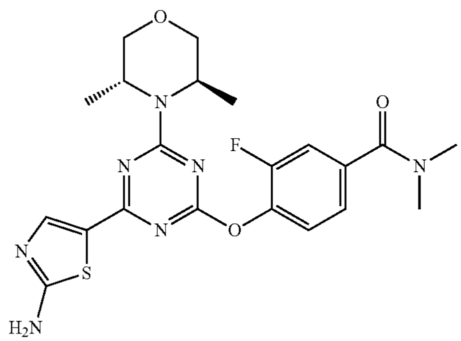 [SMILES: C[C@@H]1COC[C@@H](C)N1c1nc(Oc2ccc(C(=O)N(C)C)cc2F)nc(-c2cnc(N)s2)n1] | 4-((4-(2-Aminothiazol-5-yl)-6-((3R,5R)-3,5-dimethylmorpholino)-1,3,5-triazin-2-yl)oxy)-N,N-dimethybenzamide |
| 10086 | 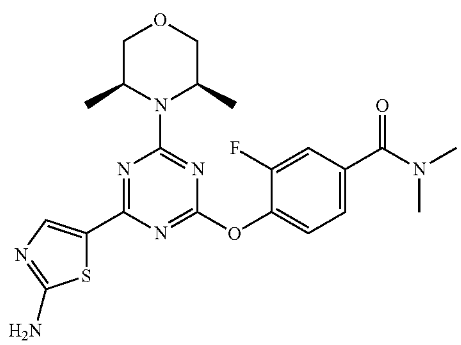 [SMILES: C[C@@H]1COC[C@H](C)N1c1nc(Oc2ccc(C(=O)N(C)C)cc2F)nc(-c2cnc(N)s2)n1] | 4-((4-(2-Aminothiazol-5-yl)-6-((3R,5S)-3,5-dimethylmorpholino)-1,3,5-triazin-2-yl)oxy)-N,N-dimethybenzamide |
| 10087 | 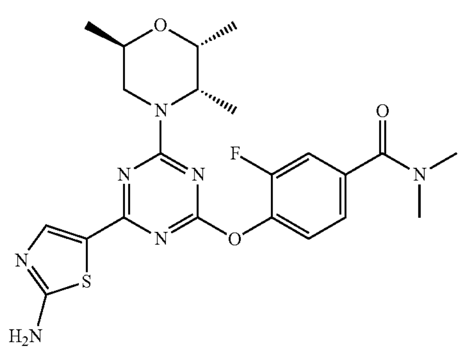 [SMILES: C[C@@H]1CN(c2nc(Oc3ccc(C(=O)N(C)C)cc3F)nc(-c3cnc(N)s3)n2)[C@@H](C)[C@@H](C)O1] | 4-((4-(2-Aminothiazol-5-yl)-6-((2R,3S,6R)-2,3,6-trimethylmorpholino)-1,3,5-triazin-2-yl)-oxy)-3-fluoro-N,N-dimethylbenzamide |
| 10088 | 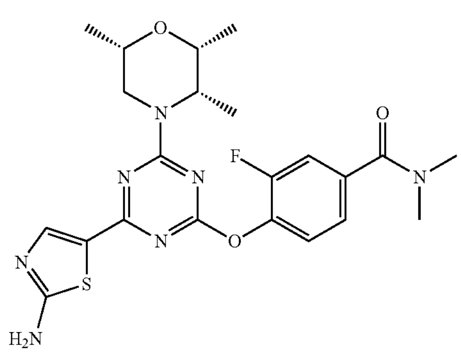 [SMILES: C[C@H]1CN(c2nc(Oc3ccc(C(=O)N(C)C)cc3F)nc(-c3cnc(N)s3)n2)[C@@H](C)[C@@H](C)O1] | 4-((4-(2-Aminothiazol-5-yl)-6-((2R,3S,6S)-2,3,6-trimethylmorpholino)-1,3,5-triazin-2-yl)-oxy)-3-fluoro-N,N-dimethylbenzamide |

TABLE 1-continued

Certain exemplified compound of the present invention

| Chemical Number | Chemical Structure | Chemical Name |
|---|---|---|
| 10090 | 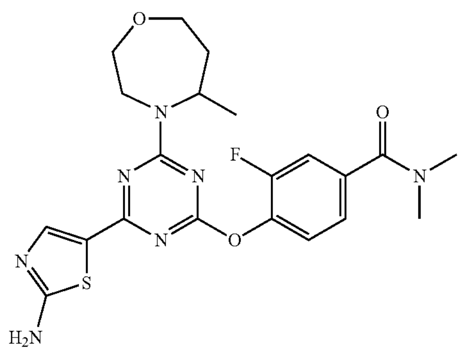 [SMILES: CC1CCOCCN1c1nc(Oc2ccc(C(=O)N(C)C)cc2F)nc(-c2cnc(N)s2)n1] | 4-((4-(2-Aminothiazol-5-yl)-6-(5-methyl-1,4-oxazepan-4-yl)-1,3,5-triazin-2-yl)oxy)-3-fluoro-N,N-dimethylbenzamide |
| 10091 | 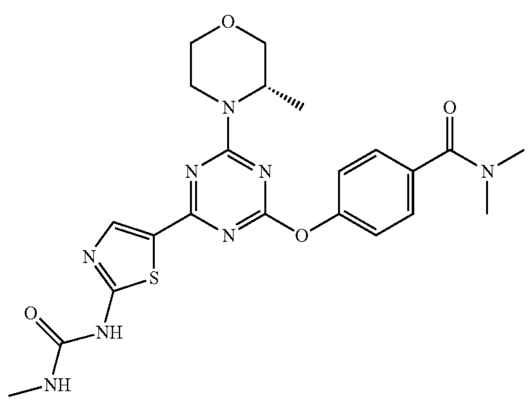 | (S)-N,N-dimethyl-4-((4-(3-methylmorpholino)-6-(2-(3-methylureido)thiazol-5-yl)-1,3,5-triazin-2-yl)oxy)benzamide |
| 10092 | 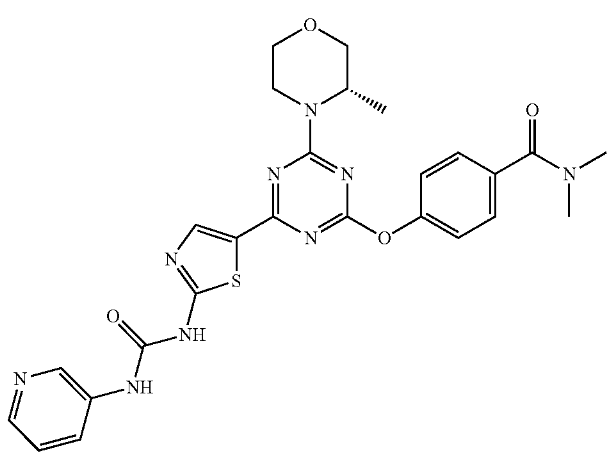 [SMILES: C[C@H]1COCCN1c1nc(Oc2ccc(C(=O)N(C)C)cc2)nc(-c2cnc(NC(=O)Nc3cccnc3)s2)n1] | (S)-N,N-dimethyl-4-((4-(3-methylmorpholino)-6-(2-(3-pyridin-3-yl)ureido)thiazol-5-yl)-1,3,5-triazin-2-yl)oxy)benzamide |

TABLE 1-continued

Certain exemplified compound of the present invention

| Chemical Number | Chemical Structure | Chemical Name |
|---|---|---|
| 10093 | 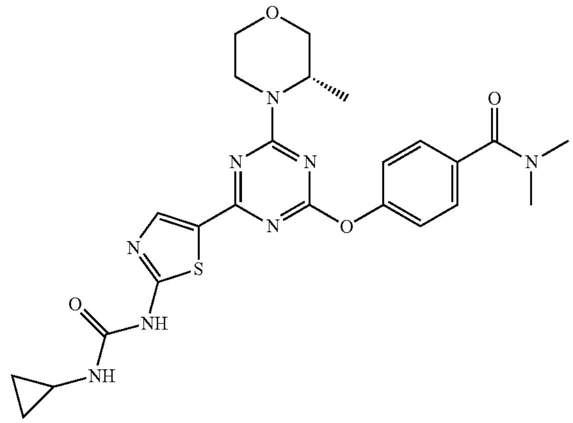 [SMILES: C[C@H]1COCCN1c1nc(Oc2ccc(C(=O)N(C)C)cc2)nc(-c2cnc(NC(=O)NC3CC3)s2)n1] | (S)-4-((4-(2-(3-cyclopropylureido)thiazol-5-yl)-6-(3-methylmorpholino)-1,3,5-triazin-2-yl)oxy-N,N-dimethylbenzamide |
| 10094 | 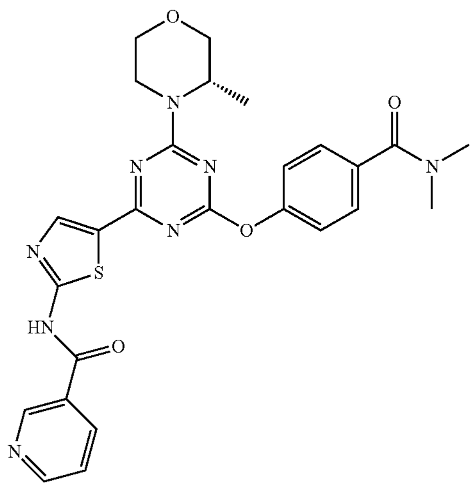 [SMILES: C[C@H]1COCCN1c1nc(Oc2ccc(C(=O)N(C)C)cc2)nc(-c2cnc(NC(=O)c3cccnc3)s2)n1] | (S)-N-(5-(4-(4-(dimethylcarbamoyl)phenoxy)-6-(3-methylmorpholino)-1,3,5-triazin-2-yl)thiazol-2-yl)nicotinamide |
| 10095 | 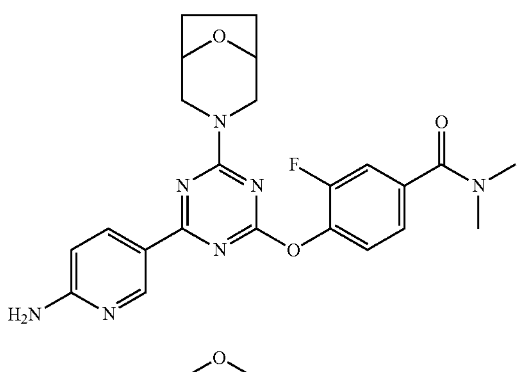 | 4-((4-6-Aminopyridin-3-yl)-6-(8-oxa-3-azabicyclo[3.2.1]octan-3-yl)-1,3,5-triazin-2-yl)oxy)-3-fluoro-N,N-dimethylbenzamide |
| 10096 | 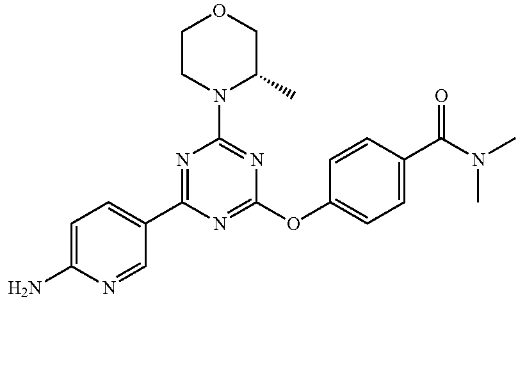 | (S)-4-((4-(6-Aminopyridin-3-yl)-6-(3-methylmorpholino)-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10097 | 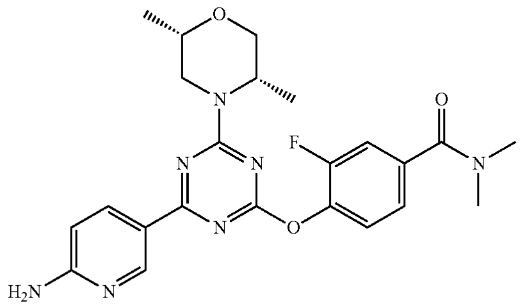 [SMILES: C[C@H]1CN(c2nc(Oc3ccc(C(=O)N(C)C)cc3F)nc(-c3ccc(N)nc3)n2)[C@@H](C)CO1] | 4-((4-(6-Aminopyridin-3-yl)-6-((2S,5S)-2,5-dimethylmorpholino)-1,3,5-triazin-2-yl)oxy)-3-fluoro-N,N-dimethylbenzamide |
| 10098 | 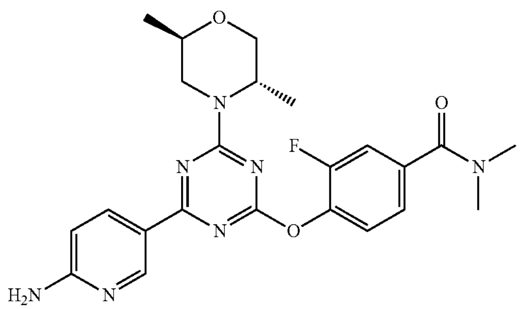 [SMILES: C[C@@H]1CN(c2nc(Oc3ccc(C(=O)N(C)C)cc3F)nc(-c3ccc(N)nc3)n2)[C@@H](C)CO1] | 4-((4-(6-Aminopyridin-3-yl)-6-((2R,5S)-2,5-dimethylmorpholino)-1,3,5-triazin-2-yl)oxy)-3-fluoro-N,N-dimethylbenzamide |
| 10099 | 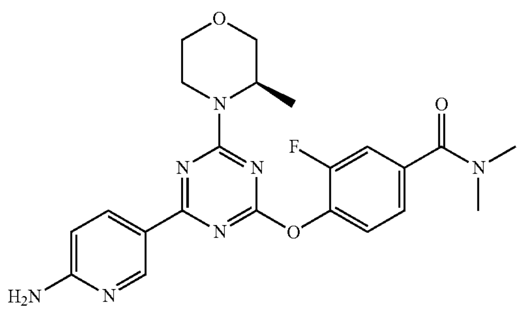 [SMILES: C[C@@H]1COCCN1c1nc(Oc2ccc(C(=O)N(C)C)cc2F)nc(-c2ccc(N)nc2)n1] | (R)-4-((4-(6-Aminopyridin-3-yl)-6-(3-methylmorpholino)-1,3,5-triazin-2-yl)oxy)-3-fluoro-N,N-dimethylbenzamide |
| 10100 | 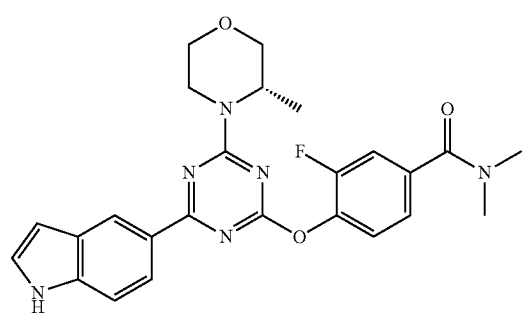 [SMILES: C[C@H]1COCCN1c1nc(Oc2ccc(C(=O)N(C)C)cc2F)nc(-c2ccc3[nH]ccc3c2)n1] | (S)-4-((4-(1H-indol-5-yl)-6-(3-methylmorpholino)1,3,5-triazin-2-yl)oxy)3-fluoro-N,N-dimethylbenzamide |
| 10101 | 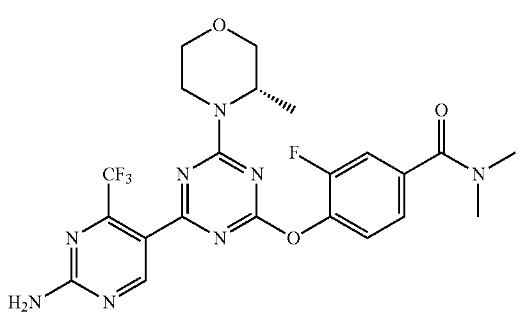 | (S)-4-((4-(2-Amino-4-(trifluoromethyl)pyrimidin-5-yl)-6-(3-methylmorpholino)-1,3,5-triazin-2-yl)-oxy-3-fluoro-N,N-dimethylbenzamide |

TABLE 1-continued

Certain exemplified compound of the present invention

| Chemical Number | Chemical Structure | Chemical Name |
|---|---|---|
| 10102 | 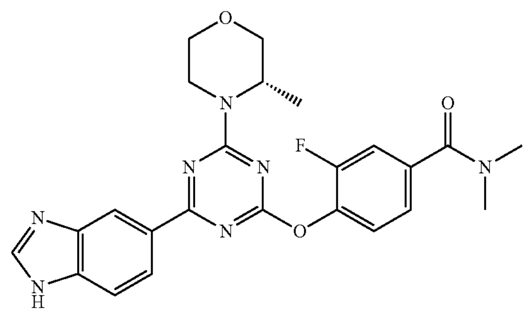 [SMILES: C[C@H]1COCCN1c1nc(Oc2ccc(C(=O)N(C)C)cc2F)nc(-c2ccc3[nH]cnc3c2)n1] | (S)-4-((4-(1H-benzo[d]imidazol-5-yl)-6-(3-methylmorpholino)-1,3,5-triazin-2-yl)oxy)-3-fluoro-N,N-dimethylbenzamide |
| 10103 | 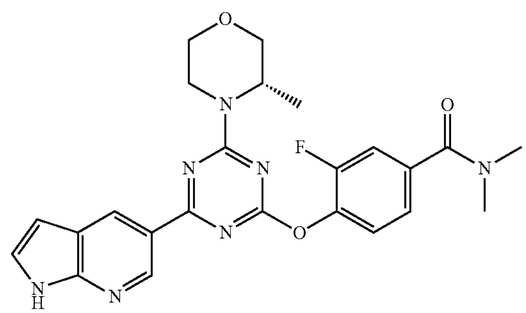 [SMILES: C[C@H]1COCCN1c1nc(Oc2ccc(C(=O)N(C)C)cc2F)nc(-c2cnc3[nH]ccc3c2)n1] | (S)-3-Fluoro-N,N-dimethyl-4-((4-(3-methylmorpholino)-6-(1H-pyrrolo-[2,3-b]pyridin-5-yl)-1,3,5-triazin-2-yl)oxy)benzamide |
| 10104 | 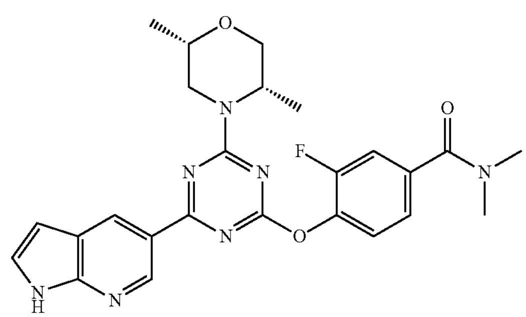 [SMILES: C[C@H]1CN(c2nc(Oc3ccc(C(=O)N(C)C)cc3F)nc(-c3cnc4[nH]ccc4c3)n2)[C@@H](C)CO1] | 4-((4-((2S,5S)-2,5-dimethylmorpholino)-6-(1H-pyrrolo[2,3-b]pyridine-5-yl)-1,3,5-triazin-2-yl)oxy)-3-fluoro-N,N-dimethylbenzamide |
| 10105 | 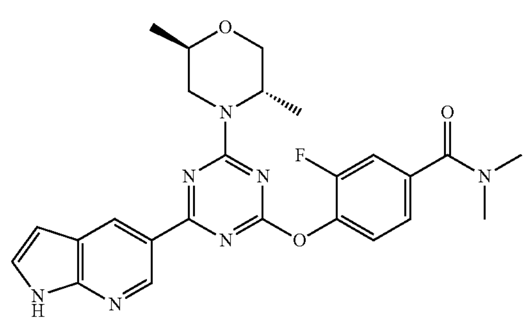 [SMILES: C[C@@H]1CN(c2nc(Oc3ccc(C(=O)N(C)C)cc3F)nc(-c3cnc4[nH]ccc4c3)n2)[C@@H](C)CO1] | 4-((4-((2R,5S)-2,5-dimethylmorpholino)-6-(1H-pyrrolo[2,3-b]pyridine-5-yl)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10106 | 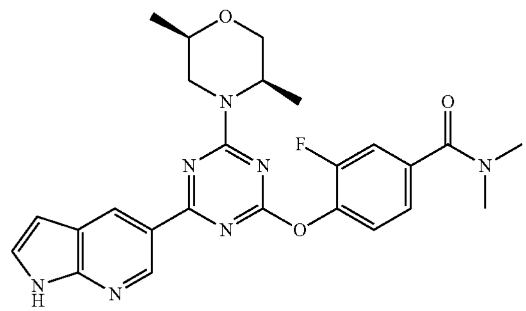 [SMILES: C[C@@H]1CN(c2nc(Oc3ccc(C(=O)N(C)C)cc3F)nc(-c3cnc4[nH]ccc4c3)n2)[C@H](C)CO1] | 4-((4-((2R,3R)-2,5-dimethylmorpholino)-6-(1H-pyrrolo[2,3-b]pyridine-5-yl)-1,3,5-triazin-2-yl)oxy)-3-fluoro-N,N-dimethylbenzamide |
| 10107 | 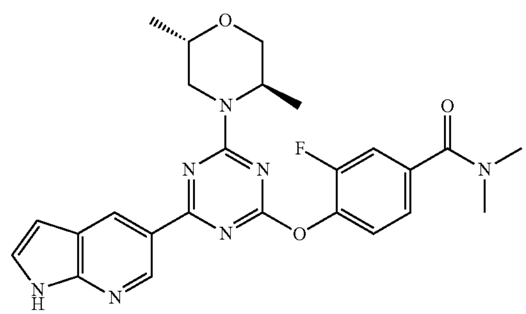 [SMILES: C[C@@H]1CO[C@@H](C)CN1c1nc(Oc2ccc(C(=O)N(C)C)cc2F)nc(-c2cnc3[nH]ccc3c2)n1] | 4-((4-((2S,5R)-2,5-dimethylmorpholino)-6-(1H-pyrrolo[2,3-b]pyridine-5-yl)-1,3,5-triazin-2-yl)oxy)-3-fluoro-N,N-dimethylbenzamide |
| 10108 | 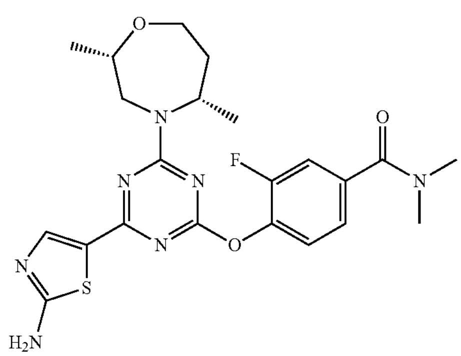 [SMILES: C[C@H]1CN(c2nc(Oc3ccc(C(=O)N(C)C)cc3F)nc(-c3cnc(N)s3)n2)[C@@H](C)CCO1] | 4-((4-(2-Aminothiazol-5-yl)-6-((2S,5S)-2,5-dimethyl-1,4-oxazepan-4-yl)-1,3,5-triazin-2-yl)oxy-3-fluoro-N,N-dimethylbenzamide |
| 10109 | 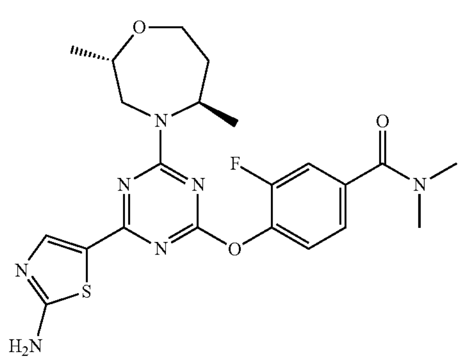 [SMILES: C[C@@H]1CCO[C@@H](C)CN1c1nc(Oc2ccc(C(=O)N(C)C)cc2F)nc(-c2cnc(N)s2)n1] | 4-((4-(2-Aminothiazol-5-yl)-6-((2S,5R)-2,5-dimethyl-1,4-oxazepan-4-yl)-1,3,5-triazin-2-yl)oxy-3-fluoro-N,N-dimethylbenzamide |

TABLE 1-continued

Certain exemplified compound of the present invention

| Chemical Number | Chemical Structure | Chemical Name |
|---|---|---|
| 10110 | 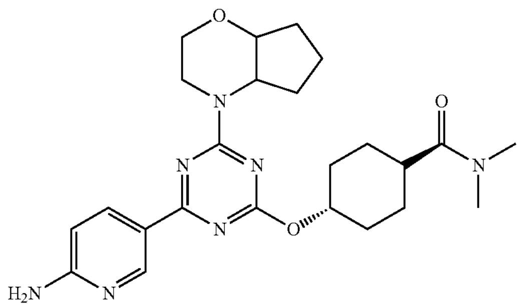 | (1s,4s)-4-((4-(6-Aminopyridin-3-yl)-6-(hexahydrocyclopenta[b][1,4]oxazin-4(4aH)-yl)-1,3,5-triazin-2-yl)oxy)-N,N-dimethylcyclohexane-1-carboxamide |
| 10111 | 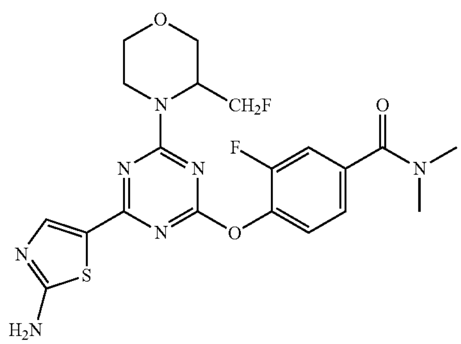 | 4-((4-(2-Aminothiazol-5-yl)-6-(3-(fluoromethyl)morpholino)-1,3,5-triazin-2-yl)oxy)-3-fluoro-N,N-dimethylbenzamide |
| 10112 | 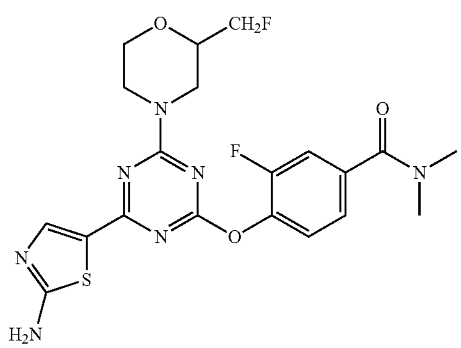 | 4-((4-(2-Aminothiazol-5-yl)-6-(2-(fluoromethyl)morpholino)-1,3,5-triazin-2-yl)oxy)-3-fluoro-N,N-dimethylbenzamide |
| 10113 | 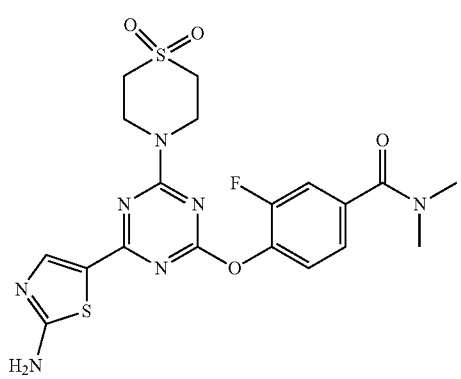 [SMILES: CN(C)C(=O)c1ccc(Oc2nc(-c3cnc(N)s3)nc(N3CCS(=O)(=O)CC3)n2)c(F)c1] | 4-((4-(2-Aminothiazol-5-yl)-6-(1,1-dioxidothiomorpholino)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10114 | 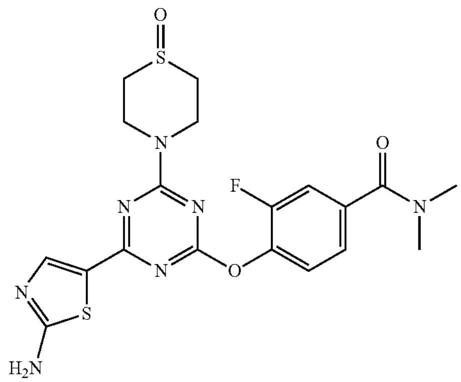 [SMILES: CN(C)C(=O)c1ccc(Oc2nc(-c3cnc(N)s3)nc(N3CCS(=O)CC3)n2)c(F)c1] | 4-((4-2-Aminothiazol-5-yl)-6-(1-oxidothiomorpholino)-1,3,5-triazin-2-yl)oxy)-3-fluoro-N,N-dimethylbenzamide |
| 10115 | 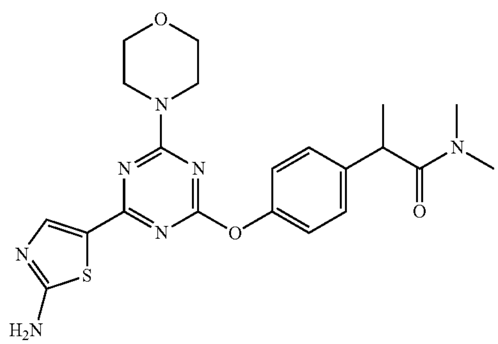 [SMILES: CC(C(=O)N(C)C)c1ccc(Oc2nc(-c3cnc(N)s3)nc(N3CCOCC3)n2)cc1] | 2-(4-(4-(2-aminothiazol-5-yl)-6-morpholino-1,3,5-triazin-2-yloxy)phenyl)-N,N-dimethylpropanamide |
| 10118 | 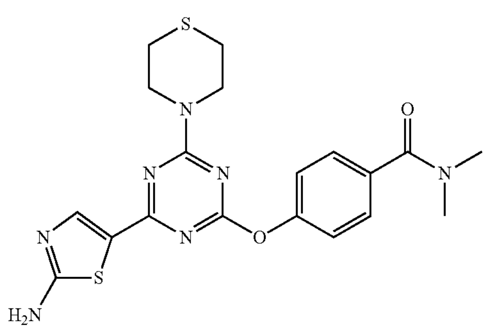 [SMILES: CN(C)C(=O)c1ccc(Oc2nc(-c3cnc(N)s3)nc(N3CCSCC3)n2)cc1] | 4-(4-(2-aminothiazol-5-yl)-6-thiomorpholino-1,3,5-triazin-2-yloxy)-N,N-dimethylbenzamide |
| 10119 | 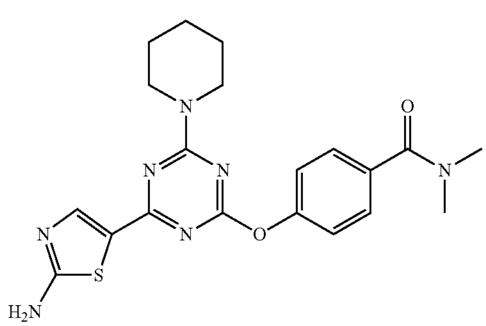 [SMILES: CN(C)C(=O)c1ccc(Oc2nc(-c3cnc(N)s3)nc(N3CCCCC3)n2)cc1] | 4-(4-(2-aminothiazol-5-yl)-6-(piperidin-1-yl)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10122 | 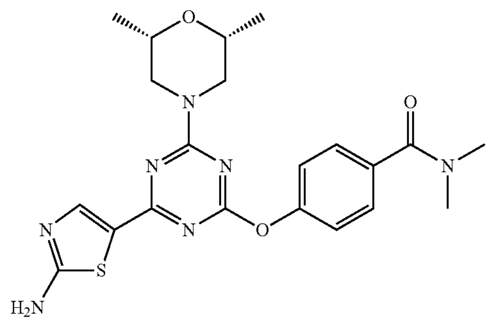 [SMILES: C[C@@H]1CN(c2nc(Oc3ccc(C(=O)N(C)C)cc3)nc(-c3cnc(N)s3)n2)C[C@H](C)O1] | 4-(4-(2-aminothiazol-5-yl)-6-((2S,6R)-2,6-dimethylmorpholino)-1,3,5-triazin-2-yloxy)-N,N-dimethylbenzamide |
| 10123 | 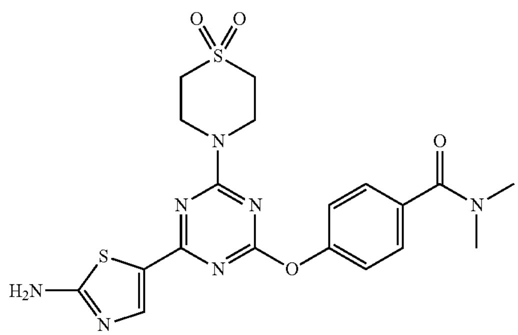 [SMILES: CN(C)C(=O)c1ccc(Oc2nc(-c3cnc(N)s3)nc(N3CCS(=O)(=O)CC3)n2)cc1] | |
| 10124 | 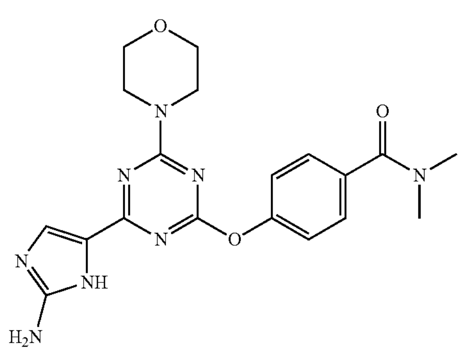 [SMILES: CN(C)C(=O)c1ccc(Oc2nc(-c3cnc(N)[nH]3)nc(N3CCOCC3)n2)cc1] | 4-(4-(2-amino-1H-imidazol-5-yl)-6-morpholino-1,3,5-triazin-2-yloxy)-N,N-dimethylbenzamide |
| 10125 | 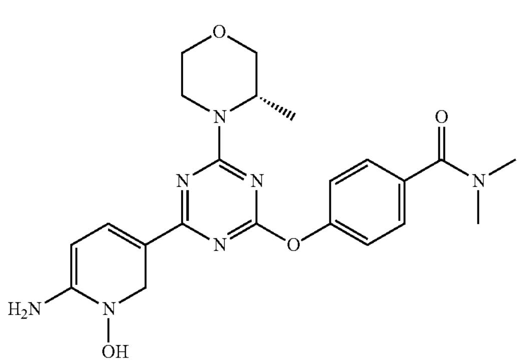 [SMILES: C[C@H]1COCCN1c1nc(Oc2ccc(C(=O)N(C)C)cc2)nc(C2=CC=C(N)N(O)C2)n1] | |

TABLE 1-continued

Certain exemplified compound of the present invention

| Chemical Number | Chemical Structure | Chemical Name |
|---|---|---|
| 10126 | 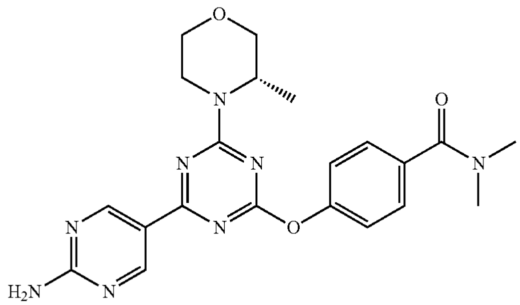 [SMILES: C[C@H]1COCCN1c1nc(Oc2ccc(C(=O)N(C)C)cc2)nc(-c2cnc(N)nc2)n1] | 4-(4-(2-aminopyrimidin-5-yl)-6-((S)-3-methylmorpholino)-1,3,5-triazin-2-yloxy)-N,N-dimethylbenzamide |
| 10127 | 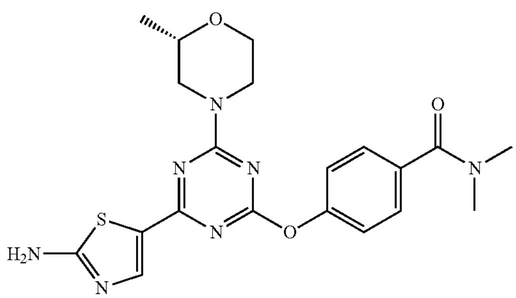 [SMILES: C[C@H]1CN(c2nc(Oc3ccc(C(=O)N(C)C)cc3)nc(-c3cnc(N)s3)n2)CCO1] | 4-(4-(2-aminothiazol-5-yl)-6-((S)-2-methylmorpholino)-1,3,5-triazin-2-yloxy)-N,N-dimethylbenzamide |
| 10128 | 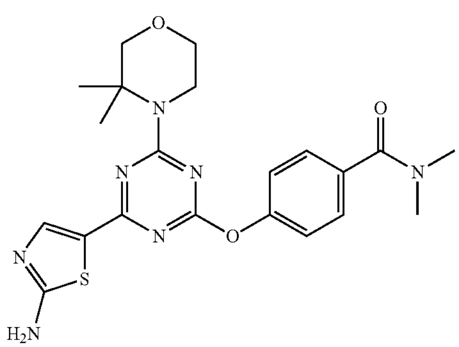 [SMILES: CN(C)C(=O)c1ccc(Oc2nc(-c3cnc(N)s3)nc(N3CCOCC3(C)C)n2)cc1] | 4-(4-(2-aminothiazol-5-yl)-6-(3,3-dimethylmorpholino)-1,3,5-triazin-2-yloxy)-N,N-dimethylbenzamide |
| 10129 | 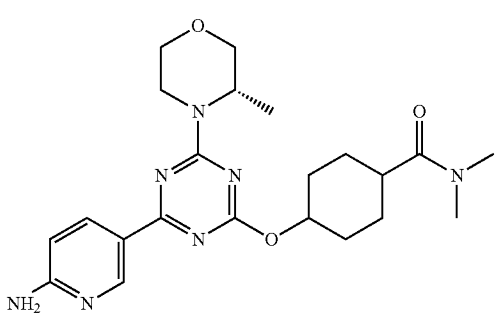 [SMILES: C[C@H]1COCCN1c1nc(OC2CCC(C(=O)N(C)C)CC2)nc(-c2ccc(N)nc2)n1] | 4-(4-(6-aminopyridin-3-yl)-6-((S)-3-methylmorpholino)-1,3,5-triazin-2-yloxy)-N,N-dimethylcyclohexanecarboxamide |

TABLE 1-continued

Certain exemplified compound of the present invention

| Chemical Number | Chemical Structure | Chemical Name |
|---|---|---|
| 10130 | 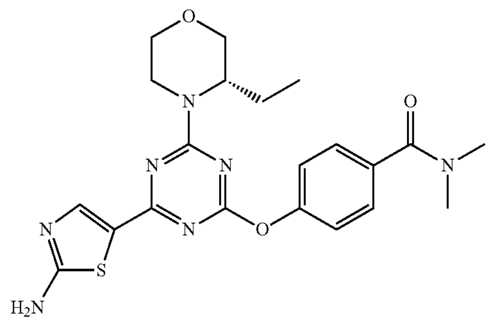 [SMILES: CC[C@H]1COCCN1c1nc(Oc2ccc(C(=O)N(C)C)cc2)nc(-c2cnc(N)s2)n1] | 4-(4-((S)-3-aminomorpholino)-6-(2-methylthiazol-5-yl)-1,3,5-triazin-2-yloxy)-N,N-dimethylbenzamide |
| 10131 | 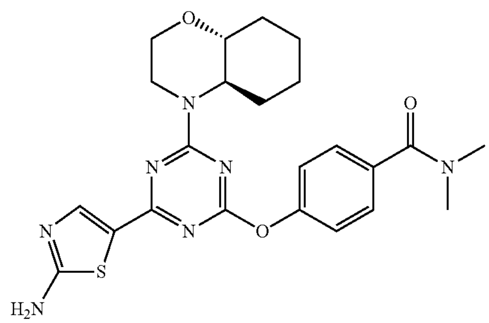 [SMILES: CN(C)C(=O)c1ccc(Oc2nc(-c3cnc(N)s3)nc(N3CCO[C@@H]4CCCC[C@H]43)n2)cc1] | 4-(4-(2-aminothiazol-5-yl)-6-((4aR,8aR)-octahydrobenzo[b][1,4]oxazin-4-yl)-1,3,5-triazin-2-yloxy)-N,N-dimethylbenzamide |
| 10132 | 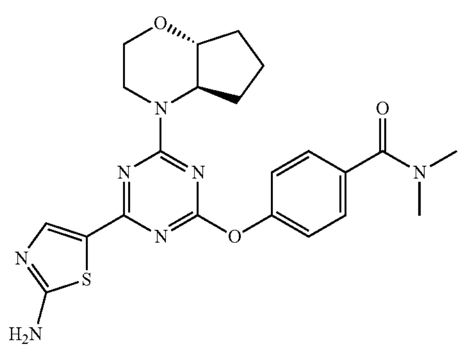 [SMILES: CN(C)C(=O)c1ccc(Oc2nc(-c3cnc(N)s3)nc(N3CCO[C@@H]4CCC[C@H]43)n2)cc1] | 4-(4-(2-aminothiazol-5-yl)-6-((4aR,7aR)-hexahydrocyclopenta[b][1,4]oxazin-4(4aH)-yl)-1,3,5-triazin-2-yloxy)-N,N-dimethylbenzamide |
| 10133 | 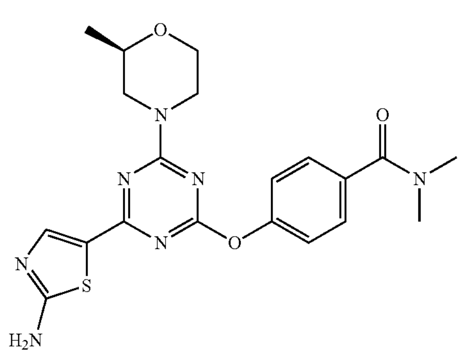 [SMILES: C[C@@H]1CN(c2nc(Oc3ccc(C(=O)N(C)C)cc3)nc(-c3cnc(N)s3)n2)CCO1] | 4-(4-(2-aminothiazol-5-yl)-6-((R)-2-methylmorpholino)-1,3,5-triazin-2-yloxy)-N,N-dimethylbenzamide |

TABLE 1-continued

Certain exemplified compound of the present invention

| Chemical Number | Chemical Structure | Chemical Name |
|---|---|---|
| 10134 | 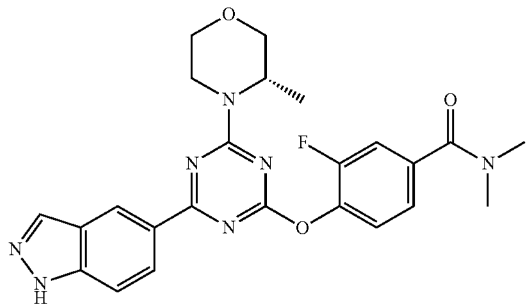 [SMILES: C[C@H]1COCCN1c1nc(Oc2ccc(C(=O)N(C)C)cc2F)nc(-c2ccc3[nH]ncc3c2)n1] | 4-(4-(1H-indazol-5-yl)-6-((S)-3-methylmorpholino)-1,3,5-triazin-2-yloxy)-3-fluoro-N,N-dimethylbenzamide |
| 10135 | 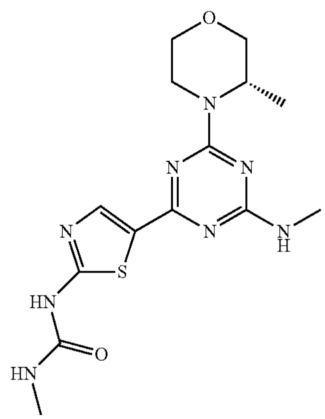 [SMILES: CNC(=O)Nc1ncc(-c2nc(NC)nc(N3CCOC[C@@H]3C)n2)s1] | 1-methyl-3-(5-(4-(methylamino)-6-((S)-3-methylmorpholino)-1,3,5-triazin-2-yl)thiazol-2-yl)urea |
| 10136 | 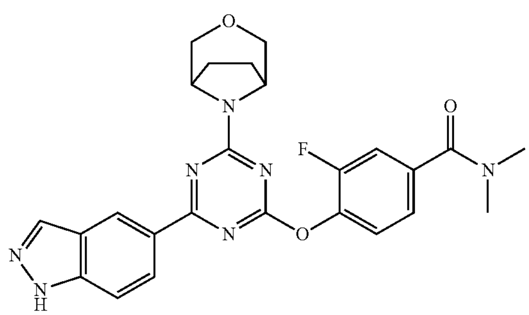 [SMILES: CN(C)C(=O)c1ccc(Oc2nc(-c3ccc4[nH]ncc4c3)nc(N3C4CCC3COC4)n2)c(F)c1] | 4-(4-(3-oxa-8-aza-bicyclo[3.2.1]octan-8-yl)-6-(1H-indazol-5-yl)-1,3,5-triazin-2-yloxy)-3-fluoro-N,N-dimethylbenzamide |
| 10137 | 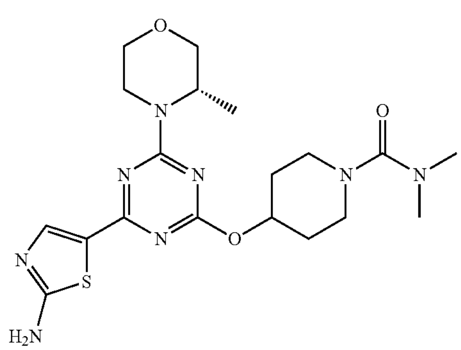 [SMILES: C[C@H]1COCCN1c1nc(OC2CCN(C(=O)N(C)C)CC2)nc(-c2cnc(N)s2)n1] | 4-(4-(2-aminothiazol-5-yl)-6-((S)-3-methylmorpholino)-1,3,5-triazin-2-yloxy)-N,N-dimethylpiperidine-1-carboxamide |

TABLE 1-continued

Certain exemplified compound of the present invention

| Chemical Number | Chemical Structure | Chemical Name |
|---|---|---|
| 10138 | 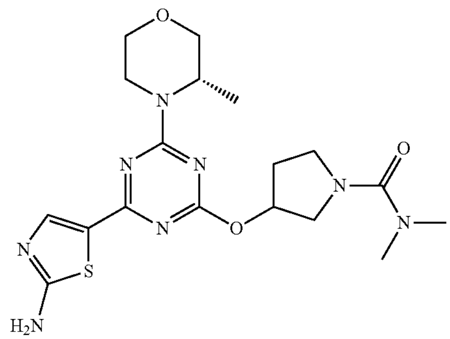 | 3-(4-(2-aminothiazol-5-yl)-6-((S)-3-methylmorpholino)-1,3,5-triazin-2-yloxy)-N,N-dimethylpyrrolidine-1-carboxamide |
| 10139 | 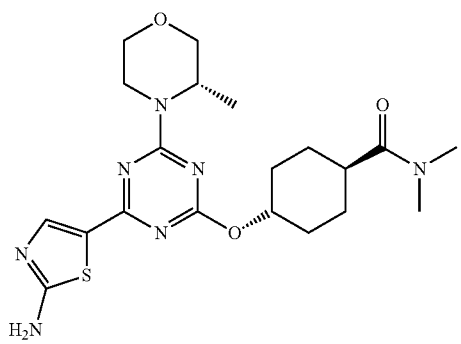 | (1S,4r)-4-(4-(2-aminothiazol-5-yl)-6-((S)-3-methylmorpholino)-1,3,5-triazin-2-yloxy)-N,N-dimethylcyclohexanecarboxamide |
| 10140 | 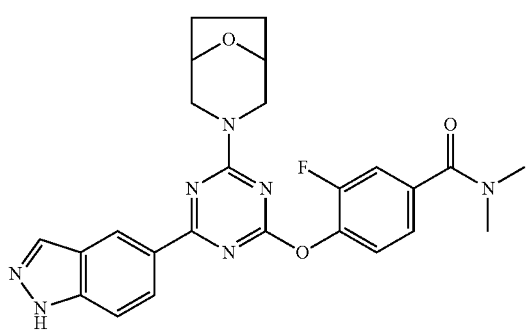 [SMILES: CN(C)C(=O)c1ccc(Oc2nc(-c3ccc4[nH]ncc4c3)nc(N3CC4CCC(C3)O4)n2)c(F)c1] | 4-(4-(8-oxa-3-azabicyclo[3.2.1]octan-3-yl)-6-(1H-indazol-5-yl)-1,3,5-triazin-2-yloxy)-3-fluoro-N,N-dimethylbenzamide |
| 10141 | 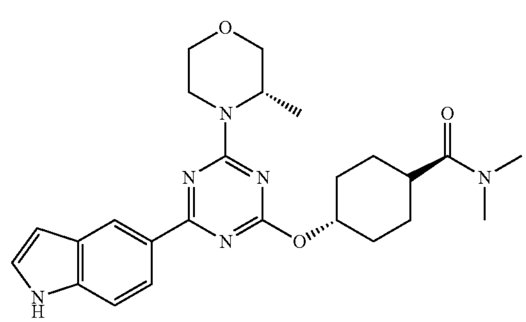 | (1R,4s)-4-(4-(1H-indol-5-yl)-6-((S)-3-methylmorpholino)-1,3,5-triazin-2-yloxy)-N,N-dimethylcyclohexanecarboxamide |

TABLE 1-continued

Certain exemplified compound of the present invention

| Chemical Number | Chemical Structure | Chemical Name |
|---|---|---|
| 10142 | 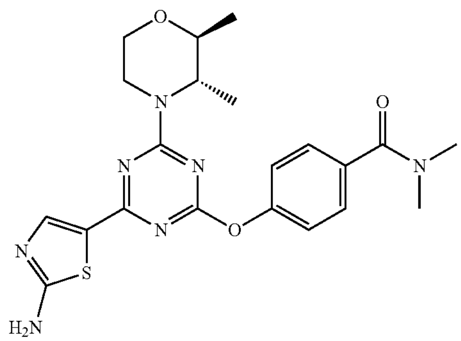 [SMILES: C[C@@H]1OCCN(c2nc(Oc3ccc(C(=O)N(C)C)cc3)nc(-c3cnc(N)s3)n2)[C@H]1C] | 4-(4-(2-aminothiazol-5-yl)-6-((2S,3S)-2,3-dimethylmorpholino)-1,3,5-triazin-2-yloxy)-N,N-dimethylbenzamide |
| 10143 | 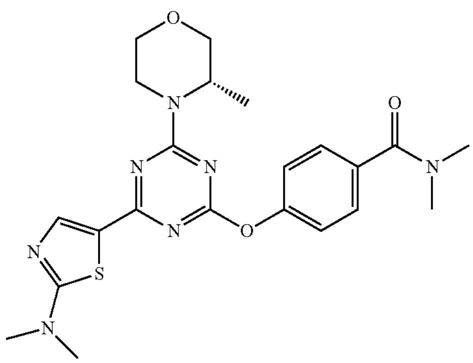 | 4-(4-(2-(dimethylamino)thiazol-5-yl)-6-((S)-3-methylmorpholino)-1,3,5-triazin-2-yloxy)-N,N-dimethylbenzamide |
| 10144 | 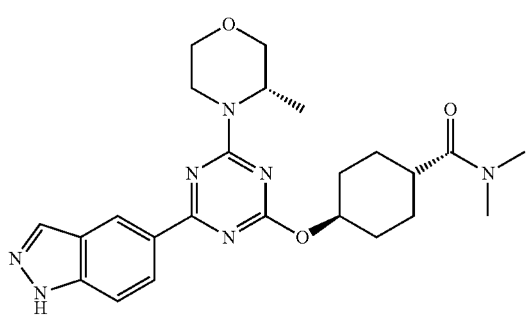 | (1S,4r)-4-(4-(1H-indazol-5-yl)-6-((S)-3-methylmorpholino)-1,3,5-triazin-2-yloxy)-N,N-dimethylcyclohexanecarboxamide |
| 10145 | 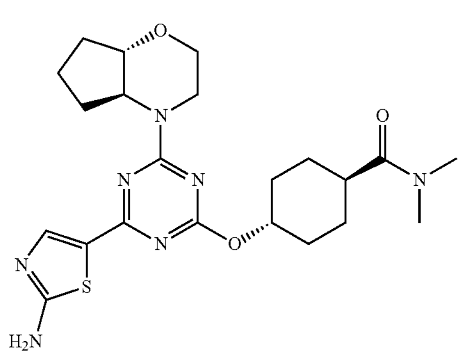 [SMILES: CN(C)C(=O)[C@H]1CC[C@H](Oc2nc(-c3cnc(N)s3)nc(N3CCO[C@H]4CCC[C@@H]43)n2)CC1] | (1S,4r)-4-(4-(2-aminothiazol-5-yl)-6-((4aS,7aS)-hexahydrocyclopenta[b][1,4]oxazin-4(4aH)-yl)-1,3,5-triazin-2-yloxy)-N,N-dimethylcyclohexanecarboxamide |

TABLE 1-continued

Certain exemplified compound of the present invention

| Chemical Number | Chemical Structure | Chemical Name |
|---|---|---|
| 10146 | 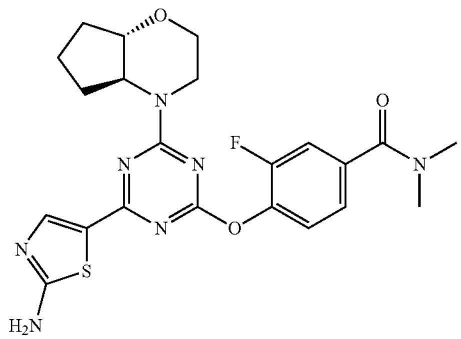 [SMILES: CN(C)C(=O)c1ccc(Oc2nc(-c3cnc(N)s3)nc(N3CCO[C@H]4CCC[C@@H]43)n2)c(F)c1] | 4-(4-(2-aminothiazol-5-yl)-6-((4aS,7aS)-hexahydrocyclopenta[b][1,4]oxazin-4(4aH)-yl)-1,3,5-triazin-2-yloxy)-3-fluoro-N,N-dimethylbenzamide |
| 10147 | 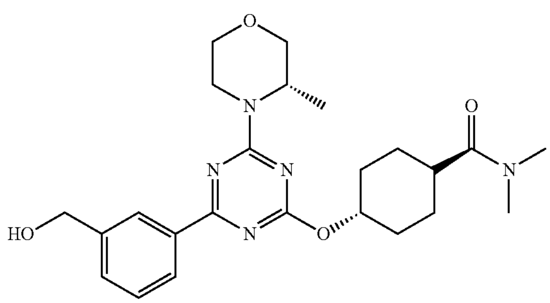 | (1R,4s)-4-(4-(3-(hydroxymethyl)phenyl)-6-((S)-3-methylmorpholino)-1,3,5-triazin-2-yloxy)-N,N-dimethylcyclohexanecarboxamide |
| 10148 | 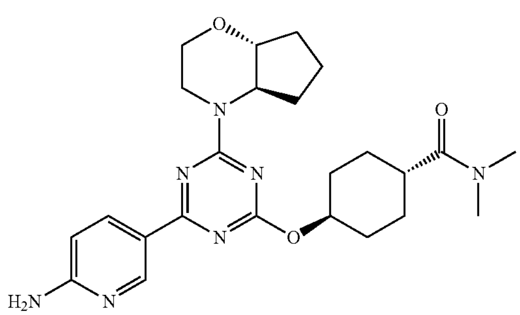 [SMILES: CN(C)C(=O)[C@H]1CC[C@H](Oc2nc(-c3ccc(N)nc3)nc(N3CCO[C@@H]4CCC[C@H]43)n2)CC1] | (1R,4r)-4-(4-(6-aminopyridin-3-yl)-6-((4aR,7aR)-hexahydrocyclopenta[b][1,4]oxazin-4(4aH)-yl)-1,3,5-triazin-2-yloxy)-N,N-dimethylcyclohexanecarboxamide |
| 10149 | 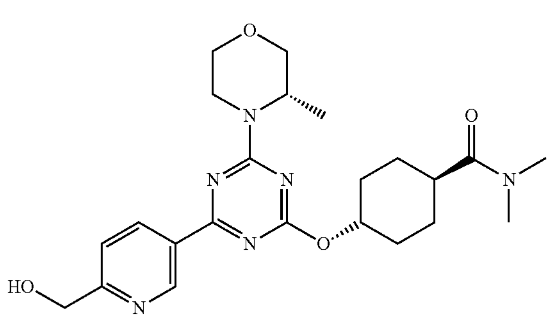 | (1S,4r)-4-(4-(6-(hydroxymethyl)pyridin-3-yl)-6-((S)-3-methylmorpholino)-1,3,5-triazin-2-yloxy)-N,N-dimethylcyclohexanecarboxamide |

TABLE 1-continued

Certain exemplified compound of the present invention

| Chemical Number | Chemical Structure | Chemical Name |
|---|---|---|
| 10150 | 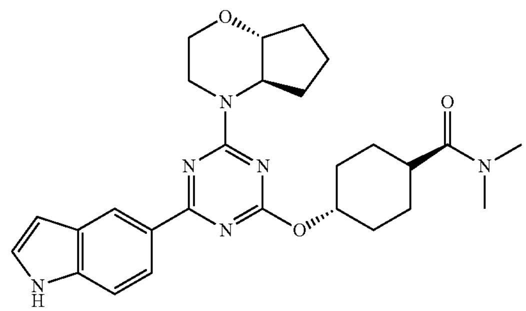 | (1S,4s)-4-(4-((4aR,7aR)-hexahydrocyclopenta[b][1,4]oxazin-4(4aH)-yl)-6-(1H-indol-5-yl)-1,3,5-triazin-2-yloxy)-N,N-dimethylcyclohexanecarboxamide |
| 10153 | 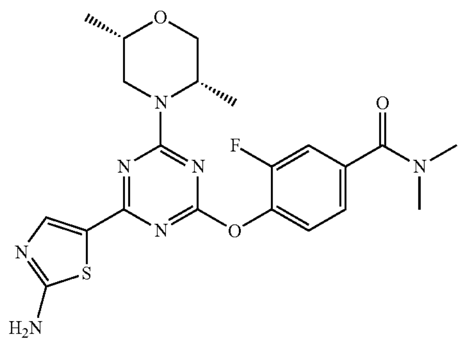 [SMILES: C[C@H]1CN(c2nc(Oc3ccc(C(=O)N(C)C)cc3F)nc(-c3cnc(N)s3)n2)[C@@H](C)CO1] | 4-(4-(2-aminothiazol-5-yl)-6-((2S,5S)-2,5-dimethylmorpholino)-1,3,5-triazin-2-yloxy)-3-fluoro-N,N-dimethylbenzamide |
| 10154 | 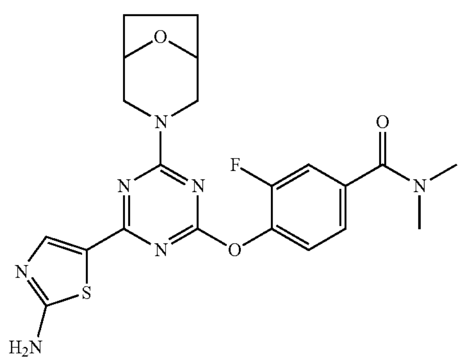 [SMILES: CN(C)C(=O)c1ccc(Oc2nc(-c3cnc(N)s3)nc(N3CC4CCC(C3)O4)n2)c(F)c1] | 4-(4-(8-oxa-3-aza-bicyclo[3.2.1]octan-3-yl)-6-(2-aminothiazol-5-yl)-1,3,5-triazin-2-yloxy)-3-fluoro-N,N-dimethylbenzamide |
| 10156 | 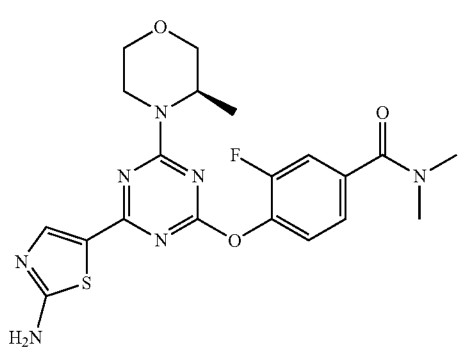 [SMILES: C[C@@H]1COCCN1c1nc(Oc2ccc(C(=O)N(C)C)cc2F)nc(-c2cnc(N)s2)n1] | 4-(4-(2-aminothiazol-5-yl)-6-((R)-3-methylmorpholino)-1,3,5-triazin-2-yloxy)-3-fluoro-N,N-dimethylbenzamide |

TABLE 1-continued

Certain exemplified compound of the present invention

| Chemical Number | Chemical Structure | Chemical Name |
|---|---|---|
| 10157 | 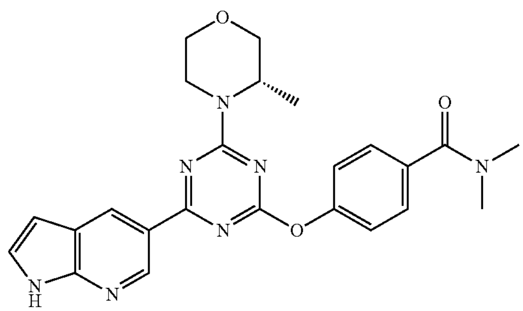 [SMILES: C[C@H]1COCCN1c1nc(Oc2ccc(C(=O)N(C)C)cc2)nc(-c2cnc3[nH]ccc3c2)n1] | 4-(4-((S)-3-methylmorpholino)-6-(1H-pyrrolo[2,3-b]pyridin-5-yl)-1,3,5-triazin-2-yloxy)-N,N-dimethylbenzamide |
| 10158 | 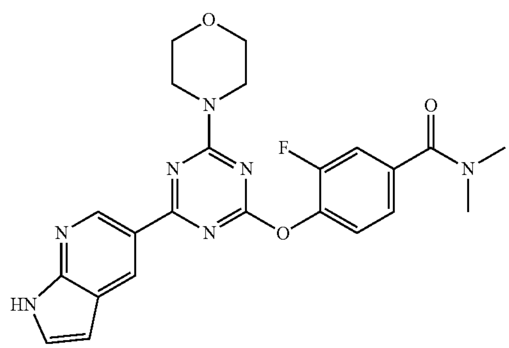 [SMILES: CN(C)C(=O)c1ccc(Oc2nc(-c3cnc4[nH]ccc4c3)nc(N3CCOCC3)n2)c(F)c1] | 4-(4-morpholino-6-(1H-pyrrolo[2,3-b]pyridin-5-yl)-1,3,5-triazin-2-yloxy)-3-fluoro-N,N-dimethylbenzamide |
| 10159 | 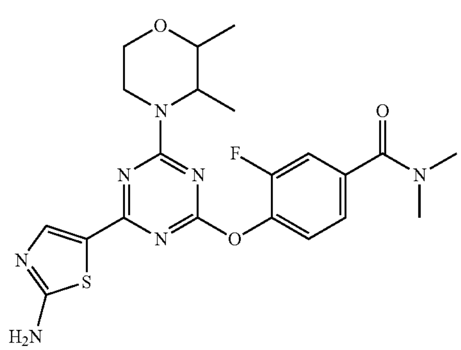 [SMILES: CC1OCCN(c2nc(Oc3ccc(C(=O)N(C)C)cc3F)nc(-c3cnc(N)s3)n2)C1C] | 4-(4-(2-aminothiazol-5-yl)-6-(2,3-dimethylmorpholino)-1,3,5-triazin-2-yloxy)-3-fluoro-N,N-dimethylbenzamide |
| 10160 | 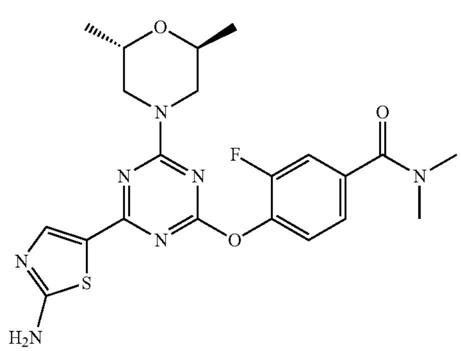 [SMILES: C[C@H]1CN(c2nc(Oc3ccc(C(=O)N(C)C)cc3F)nc(-c3cnc(N)s3)n2)C[C@H](C)O1] | 4-(4-(2-aminothiazol-5-yl)-6-((2S,6S)-2,6-dimethylmorpholino)-1,3,5-triazin-2-yloxy)-3-fluoro-N,N-dimethylbenzamide |

TABLE 1-continued

Certain exemplified compound of the present invention

| Chemical Number | Chemical Structure | Chemical Name |
|---|---|---|
| 10161 | 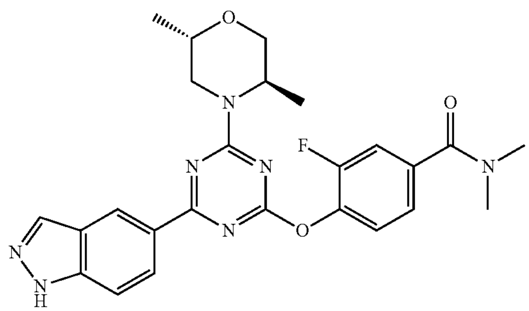 [SMILES: C[C@@H]1CO[C@@H](C)CN1c1nc(Oc2ccc(C(=O)N(C)C)cc2F)nc(-c2ccc3[nH]ncc3c2)n1] | 4-(4-(1H-indazol-5-yl)-6-((2S,5R)-2,5-dimethylmorpholino)-1,3,5-triazin-2-yloxy)-3-fluoro-N,N-dimethylbenzamide |
| 10162 | 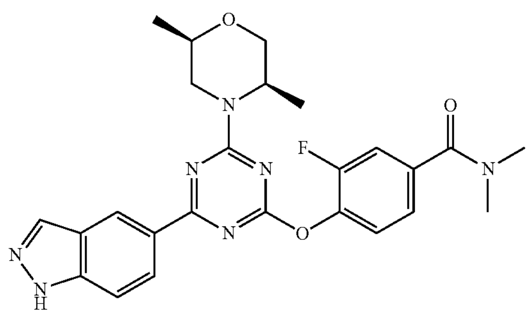 [SMILES: C[C@@H]1CN(c2nc(Oc3ccc(C(=O)N(C)C)cc3F)nc(-c3ccc4[nH]ncc4c3)n2)[C@H](C)CO1] | 4-(4-(1H-indazol-5-yl)-6-((2R,5R)-2,5-dimethylmorpholino)-1,3,5-triazin-2-yloxy)-3-fluoro-N,N-dimethylbenzamide |
| 10163 | 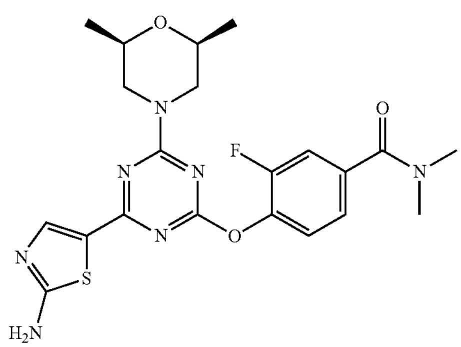 [SMILES: C[C@@H]1CN(c2nc(Oc3ccc(C(=O)N(C)C)cc3F)nc(-c3cnc(N)s3)n2)C[C@H](C)O1] | 4-(4-(2-aminothiazol-5-yl)-6-((2S,6R)-2,6-dimethylmorpholino)-1,3,5-triazin-2-yloxy)-3-fluoro-N,N-dimethylbenzamide |
| 10164 | 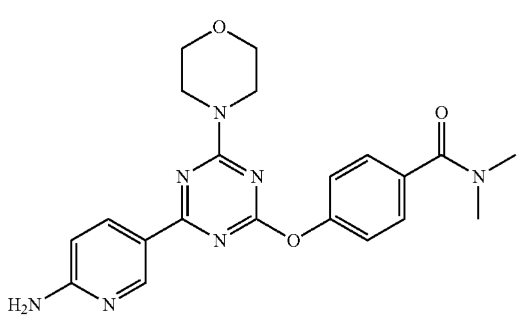 [SMILES: CN(C)C(=O)c1ccc(Oc2nc(-c3ccc(N)nc3)nc(N3CCOCC3)n2)cc1] | 4-((4-(6-Aminopyridin-3-yl)-6-morpholino-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10165 | 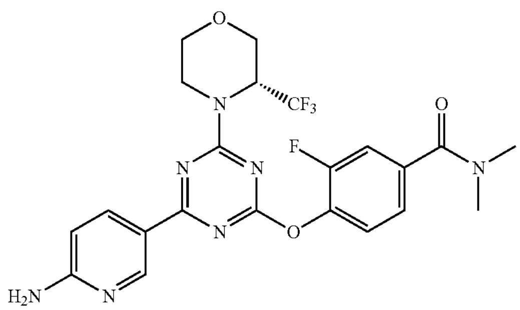 | (R)-4-((4-(6-Aminopyridin-3-yl)-6-(3-(trifluoromethylmorpholino)-1,3,5-triazin-2yl)oxy)-3-fluoro-N,N-dimethylbenzamide |
| 10166 | 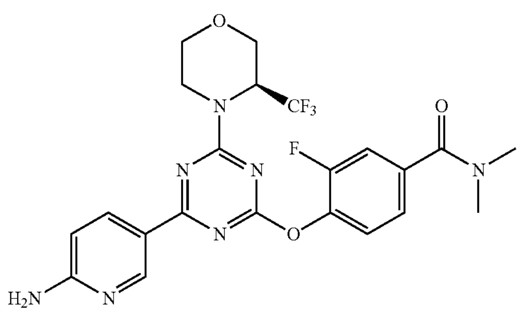 [SMILES: CN(C)C(=O)c1ccc(Oc2nc(-c3ccc(N)nc3)nc(N3CCOC[C@H]3C(F)(F)F)n2)c(F)c1] | (S)-4-((4-(6-Aminopyridin-3-yl)-6-(3-(trifluoromethylmorpholino)-1,3,5-triazin-2yl)oxy)-3-fluoro-N,N-dimethylbenzamide |
| 10167 | 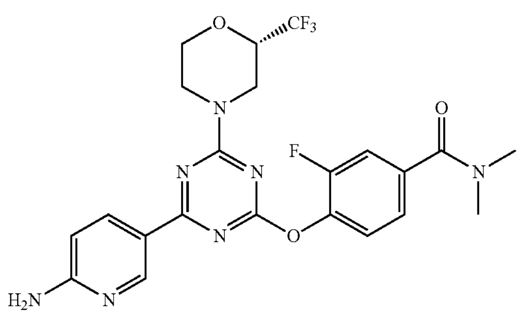 [SMILES: CN(C)C(=O)c1ccc(Oc2nc(-c3ccc(N)nc3)nc(N3CCO[C@H](C(F)(F)F)C3)n2)c(F)c1] | (S)-4-((4-(6-Aminopyridin-3-yl)-6-(2-(trifluoromethylmorpholino)-1,3,5-triazin-2yl)oxy)-3-fluoro-N,N-dimethylbenzamide |
| 10168 | 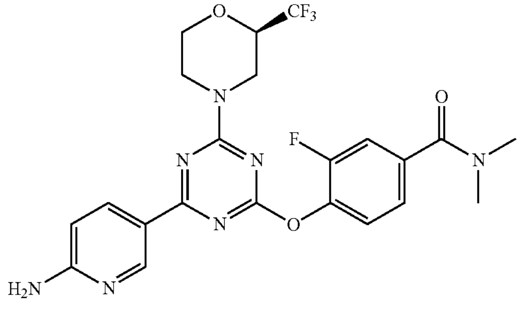 [SMILES: CN(C)C(=O)c1ccc(Oc2nc(-c3ccc(N)nc3)nc(N3CCO[C@@H](C(F)(F)F)C3)n2)c(F)c1] | (R)-4-((4-(6-Aminopyridin-3-yl)-6-(2-(trifluoromethylmorpholino)-1,3,5-triazin-2yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10169 | 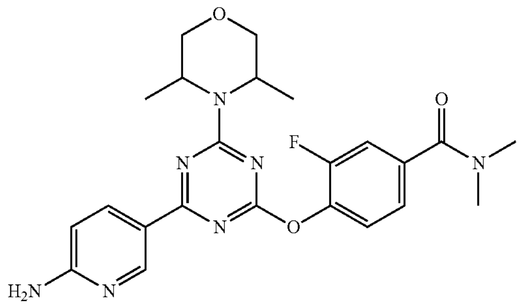 [SMILES: CC1COCC(C)N1c1nc(Oc2ccc(C(=O)N(C)C)cc2F)nc(-c2ccc(N)nc2)n1] | 4-((4-(6-Aminopyridin-3-yl)-6-(3,5-dimethylmorpholino)-1,3,5-triazin-2yl)oxy)-3-fluoro-N,N-dimethylbenzamide |
| 10170 | 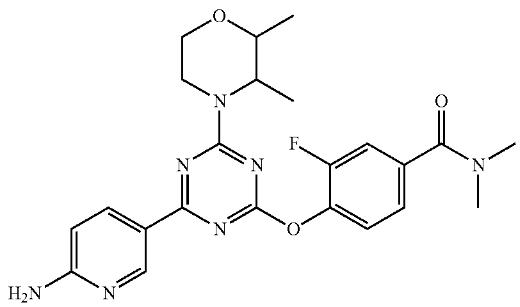 | 4-((4-(6-Aminopyridin-3-yl)-6-(2,3-dimethylmorpholino)-1,3,5-triazin-2yl)oxy)-3-fluoro-N,N-dimethylbenzamide |
| 10171 | 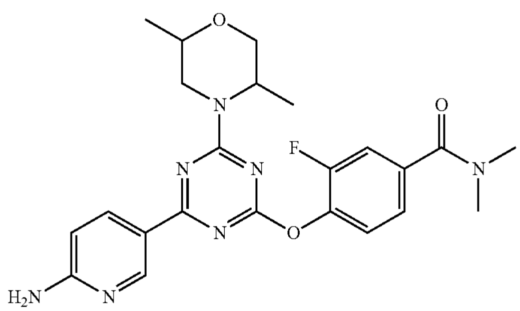 | 4-((4-(6-Aminopyridin-3-yl)-6-(2,5-dimethylmorpholino)-1,3,5-triazin-2yl)oxy)-3-fluoro-N,N-dimethylbenzamide |
| 10172 | 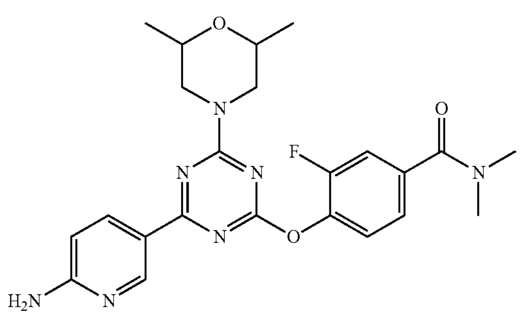 | 4-((4-(6-Aminopyridin-3-yl)-6-(2,6-dimethylmorpholino)-1,3,5-triazin-2yl)oxy)-3-fluoro-N,N-dimethylbenzamide |
| 10173 | 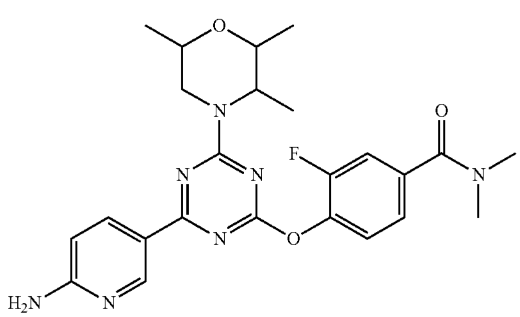 [SMILES: CC1CN(c2nc(Oc3ccc(C(=O)N(C)C)cc3F)nc(-c3ccc(N)nc3)n2)C(C)C(C)O1] | 4-((4-(6-Aminopyridin-3-yl)-6-(2,3,6-dimethylmorpholino)-1,3,5-triazin-2yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10174 | 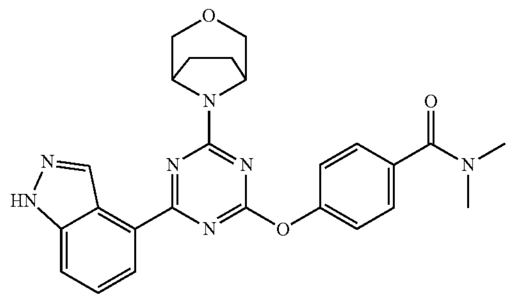 [SMILES: CN(C)C(=O)c1ccc(Oc2nc(-c3cccc4[nH]ncc34)nc(N3C4CCC3COC4)n2)cc1] | 4-((4-((1R,5S)-3-oxa-8-azabicyclo[3.2.1]octan-8-yl)-6-(1H-indazol-4-yl)-1,3,5-triazin-2-yl)oxy)-N,N-dimethylbenzamide |
| 10175 | 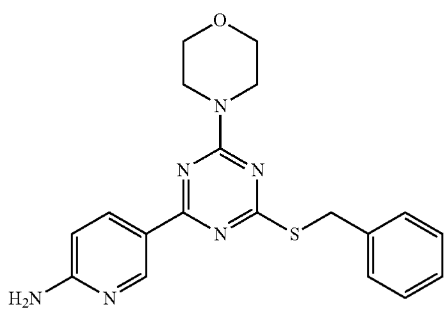 [SMILES: Nc1ccc(-c2nc(SCc3ccccc3)nc(N3CCOCC3)n2)cn1] | 5-(4-(benzylthio)-6-morpholino-1,3,5-triazin-2-yl)pyridine-2-amine |
| 10176 | 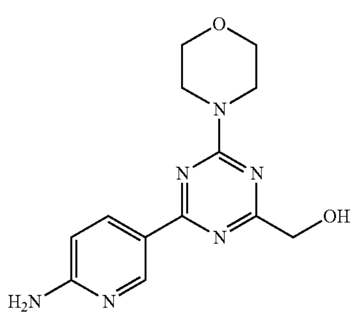 [SMILES: Nc1ccc(-c2nc(CO)nc(N3CCOCC3)n2)cn1] | (4-(6-aminopyridin-3-yl)-6-morpholino-1,3,5-triazin-2-yl)methanol |
| 10177 | 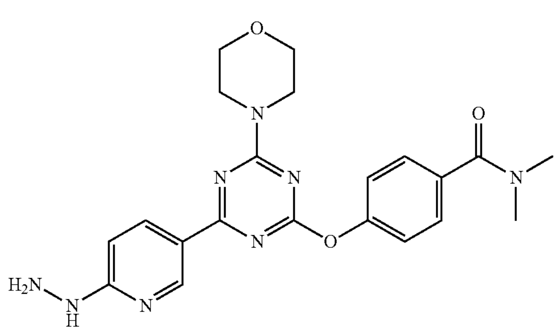 [SMILES: CN(C)C(=O)c1ccc(Oc2nc(-c3ccc(NN)nc3)nc(N3CCOCC3)n2)cc1] | 4-((4-(6-hydrazinylpyridin-3-yl)-6-morpholino-1,3,5-triazin-2-yl)oxy)-N,N-dimethylbenzamide |

TABLE 1-continued

Certain exemplified compound of the present invention

| Chemical Number | Chemical Structure | Chemical Name |
|---|---|---|
| 10178 | 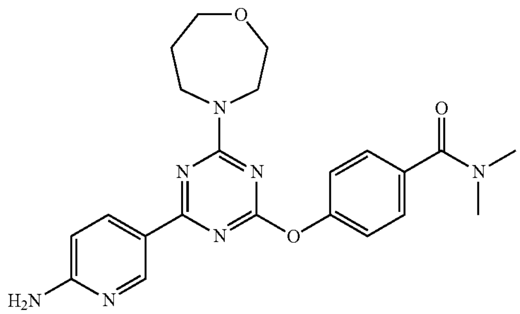 [SMILES: CN(C)C(=O)c1ccc(Oc2nc(-c3ccc(N)nc3)nc(N3CCCOCC3)n2)cc1] | 4-((4-(6-aminopyridin-3-yl)-6-(1,4-oxazepan-4-yl)-1,3,5-triazin-2-yl)oxy)-N,N-dimethylbenzamide |
| 10179 | 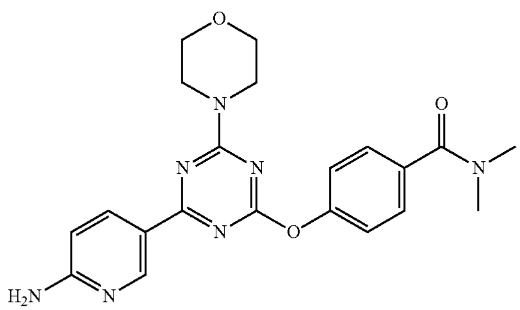 [SMILES: CN(C)C(=O)c1ccc(Oc2nc(-c3ccc(N)nc3)nc(N3CCOCC3)n2)cc1] | 4-((4-(6-aminopyridin-3-yl)-6-morpholino-1,3,5-triazin-2-yl)amino)-N,N-dimethylbenzamide |
| 10180 | 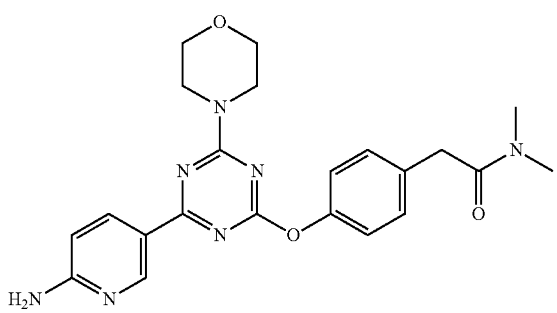 | 2-(4-((4-(6-aminopyridin-3-yl)-6-morpholino-1,3,5-triazin-2-yl)oxy)phenyl)-N,N-dimethylacetamide |
| 10181 | 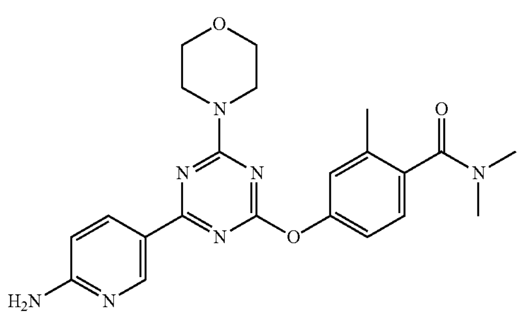 [SMILES: Cc1cc(Oc2nc(-c3ccc(N)nc3)nc(N3CCOCC3)n2)ccc1C(=O)N(C)C] | 4-((4-(6-aminopyridin-3-yl)-6-morpholino-1,3,5-triazin-2-yl)oxy)-N,N,2-trimethylbenzamide |

TABLE 1-continued

Certain exemplified compound of the present invention

| Chemical Number | Chemical Structure | Chemical Name |
|---|---|---|
| 10182 | 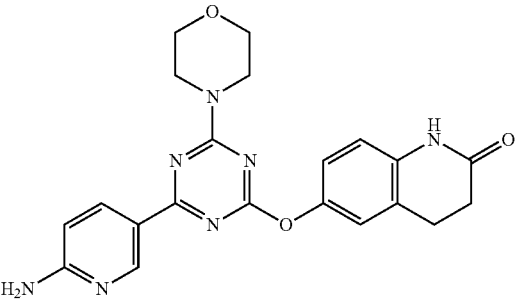 [SMILES: Nc1ccc(-c2nc(Oc3ccc4c(c3)CCC(=O)N4)nc(N3CCOCC3)n2)cn1] | 6-((4-(6-aminopyridin-3-yl)-6-morpholino-1,3,5-triazin-2-yl)oxy)-3,4-dihydroquinolin-2(1H)-one |
| 10183 | 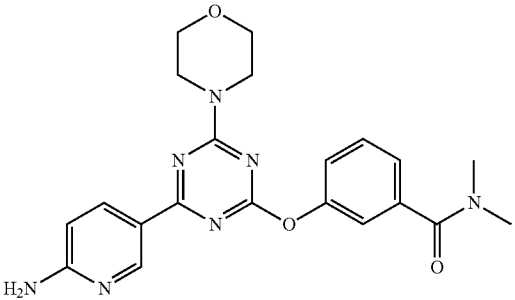 [SMILES: CN(C)C(=O)c1cccc(Oc2nc(-c3ccc(N)nc3)nc(N3CCOCC3)n2)c1] | 3-((4-(6-aminopyridin-3-yl)-6-morpholino-1,3,5-triazin-2-yl)oxy)-N,N-dimethylbenzamide |
| 10184 | 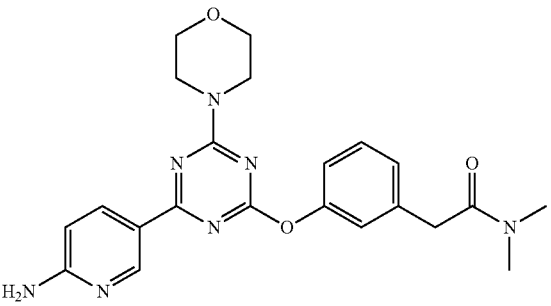 [SMILES: CN(C)C(=O)Cc1cccc(Oc2nc(-c3ccc(N)nc3)nc(N3CCOCC3)n2)c1] | 2-(3-((4-(6-aminopyridin-3-yl)-6-morpholino-1,3,5-triazin-2-yl)oxy)phenyl)-N,N-dimethylacetamide |
| 10185 | 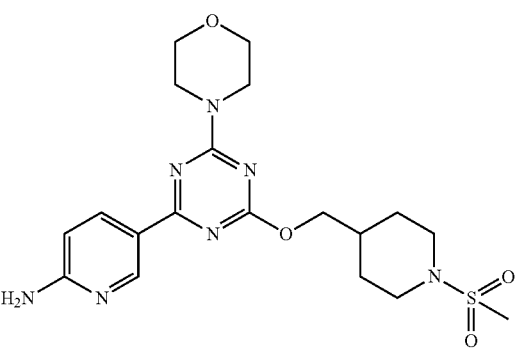 [SMILES: CS(=O)(=O)N1CCC(COc2nc(-c3ccc(N)nc3)nc(N3CCOCC3)n2)CC1] | 5-(4-((1-(methylsulfonyl)piperidin-4-yl)methoxy)-6-morpholino-1,3,5-triazin-2-yl)pyridin-2-amine |

TABLE 1-continued

Certain exemplified compound of the present invention

| Chemical Number | Chemical Structure | Chemical Name |
|---|---|---|
| 10186 | 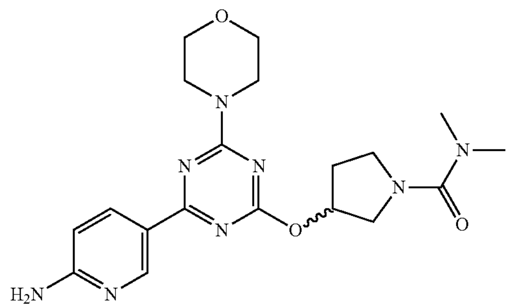 [SMILES: CN(C)C(=O)N1CCC(Oc2nc(-c3ccc(N)nc3)nc(N3CCOCC3)n2)C1] | 3-((4-(6-aminopyridin-3-yl)-6-morpholino-1,3,5-triazin-2-yl)oxy)-N,N-dimethylpyrrolidine-1-carboxamide |
| 10187 | 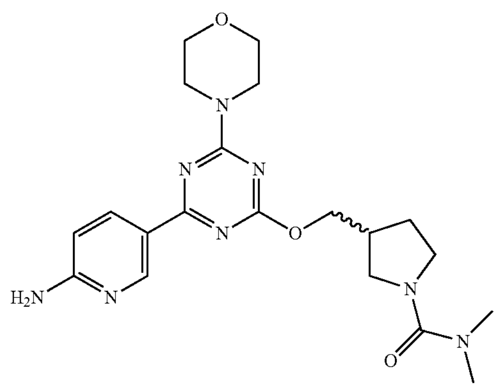 [SMILES: CN(C)C(=O)N1CCC(COc2nc(-c3ccc(N)nc3)nc(N3CCOCC3)n2)C1] | 3-(((4-(6-aminopyridin-3-yl)-6-morpholino-1,3,5-triazin-2-yl)oxy)methyl)-N,N-dimethylpyrrolidine-1-carboxamide |
| 10188 | 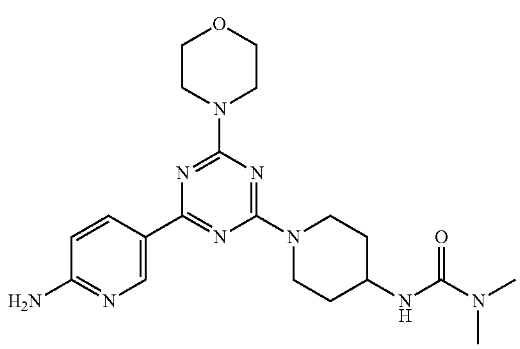 [SMILES: CN(C)C(=O)NC1CCN(c2nc(-c3ccc(N)nc3)nc(N3CCOCC3)n2)CC1] | 3-(1-(4-(6-aminopyridin-3-yl)-6-morpholino-1,3,5-triazin-2-yl)piperidin-4-yl)-1,1-dimethylurea |
| 10189 | 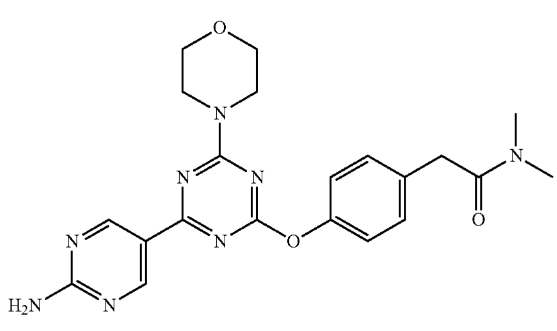 [SMILES: CN(C)C(=O)Cc1ccc(Oc2nc(-c3cnc(N)nc3)nc(N3CCOCC3)n2)cc1] | 2-(4-((4-(2-aminopyrimidin-5-yl)-6-morpholino-1,3,5-triazin-2-yl)oxy)phenyl)-N,N-dimethylacetamide |

TABLE 1-continued

Certain exemplified compound of the present invention

| Chemical Number | Chemical Structure | Chemical Name |
|---|---|---|
| 10190 | 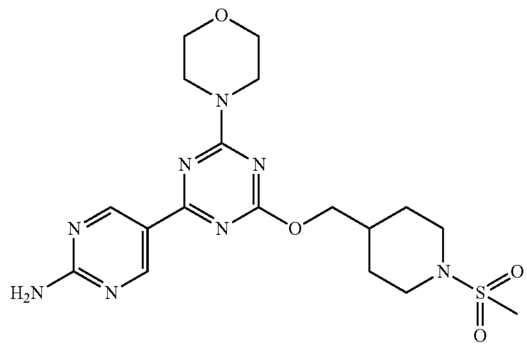 [SMILES: CS(=O)(=O)N1CCC(COc2nc(-c3cnc(N)nc3)nc(N3CCOCC3)n2)CC1] | 5-(4-((1-(methylsulfonyl)piperidin-4-yl)methoxy)-6-morpholino-1,3,5-triazin-2-yl)pyrimidin-2-amine |
| 10191 | 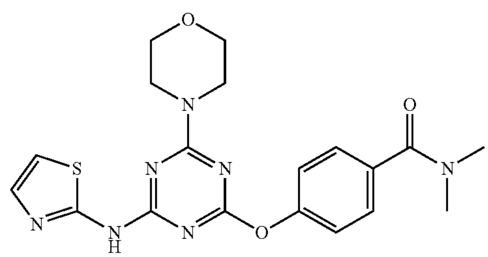 [SMILES: CN(C)C(=O)c1ccc(Oc2nc(Nc3nccs3)nc(N3CCOCC3)n2)cc1] | N,N-dimethyl-4-((4-morpholino-6-(thiazol-2-ylamino)-1,3,5-triazin-2-yl)oxy)benzamide |
| 10192 | 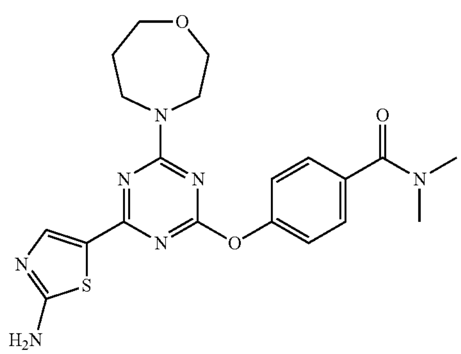 [SMILES: CN(C)C(=O)c1ccc(Oc2nc(-c3cnc(N)s3)nc(N3CCCOCC3)n2)cc1] | 4-((4-(2-aminothiazol-5-yl)-6-(1,4-oxazepan-4-yl)-1,3,5-triazin-2-yl)oxy)-N,N-dimethylbenzamide |
| 10193 | 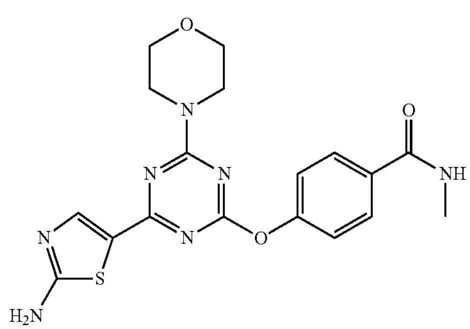 [SMILES: CNC(=O)c1ccc(Oc2nc(-c3cnc(N)s3)nc(N3CCOCC3)n2)cc1] | 4-((4-(2-aminothiazol-5-yl)-6-morpholino-1,3,5-triazin-2-yl)oxy)-N-methylbenzamide |

TABLE 1-continued

Certain exemplified compound of the present invention

| Chemical Number | Chemical Structure | Chemical Name |
|---|---|---|
| 10194 | 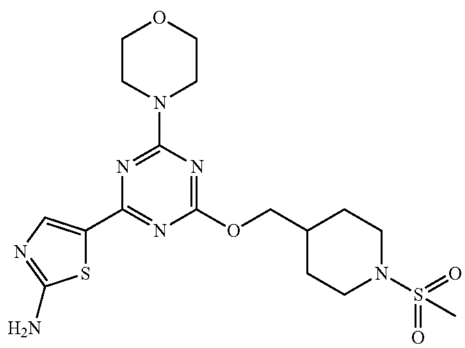 [SMILES: CS(=O)(=O)N1CCC(COc2nc(-c3cnc(N)s3)nc(N3CCOCC3)n2)CC1] | 5-(4-((1-(methylsulfonyl)piperidin-4-yl)methoxy)-6-morpholino-1,3,5-triazin-2-yl)thiazol-2-amine |
| 10195 | 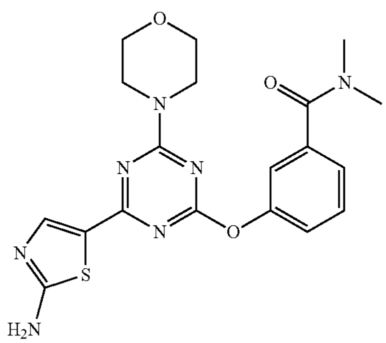 [SMILES: CN(C)C(=O)c1cccc(Oc2nc(-c3cnc(N)s3)nc(N3CCOCC3)n2)c1] | 3-((4-(2-aminothiazol-5-yl)-6-morpholino-1,3,5-triazin-2-yl)oxy)-N,N-dimethylbenzamide |
| 10196 | 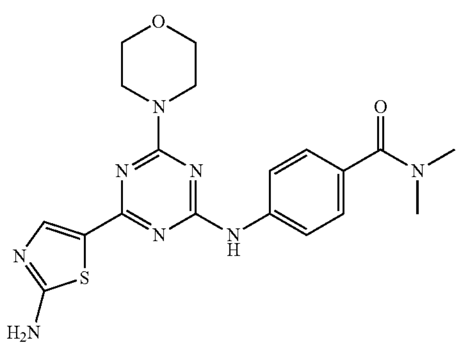 [SMILES: CN(C)C(=O)c1ccc(Nc2nc(-c3cnc(N)s3)nc(N3CCOCC3)n2)cc1] | 4-((4-(2-aminothiazol-5-yl)-6-morpholino-1,3,5-triazin-2-yl)amino)-N,N-dimethylbenzamide |
| 10197 | 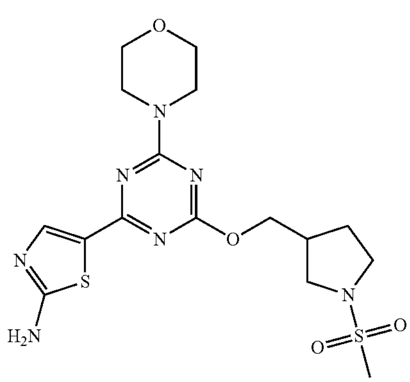 [SMILES: CS(=O)(=O)N1CCC(COc2nc(-c3cnc(N)s3)nc(N3CCOCC3)n2)C1] | 5-(4-((1-(methylsulfonyl)pyrrolidin-3-yl)methoxy)-6-morpholino-1,3,5-triazin-2-yl)thiazol-2-amine |

TABLE 1-continued

Certain exemplified compound of the present invention

| Chemical Number | Chemical Structure | Chemical Name |
|---|---|---|
| 10198 | 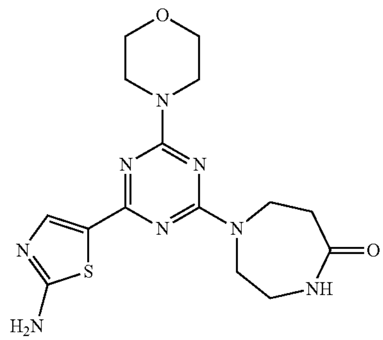 [SMILES: Nc1ncc(-c2nc(N3CCOCC3)nc(N3CCNC(=O)CC3)n2)s1] | 1-(4-(2-aminothiazol-5-yl)-6-morpholino-1,3,5-triazin-2-yl)-1,4-diazepan-5-one |
| 10199 | 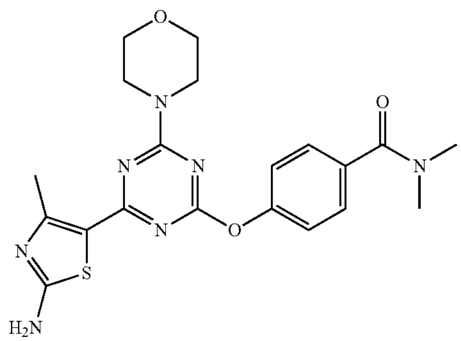 [SMILES: Cc1nc(N)sc1-c1nc(Oc2ccc(C(=O)N(C)C)cc2)nc(N2CCOCC2)n1] | 4-((4-(2-amino-4-methylthiazol-5-yl)-6-morpholino-1,3,5-triazin-2-yl)oxy)-N,N-dimethylbenzamide |
| 10200 | 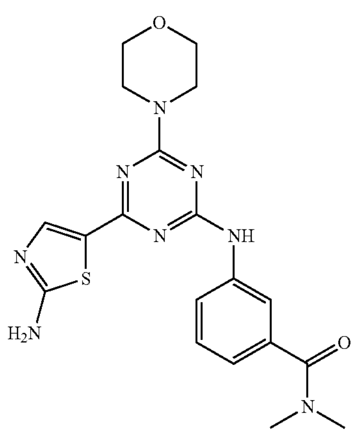 [SMILES: CN(C)C(=O)c1cccc(Nc2nc(-c3cnc(N)s3)nc(N3CCOCC3)n2)c1] | 3-((4-(2-aminothiazol-5-yl)-6-morpholino-1,3,5-triazin-2-yl)amino)-N,N-dimethylbenzamide |
| 10201 | 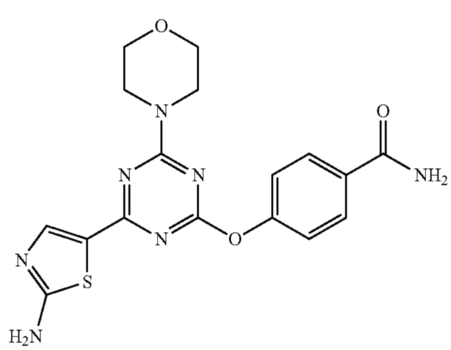 [SMILES: NC(=O)c1ccc(Oc2nc(-c3cnc(N)s3)nc(N3CCOCC3)n2)cc1] | 4-((4-(2-aminothiazol-5-yl)-6-morpholino-1,3,5-triazin-2-yl)oxy)benzamide |

US 9,630,958 B2

TABLE 1-continued

Certain exemplified compound of the present invention

| Chemical Number | Chemical Structure | Chemical Name |
|---|---|---|
| 10202 | 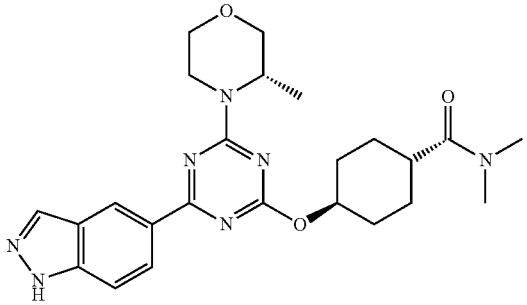 | (1S,4r)-4-((4-(1H-indazol-5-yl)-6-((S)-3-methylmorpholino)-1,3,5-triazin-2-yl)oxy)-N,N-dimethylcyclohexane-1-carboxamide |
| 10203 | 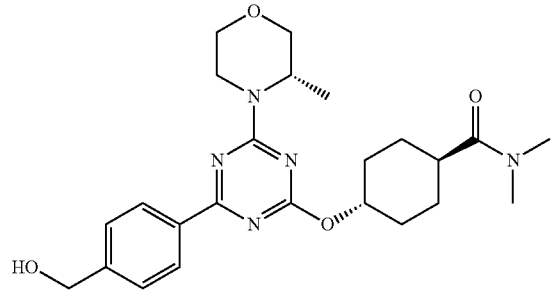 [SMILES: C[C@H]1COCCN1c1nc(O[C@H]2CC[C@H](C(=O)N(C)C)CC2)nc(-c2ccc(CO)cc2)n1] | (1S,4r)-4-((4-(4-(hydroxymethyl)phenyl)-6-((S)-3-methylmorpholino)-1,3,5-triazin-2-yl)oxy)-N,N-dimethylcyclohexane-1-carboxamide |
| 10204 | 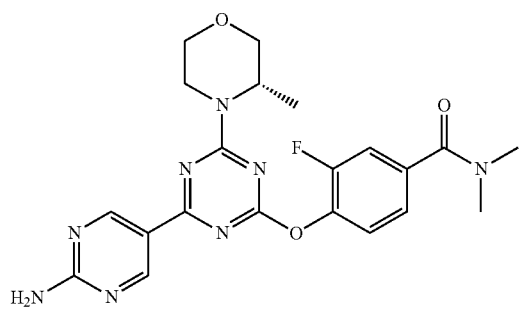 [SMILES: C[C@H]1COCCN1c1nc(Oc2ccc(C(=O)N(C)C)cc2F)nc(-c2cnc(N)nc2)n1] | (S)-4-((4-(2-aminopyrimidin-5-yl)-6-(3-methylmorpholino)-1,3,5-triazin-2-yl)oxy)-3-fluoro-N,N-dimethylbenzamide |
| 10205 | 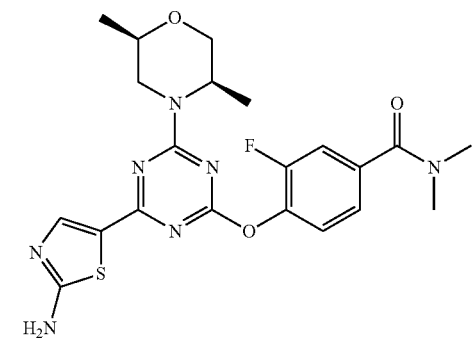 [SMILES: C[C@@H]1CN(c2nc(Oc3ccc(C(=O)N(C)C)cc3F)nc(-c3cnc(N)s3)n2)[C@H](C)CO1] | 4-((4-(2-aminothiazol-5-yl)-6-((2R,5R)-2,5-dimethylmorpholino)-1,3,5-triazin-2-yl)oxy)-3-fluoro-N,N-dimethylbenzamide |

TABLE 1-continued

Certain exemplified compound of the present invention

| Chemical Number | Chemical Structure | Chemical Name |
|---|---|---|
| 10206 | 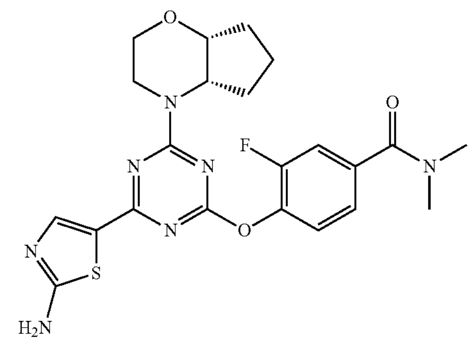 [SMILES: CN(C)C(=O)c1ccc(Oc2nc(-c3cnc(N)s3)nc(N3CCO[C@@H]4CCC[C@@H]43)n2)c(F)c1] | 4-((4-(2-aminothiazol-5-yl)-6-((4aS,7aR)-hexahydrocyclopenta[b][1.4]oxazin-4(4aH)-yl)-1,3,5-triazin-2-yl)oxy)-3-dimethylbenzamide |
| 10207 | 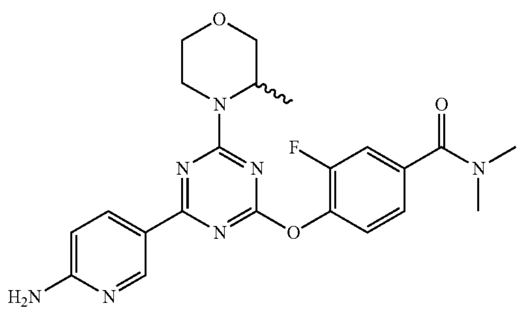 [SMILES: CC1COCCN1c1nc(Oc2ccc(C(=O)N(C)C)cc2F)nc(-c2ccc(N)nc2)n1] | 4-((4-(6-aminopyridin-3-yl)-6-(3-methylmorpholino)-1,3,5-triazin-2-yl)oxy)-3-fluoro-N,N-dimethylbenzamide |

The present invention also provides for compounds of formula I, as below:

i. 6-(4-(1H-indazol-4-yl)-6-morpholino-1,3,5-triazin-2-yloxy)-3,4-dihydroquinolin-2(1H)-one;
ii. 4-(4-(1H-indazol-4-yl)-6-morpholino-1,3,5-triazin-2-yloxy)-N,N-dimethylpiperidine-1-carboxamiide;
iii. 4-(4-(2-aminothiazol-5-yl)-6-morpholino-1,3,5-trizin-2-yloxy)-N,N-dimethylpiperidine-1-carboxamide;
iv. (R)-4-(4-(2-aminothiazol-5-yl)-6-(3-methylmorpholino)-1,3,5-triazin-2-yloxy)-N,N-dimethylbenzamide;
v. (S)-4-(4-(2-aminothiazol-5-yl)-6-(3-methylmorpholino)-1,3,5-triazin-2-yloxy)-N,N-dimethylbenzamide;
vi. 4-(4-(2-aminothiazol-5-yl)-6-(3-methylmorpholino)-1,3,5-triazin-2-yloxy)-N,N-dimethylbenzamide;
vii. N,N-dimethyl-4-(4-(2-(methylamino)thiazol-5-yl)-6-morpholino-1,3,5-triazin-2-yloxy)benzamide;
viii. 4-(4-(2-aminopyrimidin-5-yl)-6-morpholino-1,3,5-triazin-2-yloxy)-N,N-dimethylbenzamide;
ix. 4-(4-(1H-indol-5-yl)-6-morpholino-1,3,5-triazin-2-yloxy)-N,N-dimethylbenzamide;
x. (S)-4-(4-(2-aminothiazol-5-yl)-6-(3-methylmorpholino)-1,3,5-triazin-2-yloxy)-3-fluoro-N,N-di methylbenzamide;
xi. 4-(4-(2-aminothiazol-5-yl)-6-((1R,5S)-3-oxa-S-azabicyclo[3.2.1]octan-8-yl)-1,3,5-triazin-2-yloxy)-N,N-dimethylbenzamide;
xii. 3-(4-(1H-indazol-4-yl)-6-morpholino-1,3,5-triazin-2-ylamino)-N,N-dimethylpropanamide;
xiii. (1r,4r)-4-(4-(1H-indazol-4-yl)-6-morpholino-1,3,5-triazin-2-yloxy)-N,N-dimethylcyclohexanecarboxamide;
xiv. N,N-dimethyl-4-(4-morpholino-6-(1H-pyrrolo[2,3-b]pyridin-5-yl)-1,3,5-triazin-2-yloxy)benzamide;
xv. 4-(4-(6-amino-4-(trifluoromethyl)pyridin-3-yl)-6-morpholino-1,3,5-triazin-2-yloxy)-N,N-dimethylbenzamide;
xvi. 1-(4-(2-aminopyrimidin-S-yl)-6-morpholino-1,3,5-triazin-2-yl)-1,4-diazepan-5-one;
xvii. 4-(4-(2-aminothiazol-5-yl)-6-morpholino-1,3,5-triazin-2-yloxy)-N,N-dimethylbenzamide;
xviii. N1-((1r,4r)-4-(4-(1H-indazol-4-yl)-6-morpholino-1,3,5-triazin-2-yloxy)cyclohexyl)-N2-methyloxalamiide;
xix. 4-(4-(2-aminopyrimidin-5-yl)-6-morpholino-1,3,5-triazin-2-yloxy)-N,N-dimethylpiperidine-1-carboxamiide;
xx. 4-(4-(1H-indazol-4-yl)-6-(3-methylmorpholino)-1,3,5-triazin-2-yloxy)-N,N-dimethylbenzamide;
xxi. 4-(4-(6-aminopyridin-3-yl)-6-morpholino-1,3,5-triazin-2-yloxy)-N,N-dimethylpiperidine-1-carboxamide;
xxii. 4-(4-(2-aminothiazol-5-yl)-6-morpholino-1,3,5-triazin-2-yloxy)-3-fluoro-N,N-dimethylbenzamide;
xxiii. 3-(4-(1H-indazol-4-yl)-6-morpholino-1,3,5-triazin-2-ylamino)-N,N-dimethylpropanamide;
xxiv. 4-((4-(2-aminothiazol-5-yl)-6-(3-methylmorpholino)-1,3,5-triazin-2-yl)methyl)-N,N-dimethylpiperazine-1-carboxamide;
xxv. 4-(4-(2-aminothiazol-5-yl)-6-(3-methylmorpholino)-1,3,5-triazin-2-ylamino)-N,N-dimethylcyclohexanecarboxamide;
xxvi. N-(4-(2-aminothiazol-5-yl)-6-(3-methylmorpholino)-1,3,5-triazin-2-yl)-1-((R)-2-hydroxypropanoyl)piperidine-4-carboxamide;
xxvii. 4-(4-(2-aminothiazol-5-yl)-6-(3-methylmorpholino)-1,3,5-triazin-2-yloxy)-N,N-dimethylcyclohexanecarboxamide;
xxviii. 4-(4-(2-aminothiazol-5-yl)-6-(3-methyl-5-oxomorpholino)-1,3,5-triazin-2-yloxy)-N,N-dimethylbenzamide;
xxix. 4-(4-(2-aminothiazol-5-yl)-6-(2H-benzo[b][1,4]oxazin-4(3H)-yl)-1,3,5-triazin-2-yloxy)-N,N-dimethylbenzamide;

xxx. 4-(4-(2-aminothiazol-5-yl)-6-(2H-benzo[b][1,4]ox-azin-4(3H,4aH,5H,6H,7H,8H,8aH)-yl)-1,3,5-triazin-2-yloxy)-N,N-dimethylbenzamide;

xxxi. 4-(4-(6-aminopyridin-3-yl)-6-(3-methylmorpholino)-1,3,5-triazin-2-yloxy)-N,N-dimethylbenzamide;

xxxii. 4-(4-(2-aminopyrimidin-5-yl)-6-(3-methylmorpholino)-1,3,5-triazin-2-yloxy)-N,N-dimethylbenzamide;

xxxiii. 4-(4-(2-aminothiazol-5-yl)-6-(3,5-dimethylmorpholino)-1,3,5-triazin-2-yloxy)-N,N-dimethylbenzamide;

xxxiv. 3-(4-(2-aminothiazol-5-yl)-6-(3-methylmorpholino)-1,3,5-triazin-2-yloxy)-N,N-dimethylpyrrolidine-1-carboxamide;

xxxv. (R)-1-(4-(2-(4-(2-aminothiazol-5-yl)-6-morpholino-1,3,5-triazin-2-yl)acetyl)piperazin-1-yl)-2-hydroxypropan-1-one;

xxxvi. 4-(4-(2-aminothiazol-5-yl)-6-(3,3-dimethylmorpholino)-1,3,5-triazin-2-yloxy)-N,N-dimethylbenzamide;

xxxvii. 4-(4-(2-aminothiazol-5-yl)-6-(3-ethylmorpholino)-1,3,5-triazin-2-yloxy)-N,N-dimethylbenzamide;

xxxviii. 1-((4-(2-aminothiazol-5-yl)-6-(3-methyl morpholino)-1,3,5-triazin-2-yl)methyl)-N,N-dimethylpiperidine-4-carboxamiide;

xxxix. 4-((4-(2-Aminopyrimidin-5-yl)-6-morpholino, 1,3,5-triazin-2-yl)oxy)-3-fluoro-N,N-dimethylbenzamide;

xl. (2R)-1-(4-((4-(2-aminothiazol-5-yl)-6-(3-methylmorpholino)-1,3,5-triazin-2-yloxy)methyl)piperidin-1-yl)-2-hydroxypropan-1-one;

xli. (R)-1-(4-(2-(4-(2-aminothiazol-5-yl)-6-morpholino-1,3,5-triazin-2-yl)acetyl)piperidin-1-yl)-2-hydroxypropan-1-one;

xlii. 4-(4-(2-aminothiazol-5-yl)-6-(2,5-dimethylmorpholino)-1,3,5-triazin-2-yloxy)-N,N-dimethylbenzamide;

xliii. 4-(4-(2-aminothiazol-5-yl)-6-(3-methylmorpholino)-1,3,5-triazin-2-yloxy)-N,N-dimethylpiperidine-1-carboxamide;

xliv. 4-(4-(2-aminothiazol-5-yl)-6-(2-(fluoromethyl)morpholino)-1,3,5-triazin-2-yloxy)-N,N-dimethylbenzamide;

xlv. 4-(4-(2-aminothiazol-5-yl)-6-(2,3-dimethylmorpholino)-1,3,5-triazin-2-yloxy)-N,N-dimethylbenzamide;

xlvi. 4-(4-(2-aminothiazol-5-yl)-6-((1R,5S)-6-oxa-3-azabicyclo[3.1.1]heptan-3-yl)-1,3,5-triazin-2-yloxy)-N,N-dimethylbenzamide;

xlvii. 4-(4-(1H-indazol-4-yl)-6-(3-methylmorpholino)-1,3,5-triazin-2-yloxy)-N,N-dimethylbenzamide;

xlviii. 4-(4-(2-aminothiazol-5-yl)-6-(3-methylmorpholino)pyrimidin-2-yloxy)-N,N-dimethylbenzamide;

xlix. (1r,4r)-4-(4-(6-aminopyridin-3-yl)-6-morpholino-1,3,5-triazin-2-yloxy)-N,N-dimethylcyclohexanecarboxamide;

l. 4-(4-(6-aminopyridin-3-yl)-6-((1R,5S)-3-oxa-8-azabicyclo[3.2.1]octan-8-yl)-1,3,5-triazin-2-yloxy)-N,N-dimethylbenzamide;

li. (S)-4-((4-(1H-indazol-5-yl)-6-(3-methylmorpholino)-1,3,5-triazin-2-yl)oxy)-3-fluoro-N,N-dimethylbenzamide;

lii. 4-((4-(2-Aminothiazol-5-yl)-6-((2R,3S)-2,3-dimethylmorpholino)-1,3,5-triazin-2-yl)oxy)-3-fluoro-N,N-dimethylbenzamide;

liii. 4-((4-(2-Aminothiazol-5-yl)-6-((2S,3S)-2,3-dimethylmorpholino)-1,3,5-triazin-2-yl)oxy)-3-fluoro-N,N-dimethylbenzamide;

liv. 4-((4-(2-Aminothiazol-5-yl)-6-((2R,3R)-2,3-dimethylmorpholino)-1,3,5-triazin-2-yl)oxy)-3-fluoro-N,N-dimethylbenzamide;

lv. 4-((4-(2-Aminothiazol-5-yl)-6-((3S,5S)-3,5-dimethylmorpholino)-1,3,5-triazin-2-yl)oxy)-3-fluoro-N,N-dimethylbenzamide;

lvi. 4-((4-(2-Aminothiazol-5-yl)-6-((3R,5S)-3,5-dimethylmorpholino)-1,3,5-triazin-2-yl)oxy)-3-fluoro-N,N-dimethylbenzamide;

lvii. 4-((4-(2-Aminothiazol-5-yl)-6-((2R,5S)-2,5-dimethylmorpholino)-1,3,5-triazin-2-yl)oxy)-3-fluoro-N,N-dimethylbenzamide;

lviii. (S)-4-((4-(6-Aminopyridin-3-yl)-6-(3-methylmorpholino)-1,3,5-triazin-2-yl)oxy)-3-fluoro-N,N-dimethylbenzamide;

lix. 4-((4-(2-Aminothiazol-5-yl)-6-(3-(trifluoromethyl)morpholino)-1,3,5-triazin-2-yl)oxy)-3-fluoro-N,N-dimethylbenzamide;

lx. 4-((4-(2-Aminothiazol-5-yl)-6-(2-(trifluoromethyl)morpholino)-1,3,5-triazin-2-yl)oxy)-3-fluoro-N,N-dimethylbenzamide;

lxi. 4-((4-(2-Aminothiazol-5-yl)-6-(3-(difluoromethyl)morpholino)-1,3,5-triazin-2-yl)oxy)-3-fluoro-N,N-dimethylbenzamide;

lxii. 4-((4-(2-Aminothiazol-5-yl)-6-(2-(difluoromethyl)morpholino)-1,3,5-triazin-2-yl)oxy)-3-fluoro-N,N-dimethylbenzamide;

lxiii. 4-((4-((2S,3S)-2,5-dimethylmorpholino)-6-(1H-indazol-5-yl)-1,3,5-triazin-2-yl)oxy)-3-fluoro-N,N-dimethylbenzamide;

lxiv. 4-((4-((2R,3S)-2,5-dimethylmorpholino)-6-(1H-indazol-5-yl)-1,3,5-triazin-2-yl)oxy)3-fluoro-N,N-dimethylbenzamide;

lxv. 4-((4-(6-Amino-4-(trifluoromethyl)pyridine-3-yl)-6-morpholino-1,3,5-triazin-2-yl)oxy)-3-fluoro-N,N-dimethylbenzamide;

lxvi. (S)-4-((4-(6-Amino-4-(trifluoromethyl)pyridine-3-yl)-6-(3-methylmorpholino)-1,3,5-triazin-2-yl)oxy)-N,N-dimethylbenzamide;

lxvii. (S)-4-((4-(6-Amino-4-(trifluoromethyl)pyridine-3-yl)-6-(3-methylmorpholino)-1,3,5-triazin-2-yl)oxy)-3-fluoro-N,N-dimethylbenzamide;

lxviii. 4-((4-(2-Aminothiazol-5-yl)-6-(piperidin-1-yl)-1,3,5-triazin-2-yl)oxy)-3-fluoro-N,N-dimethylbenzamide;

lxix. 4((4-(2-Aminothiazol-5-yl)-6-((2R,6S)-2,6-dimethylmorpholino-1,3,5-triazin-2-yl)-3-fluoro-N,N-dimethylbenzamide;

lxx. 4-((4-2-Aminothiazol-5-yl)-6-((2R,6R)-2,6-dimethylmorpholino)-1,3,5-triazin-2-yl)oxy-3-fluoro-N,N-dimethylbenzamide;

lxxi. 4-((4-(2-Aminothiazol-5-yl)-6-(5-oxo-1,4-diazepan-1-yl)-1,3,5-triazin-2-yl)oxy)-N,N-dimethylbenzamide;

lxxii. 4-((4-(2-Aminothiazol-5-yl)-6-(3-oxopiperazin-1-yl)-1,3,5-triazin-2-yl)oxy)-N,N-dimethylbenzamide;

lxxiii. (R)-4-((4-(2-Aminothiazol-5-yl)-6-(2-methylmorpholino)-1,3,5-triazin-2-yl)oxy)-N,N-dimethylbenzamide;

lxxiv. 4-((4-(2-Aminothiazol-5-yl)-6-(hexahydrocyclopenta[b][1,4]oxazin-4-(4aH)-yl)-1,3,5-triazin-2-yl)oxy)-N,N-dimethylbenzamide;

lxxv. 4-((4-(2-Aminothiazol-5-yl)-6-(8-oxa-3-azabicyclo[3.2.1]octan-3-yl)-1,3,5-triazin-2-yl)oxy)-N,N-dimethylbenzamide;

lxxvi. 4-((4-(2-Aminothiazol-5-yl)-6-((2R,5S)-2,5-dimethylmorpholino)-1,3,5-triazin-2-yl)oxy)-N,N-dimethylbenzamide;

lxxvii. 4-((4-(2-Aminothiazol-5-yl)-6-((2S,5S)-2,5-dimethylmorpholino)-1,3,5-triazin-2-yl)oxy)-N,N-dimethylbenzamide;

lxxviii. 4-((4-(2-Aminothiazol-5-yl)-6-((3S,5S)-3,5-dimethylmorpholino)-1,3,5-triazin-2-yl)oxy)-N,N-dimethylbenzamide;

lxxix. 4-((4-(2-Aminothiazol-5-yl)-6-((3S,5R)-3,5-dimethylmorpholino)-1,3,5-triazin-2-yl)oxy)-N,N-dimethylbenzamide;

lxxx. (S)-4-((4-(2-Aminothiazol-5-yl)-6-(2-methylmorpholino)-1,3,5-triazin-2-yl)oxy)-N,N-dimethylbenzamide;

lxxxi. (S)-4-((4-(2-Aminothiazol-5-yl)-6-(3-ethylmorpholino)-1,3,5-triazin-2-yl)oxy)-N,N-dimethylbenzamide;

lxxxii. (R)-4-((4-(2-Aminothiazol-5-yl)-6-(3-ethylmorpholino)-1,3,5-triazin-2-yl)oxy)-N,N-dimethylbenzamide;

lxxxiii. 4-((4-(2-Aminothiazol-5-yl)-6-(9-oxa-6-azaspiro[4.5]decan-6-yl)-1,3,5-triazin-2-yl)oxy)-3-fluoro-N,N-dimethylbenzamide;

lxxxiv. 4-((4-2-Aminothiazol-5-yl)-6-((2S,6S)-2,6-dimethylmorpholino)-1,3,5-triazin-2-yl)oxy-3-fluoro-N,N-dimethylbenzamide;

lxxxv. 4-((4-(2-Aminothiazol-5-yl)-6-((3R,5R)-3, 5-dimethylmorpholino)-1,3,5-triazin-2-yl)oxy)-N,N-dimethylbenzamide;

lxxxvi. 4-((4-(2-Aminothiazol-5-yl)-6-((3R,5S)-3,5-dimethylmorpholino)-1,3,5-triazin-2-yl)oxy)-N,N-dimethylbenzamide;

lxxxvii. 4-((4-(2-Aminothiazol-5-yl)-6-((2R,3S,6R)-2,3,6-trimethylmorpholino)-1,3,5-triazin-2-yl)-oxy)-3-fluoro-N,N-dimethylbenzamide;

lxxxviii. 4-((4-(2-Aminothiazol-5-yl)-6-((2R,3S,6S)-2,3,6-trimethylmorpholino)-1,3,5-triazin-2-yl)-oxy)-3-fluoro-N,N-dimethylbenzamide;

lxxxix. 4-((4-(2-Aminothiazol-5-yl)-6-(5-methyl-1,4-oxazepan-4-yl)-1,3,5-triazin-2-yl)oxy)-3-fluoro-N,N-dimethylbenzamide;

xc. (S)—N,N-dimethyl-4-((4-(3-methylmorpholino)-6-(2-(3-methylureido)thiazol-5-yl)-1,3,5-triazin-2-yl)oxy)benzamide;

xci. (S)—N,N-dimethyl-4-((4-(3-methylmorpholino)-6-(2-(3-pyridin-3-yl)ureido)thiazol-5-yl)-1,3,5-triazin-2-yl)oxy)benzamide;

xcii. (S)-4-((4-(2-(3-cyclopropylureido)thiazol-5-yl)-6-(3-methylmorpholino)-1,3,5-triazin-2-yl)oxy-N,N-dimethylbenzamide;

xciii. (S)—N-(5-(4-(4-(dimethylcarbamoyl)phenoxy)-6-(3-methylmorpholino)-1,3,5-triazin-2-yl)thiazol-2-yl)nicotinamide;

xciv. 4-6-Aminopyridin-3-yl)-6-(8-oxa-3-azabicyclo[3.2.1]octan-3-yl)-1,3,5-triazin-2-yl)oxy)-3-fluoro-N,N-dimethylbenzamide;

xcv. (S)-4-((4-(6-Aminopyridin-3-yl)-6-(3-methylmorpholino)-1,3,5-triazin-2-yl)oxy)-N,N-dimethylbenzamide;

xcvi. 4-((4-(6-Aminopyridin-3-yl)-6-((2S,5S)-2,5-dimethylmorpholino)-1,3,5-triazin-2-yl)oxy)-3-fluoro-N,N-dimethylbenzamide;

xcvii. 4-((4-(6-Aminopyridin-3-yl)-6-((2R,5S)-2,5-dimethylmorpholino)-1,3,5-triazin-2-yl)oxy)-3-fluoro-N,N-dimethylbenzamide;

xcviii. (R)-4-((4-(6-Aminopyridin-3-yl)-6-(3-methylmorpholino)-1,3,5-triazin-2-yl)oxy)-3-fluoro-N,N-dimethylbenzamide;

xcix. (S)-4-((4-(1H-indol-5-yl)-6-(3-methylmorpholino)1,3,5-triazin-2-yl)oxy)3-fluoro-N,N-dimethylbenzamide;

c. (S)-4-((4-(2-Amino-4-(trifluoromethyl)pyrimidin-5-yl)-6-(3-methylmorpholino)-1,3,5-triazin-2-yl)-oxy-3-fluoro-N,N-dimethylbenzamide;

ci. (S)-4-((4-(1H-benzo[d]imidazol-5-yl)-6-(3-methylmorpholino)-1,3,5-triazin-2-yl)oxy)-3-fluoro-N,N-dimethylbenzamide;

cii. (S)-3-Fluoro-N,N-dimethyl-4-((4-(3-methylmorpholino)-6-(1H-pyrrolo-[2,3-b]pyridin-5-yl)-1,3,5-triazin-2-yl)oxy)benzamide;

ciii. 4-((4-((2S,5S)-2,5-dimethylmorpholino)-6-(1H-pyrrolo[2,3-b]pyridine-5-yl)-1,3,5-triazin-2-yl)oxy)-3-fluoro-N,N-dimethylbenzamide;

civ. 4-((4-((2R,5S)-2,5-dimethylmorpholino)-6-(1H-pyrrolo[2,3-b]pyridine-5-yl)-1,3,5-triazin-2-yl)oxy)-3-fluoro-N,N-dimethylbenzamide;

cv. 4-((4-((2R,3R)-2,5-dimethylmorpholino)-6-(1H-pyrrolo[2,3-b]pyridine-5-yl)-1,3,5-triazin-2-yl)oxy)-3-fluoro-N,N-dimethylbenzamide;

cvi. 4-((4-((2S,5R)-2,5-dimethylmorpholino)-6-(1H-pyrrolo[2,3-b]pyridine-5-yl)-1,3,5-triazin-2-yl)oxy)-3-fluoro-N,N-dimethylbenzamide;

cvii. 4-((4-(2-Aminothiazol-5-yl)-6-((2S,5S)-2,5-dimethyl-1,4-oxazepan-4-yl)-1,3,5-triazin-2-yl)oxy-3-fluoro-N,N-dimethylbenzamide;

cviii. 4-((4-(2-Aminothiazol-5-yl)-6-((2S,5R)-2,5-dimethyl-1,4-oxazepan-4-yl)-1,3,5-triazin-2-yl)oxy-3-fluoro-N,N-dimethylbenzamide;

cix. (1s,4s)-4-((4-(6-Aminopyridin-3-yl)-6-(hexahydrocyclopenta[b][1,4]oxazin-4(4aH)-yl)-1,3,5-triazin-2-yl)oxy)-N,N-dimethylcyclohexane-1-carboxamide;

cx. 4-((4-(2-Aminothiazol-5-yl)-6-(3-(fluoromethyl)morpholino)-1,3,5-triazin-2-yl)oxy)-3-fluoro-N,N-dimethylbenzamide;

cxi. 4-((4-(2-Aminothiazol-5-yl)-6-(2-(fluoromethyl)morpholino)-1,3,5-triazin-2-yl)oxy)-3-fluoro-N,N-dimethylbenzamide;

cxii. 4-((4-(2-Aminothiazol-5-yl)-6-(1,1-dioxidothiomorpholino)-1,3,5-triazin-2-yl)oxy)-3-fluoro-N,N-dimethylbenzamide;

cxiii. 4-((4-2-Aminothiazol-5-yl)-6-(1-oxidothiomorpholino)-1,3,5-triazin-2-yl)oxy)-3-fluoro-N,N-dimethylbenzamide;

cxiv. 2-(4-(4-(2-aminothiazol-5-yl)-6-morpholino-1,3,5-triazin-2-yloxy)phenyl)-N,N-dimethylpropanamide;

cxv. 4-(4-(2-aminothiazol-5-yl)-6-thiomorpholino-1,3,5-triazin-2-yloxy)-N,N-dimethylbenzamide;

cxvi. 4-(4-(2-aminothiazol-5-yl)-6-(piperidin-1-yl)-1,3,5-triazin-2-yloxy)-N,N-dimethylbenzamide;

cxvii. 4-4-(2-aminothiazol-5-yl)-6-((2S,6R)-2,6-dimethylmorpholino)-1,3,5-triazin-2-yloxy)-N,N-dimethylbenzamide;

cxviii. 4-(4-(2-amino-1H-imidazol-5-yl)-6-morpholino-1,3,5-triazin-2-yloxy)-N,N-dimethylbenzamide;

cxix. 4-(4-(2-aminopyrimidin-5-yl)-6-((S)-3-methylmorpholino)-1,3,5-triazin-2-yloxy)-N,N-dimethylbenzamide;

cxx. 4-(4-(2-aminothiazol-5-yl)-6-((S)-2-methylmorpholino)-1,3,5-triazin-2-yloxy)-N,N-dimethylbenzamide;

cxxi. 4-(4-(2-aminothiazol-5-yl)-6-(3,3-dimethylmorpholino)-1,3,5-triazin-2-yloxy)-N,N-dimethylbenzamide;

cxxii. 4-(4-(6-aminopyridin-3-yl)-6-((S)-3-methylmorpholino)-1,3,5-triazin-2-yloxy)-N,N-dimethylcyclohexanecarboxamide;

cxxiii. 4-(4-((S)-3-aminomorpholino)-6-(2-methylthiazol-5-yl)-1,3,5-triazin-2-yl oxy)-N,N-dimethylbenzamide;

cxxiv. 4-(4-(2-aminothiazol-5-yl)-6-((4aR,8aR)-octahydrobenzo[b][1,4]oxazin-4-yl)-1,3,5-triazin-2-yloxy)-N,N-dimethylbenzamide;

cxxv. 4-(4-(2-aminothiazol-5-yl)-6-((4aR,7aR)-hexahydrocyclopenta[b][1,4]oxazin-4(4aH)-yl)-1,3,5-triazin-2-yloxy)-N,N-dimethylbenzamide;

cxxvi. 4-(4-(2-aminothiazol-5-yl)-6-((R)-2-methylmorpholino)-1,3,5-triazin-2-yloxy)-N,N-dimethylbenzamide;
cxxvii. 4-(4-(1H-indazol-5-yl)-6-((S)-3-methylmorpholino)-1,3,5-triazin-2-yloxy)-3-fluoro-N,N-dimethylbenzamide;
cxxviii. 1-methyl-3-(5-(4-(methylamino)-6-((S)-3-methylmorpholino)-1,3,5-triazin-2-yl)thiazol-2-yl)urea;
cxxix. 4-(4-(3-oxa-8-aza-bicyclo[3.2.1]octan-8-yl)-6-(1H-indazol-5-yl)-1,3,5-triazin-2-yloxy)-3-fluoro-N,N-dimethylbenzamide;
cxxx. 4-(4-(2-aminothiazol-5-yl)-6-((S)-3-methylmorpholino)-1,3,5-triazin-2-yloxy)-N,N-dimethylpiperidine-1-carboxamide;
cxxxi. 3-(4-(2-aminothiazol-5-yl)-6-((S)-3-methylmorpholino)-1,3,5-triazin-2-yloxy)-N,N-dimethylpyrrolidine-1-carboxamide;
cxxxii. (1S,4r)-4-(4-(2-aminothiazol-5-yl)-6-((S)-3-methylmorpholino)-1,3,5-triazin-2-yloxy)-N,N-dimethylcyclohexanecarboxamide;
cxxxiii. 4-(4-(8-oxa-3-aza-bicyclo[3.2.1]octan-3-yl)-6-(1H-indazol-5-yl)-1,3,5-triazin-2-yloxy)-3-fluoro-N,N-dimethylbenzamide;
cxxxiv. (1R,4s)-4-(4-(1H-indol-5-yl)-6-((S)-3-methylmorpholino)-1,3,5-triazin-2-yloxy)-N,N-dimethylcyclohexanecarboxamide;
cxxxv. 4-(4-(2-aminothiazol-5-yl)-6-((2S,3S)-2,3-dimethylmorpholino)-1,3,5-triazin-2-yloxy)-N,N-dimethylbenzamide;
cxxxvi. 4-(4-(2-(dimethylamino) thiazol-5-yl)-6-((S)-3-methylmorpholino)-1,3,5-triazin-2-yloxy)-N,N-dimethylbenzamide;
cxxxvii. (1S,4r)-4-(4-(1H-indazol-5-yl)-6-((S)-3-methylmorpholino)-1,3,5-triazin-2-yloxy)-N,N-dimethylcyclohexanecarboxamide;
cxxxviii. (1S,4r)-4-(4-(2-aminothiazol-5-yl)-6-((4aS,7aS)-hexahydrocyclopenta[b][1,4]oxazin-4(4aH)-yl)-1,3,5-triazin-2-yloxy)-N,N-dimethylcyclohexanecarboxamide;
cxxxix. 4-(4-(2-aminothiazol-5-yl)-6-((4aS,7aS)-hexahydrocyclopenta[b][1,4]oxazin-4(4aH)-yl)-1,3,5-triazin-2-yloxy)-3-fluoro-N,N-dimethylbenzamide;
cxl. (1R,4s)-4-(4-(3-(hydroxymethyl)phenyl)-6-((S)-3-methylmorpholino)-1,3,5-triazin-2-yloxy)-N,N-dimethylcyclohexanecarboxamide;
cxli. (1R,4r)-4-(4-(6-aminopyridin-3-yl)-6-((4aR,7aR)-hexahydrocyclopenta[b][1,4]oxazin-4(4aH)-yl)-1,3,5-triazin-2-yloxy)-N,N-dimethylcyclohexanecarboxamide;
cxlii. (1S,4r)-4-(4-(6-(hydroxymethyl)pyridin-3-yl)-6-((S)-3-methylmorpholino)-1,3,5-triazin-2-yloxy)-N,N-dimethylcyclohexanecarboxamide;
cxliii. (1S,4s)-4-(4-((4aR,7aR)-hexahydrocyclopenta[b][1,4]oxazin-4(4aH)-yl)-6-(1H-indol-5-yl)-1,3,5-triazin-2-yloxy)-N,N-dimethylcyclohexanecarboxamide;
cxliv. 4-(4-(2-aminothiazol-5-yl)-6-((2S,5S)-2,5-dimethylmorpholino)-1,3,5-triazin-2-yloxy)-3-fluoro-N,N-dimethylbenzamide;
cxlv. 4-(4-(8-oxa-3-aza-bicyclo[3.2.1]octan-3-yl)-6-(2-aminothiazol-5-yl)-1,3,5-triazin-2-yloxy)-3-fluoro-N,N-dimethylbenzamide;
cxlvi. 4-(4-(2-aminothiazol-5-yl)-6-((R)-3-methylmorpholino)-1,3,5-triazin-2-yloxy)-3-fluoro-N,N-dimethylbenzamide;
cxlvii. 4-(4-((S)-3-methylmorpholino)-6-(1H-pyrrolo[2,3-b]pyridin-5-yl)-1,3,5-triazin-2-yloxy)-N,N-dimethylbenzamide;
cxlviii. 4-(4-morpholino-6-(1H-pyrrolo[2,3-b]pyridin-5-yl)-1,3,5-triazin-2-yloxy)-3-fluoro-N,N-dimethylbenzamide;
cxlix. 4-(4-(2-aminothiazol-5-yl)-6-(2,3-dimethylmorpholino)-1,3,5-triazin-2-yloxy)-3-fluoro-N,N-dimethylbenzamide;
cl. 4-(4-(2-aminothiazol-5-yl)-6-((2S,6S)-2,6-dimethylmorpholino)-1,3,5-triazin-2-yloxy)-3-fluoro-N,N-dimethylbenzamide;
cli. 4-(4-(1H-indazol-5-yl)-6-((2S,5R)-2,5-dimethylmorpholino)-1,3,5-triazin-2-yloxy)-3-fluoro-N,N-dimethylbenzamide;
ciii. 4-(4-(1H-indazol-5-yl)-6-((2R,5R)-2,5-dimethylmorpholino)-1,3,5-triazin-2-yloxy)-3-fluoro-N,N-dimethylbenzamide;
cliii. 4-(4-(2-aminothiazol-5-yl)-6-((2S,6R)-2,6-dimethylmorpholino)-1,3,5-triazin-2-yloxy)-3-fluoro-N,N-dimethylbenzamide;
cliv. 4-((4-(6-Aminopyridin-3-yl)-6-morpholino-1,3,5-triazin-2-yl)oxy)-N,N-dimethylbenzamide;
clv. (R)-4-((4-(6-Aminopyridin-3-yl)-6-(3-(trifluoromethylmorpholino)-1,3,5-triazin-2yl)oxy)-3-fluoro-N,N-dimethylbenzamide;
clvi. (S)-4-((4-(6-Aminopyridin-3-yl)-6-(3-(trifluoromethylmorpholino)-1,3,5-triazin-2yl)oxy)-3-fluoro-N,N-dimethylbenzamide;
clvii. (S)-4-((4-(6-Aminopyridin-3-yl)-6-(2-(trifluoromethylmorpholino)-1,3,5-triazin-2yl)oxy)-3-fluoro-N,N-dimethylbenzamide;
clviii. (R)-4-((4-(6-Aminopyridin-3-yl)-6-(2-(trifluoromethylmorpholino)-1,3,5-triazin-2yl)oxy)-3-fluoro-N,N-dimethylbenzamide;
clix. 4-((4-(6-Aminopyridin-3-yl)-6-(3,5-dimethylmorpholino)-1,3,5-triazin-2yl)oxy)-3-fluoro-N,N-dimethylbenzamide;
clx. 4-((4-(6-Aminopyridin-3-yl)-6-(2,3-dimethylmorpholino)-1,3,5-triazin-2yl)oxy)-3-fluoro-N,N-dimethylbenzamide;
clxi. 4-((4-(6-Aminopyridin-3-yl)-6-(2,5-dimethylmorpholino)-1,3,5-triazin-2yl)oxy)-3-fluoro-N,N-dimethylbenzamide;
clxii. 4-((4-(6-Aminopyridin-3-yl)-6-(2,6-dimethylmorpholino)-1,3,5-triazin-2yl)oxy)-3-fluoro-N,N-dimethylbenzamide;
clxiii. 4-((4-(6-Aminopyridin-3-yl)-6-(2,3,6-dimethylmorpholino)-1,3,5-triazin-2yl)oxy)-3-fluoro-N,N-dimethylbenzamide;
clxiv. 4-((4-((1R,5S)-3-oxa-8-azabicyclo[3.2.1]octan-8-yl)-6-(1H-indazol-4-yl)-1,3,5-triazin-2-yl)oxy)-N,N-dimethylbenzamide;
clxv. 5-(4-(benzylthio)-6-morpholino-1,3,5-triazin-2-yl)pyridine-2-amine;
clxvi. (4-(6-aminopyridin-3-yl)-6-morpholino-1,3,5-triazin-2-yl)methanol;
clxvii. 4-((4-(6-hydrazinylpyridin-3-yl)-6-morpholino-1,3,5-triazin-2-yl)oxy)-N,N-dimethylbenzamide;
clxviii. 4-((4-(6-aminopyridin-3-yl)-6-(1,4-oxazepan-4-yl)-1,3,5-triazin-2-yl)oxy)-N,N-dimethylbenzamide;
clxix. 4-((4-(6-aminopyridin-3-yl)-6-morpholino-1,3,5-triazin-2-yl)amino)-N,N-dimethylbenzamide;
clxx. 2-(4-((4-(6-aminopyridin-3-yl)-6-morpholino-1,3,5-triazin-2-yl)oxy)phenyl)-N,N-dimethylacetamide;
clxxi. 4-((4-(6-aminopyridin-3-yl)-6-morpholino-1,3,5-triazin-2-yl)oxy)-N,N,2-trimethylbenzamide;
clxxii. 6-((4-(6-aminopyridin-3-yl)-6-morpholino-1,3,5-triazin-2-yl)oxy)-3,4-dihydroquinolin-2(1H)-one;
clxxiii. 3-((4-(6-aminopyridin-3-yl)-6-morpholino-1,3,5-triazin-2-yl)oxy)-N,N-dimethylbenzamide;
clxxiv. 2-(3-((4-(6-aminopyridin-3-yl)-6-morpholino-1,3,5-triazin-2-yl)oxy)phenyl)-N,N-dimethylacetamide;

clxxv. 5-(4-((1-(methylsulfonyl)piperidin-4-yl)methoxy)-6-morpholino-1,3,5-triazin-2-yl)pyridin-2-amine;

clxxvi. 3-((4-(6-aminopyridin-3-yl)-6-morpholino-1,3,5-triazin-2-yl)oxy)-N,N-dimethylpyrrolidine-1-carboxamide;

clxxvii. 3-(((4-(6-aminopyridin-3-yl)-6-morpholino-1,3,5-triazin-2-yl)oxy)methyl)-N,N-dimethylpyrrolidine-1-carboxamide;

clxxviii. 3-(1-(4-(6-aminopyridin-3-yl)-6-morpholino-1,3,5-triazin-2-yl)piperidin-4-yl)-1,1-dimethylurea;

clxxix. 2-(4-((4-(2-aminopyrimidin-5-yl)-6-morpholino-1,3,5-triazin-2-yl)oxy)phenyl)-N,N-dimethylacetamide;

clxxx. 5-(4-((1-(methylsulfonyl)piperidin-4-yl)methoxy)-6-morpholino-1,3,5-triazin-2-yl)pyrimidin-2-amine;

clxxxi. N,N-dimethyl-4-((4-morpholino-6-(thiazol-2-ylamino)-1,3,5-triazin-2-yl)oxy)benzamide;

clxxxii. 4-((4-(2-aminothiazol-5-yl)-6-(1,4-oxazepan-4-yl)-1,3,5-triazin-2-yl)oxy)-N,N-dimethylbenzamide;

clxxxiii. 4-((4-(2-aminothiazol-5-yl)-6-morpholino-1,3,5-triazin-2-yl)oxy)-N-methylbenzamide;

clxxxiv. 5-(4-((1-(methylsulfonyl)piperidin-4-yl)methoxy)-6-morpholino-1,3,5-triazin-2-yl)thiazol-2-amine;

clxxxv. 3-((4-(2-aminothiazol-5-yl)-6-morpholino-1,3,5-triazin-2-yl)oxy)-N,N-dimethylbenzamide;

clxxxvi. 4-((4-(2-aminothiazol-5-yl)-6-morpholino-1,3,5-triazin-2-yl)amino)-N,N-dimethylbenzamide;

clxxxvii. 5-(4-((1-(methylsulfonyl)pyrrolidin-3-yl)methoxy)-6-morpholino-1,3,5-triazin-2-yl)thiazol-2-amine;

clxxxviii. 1-(4-(2-aminothiazol-5-yl)-6-morpholino-1,3,5-triazin-2-yl)-1,4-diazepan-5-one;

clxxxix. 4-((4-(2-amino-4-methylthiazol-5-yl)-6-morpholino-1,3,5-triazin-2-yl)oxy)-N,N-dimethylbenzamide;

cxc. 3-((4-(2-aminothiazol-5-yl)-6-morpholino-1,3,5-triazin-2-yl)amino)-N,N-dimethylbenzamide;

cxci. 4-((4-(2-aminothiazol-5-yl)-6-morpholino-1,3,5-triazin-2-yl)oxy)benzamide;

cxcii. (1S,4r)-4-((4-(1H-indazol-5-yl)-6-((S)-3-methylmorpholino)-1,3,5-triazin-2-yl)oxy)-N,N-dimethylcyclohexane-1-carboxamide;

cxciii. (1S,4r)-((4-(4-(hydroxymethyl)phenyl)-6-((S)-3-methylmorpholino)-1,3,5-triazin-2-yl)oxy)-N,N-dimethylcyclohexane-1-carboxamide;

cxciv. (S)-4-((4-(2-aminopyrimidin-5-yl)-6-(3-methylmorpholino)-1,3,5-triazin-2-yl)oxy)-3-fluoro-N,N-dimethylbenzamide;

cxcv. 4-((4-(2-aminothiazol-5-yl)-6-((2R,5R)-2,5-dimethylmorpholino)-1,3,5-triazin-2-yl)oxy)-3-fluoro-N,N-dimethylbenzamide;

cxcvi. 4-((4-(2-aminothiazol-5-yl)-6-((4aS,7aR)-hexahydrocyclopenta[b][1,4]oxazin-4(4aH)-yl)-1,3,5-triazin-2-yl)oxy)-3-fluoro-N,N-dimethylbenzamide;

cxcvii. 4-((4-(6-aminopyridin-3-yl)-6-(3-methylmorpholino)-1,3,5-triazin-2-yl)oxy)-3-fluoro-N,N-di methylbenzamide.

The compounds of the present invention include the compounds:

i. (S)-4-(4-(2-aminothiazol-5-yl)-6-(3-methylmorpholino)-1,3,5-triazin-2-yloxy)-N,N-dimethylbenzamide;

ii. 4-(4-(2-aminopyrimidin-5-yl)-6-morpholino-1,3,5-triazin-2-yloxy)-N,N-dimethylbenzamide;

iii. (S)-4-(4-(2-aminothiazol-5-yl)-6-(3-methylmorpholino)-1,3,5-triazin-2-yloxy)-3-fluoro-N,N-dimethylbenzamide;

iv. 4-(4-(6-amino-4-(trifluoromethyl)pyridin-3-yl)-6-morpholino-1,3,5-triazin-2-yloxy)-N,N-dimethylbenzamide;

v. 4-(4-(2-aminothiazol-5-yl)-6-morpholino-1,3,5-triazin-2-yloxy)-N,N-dimethylbenzamide;

vi. 4-(4-(2-aminothiazol-5-yl)-6-morpholino-1,3,5-triazin-2-yloxy)-3-fluoro-N,N-dimethylbenzamide;

vii. 4-(4-(6-aminopyridin-3-yl)-6-(3-methylmorpholino)-1,3,5-triazin-2-yloxy)-N,N-dimethylbenzamide;

viii. 4-(4-(2-aminopyrimidin-5-yl)-6-(3-methylmorpholino)-1,3,5-triazin-2-yloxy)-N,N-dimethylbenzamide;

ix. 4-((4-(2-Aminopyrimidin-5-yl)-6-morpholino,1,3,5-triazin-2-yl)oxy)-3-fluoro-N,N-dimethylbenzamide;

x. 4-(4-(2-aminothiazol-5-yl)-6-(2,3-dimethylmorpholino)-1,3,5-triazin-2-yloxy)-N,N-dimethylbenzamide;

xi. 4-(4-(2-aminothiazol-5-yl)-6-(3-methylmorpholino)pyrimidin-2-yloxy)-N,N-dimethylbenzamide;

xii. (S)-4-((4-(1H-indazol-6-yl)-6-(3-methylmorpholino)-1,3,5-triazin-2-yl)oxy)-3-fluoro-N,N-dimethylbenzamide;

xiii. 4-((4-(2-Aminothiazol-5-yl)-6-((2R,3S)-2,3-dimethylmorpholino)-1,3,5-triazin-2-yl)oxy)-3-fluoro-N,N-dimethylbenzamide;

xiv. 4-((4-(2-Aminothiazol-5-yl)-6-((2S,3S)-2,3-dimethylmorpholino)-1,3,5-triazin-2-yl)oxy)-3-fluoro-N,N-dimethylbenzamide;

xv. 4-((4-(2-Aminothiazol-5-yl)-6-((2R,3R)-2,3-dimethylmorpholino)-1,3,5-triazin-2-yl)oxy)-3-fluoro-N,N-dimethylbenzamide;

xvi. 4-((4-(2-Aminothiazol-5-yl)-6-((2R,5S)-2,5-dimethylmorpholino)-1,3,5-triazin-2-yl)oxy)-3-fluoro-N,N-dimethylbenzamide;

xvii. (S)-4-((4-(6-Aminopyridin-3-yl)-6-(3-methylmorpholino)-1,3,5-triazin-2-yl)oxy)-3-fluoro-N,N-dimethylbenzamide;

xviii. 4-((4-(6-Amino-4-(trifluoromethyl)pyridine-3-yl)-6-morpholino-1,3,5-triazin-2-yl)oxy)-3-fluoro-N,N-dimethylbenzamide;

xix. (S)-4-((4-(6-Amino-4-(trifluoromethyl)pyridine-3-yl)-6-(3-methylmorpholino)-1,3,5-triazin-2-yl)oxy)-N,N-dimethylbenzamide;

xx. (S)-4-((4-(6-Amino-4-(trifluoromethyl)pyridine-3-yl)-6-(3-methylmorpholino)-1,3,5-triazin-2-yl)oxy)-3-fluoro-N,N-dimethylbenzamide;

xxi. 4-((4-(2-Aminothiazol-5-yl)-6-((2S,5S)-2,5-dimethylmorpholino)-1,3,5-triazin-2-yl)oxy)-N,N-dimethylbenzamide;

xxii. 4-((4-6-Aminopyridin-3-yl)-6-(8-oxa-3-azabicyclo[3.2.1]octan-3-yl)-1,3,5-triazin-2-yl)oxy)-3-fluoro-N,N-dimethylbenzamide;

xxiii. (S)-4-((4-(6-Aminopyridin-3-yl)-6-(3-methylmorpholino)-1,3,5-triazin-2-yl)oxy)-N,N-dimethylbenzamide;

xxiv. 4-((4-(6-Aminopyridin-3-yl)-6-((2S,5S)-2,5-dimethylmorpholino)-1,3,5-triazin-2-yl)oxy)-3-fluoro-N,N-dimethylbenzamide;

xxv. (S)-4-((4-(1H-indol-5-yl)-6-(3-methylmorpholino) 1,3,5-triazin-2-yl)oxy)3-fluoro-N,N-dimethylbenzamide;

xxvi. (S)-3-Fluoro-N,N-dimethyl-4-((4-(3-methylmorpholino)-6-(1H-pyrrolo-[2,3-b]pyridin-5-yl)-1,3,5-triazin-2-yl)oxy)benzamide;

xxvii. 4-(4-(1H-indazol-5-yl)-6-((S)-3-methylmorpholino)-1,3,5-triazin-2-yloxy)-3-fluoro-N,N-dimethylbenzamide;

xxviii. 4-(4-(2-aminothiazol-5-yl)-6-((2S,3S)-2,3-dimethylmorpholino)-1,3,5-triazin-2-yloxy)-N,N-dimethylbenzamide;

xxix. 4-(4-(2-aminothiazol-5-yl)-6-((2S,5S)-2,5-dimethylmorpholino)-1,3,5-triazin-2-yloxy)-3-fluoro-N,N-dimethylbenzamide;

xxx. 4-(4-(8-oxa-3-aza-bicyclo[3.2.1]octan-3-yl)-6-(2-aminothiazol-5-yl)-1,3,5-triazin-2-yloxy)-3-fluoro-N,N-dimethylbenzamide;

xxxi. 4-(4-(2-aminothiazol-5-yl)-6-(2,3-dimethylmorpholino)-1,3,5-triazin-2-yloxy)-3-fluoro-N,N-dimethylbenzamide;

xxxii. 4-((4-(6-Aminopyridin-3-yl)-6-(2,3-dimethylmorpholino)-1,3,5-triazin-2yl)oxy)-3-fluoro-N,N-dimethylbenzamide;

xxxiii. 4-((4-(6-Aminopyridin-3-yl)-6-(2,5-dimethylmorpholino)-1,3,5-triazin-2yl)oxy)-3-fluoro-N,N-dimethylbenzamide.

B. SYNTHESIS OF THE COMPOUNDS OF THE PRESENT INVENTION

The compounds of the present invention may be synthesized by the any of the synthetic schemes as shown below:

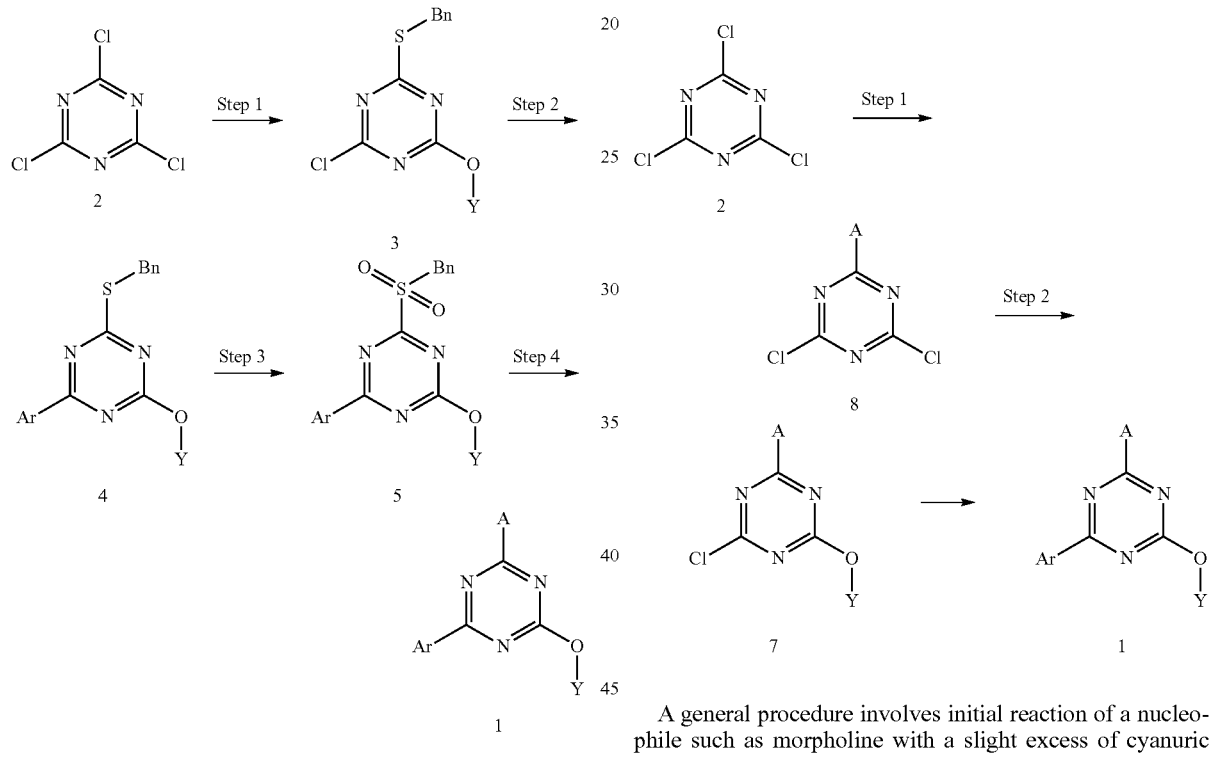

A general procedure involves initial reaction of thiol such as benzyl mercaptan with a slight excess of cyanuric chloride [2] in a solvent such as THF in the presence of a suitable base, followed by addition of hydroxy amide. The base may be a non-reactive tertiary amine. The desired product [3] may be further purified using standard lab purification methods such as column chromatography. Intermediate [3] under general Suzuki or Stille coupling conditions with an appropriate boronate or boronic acid or organotin reagent may provide [4]. Intermediate [4] may be converted to [5] under oxidation conditions with reagents such as oxone. The desired compound [1] may be obtained with reaction of an appropriate morpholine on [5]. In certain circumstances the substituent(s) on the rings of the compound(s) of formula 1 produced by this procedure were further elaborated using standard techniques to arrive at other members of the series.

General Synthetic Scheme B

A process for synthesis of the compounds of formula (I) of the present invention comprises the steps of:

i. reacting a nucleophile with a slight excess of cyanuric chloride in a suitable solvent in the presence of a suitable base to get an intermediate;

ii. treating the Intermediate of step (i) with a nucleophilic reactant in the presence of a base;

iii. optionally purifying the compound of step (ii);

iv. Subjecting the intermediate of step (ii) or step (iii) to palladium catalyzed Suzuki or Stille coupling reactions.

In the scheme above, the nucleophile of step (i) may be morpholine or similar compounds. The solvent may be any solvent suitable for dissolving the compounds. A mixture of solvents may also be used. The base may be a non-reactive tertiary amine or an appropriate inorganic salt such as sodium bicarbonate. The purification may be conducted by any technique including chromatography.

This scheme is illustrated herein below:

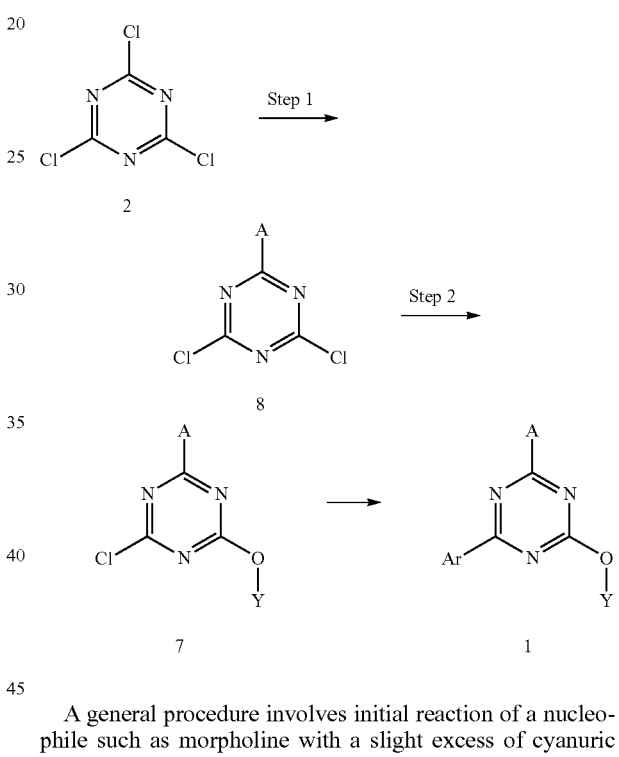

A general procedure involves initial reaction of a nucleophile such as morpholine with a slight excess of cyanuric chloride [2] in a solvent such as acetone/THF and water in the presence of a suitable base. The base may be a non-reactive tertiary amine or an appropriate inorganic salt such as sodium bicarbonate. Although the mono addition product predominates, small quantities of 2-chloro-4,6-di-morpholin-4-yl-[1, 3, 5]-triazine, resulting from the addition of two molecules of morpholine, are generally formed but may be efficiently removed during purification in the final steps. Intermediate [8] is then treated with a nucleophilic reactant in the presence of a base such as a tertiary amine or sodium bicarbonate. Purification by chromatography at this stage will yield a very pure intermediate [7] for the final palladium catalyzed Suzuki or Stille coupling reactions. The boronic acids, esters and organotin employed were generally commercially available or could be prepared in a straightforward manner using procedures known to one versed in the art. In certain circumstances the substituent(s) on the ring of the compound(s) of formula [1] produced by this procedure were further elaborated using standard techniques to arrive at other members of the series.

General Synthetic Scheme C:

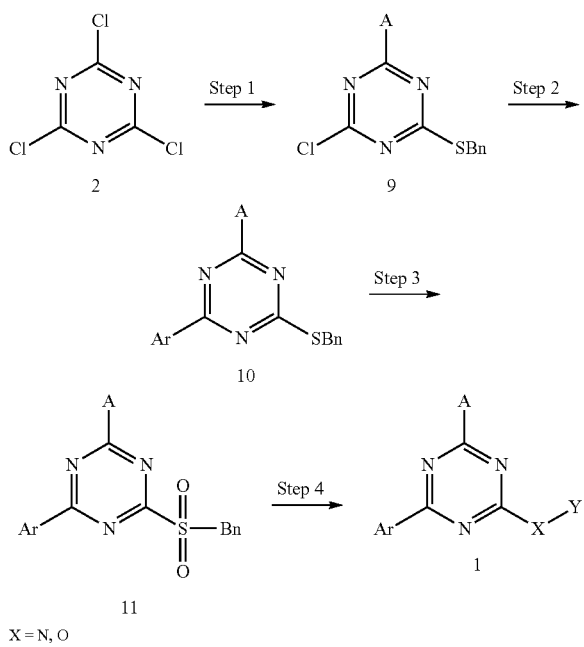

X = N, O

A general procedure involves initial reaction of a nucleophile such as morpholine with a slight excess of cyanuric chloride [2] in a solvent such as acetone/THF and water in the presence of a suitable base followed by addition of thiol such as benzyl mercaptan. The base may be a non-reactive tertiary amine or an appropriate inorganic salt such as sodium bicarbonate. The desired product [9] may be further purified using standard lab purification methods such as column chromatography. Intermediate [9] under general Suzuki or Stille coupling conditions with an appropriate boronate or boronic acid or organotin reagent may provide [10]. Intermediate [10] may be converted to [11] under oxidation conditions with reagents such as oxone. The desire structure [1] may be obtained with attack of an appropriate nucleophile on [11]. In certain circumstances the substituent(s) on the rings of the compound(s) of formula 1 produced by this procedure were further elaborated using standard techniques to arrive at other members of the series.

General Synthetic Scheme D

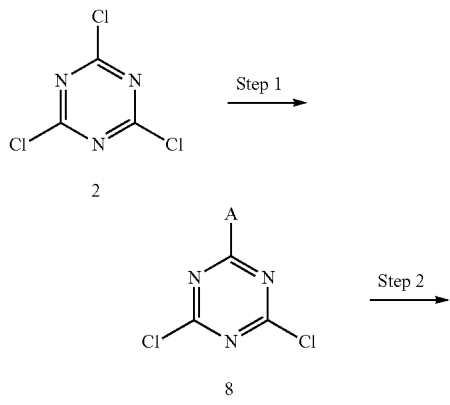

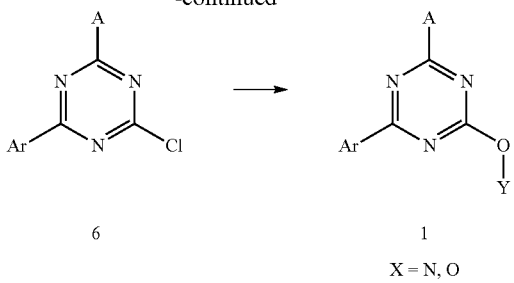

X = N, O

A general procedure involves initial reaction of a nucleophile such as morpholine with a slight excess of cyanuric chloride [2] in a solvent such as acetone/THF and water in the presence of a suitable base. The base may be a non-reactive tertiary amine or an appropriate inorganic salt such as sodium bicarbonate. Although the mono addition product predominates, small quantities of 2-chloro-4,6-di-morpholin-4-yl-[1, 3, 5]-triazine, resulting from the addition of two molecules of morpholine, are generally formed but may be efficiently removed during purification in the final steps. Intermediate [8] under Suzuki or Stille coupling conditions with an appropriate boronate or boronic acid or organotin reagent may provide [6]. The desire structure [1] may be obtained by the attack of an appropriate nucleophile on [6] using non-reactive base such as tertiary amine or an appropriate inorganic salt such as sodium bicarbonate. In certain circumstances the substituent(s) on the ring of the compound(s) of formula [1] produced by this procedure were further elaborated using standard techniques to arrive at other members of the series.

General Synthetic Scheme E:

One of process for synthesizing the compounds of the present invention of Formula (I) includes a reaction scheme, comprising the steps of:

i. reacting a substituted heteroaromatic amide with a slight excess of phosphoryl chloride;

ii. cyclization with an substituted amidine leading to the formation of aryl substituted 3,5-dichloro triazine core;

iii. treating aryl substituted 3,5-dichloro triazine core with a nucleophile in the presence of an organic/inorganic base to yield an intermediate;

iv. coupling the intermediate of step (iii) with another nucleophile in presence an inorganic base such as to yield a further intermediate;

v. optionally purifying the intermediate of step (iv);

vi. amination (when G=Cl, Br or iodo), of intermediate of step (iv) or (v) by attack of an appropriate nucleophile such as ammonia to yield the desired compound.

In the scheme above, the heteroaromatic amide may be 6-substituted N,N-dimethyl aryl amide or similar. The substituted amidine may be such as N-cyanocarbamimidic chloride or similar compounds. The nucleophile may be such as morpholine or equivalent. The organic/inorganic base may be such as a tertiary amine or sodium bicarbonate or potassium bicarbonate or equivalent. The nucleophile in step (iv) may be such as substituted hydroxyl-benzamide or equivalent and the nucleophile in step (v) may be such as ammonia or equivalent.

This scheme may be illustrated herein below:

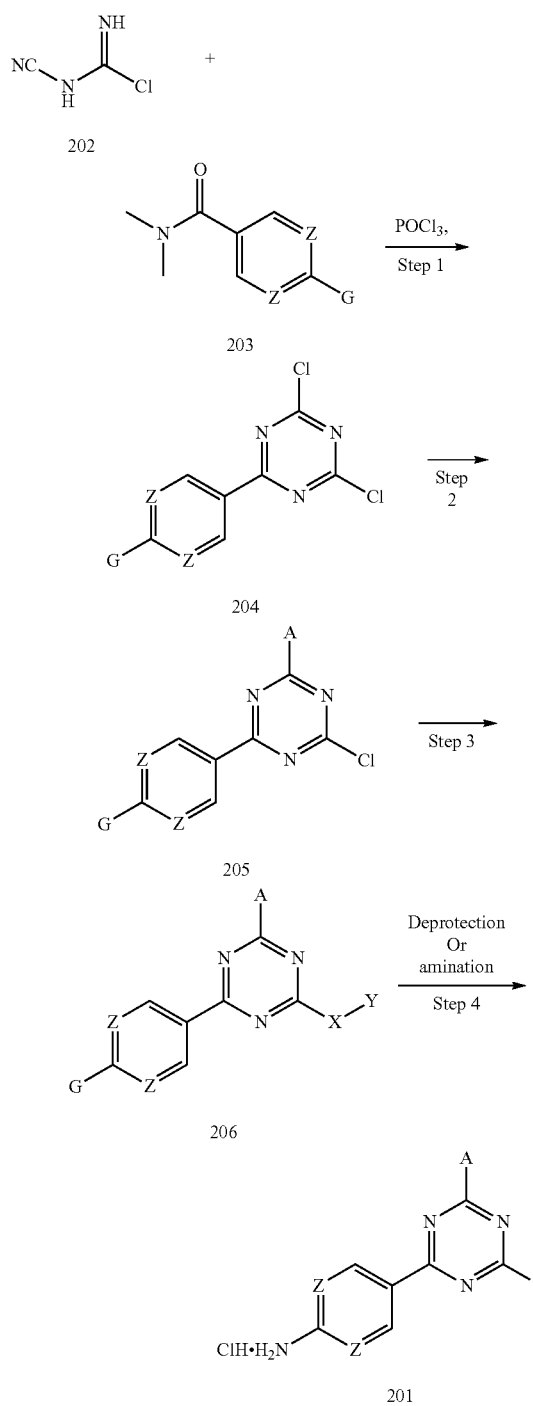

Z = N, C
X = O, N
G = Cl, Br, I, NO$_2$ NH$_2$, NHCOCH$_3$, N(COCH$_3$)$_2$
NHBoc, NHPMB

A general procedure involves initial reaction of a 6-substituted N,N-dimethyl aryl amide [203] with a slight excess of phosphoryl chloride (formation of iminium salt) and cyclization with N-cyanocarbamimidic chloride [202] leading to the formation of Aryl substituted 3,5-dichloro triazine core [204]. Intermediate [204] is then treated with a nucleophilic reactant such as morpholines in the presence of a base such as a tertiary amine or sodium bicarbonate or potassium Carbonate will yield a intermediate [205] which further coupling with nucleophilic reactant such as substituted hydroxyl-benzamide and an appropriate inorganic salt such as potassium carbonate will provide [206]. The desired structure [206] may be obtained with substituted pyridine on [203]. Purification by chromatography at this stage will yield a very pure intermediate [206] for the final deprotection reactions. The desire structure [201] may be obtained by deprotection or amination by attack of an appropriate nucleophile such as ammonia on [206]. In certain circumstances the substituent(s) on the rings of the compound(s) of formula 1 produced by this procedure were further elaborated using standard techniques to arrive at other members of the series.

General Schemes for the Synthesis of Aryl/Heteroaryl Boronates

The aryl/heteroaryl boronates may be synthesized by methods such as those represented in Scheme F or Scheme G.

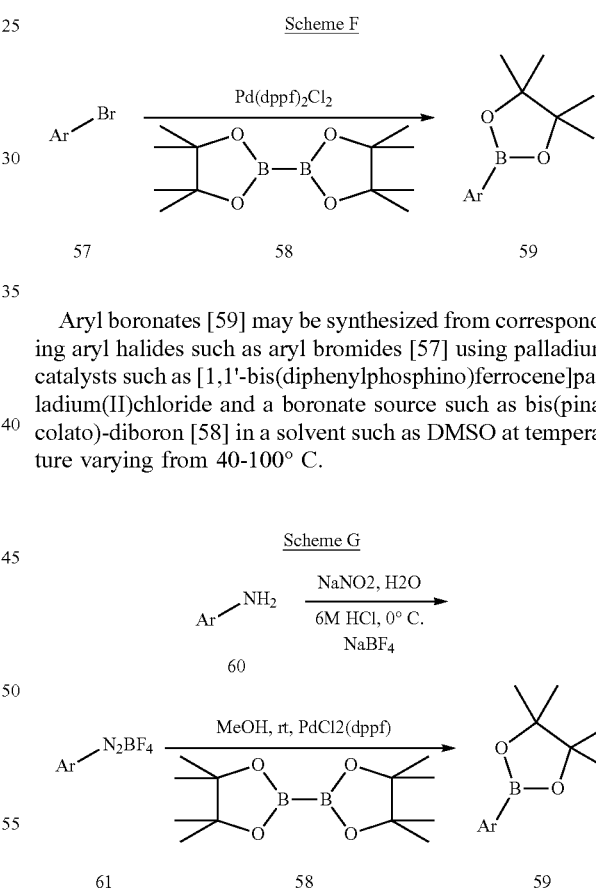

Aryl boronates [59] may be synthesized from corresponding aryl halides such as aryl bromides [57] using palladium catalysts such as [1,1'-bis(diphenylphosphino)ferrocene]palladium(II)chloride and a boronate source such as bis(pinacolato)-diboron [58] in a solvent such as DMSO at temperature varying from 40-100° C.

Aryl boronates [59] may also be synthesized from corresponding aryl amines [60] as shown in Scheme G. An aryl amine may be converted to corresponding diazonium tetrafluoroborate salt [61] by treating with reagents such as aqueous sodium nitrite and hydrochloric acid. The corresponding diazonium tetrafluoroborate salt when reacted with a boronate source such as bis(pinacolato)-diboron [58] in presence of a suitable palladium catalyst such as [1,1'-bis(diphenylphosphino)ferrocene]palladium(II)chloride in a solvent such as methanol at RT may provide aryl boronate [59].

C. PHARMACEUTICAL COMPOSITIONS

In one embodiment, provided herein is a pharmaceutical composition comprising the compound of Formula 1 as defined herein, and a pharmaceutically acceptable excipient, such as an adjuvant, carrier, buffer, or stabilizer. The pharmaceutically acceptable excipients, such as an adjuvant, carrier, buffer, or stabilizer is non-toxic and does not interfere with the efficacy of the active ingredient. The precise nature of the carrier or other material may depend on the route of administration, which may be oral or by injection, such as cutaneous, subcutaneous, or intravenous injection.

The pharmaceutical compositions are provided in a dosage form for oral administration, which comprise a compound provided herein, and one or more pharmaceutically acceptable excipients or carriers. The pharmaceutical compositions provided herein that may be formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin. The pharmaceutical compositions may be provided in a dosage form for parenteral administration, and one or more pharmaceutically acceptable excipients or carriers. Where pharmaceutical compositions may be formulated for intravenous, cutaneous or subcutaneous injection, the active ingredient may be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilizers, buffers, antioxidants, and/or other additives may be included as required. The pharmaceutical compositions are provided in a dosage form for topical administration, which comprise a compound provided herein, and one or more pharmaceutically acceptable excipients or carriers. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms.

The pharmaceutical compositions provided herein may be provided in a unit dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time.

D. METHODS OF USE

The compounds of the present invention may be designed to inhibit mTOR alone or with other enzymes in PI3K/mTOR pathway. Accordingly the inventors provides a method of prevention of any disorder or a therapy for disorder in which increased mTOR is indicated. The therapy comprises, administering a compound of Formula I as defined herein to a subject in need thereof. In an aspect, the compound may also inhibit PI3 Kinase and thus may also be used in the therapy for disorder indicated by increase in PI3 Kinase activity.

E. EXPERIMENTALS

Scheme 1: Synthesis of (S)-4-((4-(2-aminothiazol-5-yl)-6-(3-methylmorpholino)-1,3,5-triazin-2-yl)oxy)-N,N-dimethylbenzamide using scheme A

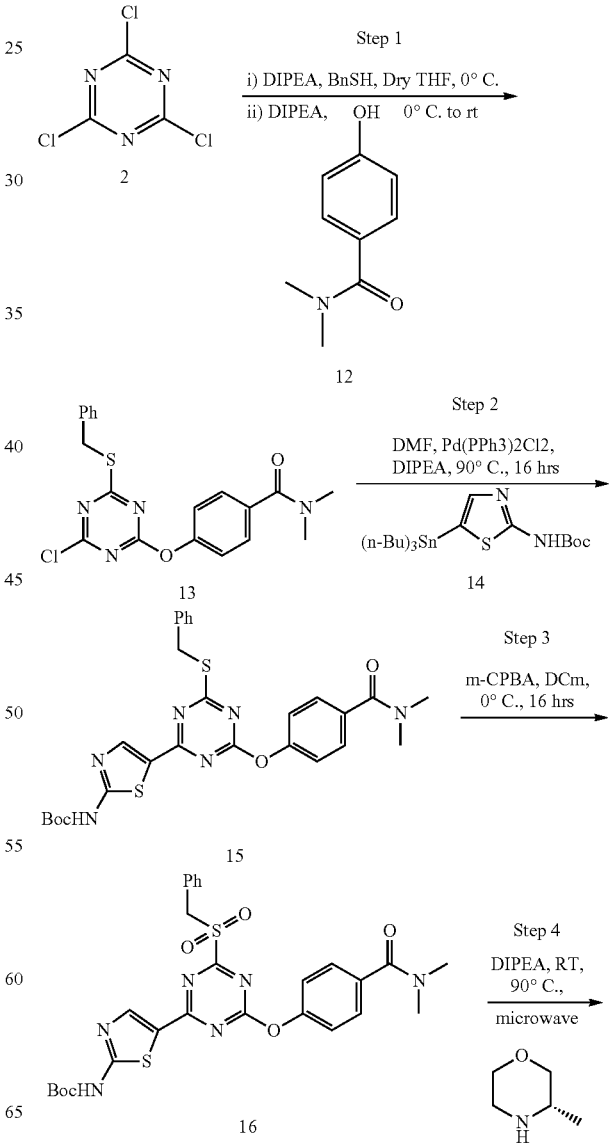

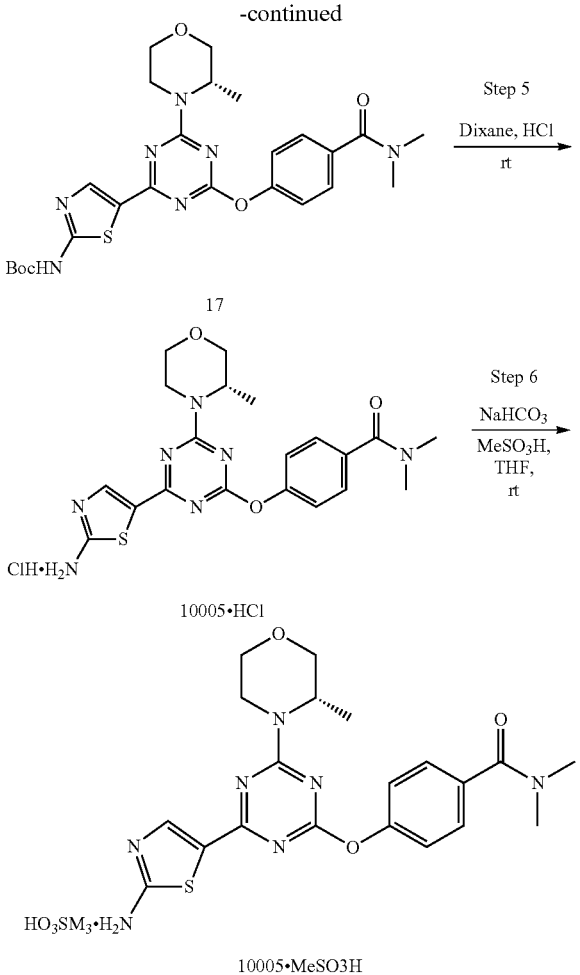

17

10005·HCl

10005·MeSO3H

Step 1

Cyanuric chloride [2] (1.0 g, 5.4 mmol) was suspended in anhydrous THF (20 ml) in a three neck RB flask under inert atmosphere and cooled using ice-bath, followed by addition of DIPEA (5.16 mmol) and benzyl mercaptan (5.08 mmol). The reaction mixture was allowed to stir at 0-4° C. for 1 h and monitored by TLC examination (5% EtOAc/Hexane). A mixture of DIPEA (5.40 mmol) and 4-hydroxy-N,N-dimethylbenzamide [12] (5.40 mmol) was added to reaction mixture followed by an addition stirring for 3 h at RT. The excess solvent was evaporated under reduced pressure to obtained crude product which was purified using silica gel column chromatography (eluent, 25% EtOAc/Hexane) to obtain product [13] in 87% yield. ESIMS: 401 (M$^+$+1).

Step 2

Compound [13] (1.0 g, 2.5 mmol) was dissolved in 10 ml of DMF in three neck round bottom flask followed by addition of [14] (1.84 g, 3.75 mmol) and DIPEA (7.5 mmol). The reaction mixture was degassed using nitrogen for 30 min followed by addition of palladium catalyst (0.125 mmol). The reaction mixture was heated at 90° C. for 16 h and monitored by TLC (5% MeOH/DCM). After completion, the reaction mixture was diluted with DCM and washed with water, followed by brine. The organic layer was dried over Na$_2$SO$_4$ and evaporated under reduced pressure to obtained crude product which was purified using silica gel column chromatography using 2% MeOH/DCM affording product [15] in 30% yield. ESIMS: 565 (M$^+$+1).

Step 3

Compound [15] (0.400, 0.709 mmol) was dissolved in 20 ml DCM at 0-4° C. under inert atmosphere followed by addition of m-CPBA (1.77 mmol) portion-wise. Reaction temperature was allowed to rise until reaching room temperature and stirred for 16 h. The reaction progress was monitored by TLC (5% MeOH/DCM). After completion, the reaction mixture was diluted with DCM and washed successively with saturated NaHCO$_3$ solution. The organic layer was dried over anhydrous Na$_2$SO$_4$, filtered and evaporated under reduced pressure. The product obtained [16] was pure enough to be used for next step without any further purification. ESIMS: 597 (M$^+$+1).

Step 4

Compound [16] (0.400 g, 0.689 mmol), 3-(S)-methyl morpholine (0.074 g, 0.757 mmol) was dissolved in acetonitrile in a microwave reaction vessel followed by addition of DIPEA (1.378 mmol). The reaction mixture was heated to 90° C. under microwave conditions for 30 min. Excess solvent was removed under reduced pressure yielding the crude product which was subjected to silica gel column chromatography using 3% MeOH/DCM to obtain pure product [17] in 42% yield. ESIMS: 542 (M$^+$+1).

Step 5

Compound [17] (0.150 g, 0.277 mmol) was taken in dioxane HCl (4 M) and mixture was stirred for 24 h at rt. The solvent was evaporated and crude was purified by washing with DCM, ether and pentane to obtain compound [10005.HCl] in 88% yield. ESIMS: 442 (M$^+$+1).

Step 6

Compound [10005.HCl] (0.100 g, 0.226 mmol) was taken in water. To this NaHCO$_3$ (aq.) was added dropwise until pH=7 was achieved. The mixture was stirred at RT for 1 hrs. A white precipitate was filtered and dried to give product. The product was taken in THF and to this methanesulfonic acid (0.013 ml, 0.204 mmol) was added and resulting mixture was stirred at RT for 2 hrs. The solvent was evaporated and crude was crystallized from CHCl$_3$:Cyclohexane (7:3) to yield 10005.MeSO$_3$H as white powder (0.098 g, 90%, yield). ESIMS: 442 (M$^+$+1).

Scheme 2: Synthesis of 4-((4-(2-aminothiazol-5-yl)-6-morpholino-1,3,5-triazin-2-yl)oxy)-N,N-dimethylbenzamide using scheme B

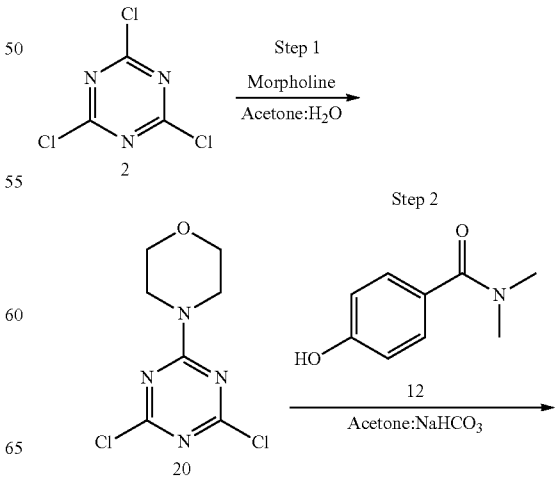

-continued

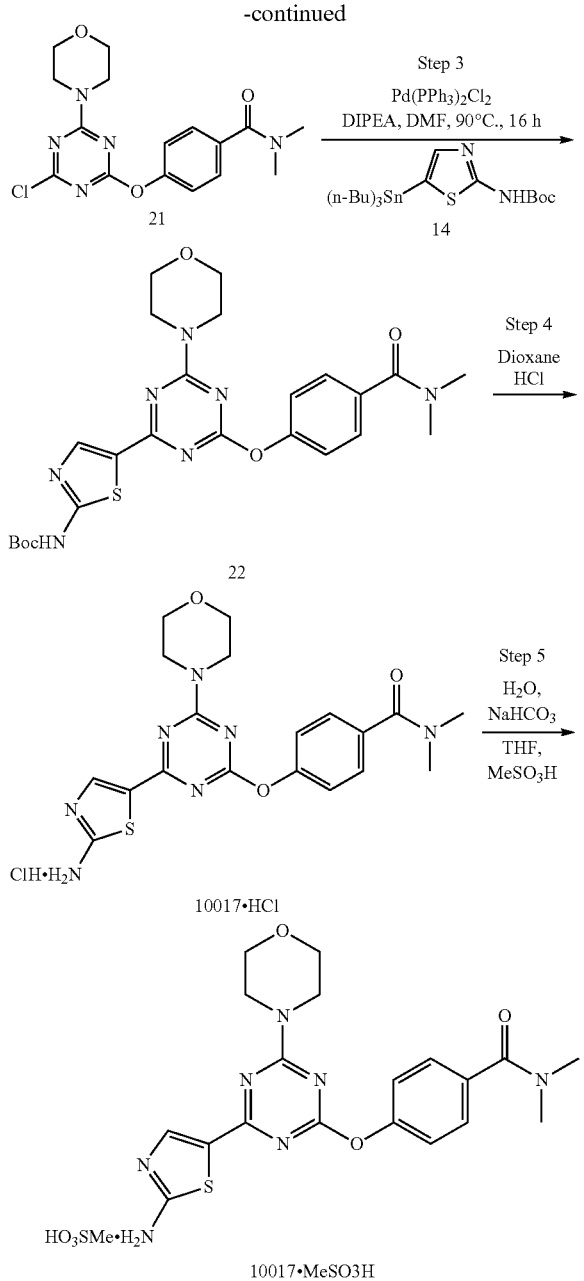

Step 1
Compound [2] (20 g, 108.4 mmol) was dissolved in acetone (100 ml):water (30 ml). An acetone solution (10 ml) of morpholine (9.44 ml, 108.4 mmol) was added dropwise at 0° C. The reaction mixture was stirred at 0° C. for 3 hrs; a solid formed during reaction and was filtered off. The filtrate was concentrated and again diluted with acetone: water (3:1); the precipitated solid was filtered again, both the solids were combined and dried to give compound [20] as white solid (14 g, 55%).
ESIMS: 235 (M$^+$+1).
Step 2
Compound [20] (3.2 g, 13.6 mmol) was taken in a solution of acetone: NaHCO$_3$(aq.) [1:1] (30 ml). The reaction mass turned hazy and was stirred at RT until effervescence ceased. Compound [12] was added (1.49 g, 10.8 mmol) and the reaction mass was further stirred at RT for 2 hrs. The excess of acetone from the reaction mixture was evaporated to dryness. More water (20 ml) was added and the mixture was filtered through Buchner funnel. The filtrate was washed with DCM; the DCM layer was discarded and the water layer was acidified to pH=4. A precipitate formed, was filtered, washed with water and dried to give compound [21] (3.5 g, 76%) as white solid.
ESIMS: 364 (M$^+$+1).
Step 3
Compound [21] (2.0 g, 5.4 mmol) was taken in DMF (10 ml). Compound [14] (4.04 g, 8.10 mmol) Pd(PPh$_3$)$_2$Cl$_2$ (0.386 g, 0.554 mmol), DIPEA (1.95 ml, 10.8 mmol) were added. The mixture was heated at 95° C. for 16 hrs. After completion, the mixture was cooled to RT, poured to ice-water mixture, the precipitate formed were filtered to obtain compound [22] (1.5 g, 50% yield) as off while solid.
ESIMS: 528 (M$^+$+1).
Step 4
Compound [22] (1.00 g, 1.89 mmol) was taken in dioxane HCl (4 M, 20 ml) and mixture was stirred for 24 hrs at RT. The solvent was evaporated and crude was purified by washing with DCM, ether and pentane to obtain compound [10017. HCl] (0.700 g, 86% yield) as white solid.
ESIMS: 428 (M$^+$+1).
Step 5
Compound [10017. HCl] (0.500 g, 1.17 mol) was taken in water. To this NaHCO$_3$ (aq.) was added dropwise until pH=7 was achieved. The mixture was stirred at RT for 1 hrs. White precipitates were filtered and dried to give product. The product was taken in THF and to this methanesulfonic acid (0.075 ml, 1.17 mmol) was added and resulting mixture was stirred at RT for 24 hrs. The solvent was evaporated and crude was crystallized from CHCl$_3$:Cyclohexane (7:3) to yield [10017. MeSO3H] as white powder (0.580 g, 95%, yield).

Compounds, 10005, 10009, 10016, 10015, 10014, 10022, 10051, 10058, 10129, 10137, 10138, 10139, 10141, 10144, 10145, 10147, 10175 was synthesized using above synthetic procedure.

Scheme 3: (1r,4r)-4((4-(2H-indazol-4-yl)-6-morpholino-1,3,5-triazine-2-yl)oxy)-N,N-dimethylcyclohexanecarboxamide using scheme C

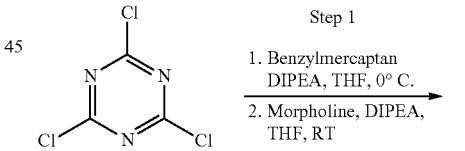

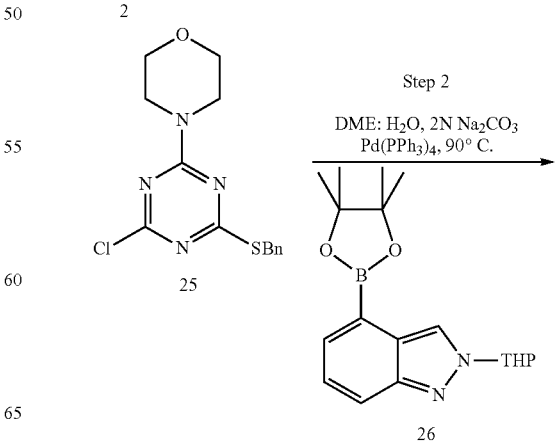

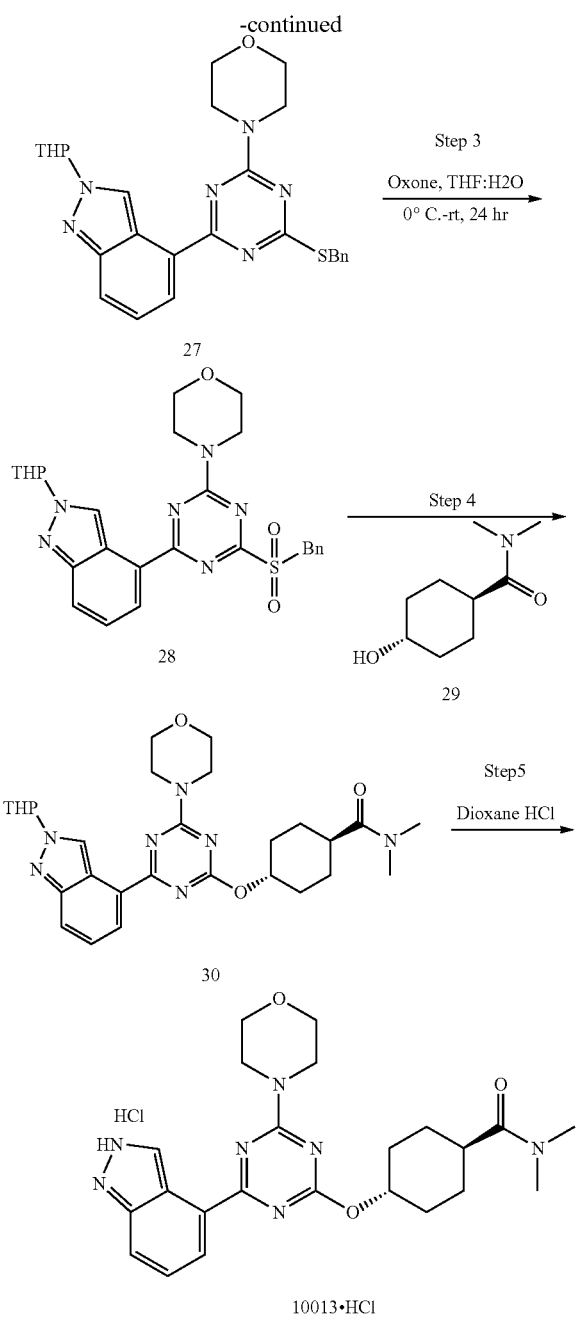

addition of compound [26] (2.16 g, 6.78 mmol). After that, tetrakis palladium (323 mg, 0.279 mmol) was added and the reaction was heated under inert condition at 90° C. overnight. DME was removed under vacuum and the reaction mass was extracted with (2×200 ml of DCM. The DCM extracts were combined, washed with brine, dried over anhydrous sodium sulphate, and then evaporated to obtain a viscous dark brown material. This material was purified by silica gel chromatography with 40% EtOAC/Hexane to obtain compound [27] as a pale yellow solid (1.2 g, 45% yield).

ESIMS: 489 ($M^+$+1)

Step 3

To a solution of compound [27] (1.0 g, 2.04 mmol,) in THF:water: 1:1 (50 ml), was added portion wise oxone (3.14 g, 5.12 mmol) at 0° C. After stirring at 0° C. for 1 h, the reaction mixture was stirred at room temperature for additional 24 h. After completion of the reaction, 50 ml of water was added, and the reaction mass was extracted with 2×100 ml EtOAc. The EtOAc layers were combined, washed with brine, dried over anhydrous sodium sulphate and concentrated to get compound [28] as a pale yellow solid (0.9 g, 85% yield).

ESIMS: 521 ($M^+$+1)

Step 4

To a solution of compound [29] (0.090 g, 0.528 mmol) in THF (10 ml) at 0° C. under inert atmosphere was added sodium hydride (0.021 g, 0.528 mmol). After stirring at 0° C. for 1 h, compound [28] (0.25 g, 0.48 mmol) was added. The mixture was then stirred at RT for 3 h, followed by removal of the solvent under reduced pressure. Purification was done by silica gel column chromatography with 50% EtOAc/cyclohexane to give compound [30] as a white solid (0.105 g, 44% yield).

ESIMS: 536 ($M^+$+1)

Step 5

Compound [30] (0.100 g, 0.186 mmol) was taken in dioxane HCl (4 M, 20 ml) and mixture was stirred for 24 hrs at RT. The solvent was evaporated and crude was purified by washing with DCM, ether and pentane to obtain compound [10013.HCl] (0.070 g, 86% yield) as white solid

ESIMS: 452 ($M^+$+1)

Compound 10001, 10002, 10008, 10018, 10019, 10021 were synthesized using above synthetic scheme.

Scheme 4: Synthesis of (S)-4-((4-(6-aminopyridin-3-yl)-6(3-methylmorpholino)-1,3,5-triazin-2-yl)oxy-N,N-dimethylbenzamide

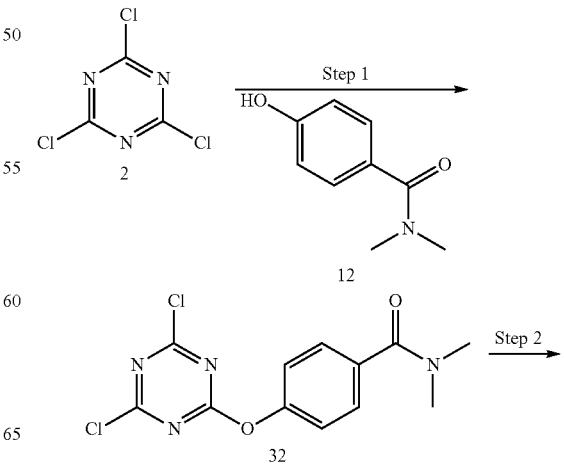

Step 1

Benzyl mercaptan (1.3 ml, 10.26 mmol) and DIPEA (1.7 ml, 10.37 mmol, 0.95 eq) were added to a solution of compound [2] (2 g, 10.92 mmol) in dry THF at 0° C. under a nitrogen atmosphere for 2 hrs. TLC was used to monitor for consumption of starting material [2]. Once the starting material was consumed, morpholine (0.95 ml, 10.92 mmol) and DIPEA (1.8 ml, 10.92 mmol) were added. The mixture was then stirred at RT for 3 h, followed by removal of the solvent under reduced pressure. Purification was done by silica gel column chromatography with 50% EtOAc/cyclohexane to give compound [25] as a white solid (2.5 g, 71%).

ESIMS: 323 ($M^+$+1)

Step 2

To a solution of compound [25] (2 g, 5.59 mmol) in DME:$H_2O$: 4:1, 5 ml of 2 M $Na_2CO_3$ was added followed by

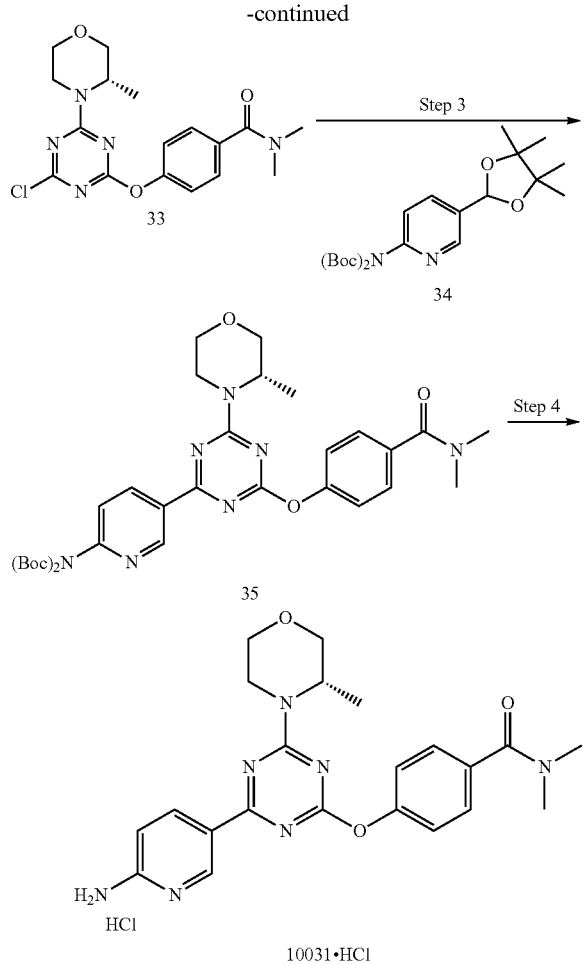

10031·HCl

Step 1

To a solution of compound [2] (5.00 g, 27.17 mmol) in THF at 0° C. was added DIPEA (4.89 ml, 27.17 mmol) and compound [12] (4.45 g, 27.17 mmol). The mixture was stirred at 0° C. for 4 hrs. TLC was used to monitor for consumption of starting material [2]. Once the starting material was consumed, solvent was removed under reduced pressure. Purification was done by silica gel column chromatography with 20% EtOAc/cyclohexane to give compound [32] as a white solid (6.0 g, 71%).

ESIMS: 313 (M$^+$+1)

Step 2

To a solution of compound [32] (2.0 g, 6.14 mmol) in chloroform at 0° C. was added TEA (0.89 ml, 6.14 mmol) and (S)-3-methylmorpholine (0.647 g, 6.14 mmol). The resulting mixture was stirred at 0° C. for 3 hrs. TLC was used to monitor for consumption of starting material [32]. Once the starting material was consumed, solvent was removed under reduced pressure. Purification was done by silica gel column chromatography with 20% EtOAc/cyclohexane to give compound [33] as a white solid (1.65 g, 68%).

ESIMS: 378 (M$^+$+1)

Step 3

To a solution of compound [33] (0.500 g, 1.32 mmol) in DME:H$_2$O: 4:1, 5 ml of 2 M Na$_2$CO$_3$ was added followed by addition of compound [34] (0.850 g, 2.10 mmol). After that, tetrakis palladium (76 mg, 0.066 mmol) was added and the reaction was heated under inert condition at 120° C. overnight. DME was removed under vacuum and the reaction mass was extracted with (2×200 ml of DCM. The DCM extracts were combined, washed with brine, dried over anhydrous sodium sulphate, and then evaporated to obtain a viscous dark brown material. This material was purified by silica gel chromatography with 2% MeOH/DCM to obtain compound [35] as a pale yellow solid (0.150 g, 18% yield).

ESIMS: 636 (M$^+$+1)

Step 4

Compound [35] (0.100 g, 0.157 mmol) was taken in dioxane HCl (4 M, 20 ml) and mixture was stirred for 24 hrs at RT. The solvent was evaporated and crude was purified by washing with DCM, ether and pentane to obtain compound [10031.HCl] (0.035 g, 51% yield) as white solid.

ESIMS: 436 (M$^+$+1)

Compounds 10004, 10005 10006, 10010, 10011, 10020, 10029, 10053, 10057, 10058, 10064, 10069, 10070, 10071, 10072, 10075, 10076, 10077, 10078, 10079, 10082, 10083, 10085, 10086, 10088, 10090, 10095, 10096, 10097, 10098, 10099, 10100, 10103, 10104, 10105, 10115, 10118, 10119, 10122, 10123, 10124, 10125, 10126, 10127, 10128, 10130, 10131, 10132, 10134, 10136, 10137, 10138, 10138, 10140, 10142, 10144, 10146, 10147, 10153, 10154, 10156, 10157, 10158, 10159, 10160, 10175 10913, 10925 are synthesized following scheme 7 by using appropriate boronic ester and stanyl reagents.

Scheme 5: Synthesis of (S)-4-((4-(6-aminopyridin-3-yl)-6-(3-methylmorpholino)-1,3,5-triazin-2-yl)oxy)-3-fluoro-N,N-dimethlbenzamide hydrochloride salt[10058·HCl] following scheme E.

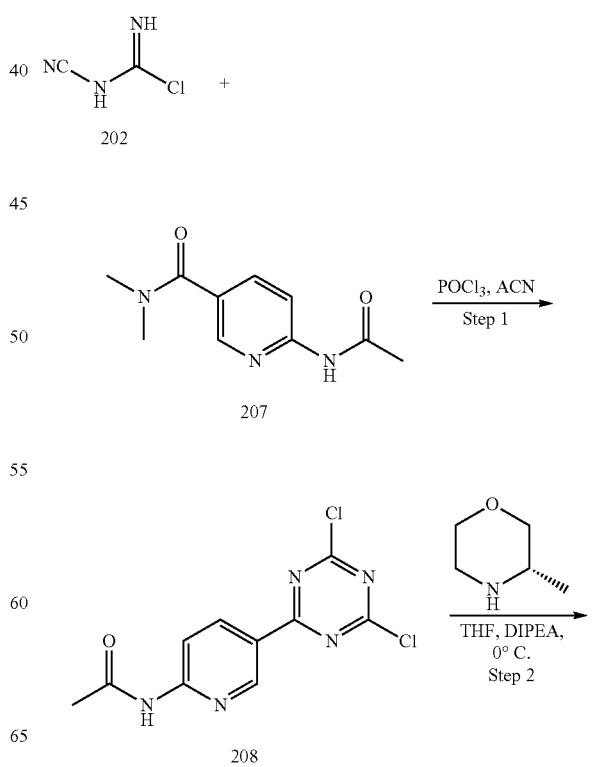

-continued

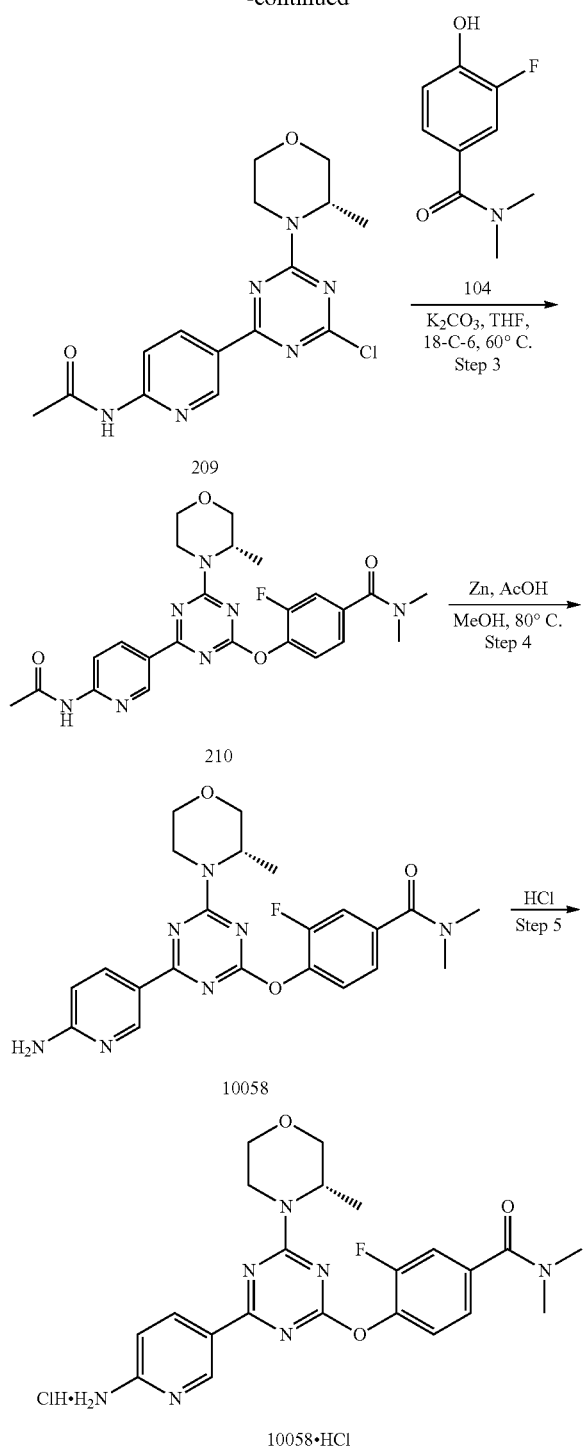

Step 1

Compound [207] (1.0 g, 4.8 mmol), POCl₃ (0.88 ml, 9.6 mmol) and 1 ml ACN stirred at RT for 3 hrs. Compound [202] (1.2 g, 12 mmol) was added and mixture was heated at 60° C. temp for 1 hr. Once the starting material was consumed reaction mixture was quenched with water (20 ml). The reaction mixture was extracted with ethyl acetate (3×50 ml). The organic layer was separated and washed with 5% NaHCO3 (30 ml) solution and brine solution (30 ml).

Dried over Na₂SO₄, concentrated under reduced pressure to obtain compound [208] (0.67 g, 50%) as yellow solid.

ESIMS: 284 (M⁺+1)

Step 2

To a solution of compound [208] (1.0 g, 3.5 mmol) in THF (100 ml) at 0° C. was added DIPEA (0.6 ml, 3.5 mmol) and (S)-3-methylmorpholine (0.353 g, 3.5 mmol). The resulting mixture was stirred at 0° C. for 2 hrs. TLC was used to monitor for consumption of starting material [208]. Once the starting material was consumed, solvent was removed under reduced pressure. Purification was done by silica gel column chromatography with 20% EtOAc/cyclohexane to give compound [209] as a brownish solid (1.1 g, 89%).

ESIMS: 349.1 (M⁺+1)

Step 3

To a solution of compound [209] (1.0 g, 2.8 mmol) in DMF (6 ml) was added K₂CO₃ (0.98 g, 7.1 mmol) and compound [104] (0.56 g, 3.08 mmol) followed by catalytic amount of 18-crown-6 (50 mg). The mixture was heated at 60° C. for 4 hrs. TLC was used to monitor for consumption of starting material [209]. Once the starting material was consumed, reaction was cooled to RT, quenched with water (40 ml). The reaction mixture was extracted with ethyl acetate (3×60 ml). The organic layer was separated, dried over Na₂SO₄, concentrated under reduced pressure to get crude product. Purification was done by silica gel column chromatography with 1.5% MeOH/DCM to obtain compound [210] as a white solid (1.33 g, 94%).

ESIMS: 496.2 (M⁺+1)

Step 4

To a solution of compound [210] (1.0 g, 2.0 mmol) in methanol (10 ml) was added Zn (0.4 g, 6.0 mmol) followed by acetic acid (0.5 ml). The mixture was heated at 80° C. for 14 hrs. TLC was used to monitor for consumption of starting material [210]. Once the starting material was consumed, reaction was cooled to RT, and filtered via celite bed and washed with DCM (100 ml). The organic layer was stirred with saturated NaHCO3 (30 ml) solution separated and washed water (50 ml) and brine solution (30 ml). Dried over Na₂SO₄, concentrated under reduced pressure to obtain compound [10058] (0.82 g, 89%) as a white solid.

ESIMS: 454.5 (M⁺+1)

Step 5

Compound [10058] (1.0 g, 2.2 mmol) was taken in diethylether HCl (20 ml) and mixture was stirred for 30 mins at RT. The solvent was concentrated under reduced pressure to obtain compound [10058.HCl] (1.05 g, 97% yield) as white solid.

ESIMS: 454.2 (M⁺+1)

Scheme 6: Synthesis of 4-(4-(2-aminothiazol-5-yl)-6-((S)-3-methylmorpholino)-1,3,5-triazin-2-yloxy)-3-fluoro-N,N-dimethylbenzamide. Hydrochloride salt

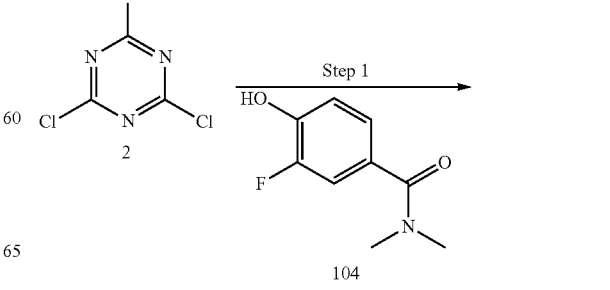

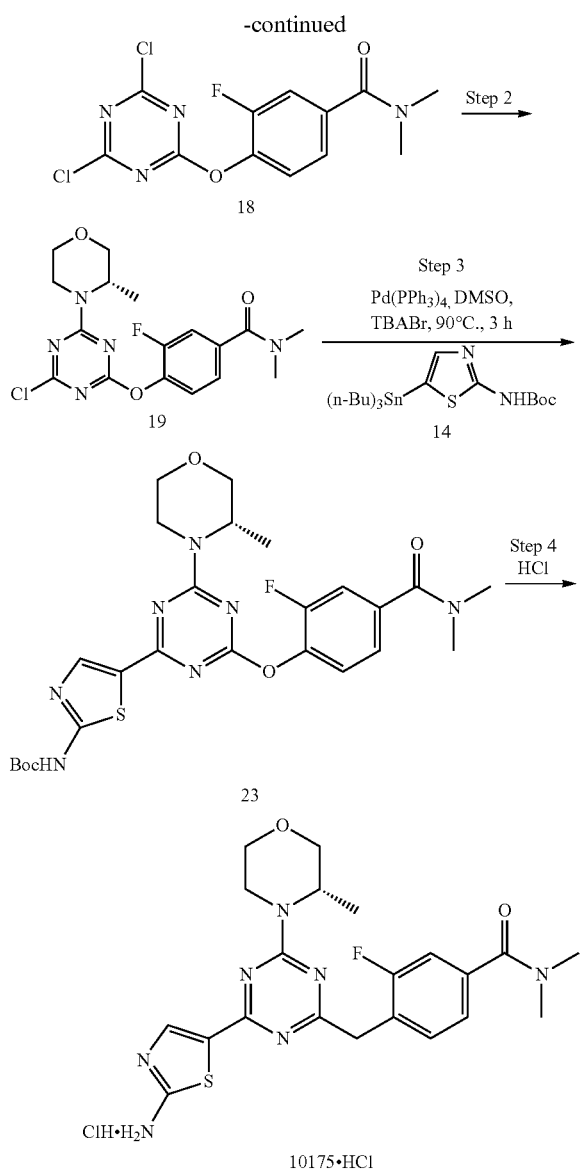

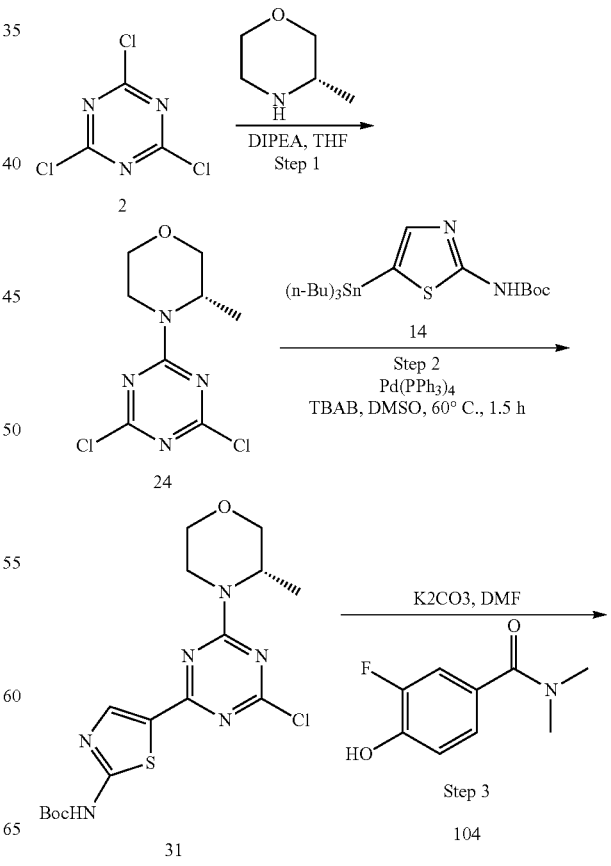

silica gel column chromatography with 20% EtOAc/cyclohexane to give compound [19] as a white solid (1.62 g, 68%).

ESIMS: 396 (M$^+$+1)

Step 3

To a solution of compound [19] (0.500 g, 1.26 mmol) in DMSO (5 ml), TBAB (0.041 g, 0.126 mmol) was added followed by addition of compound [14] (0.930 g, 1.89 mmol). The mixture was purged with nitrogen for 20 min. After that, tetrakis palladium (73 mg, 0.063 mmol) was added and the reaction was heated under inert condition at 90° C. for 3 hrs. The reaction mixture was cooled to RT, poured in to ice, washed with brine and reaction mass was extracted with ethyl acetate (2×100 ml). The organic extracts were combined, dried over anhydrous sodium sulphate, and then evaporated to obtain a viscous dark brown material. This material was purified by silica gel chromatography with 2% MeOH/DCM to obtain compound [23] as a pale yellow solid (0.424 g, 60% yield).

ESIMS: 560 (M$^+$+1)

Step 4

Compound [23] (0.100 g, 0.178 mmol) was taken in dioxane HCl (4 M, 10 ml) and mixture was stirred for 24 hrs at RT. The solvent was evaporated and crude was purified by washing with DCM, ether and pentane to obtain compound [10175.HCl] (0.049 g, 80% yield) as white solid.

ESIMS: 460 (M$^+$+1)

Scheme 7: Synthesis of 4-(4-(2-aminothiazol-5-yl)-6-((S)-3-methylmorpholino)-1,3,5-triazin-2-yloxy)-3-fluoro-N,N-dimethylbenzamide. Hydrochloride salt following scheme D Step 1

To a solution of compound [2] (5.00 g, 27.17 mmol) in THF at 0° C. was added DIPEA (4.89 ml, 27.17 mmol) and compound [104] (4.97 g, 27.17 mmol). The mixture was stirred at 0° C. for 4 hrs. TLC was used to monitor for consumption of starting material [2]. Once the starting material was consumed, solvent was removed under reduced pressure. Purification was done by silica gel column chromatography with 20% EtOAc/cyclohexane to give compound [18] as a white solid (6.38 g, 71%).

ESIMS: 332 (M$^+$+1)

Step 2

To a solution of compound [18] (2.0 g, 6.06 mmol) in chloroform at 0° C. was added TEA (0.89 ml, 6.14 mmol) and (S)-3-methylmorpholine (0.612 g, 6.06 mmol). The resulting mixture was stirred at 0° C. for 3 hrs. TLC was used to monitor for consumption of starting material [18]. Once the starting material was consumed, solvent was removed under reduced pressure. Purification was done by

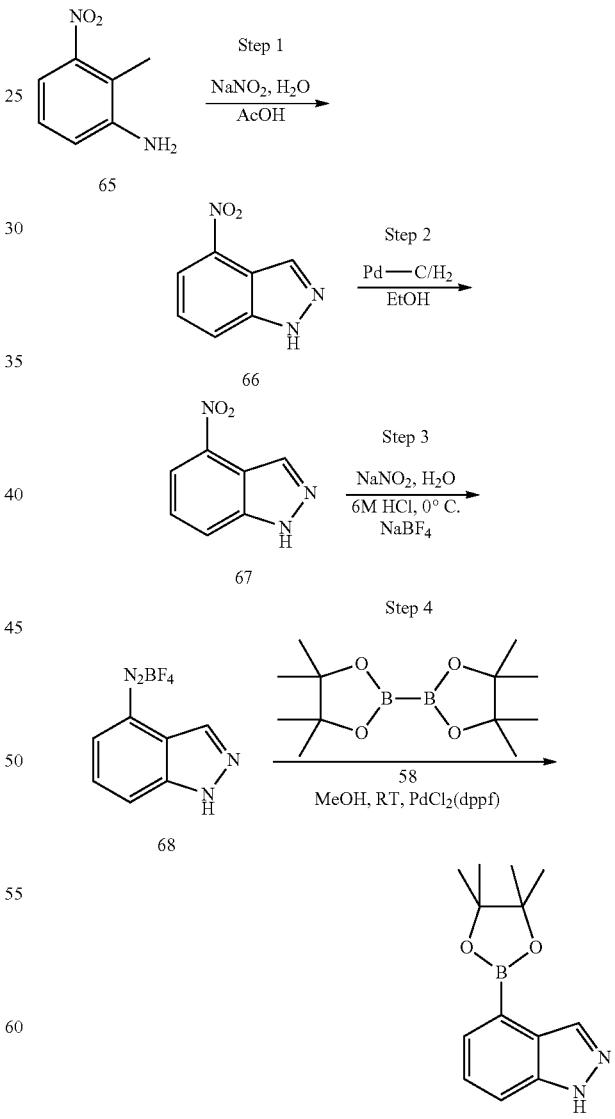

over Na₂SO₄, concentrated under reduced pressure to get crude product. Purification was done by silica gel column chromatography with 1.5% MeOH/DCM to obtain compound [23] as a white solid (1.2 g, 88%).

ESIMS: 560.1 (M$^+$+1)

Step 4

Compound [23] (0.100 g, 0.178 mmol) was taken in dioxane HCl (4 M, 10 ml) and mixture was stirred for 24 hrs at RT. The solvent was evaporated and crude was purified by washing with DCM, ether and pentane to obtain compound [10175.HCl] (0.049 g, 80% yield) as white solid.

ESIMS: 460 (M$^+$+1)

Compound 10003, 10005, 10034, 10040, 10043, 10138 are synthesized exploiting above scheme by using appropriate alkoxide reagents.

Scheme 8: Synthesis of indazole boronate [62]

Step-1

To a solution of compound [2] (5.00 g, 27.17 mmol) in THF at 0° C. was added DIPEA (4.89 ml, 27.17 mmol) and (S)-3-methyl morpholine (2.74 g, 27.17 mmol). The mixture was stirred at 0° C. for 2 hrs. TLC was used to monitor for consumption of starting material [2]. Once the starting material was consumed, solvent was removed under reduced pressure. Purification was done by silica gel column chromatography with 20% EtOAc/cyclohexane to give compound [24] as a white solid (4.7 g, 69%).

ESIMS: 249.1 (M$^-$+1).

Step-2

To a solution of compound [24] (1 g, 4.01 mmol) in DMSO (10 ml), TBAB (0.128 g, 0.4 mmol) was added followed by addition of compound [14] (1.97 g, 4.01 mmol). The mixture was purged with nitrogen for 20 min. After that, tetrakis palladium (0.23 g, 0.2 mmol) was added and the reaction was heated under inert condition at 60° C. for 1.5 hrs. The reaction mixture was cooled to RT, poured in to ice, washed with brine and reaction mass was extracted with ethyl acetate (2×100 ml). The organic extracts were combined, dried over anhydrous sodium sulphate, and then evaporated to obtain a viscous dark brown material. This material was purified by silica gel chromatography with 1% MeOH/DCM to obtain compound [31] as a off white solid (1.1 g, 65% yield).

ESIMS: 413.2 (M$^-$+1)

Step 3

To a solution of compound [31] (1.0 g, 2.42 mmol) in DMF (10 ml) was added K₂CO₃ (0.837 g, 6.06 mmol) and compound [104] (0.48 g, 2.66 mmol) followed by catalytic amount of 18-crown-6 (50 mg). The mixture was heated at 90° C. for 12 hrs. TLC was used to monitor for consumption of starting material [31]. Once the starting material was consumed, reaction was cooled to RT, quenched with water (40 ml). The reaction mixture was extracted with ethyl acetate (3×60 ml). The organic layer was separated, dried Step 1

Compound [65] (15.0 g, 0.099 mol) was dissolved in 375 ml glacial acetic acid in a 500 ml round bottom flask. An aqueous solution of sodium nitrite (8.16 g, 0.12 mol, in 35 ml of water) was added to the reaction mixture. The reaction mixture was stirred for 2 hrs at RT. TLC monitoring showed complete consumption of starting material. Reaction was ceased by the addition of ice-cold water, solid thus formed was filtered and dried well to afford yellowish solid [66] (10.0 g, 62%).

Step 2

Compound [66] (10.0 g) was suspended in ethyl alcohol (160 ml). The reaction mixture was charged with Pd—C (10%) (600 mg, 6% wt. by wt.) under nitrogen atmosphere. It was then allowed to stir at RT overnight under hydrogen atmosphere. TLC showed consumption of starting material. The reaction was worked up by filtering the reaction mass through celite and concentrated to afford [67] (7.9 g, 96%).

ESIMS: 134 (M$^+$+1)

Step 3

To compound [67] (6.0 g, 0.045 mol) was added 6 M HCl (70 ml) at −5° C. followed by drop wise addition of an aqueous solution of sodium nitrite (3.42 g, 0.049 mol, in 11 ml water). The reaction mixture was stirred at −5° C. for 30 min followed by addition of sodium tetrafluoroborate (7.4 g, 0.0675 mol). The reaction mixture was stirred for another 10 min and filtered using filter paper and dried well to yield crude [68] (6.0 g).

ESIMS: 163 (M$^+$+1)

Step 4

To a solution of compound [68] (6.0 g, 0.026 mol) in degassed MeOH (110 ml), bis(pinacolato)-diboron ([61], 6.604 g, 0.026 mol) was added followed by addition of [1,1'-bis(diphenylphosphino) ferrocene] palladium(II) chloride (546 mg). The reaction mixture was stirred at RT for overnight. After complete consumption of starting material, the reaction mixture was passed through celite and the organic layer obtained was concentrated to afford a crude product which was further purified using 100-200 mesh silica column and EtOAc-Cyclohexane as eluent to afford [62] (2.9 g, 40%).

ESIMS: 245 (M$^+$+1)

Scheme 9: Protection of Compound Indazole boronate [62]

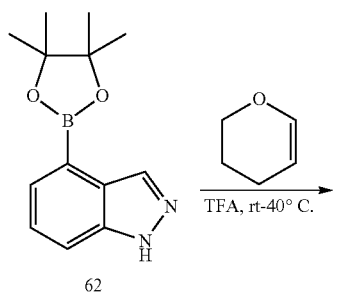

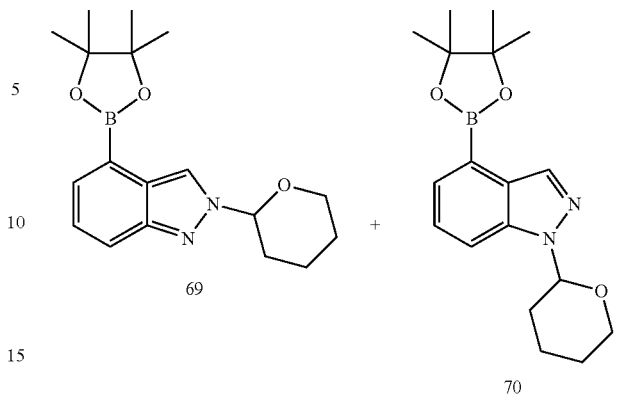

Compound [62] was dissolved in 25 ml of ethyl acetate in a two neck 100 ml round bottom flask followed by addition of 3,4-dihydro-2H-pyran. The reaction mixture was stirred for 10 min followed by addition of a catalytic addition of TFA. The reaction mixture was stirred overnight. Consumption of the starting material was monitored using TLC (20% ethyl acetate in hexane). After the complete addition of starting material, the reaction mixture was washed with water (2×25 ml). Organic layer was dried over anhydrous sodium sulfate and concentrated under reduced pressure to yield a crude product, which was a mixture of two regioisomers ([69] and [70]). Column purification of the crude product using silica gel column afforded a major regioisomer [69] as pure product (4.5 g, 85%).

ESIMS: 328 (M$^+$+1)

Scheme 10: Di-t-butyl(5-(4,4,5,5-tetramethyl-1,3,2-dioxaborolan-2-yl) pyridin-2-yl)dicarbamate [72]

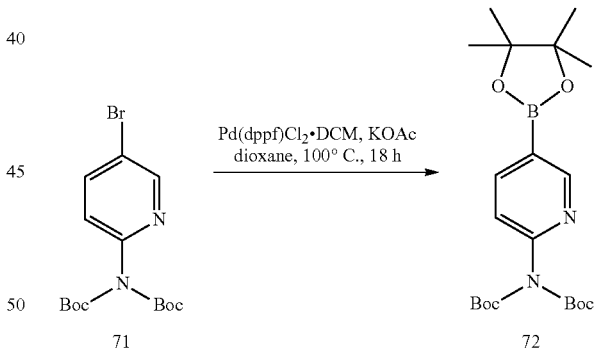

Compound [71] (1.0 g, 2.68 mmol) was dissolved in 1,4-dioxane (30 ml) in a clean oven-dried two necked RB flask (250 ml) and degassed with nitrogen. To this clear solution, bis(pinnacaloto)-diboron (0.82 g, 3.2 mmol) was added, followed by potassium acetate (0.79 g, 8.04 mmol) and [1, 1'-bis (diphenylphosphino)ferrocene]palladium(II) chloride with dichloromethane (0.22 g, 2.6 mmol). The reaction mixture was stirred and heated at 100° C. for 18 h, under nitrogen atmosphere. The reaction was monitored by TLC. The reaction mixture was filtered through celite and was washed well with ethyl acetate. The filtrate was extracted with ethyl acetate (2×30 ml). The organic extracts were combined, washed with brine and dried using Na$_2$SO$_4$.

The organic layer was evaporated to afford 72 as black oil (1.1 g) which was washed with ether to yield compound [72] (1 g, 89%) as a brown solid.

ESIMS: 421 (M++1)

Scheme 11: Synthesis of 4-(4,4,5,5-tetramethyl-1,3,2-dioxaborolan-2-yl)-1H-indole [74]

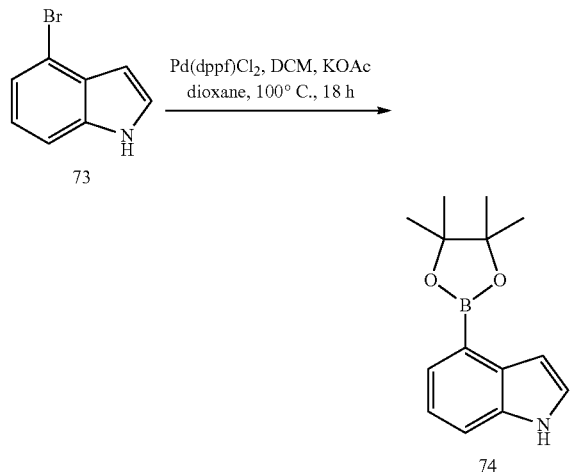

Compound [73] (1 g, 2.68 5.1 mmol) was dissolved in 1,4-dioxane (30 ml) in a clean oven-dried two necked RB flask (250 ml) and degassed with nitrogen. To this clear solution, bis(pinnacaloto)-diboron (1.64 g, 6.12 mmol) was added, followed by potassium acetate (1.5 g, 15.3 mol) and [1, 1'-bis (diphenylphosphino)ferrocene]palladium(II)chloride (0.43 g, 0.51 mmol) with dichloromethane. The reaction mixture was stirred under a nitrogen atmosphere and heated at 100° C. for 18 h. The reaction was monitored by TLC. The reaction mixture was filtered through celite and washed well with ethyl acetate. The filtrate was then extracted with ethyl acetate (2×30 ml). The organic extracts were combined, washed with brine and dried over $Na_2SO_4$. The organic layer was then evaporated to give [74] as a crude black oil (1.2 g) which was washed with ether to yield [74] (0.9 g, 72%) as a brown solid.

ESIMS: 244 (M++1)

Scheme 12: Synthesis of tert-butyl 4-(4,4,5,5-tetramethyl-1,3,2-dioxaborolan-2-yl)-1H-pyrrolo[2,3-b]pyridine-1-carboxylate [77]

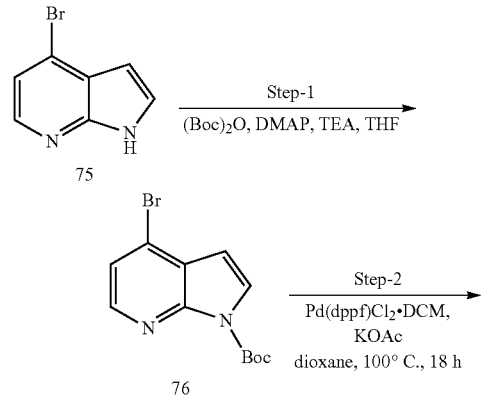

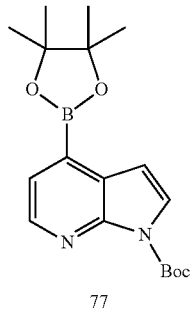

Step 1

Compound [75] (1.0 g, 5.1 mmol) was dissolved in THF (30 ml) and the temperature brought down to 0° C. with an ice bath. To this reaction mixture TEA (1.41 ml, 10.2 mmol), followed by BOC anhydride (1.33 g, 6.2 mmol) was added. A catalytic amount of DMAP (50 mg) was then added. This reaction mixture was then allowed to stirred and refluxed under nitrogen at 70° C. for 18 h. TLC and mass spectral analysis confirmed completion of the reaction. The reaction mixture was diluted with ethyl acetate (30 ml) which was washed with water and brine solution. The organic layers were combined, dried using anhydrous $Na_2SO_4$, filtered, and evaporated to yield [76] as a brown solid (1.3 g, 87%).

ESIMS: 298 (M++1)

Step 2

Compound [76] (1.3 g, 4.37 mmol) was dissolved in 1,4-dioxane (30 ml) in a clean oven-dried two necked RB flask (250 ml) and degassed with nitrogen. To this clear solution, bis(pinnacaloto)-diboron (1.3 g, 5.24 mmol) was added, followed by potassium acetate (1.28 g, 813.11 mmol) and [1, 1'-bis (diphenylphosphino)ferrocene]palladium(II) chloride with dichloromethane (0.37 g, 0.437 mmol). The reaction mixture was stirred and heated at 100° C. for 18 h, under a nitrogen atmosphere. The reaction was monitored by TLC. Upon completion of the reaction, the reaction mixture was filtered through celite, washed well with ethyl acetate. The filtrate was extracted with ethyl acetate (2×30 ml). The organic extracts were combined, washed with brine and dried over $Na_2SO_4$, filtered and evaporated under vacuum to give [77] as dark brown solid (1.3 g), which upon further washing with ether yielded [77] as a brown solid (1.15 g, 76%).

ESIMS: 345 (M++1)

Scheme 13:

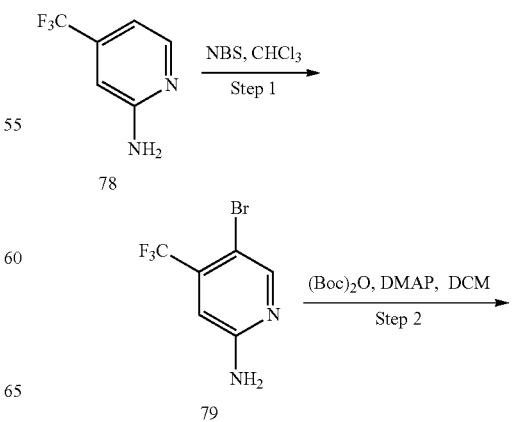

-continued

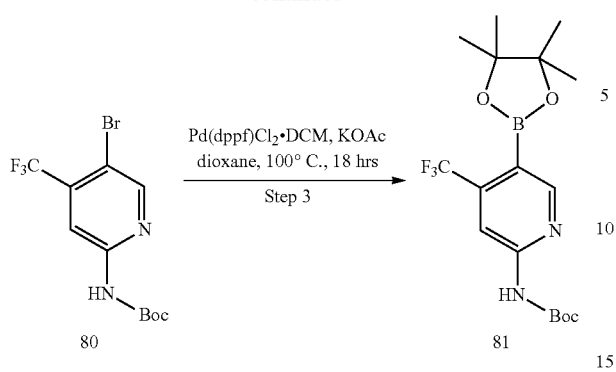

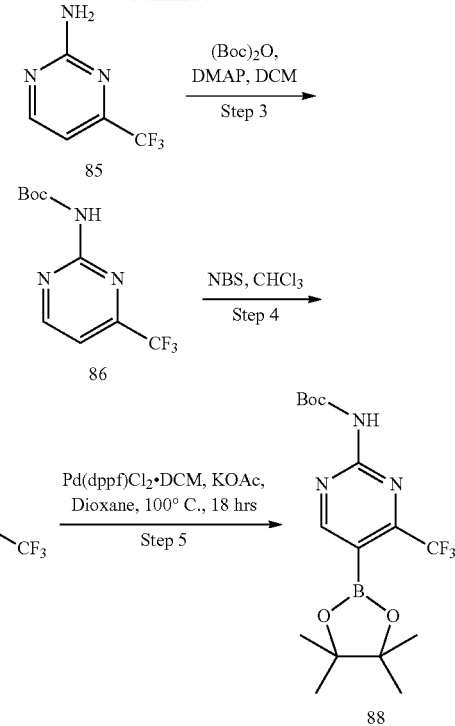

Step 1:

To a solution of compound [78] (3.5 g, 21.6 mmol, 1 eq) in chloroform (50 ml) was slowly added NBS (4.6 g, 25.9 mmol, 1.2 eq) at 0° C. temperature. The reaction mass was stirred at room temperature for 3 hrs. Reaction mass was diluted with 50 ml of chloroform and washed with water and brine, dried over anhydrous sodium sulphate, and then evaporated to obtain a brown solid as a crude material. Purification of the solid residue was done by column chromatography with silica gel (100:200 mesh) in solvent system 5% EtOAc in cyclohexane to get compound [79] as brown solid (4 g, 77%).

ESIMS: 241 ($M^+$+1e)

Step 2:

Compound [79] (1.0 g, 4.1 mmol, 1 eq) was dissolved in DCM (30 ml) and the temperature brought down to 0° C. with an ice bath. To this reaction mixture DMAP (0.050 g, 0.41 mmol, 0.1 eq), followed by BOC anhydride (1.1 g, 4.9 mmol, 1.2 eq) was added. The reaction mass was stirred at room temperature for overnight. TLC and mass spectral analysis confirmed completion of the reaction. The reaction mixture was diluted with DCM (50 ml) which was washed with water and brine solution, dried over anhydrous sodium sulphate, and then evaporated to obtain a brown solid as a crude material. Purification of solid residue was done by column chromatography with silica gel (100:200 mesh) in solvent system 7% EtOAc in cyclohexane to yield compound [80] as a yellow solid (1 g, 71%). ESIMS: 341 ($M^+$+1)

Compound [81] was synthesized following described procedure in Scheme 10.

Scheme 14:

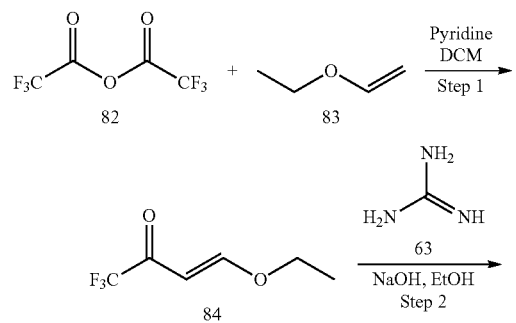

Step 1:

To a solution of compound [83] (19 ml, 1 eq.) in DCM (50 mL), pyridine (20 ml, 1.2 eq.) was added and cooled to 10-15° C. Trifluoroacetic anhydride (33 mL, 1.2 eq.) was added drop wise over 30 min. After the addition was complete, the mixture was stirred at RT for 18 hrs. The mixture was transferred to separating funnel and organic layer was washed with water (4×500 mL) to remove pyridinium salts. The resulting organic solution of compound [84] was directly used for further step.

Step 2:

To a solution of compound [63] (22.8 g, 2.4 mmol, 1 eq.), absolute ethanol (100 mL) was added and mixture was stirred at RT for 1 hrs. NaOH pellets (9.55 g, 238 mmol, 1 eq.) were added and mixture was stirred at ambient temperature for 16 hrs. A solution of compound [84] was added by mean of dropping funnel over a period of 2 hrs. The mixture was further stirred for 2 hrs. The solvent was evaporated and residue was taken in water (500 ml) and stirred vigorously for 2 hrs and allowed to stand at RT overnight. The precipitates formed were filtered, dried under vacuum to obtain compound [85] as light yellow solid (20.6 g, 53%)

ESIMS: 164 ($M^+$+1)

Step 3:

Compound [85] (1.0 g, 6.09 mmol, 1 eq.) was dissolved in DCM (30 ml) and the temperature brought down to 0° C. with an ice bath. To this reaction mixture DMAP (0.050 g, 0.41 mmol, 0.1 eq.), followed by BOC anhydride (1.1 g, 4.9 mmol, 1.2 eq) was added. The reaction mass was stirred at room temperature for overnight. TLC and mass spectral analysis confirmed completion of the reaction. The reaction mixture was diluted with DCM (50 ml) which was washed with water and brine solution, dried over anhydrous sodium sulphate, and then evaporated to obtain a brown solid as a crude material. Purification of solid residue was done by column chromatography with silica gel (100-200 mesh) in solvent system 7% EtOAc in cyclohexane to yield compound 1861 as a yellow solid (1.6 g, 75%).

ESIMS: 264 (M$^+$+1)

Step 4:

To a solution of compound [86] (3.0 g, 11.36 mmol, 1 eq.) in chloroform (50 ml) was slowly added NBS (2.4 g, 13.4 mmol, 1.2 eq) at 0° C. temperature. The reaction mass was stirred at room temperature for 4 hrs. Reaction mass was diluted with 50 ml of chloroform and washed with water and brine, dried over anhydrous sodium sulfate, and then evaporated to obtain a brown solid as a crude material. Purification of the solid residue was done by column chromatography with silica gel (100-200 mesh) in solvent system 5% EtOAc in cyclohexane to get compound [87] as brown solid (3.5 g, 73%).

ESIMS: 342 (M$^+$+1)

Compound [88] was synthesized following described procedure in Scheme 10

Scheme 15: Synthesis of 1-(tetrahydro-2H-pyran-2-yl)-5-(4,4,5,5-tetramethyl-1,3,2-dioxaborolan-2-yl)-1H-indazole [96]

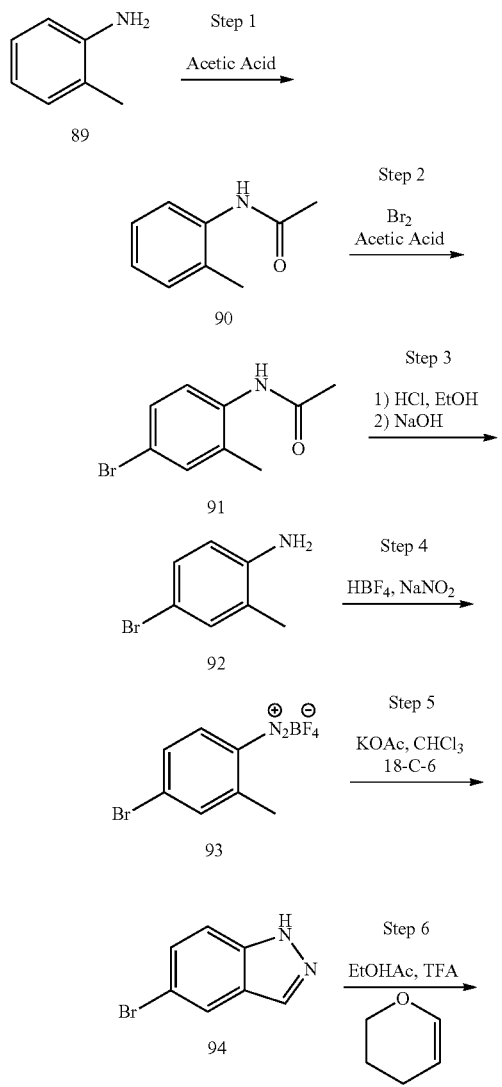

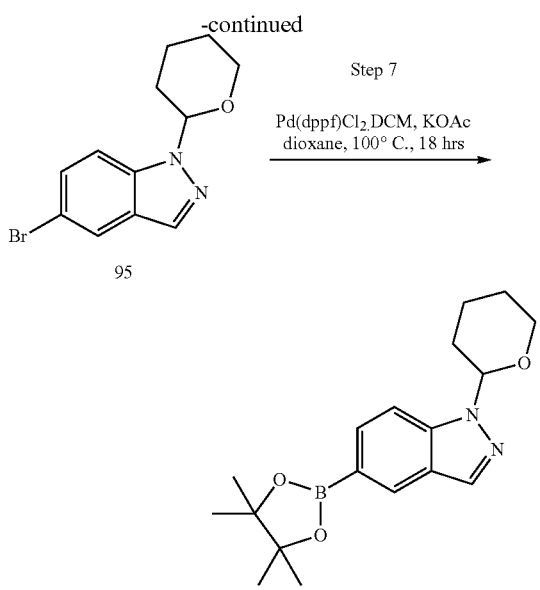

Step 1:

Compound [89] (10.0 g, 0.093 mol) was dissolved in 20 ml glacial acetic acid in two necked RBF and mixture was heated at 110-115° C. for 2 hrs. The mixture was cooled to RT and poured into ice water mixture. The mixture was extracted with DCM (3×200 ml). The organic layer was separated, dried over Na$_2$SO$_4$, concentrated under vacuum to obtain compound [90] (12.5 g, 90%) as pale pink solid.

ESIMS: 150 (M$^+$+1)

Step 2:

Compound [90] (10.0 g, 0.067 mol) was dissolved in 37 ml glacial acetic acid in two necked RBF. Bromine (11 ml, 0.067 mol, 1 eq.) was added drop wise to the mixture and then heated at 50° C. for 1.5 hrs. On completion of reaction, the mixture was poured into ice cold water. The aqueous layer was extracted with ethyl acetate (3×100 ml). The organic layer was separated, dried over Na$_2$SO$_4$, concentrated under vacuum to obtain compound [91] (15.0 g, 97%) as pink solid.

ESIMS: 229 (M$^+$+1)

Step 3:

Compound [91] (15.0 g, 0.65 mol, 1 eq.) was taken in 25 ml ethanol in two necked RBF. The mixture was refluxed. Con HCl (20 ml) was added to the mixture drop wise and refluxing was continued for 3 hrs. After completion, the mixture was cooled to RT and solid was filtered. The solid obtained was dissolved in water, basified with aq. NaOH ad stirred at RT for 30 min. The solution was extracted with ethyl acetate (3×200 ml), organic layer was separated, dried over Na$_2$SO$_4$, concentrated under reduced pressure to obtain compound [92] (7.25 g, 50%) brown colored solid.

ESIMS: 188 (M$^+$+1)

Step 4:

Compound [92] (5.0 g, 0.026 mol) was taken in aq. HBF4 (55%, 8.8 ml) in two necked RBF. The mixture was stirred at RT for 15 min. NaNO$_2$ (2.04 g, 0.028 mol, 5 ml of H2O) was drop wise to the mixture at 0-5° C. and stirring was continued for 2 hrs. The reaction contents were filtered, washed with diethyl ether, dried under vacuum to obtain compound [93] (5.2 g, 99%) as off white solid.

ESIMS: 197 (M$^+$+1)

Step 5:

To a stirred solution of 18-Crown-6 (0.225 g, 0.85 mmol) and potassium acetate (3.44 g, 35.1 mmol) in chloroform (200 ml), compound [93] (5.0 g, 25.3 mmol) was added and mixture was stirred at RT for 2 hrs. After completion, the solvent was evaporated and residue was dissolved in water (100 ml) and product was extracted with ethyl acetate (2×200 ml). The organic layer was separated, dried over $Na_2SO_4$, concentrated under reduced pressure and purified with petroleum ether to obtain compound [94] (3.0 g, 60%) as yellow solid.

ESIMS: 197 ($M^+$+1)

Step 6:

Compound [94] (3.0 g, 15.3 mmol) was dissolved in 25 ml of ethyl acetate in a two neck 100 ml round bottom flask followed by addition of 3,4-dihydro-2H-pyran (1.93 g, 22.9 mmol). The reaction mixture was stirred for 10 min followed by addition of a catalytic addition of TFA. The reaction mixture was stirred overnight. Consumption of the starting material was monitored using TLC (20% ethyl acetate in hexane). After the complete addition of starting material, the reaction mixture was washed with water (2×100 ml). Organic layer was dried over anhydrous sodium sulfate and concentrated under reduced pressure to yield a crude product, Column purification of the crude product using silica gel column afforded a major regioisomer (951 as pure product (4.0 g, 93%).

ESIMS: 281 (M++1)

Step 7:

Compound [95] (3.0 g, 10.71 mmol) was dissolved in 1,4-dioxane (30 ml) in a clean oven-dried two necked RB flask (250 ml) and degassed with nitrogen. To this clear solution, bis(pinnacaloto)-diboron (3.26 g, 12.85 mmol) was added, followed by potassium acetate (3.15 g, 32.11 mmol) and [1, 1'-bis (diphenylphosphino)ferrocene]palladium(II) chloride with dichloromethane (0.87 g, 1.07 mmol). The reaction mixture was stirred and heated at 100° C. for 18 hrs, under a nitrogen atmosphere. The reaction was monitored by TLC. Upon completion of the reaction, the reaction mixture was filtered through celite, washed well with ethyl acetate. The filtrate was extracted with ethyl acetate (2×30 ml). The organic extracts were combined, washed with brine and dried over $Na_2SO_4$, filtered and evaporated under vacuum to give [96] as dark brown solid (3.26), which upon further washing with ether yielded compound [96] as a brown solid (3.05 g, 87%).

ESIMS: 329 ($M^+$+1)

Scheme 16: Synthesis of heteroaryl organotin reagent [14]

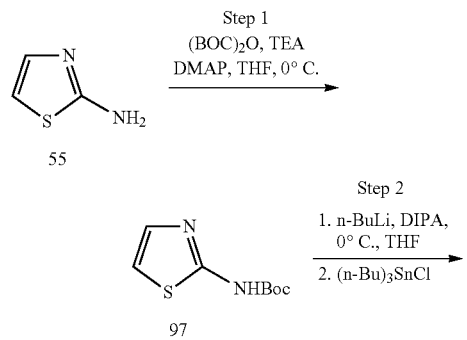

-continued

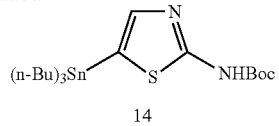

14

Step 1

Compound [55] (5.0 g, 50 mmol) was dissolved in THF (100 ml) and cooled to 0° C. TEA (8.25 ml, 60 mmol) was added dropwise followed by DMAP (0.100 g, 4.0 mmol). $(BOC)_2O$ (11.99 g 55 mmol) was added dropwise. The mixture was stirred at 0° C. for 16 hrs. After completion of the reaction, 100 ml of water was added, and the reaction mass was extracted with 3×100 ml EtOAc (3×100 ml). The EtOAc layers were combined then washed with brine, dried over anhydrous and concentrated to give crude. The product was purified with column silica gel chromatography with DCM to obtain compound [97] as a pale yellow solid (8.0 g, 80% yield).

ESIMS: 201 ($M^+$+1)

Step 2

Compound [97] (1.0 g, 5.0 mmol) was dissolved in THF and cooled to −78° C. Freshly prepared LDA (2.1 eq.) was added to it and mixture was stirred for 1 h. $(n-Bu)_3SnCl$ (1.62 g, 5.0 mmol) was added dropwise and resulting mixture was stirred for 24 h. After completion of reaction 100 ml of aqueous saturated $NH_4Cl$ was added and reaction was extracted with 3×100 ml EtOAc. The EtOAc layer was combined, washed with brine, dried over $Na_2SO_4$ and concentrated to obtain compound [14] as brown solid (2.25 g, 92% yield).

ESIMS: 491 ($M^+$+1)

Scheme 17: Synthesis of 4-hydroxy-N,N-dimethylbenzamide [12]

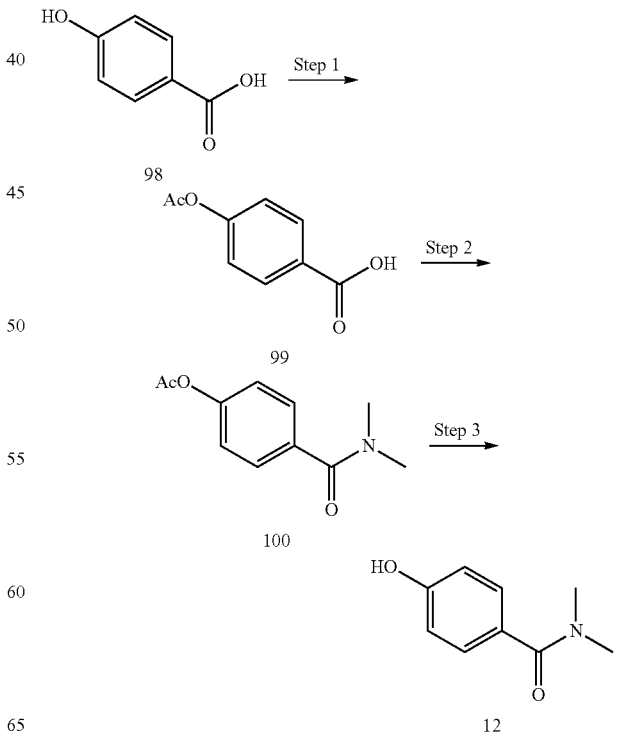

Step 1

Acetic anhydride (10 ml) was added dropwise to a cooled solution of [98] (2.0 g, 14.49 mmol) in pyridine (10 ml), and stirred at RT for 4 h. The reaction mixture was cooled and poured over crushed ice. The white precipitate formed was collected by filtration, washed with diethyl ether (50 ml) and dried to afford [99] as a white solid (2.0 g, 77%).

ESIMS: 181 (M$^+$+1)

Step 2

To a clean dried 100 ml two neck round bottom flask was added [99] (2.0 g, 11.1 mmol) in DCM (25 ml). DMF (4 drops) was added to the solution and cooled to 0° C. followed by the addition of oxalyl chloride (3.0 ml, 33.3 mmol). The resulting solution was stirred at RT for 4 hrs. After completion of the reaction, excess oxalyl chloride was evaporated on a rotary evaporator under nitrogen atmosphere to yield the corresponding acid chloride as a brown solid (2.16 g, 100%) [100]. The resulting brown solid was dissolved in DCM (50 ml) and cooled to 0° C. followed by the addition of a 2.0 M solution of dimethyl amine in THF (11.2 ml, 24.4 mmol) and DIPEA (1.33 ml, 12.2 mmol) and stirred it for 3 hrs at RT. The progress of the reaction was monitored by TLC. The solvent was evaporated under reduced pressure and crude was used as such for further step.

ESIMS: 208 (M$^+$+1)

Step 3

Compound [100] (1.5 g, 7.2 mmol) was dissolved in MeOH (20 ml) to which K$_2$CO$_3$ (3.0 g, 21.7 mmol) was added. The resulting suspension was stirred at RT for 5 hrs. The progress of the reaction was monitored by TLC. After complete conversion, the solvent was removed under reduced pressure and purification was done by silica gel chromatography 2% MeOH/DCM to obtain compound [12] as a white solid (0.80 g, 68% yield).

ESIMS: 165 (M$^+$+1)

Scheme 18: Synthesis of 3-fluoro-4-hydroxy-N,N-dimethylbenzamide [104]

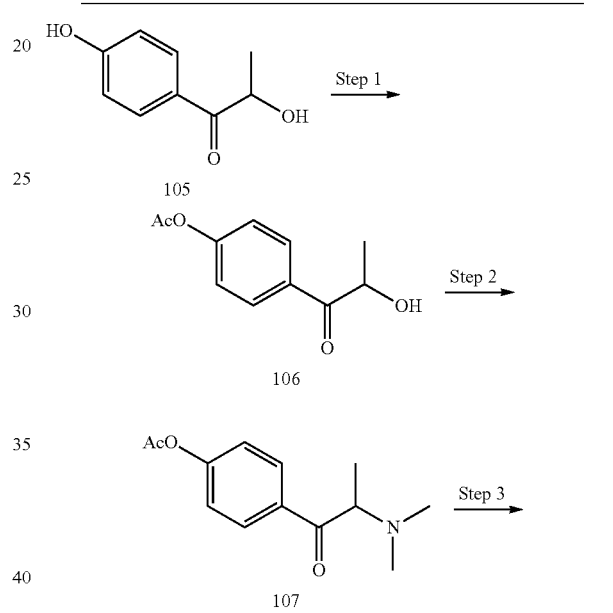

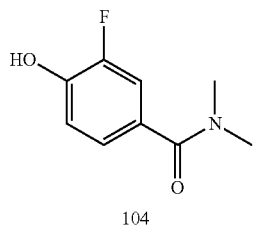

Compound [104] was synthesized using the same procedure as for compound [12] (Scheme 17).

Scheme 19. Synthesis of 2-(dimethylamino)-1-(4-hydroxyphenyl) propan-1-one

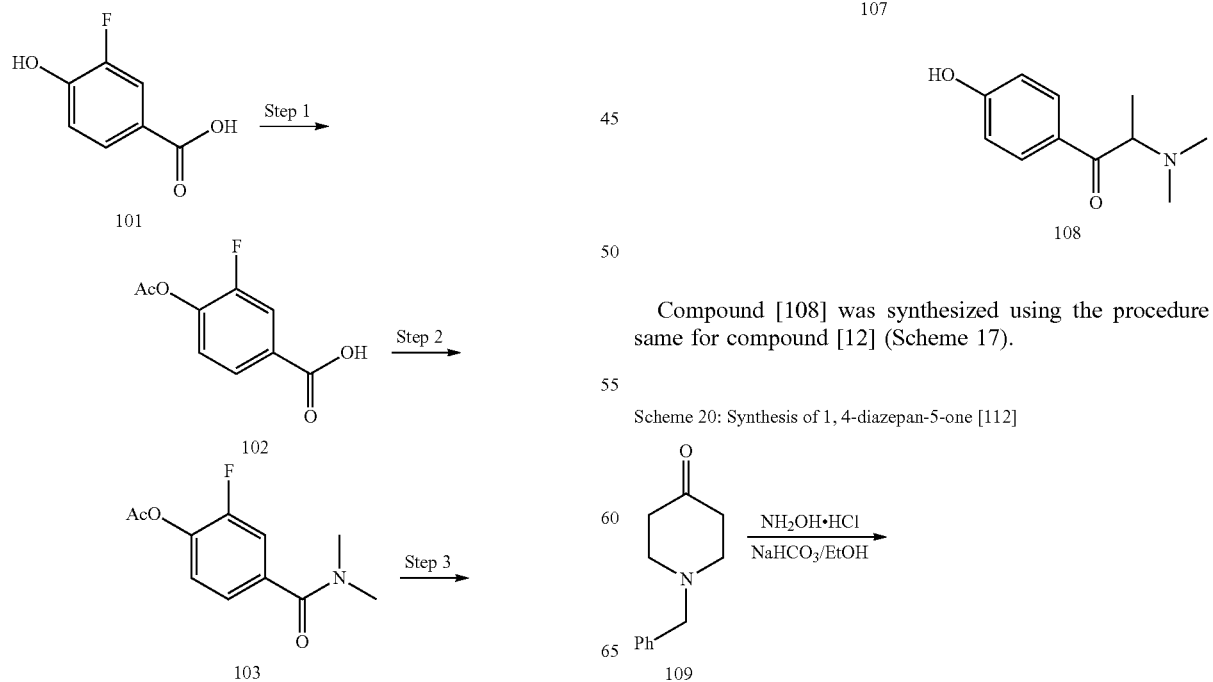

Compound [108] was synthesized using the procedure same for compound [12] (Scheme 17).

Scheme 20: Synthesis of 1, 4-diazepan-5-one [112]

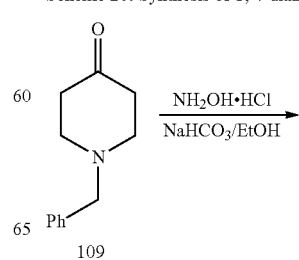

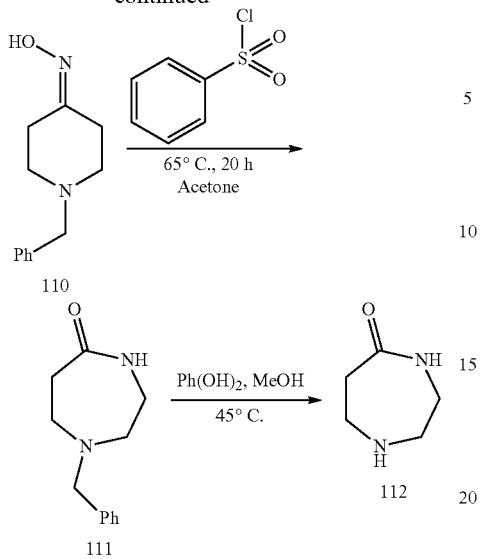

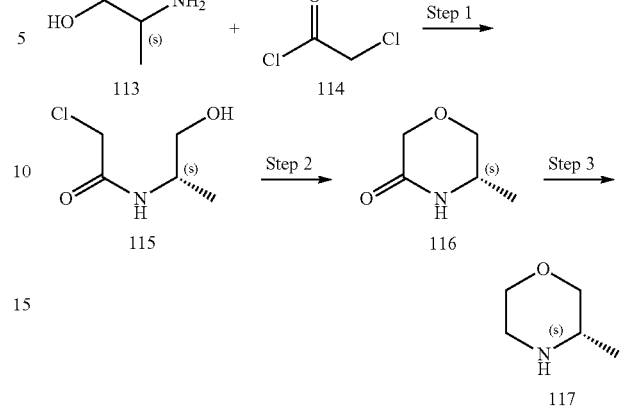

Scheme 21: Synthesis of (S)-3-methylmorphline [117]

Step 1

To a mixture of (S)-(+)-2-amino-1-propanol [113] (4.5 g, 60 mmol) in 150 ml of DCM at −40° C. under nitrogen atmosphere was added dropwise chloroacetyl chloride [114] (2.3 ml, 29.2 mmol) in 30 ml of DCM. The mixture was gradually warmed to 0° C. and stirred for 2 hours. After the removal of the solvents the residue was diluted with 50 ml of 1:1 ethyl acetate/hexanes, stirred for 30 min and filtered. The filtrate was concentrated to afford [115] as a liquid (7.73 g, 85%).

ESIMS: 152 (M$^+$+1)

Step 2

To a mixture of compound [115] (3.50 g, 23.1 mmol) in 175 ml of isopropanol and 120 ml of DCM was added t-BuOK (9.0 g, 80.35 mmol) in 120 ml of isopropanol over 40 min. The mixture was stirred for 1 h and was neutralized with concentrated HCl until the pH was brought down to 6.5. The mixture was concentrated and the residue was diluted with 150 ml of water and 150 ml of ethyl acetate. The aqueous layer was extracted with ethylacetate, the organic layers were combined and dried. Removal of the solvents afforded the desired compound [116] which was used directly at next step.

Step 3

To a mixture of [116] (0.670 g, 5.82 mmol) in 10 ml of THF was added 14.0 ml of LAH/THF (1.0M), the resulting mixture was stirred overnight at RT. The excess LAH was quenched with Fischer workup (2 ml water, 6 ml 15% NaOH, 2 ml water). The mixture was filtered through a celite bed, the filtrate was dried over Na$_2$SO$_4$ then concentrated to obtain compound [117] (0.419 g, 71% yield).

ESIMS: 102 (M$^+$+1)

Bulk synthesis of (S)-3-methylmorpholine [177]

scheme 22:-

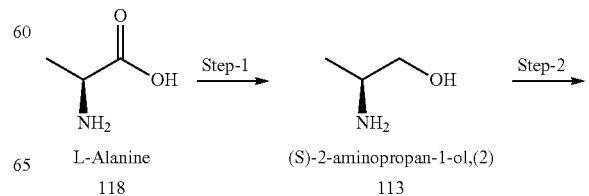

Step 1

To a clean and dried single necked round bottom flask was added hydroxyl amine hydrochloride (3.08 g, 0.04 mol), sodium bicarbonate (9.32 g, 0.11 mol), and ethanol (120 ml) at 0° C. After 5 min compound [109] (7.0 g, 0.04 mol) was added dropwise at 0° C. The reaction mixture was brought to RT in 2 h. TLC analysis showed complete consumption of starting material. The reaction was worked up by removing the ethanol by distillation followed by addition of water (50 ml), extracted into EtOAc (3×150 ml), combined the organic layer which were dried over sodium sulphate and concentrated to yield [110] as a white solid (5.5 g, 72%).

ESIMS: 205 (M$^+$+1)

Step 2

To a clean and dried two necked round bottom flask [110] (2 g, 9.76 mmol) was dissolved in acetone (20 ml) and acetonitrile (20 ml). The reaction mixture was cooled to 0° C., and then to it 15% aqueous NaOH (1.2 ml) was added drop wise, followed by the addition of benzene sulphonyl chloride (1.49 ml, 11 mmol). The reaction mixture was refluxed overnight. TLC showed complete consumption of SM. The reaction mixture was diluted with acetone, and passed through celite and concentrated. Saturated NaHCO$_3$ (50 ml) was added to the solid followed by extraction with EtOAc (3×150 ml), removal of the solvent under reduced pressure. The residue was purified by column chromatography on silica gel with MeOH:DCM (1%) as an eluent to afford [111] as a white solid (600 mg, 30%).

ESIMS: 205 (M$^+$+1)

Step 3

To a clean and dried two-necked RB flask taken compound [111] (600 mg, 2.93 mmol) was dissolved in MeOH (15 ml). Concentrated HCl (0.05 ml) and Pd(OH)$_2$ (120 mg) were added to the solution sequentially under a nitrogen atmosphere. The reaction mixture was heated to 45° C. under a hydrogen atmosphere and maintained at 45° C. overnight. The reaction was monitored by mass analysis. Crude compound [112] obtained was used as such for the next step (350 mg, crude).

ESIMS: 115 (M$^+$+1)

169
-continued

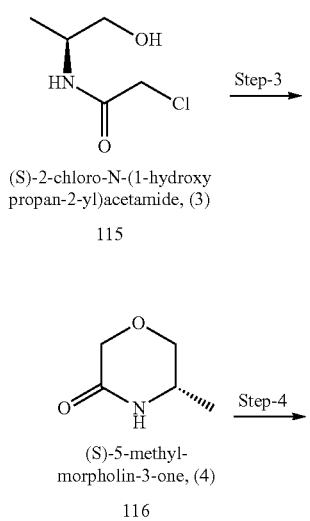

(S)-2-chloro-N-(1-hydroxy
propan-2-yl)acetamide, (3)
115

(S)-5-methyl-
morpholin-3-one, (4)
116

(S)-3-methyl
morpholine, (5)
117

Step-1: Synthesis of S-2-amino propanol (113)

Lithium aluminum hydride (104 gm; 2.2 eq) was suspended in dry THF (2000 ml) at 0° C. in 5.0 Lt three necked RBF under nitrogen. (L)-alanine (110 gm; 1.0 eq) was added slowly in small portions. The reaction mixture warmed to room temperature slowly in 1.0 Hr and further heated to reflux for 12 h. Reaction mixture cooled at 0° C. and quenched with saturated $K_2CO_3$ solution (300 ml) and stirred for 1.0 Hr. at room temperature. Added 2% MeOH/DCM (1000 ml) and stirred for additional 1.0 Hr. Crude mixture filtered with celite bed and filtrate was dried over anhydrous sodium sulfate and finally concentrated on rotavapor at low water bath temperature (20-25° C.) to get 2-(S)-Amino propan-1-ol (84 gm; 90%).

Analytical data: $^1$HNMR (300 MHz, CDCl$_3$), δ 3.55 (M, 1H), 3.22 (m, 1H), 2.99, (m, 1H), 1.05 (d, J=6.6 Hz, 3H). ESIMS: 76 (M+1).

Step-2: Synthesis of (S)-2-chloro-N-(1-hydroxypropan-2-yl)acetamide (115)

2-(S)-amino-propan-1-ol (84 gm) was dissolved in THF (1500 ml) in 5.0 Ltr RBF at 0° C. in and added $K_2CO_3$ (441 gm, 3.0 eq) (solution in 1000 ml $H_2O$) at same temperature. Chloroacetyl chloride (137.9 gm) was added drop wise at 0-5° C. and stirred for 1.0 Hr at same temperature. Added 2N—NaOH solution (100 to 120 ml) to maintain pH 13-14 and stirred at room temperature for 10 minute. Added Ethyl acetate (1000 ml) and separate layer, aqueous layer again extracted with ethyl acetate two times (1000 ml×2). Combined the organic layer and dried over anhydrous sodium sulfate and finally concentrated to yield product (145 gm, 85%).

Analytical data: $^1$HNMR (300 MHz, CDCl$_3$), δ 6.73 (br, 1H), 4.1 (m, 1H), 4.05 (s, 2H), 3.70 (m, 1H), 3.57 (m, 1H), 2.57 (br, 1H), 1.22 (d, J=6.0 Hz, 3H), ESIMS: 152 (M$^+$+1)

170

Step-3: 3-Synthesis of (S)-5-methylmorpholin-3-one (116)

Compound (3) (145 gm) dissolved in DCM (2000 ml) in 5.0 Ltr RBF at 0° C. and added potassium tert-butoxide (430 gm, 4.0 eq) dissolved in Isopropanol (1600 ml)] dropwise at 0° C. and stirred for 1 h at same temperature Crude reaction mixture was acidifying by conc. HCl (180-200 ml) to maintain pH (7-8) at 0° C. Isopropanol was evaporated on rotavapor and extracted with DCM (1000 ml×3). Total organic layer was dried over anhydrous sodium sulfate and finally concentrated yield product (88 gm; 80%).

Analytical data: $^1$HNMR (300 MHz, CDCl$_3$), δ 6.75 (br, 1H), 4.21-4.06 (m, 2H), 3.91-3.86 (m, 1H), 3.71 (m, 1H), 3.35 (m, 1H), 1.19 (d, J=6.0 Hz, 3H), ESIMS: 116 (M+1).

Step-4: Synthesis of (S)-3-methylmorpholine (117)

Lithium aluminum hydride (87 gm; 3.0 eq) was suspended in dry THF (1500 ml) in three necked RBF at 0° C. under nitrogen. Compound (4) (88 gm) dissolved in dry THF (500 ml) and added drop wise at same temperature. The reaction mixture warm to room temp and stirred over night.

Reaction mixture quenched with water (100 ml), 2N—NaOH (200 ml), and H$_2$O (300 ml) (fisher workup) and stirred for 30 minute. Added 2% MeOH/DCM (1000 ml) and stirred for additional 1.0 Hr.

Crude mixture filter on celite pad and filtrate was dried with anhydrous Na$_2$SO$_4$ and finally concentrated on rotavapor at low water bath temperature (20-25° C.) yield the final product (55 gm; 71%).

Scheme 23: Synthesis of (R)-3-methylmorphline [127]

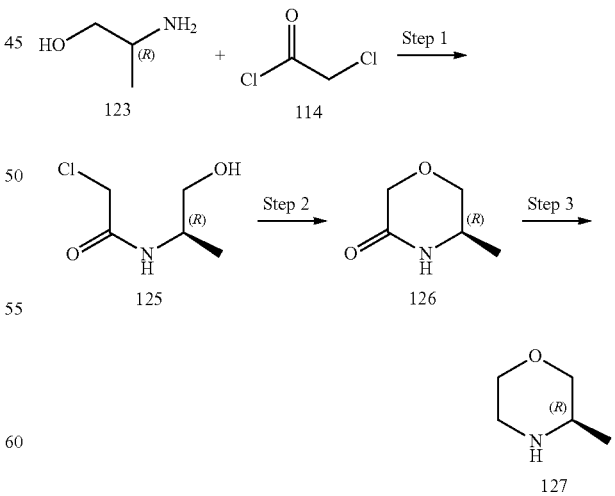

Compound [127] was synthesized using the same procedure as for compound [117] except compound [123] was used as the starting material. ESIMS: 102 (M$^+$+1)

TABLE
Synthesis of Various Substituted Morpholines
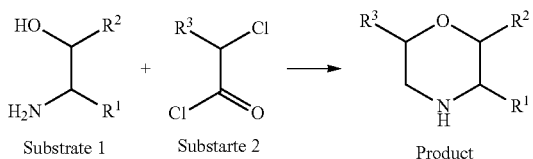
Following substituted Morpholines were synthesized using the schemes above as applicable.
| Entry | Substrate 1 | Substrate 2 | Product | Yield |
|---|---|---|---|---|
| 1. | | | | 71 |
| 2. | | | | 70 |
| 3. | | | | 75 |
| 4. | | | | 76 |
| 5. | | | | 75 |
| 6. | | | | 72 |
| 7. | | | | 75 |
| 8. | | | | 80 |
| 9. | | | | 83 |

TABLE-continued

Synthesis of Various Substituted Morpholines

Following substituted Morpholines were synthesized using the schemes above as applicable.

| Entry | Substrate 1 | Substrate 2 | Product | Yield |
|---|---|---|---|---|
| 10. | | | | 40 |
| 11. | | | | 76 |
| 12. | | | | 38 |
| 13. | | | | 76 |
| 14. | | | | 82 |
| 15. | | | | 83 |
| 16. | | | | 82 |
| 17. | | | | 78 |
| 18. | | | | 75 |

TABLE-continued
Synthesis of Various Substituted Morpholines

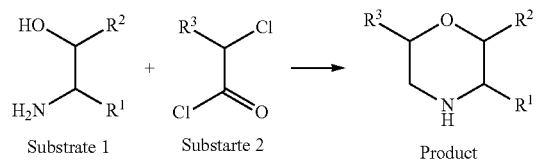

| | Substrate 1 | Substarte 2 | Product |
|---|---|---|---|
| | HO | R² | R³ | O | R² |
| | H₂N | R¹ | Cl | + | Cl | O | → | N | R¹ |
| | | | | H | |

Following substituted Morpholines were synthesized using the schemes above as applicable.

| Entry | Substrate 1 | Substrate 2 | Product | Yield |
|---|---|---|---|---|
| 19. | 1-(aminomethyl)cyclopentyl methanol | chloroacetyl chloride | 1-oxa-4-azaspiro[5.4]decane | 85 |
| 20. | 3-amino-1-butanol | chloroacetyl chloride | 5-methyl-1,4-oxazepane | 72 |
| 21. | (2R,3S)-3-amino-2-butanol | 2-chloropropanoyl chloride | (2R,3S,6S)-2,3,6-trimethylmorpholine | 68 |

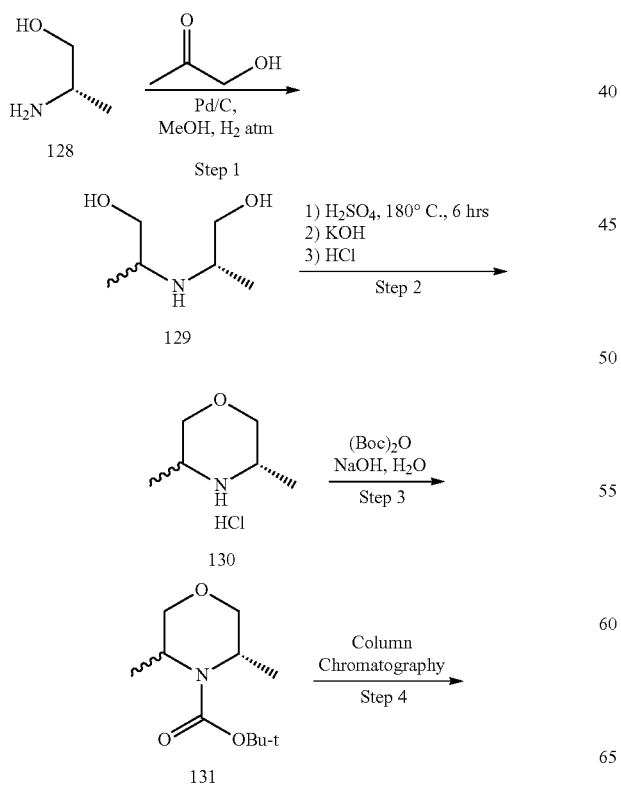

Scheme 24: Synthesis of (3R,5S)-3,5-dimethylmorpholine Hydrochloride [134] and (3S,5S)-3,5-dimethylmorpholine Hydrochloride [135]

Step 1:
To a solution of compound [128] (5.0 g, 66.67 mmol, 1 eq.) in methanol (100 ml) was added Pd/C (0.10 g, 10%). Hydroxyacetone (5.48 mL, 80.0 mmol, 1.2 eq.) was added and mixture was hydrogenated overnight in parr shaker under 55 psi. The palladium was removed by passing the mixture through celite bed and combined filtrate was concentrated under vacuum to obtain compound [129] (8.35 g, 93%) as yellow oil.

ESIMS: 134 (M⁺+1e)

Step 2:
Compound [129] (7.0 g, 52.63 mmol) was taken in sealed tube and cooled to 0° C. Conc H2SO4 (16.6 g) was added dropwise with vigorous stirring over 1 h. The cooling bath was removed and mixture was heated in an oil bath at temperature 180° C. for 6 hrs. The mixture was cooled to RT and KOH solution (20 g in 100 mL water) was added slowly. The resulting precipitates were removed by vacuum filtration and washed thoroughly with water (100 mL). The water was distilled until only 50 mL liquid remained in the flask. The mixture was acidified with 3 M HCl and solvent was removed under vacuo yielding compound [130] (5.0 g, 81%) as white syrup.

ESIMS: 116 (M$^+$+1e)

Step 3:

Compound [130] (5.0 g, 43.10 mmol, 1 eq.) was added to a solution of NaOH (5.0 g, 107.7 mmol, 2.5 eq.) in water (50 mL). (Boc)$_2$O (10 g, 64.6 mmol, 1.5 eq.) was added in portions over 15 min. Mixture was stirred overnight, the organic layer was isolated by extraction with ethyl acetate (2×250 mL). The organic phase was dried over Na$_2$SO$_4$. The solvent was removed under vacuum to obtain compound [131] (8.5 g, 91%) as white solid.

ESIMS: 216 (M$^+$+1e)

Step 5:

Compound [131] (2.5 g) was purified by column chromatography (silica gel, 100-200 mesh, EtOAc/cyclohexane) to obtain compound [132] (0.45 g) and compound [133] (1.54 g) as white solid.

Step 6:

Compound [132] (1.54, 7.12 mmol) was stirred with dioxane HCl (4N, 20 mL) at 0° C. for 2 hrs. The solvent was evaporated under vacuum to obtain compound [134] (0.70 g, 85%) as viscous oil.

ESIMS: 116 (M$^+$+1e)

Step 6:

Compound [133] (0.45 g, 2.08 mmol) was stirred with dioxane HCl (4N, 10 mL) at 0° C. for 2 hrs. The solvent was evaporated under vacuum to obtain compound [135] (0.23 g, 96%) as viscous oil.

ESIMS: 116 (M$^+$+1e)

Scheme 25: Synthesis of (3R,5R)-3,5-dimethylmorpholine Hydrochloride [142] and (3S,5R)-3,5-dimethylmorpholine Hydrochloride [143]

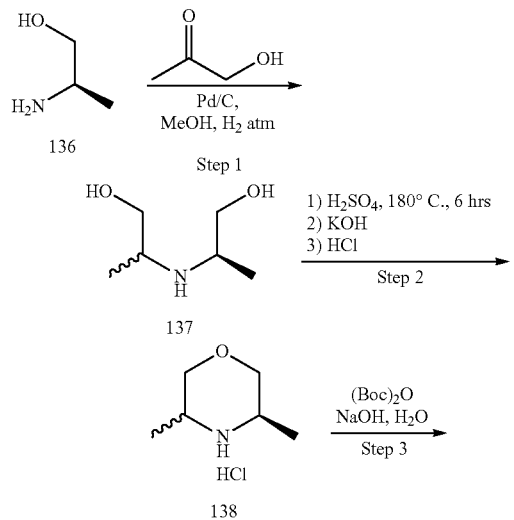

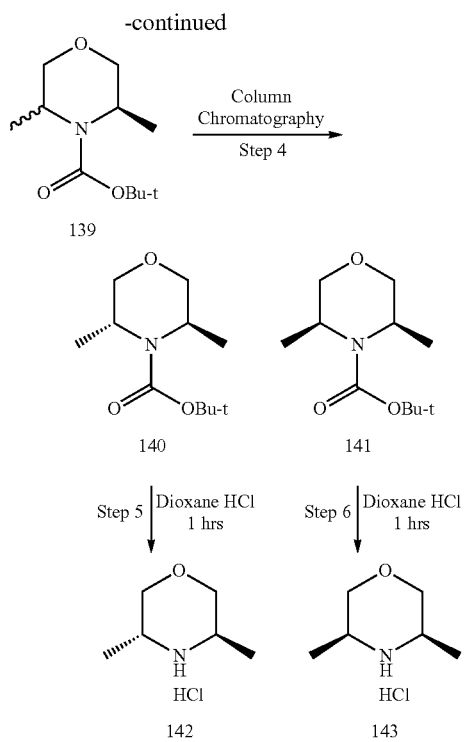

Compound [142] and compound [143] were synthesized using the same procedure as for compound [134] and compound [135] except the use of different starting materials.

Scheme 26: Synthesis of 6-oxa-3-azabicyclo[3.1.1]heptanes hydrotosylate salt [150]

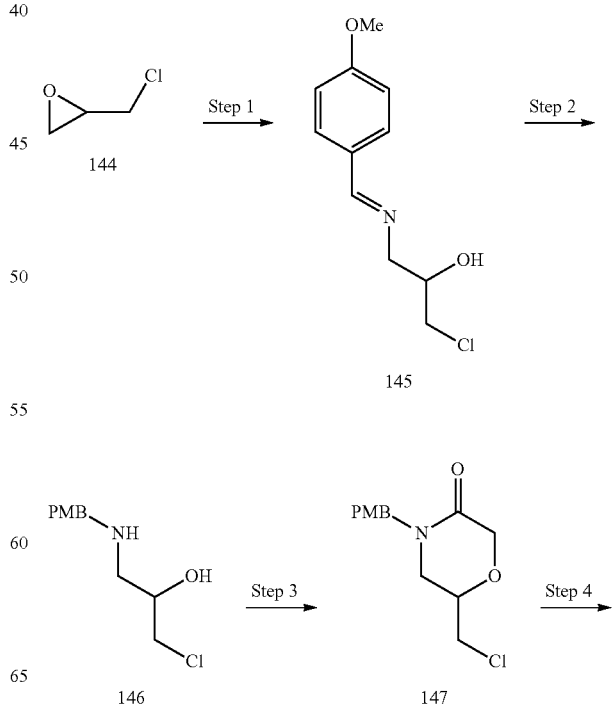

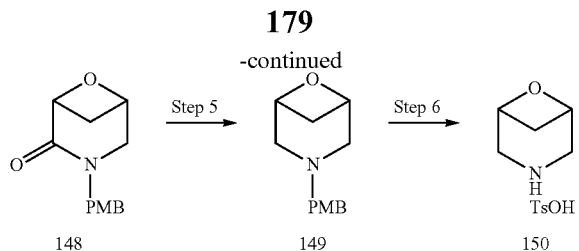

148 → Step 5 → 149 → Step 6 → 150

Step 1

To a stirred solution of 4-methoxybenzaldehyde (12.12 ml,) in t-BuOMe (100 ml) and 30% aq. ammonia (10.14 ml) in round bottom flask was added epichlorohydrin (7.84 ml, [144]) dropwise. The mixture was stirred at RT for 18 h. Additional 30% aq. ammonia (6 ml) and epichlorohydrin (5 ml) were added and stirred for an additional 4 h. The layers were separated, and the organic layer was concentrated in vacuo to yield a thick oil. Heptane (200 ml) was slowly added to a vigorously stirred solution of oil in t-BuOMe resulting in the formation of white precipitates. The mixture was stirred for 18 h at RT, followed by cooling to 0° C. The precipitate was filtered and washed with heptanes. The precipitate was dried in vacuo to afford compound [145] as an off-white solid (14.26 g, 85% yield).

ESIMS: 229 ($M^+$+1)

Step 2

To a stirred solution of compound [145] (10.00 g, 43.85 mmol) in MeOH (100 ml) at 0° C., was added $NaBH_4$ (2.5 g, 65.78 mmol) in small portions. After complete addition, the reaction was stirred at 0° C. for 1 h. The reaction was quenched at 0° C. with 1 N HCl; pH was adjusted up to 8. The mixture was concentrated to volume 100 ml and basified with 6.0 N aq. NaOH. The aqueous layer was extracted with EtOAc (2×100 ml). The organic layer was washed with brine, dried over $Na_2SO_4$, filtered and concentrated under reduced pressure to obtain compound [146] as white solid (7.78 g, 77% yield).

ESIMS: 231 ($M^+$+1)

Step 3

To a stirred solution of compound [146] (7.75 g, 33.39 mmol) in DCM (100 ml) and 1.0 N aq. NaOH (38 ml) at 0° C. was added dropwise a solution of chloroacetyl chloride (8.95 ml, 34.36 mmol) in DCM (50 ml). The mixture was stirred at 0° C. for 1 hr, followed by warming to RT. 10 N aq. NaOH (25.2 ml) was added, and the mixture was rapidly stirred for 4 hrs. The mixture was diluted with water (50 ml) and layers were separated. The aq. layer was extracted with DCM (100 ml). The combined organic extract was dried over Na2SO4, filtered, concentrated in vacuo to light yellow oil. The product [147] was purified by silica gel chromatography with 60% ETOAc/hexane. (7.36 g, 81% yield).

ESIMS: 271 ($M^+$+1)

Step 4

To a stirred solution of compound [147] (5.0 g, 18.5 mmol) in anhydrous THF:toluene (150 ml, 1:1) at 0° C. was added KHMDS in THF (37.8 ml). The mixture was stirred at 0° C. for 1.5 h. The reaction was quenched with saturated aq. $NH_4Cl$ solution followed by stirring at 0° C. for 1 h. The insoluble material was removed by filtration, and the filter cake was washed with EtOAc (50 ml). The filtrate was removed and the aqueous layer was extracted with EtOAc (50 ml). The organic layer was dried, filtered and concentrated in vacuo. Purification was done through silica gel column 80% ETOAc/hexanes to obtain compound [148] as white solid. (2.05 g, 47% yield).

ESIMS: 234 ($M^+$+1)

Step 5

To a stirred solution of compound [148] (0.90 g, 3.84 mmol) in THF (10 ml) at 0° C. under inert atmosphere was added dropwise $BH_3.SMe_2$ complex in THF (1.1 ml). After complete addition, mixture was allowed to warm to RT and stirred overnight. The mixture was cooled to 0° C. and MeOH (20 ml) was added dropwise. The mixture was allowed to warm to RT and stirred for 30 min. The solvent was removed under vacuum to afford a viscous oil. 1.0 N HCl (20 ml) was added and the mixture was heated for 30 min at 60° C. The mixture was cooled to RT, and its pH was adjusted to 13 with concentrated aq. NaOH. The aqueous layer was extracted with EtOAc (2×50 ml), separated, dried over $Na_2SO_4$, concentrated in vacuo to give oil. The purification was done with silica gel chromatography 70% EtOAc/hexanes to obtain compound [149] as colourless oil (0.700 g, 83%).

ESIMS: 221 ($M^+$+1)

Step 6

Compound [149] (0.700 g, 3.18 mmol), $TsOH.H_2O$ (0.604 g, 3.18 mmol) and $Pd(OH)_2$ on charcoal (0.200 g) in MeOH (30 ml) was placed in a Parr bottle and hydrogenated at 60 psi for 36 hrs. The mixture was filtered through celite, and the filter cake was washed with MeOH (20 ml). The filtrate was concentrated in vacuo to a semisolid. Trituration of the semisolid in EtOAc (20 ml) afforded a white precipitate. The precipitate was filtered, washed with EtOAc (20 ml), and dried in vacuo to obtain compound [150] as a white solid (0.702 g, 81% yield.)

Scheme 27: Synthesis of N,N-dimethyl-4-(4-(2-(methylamino)thiazol-5-yl)-6-morpholino-1,3,5-triazin-2-yloxy)benzamide [10007]

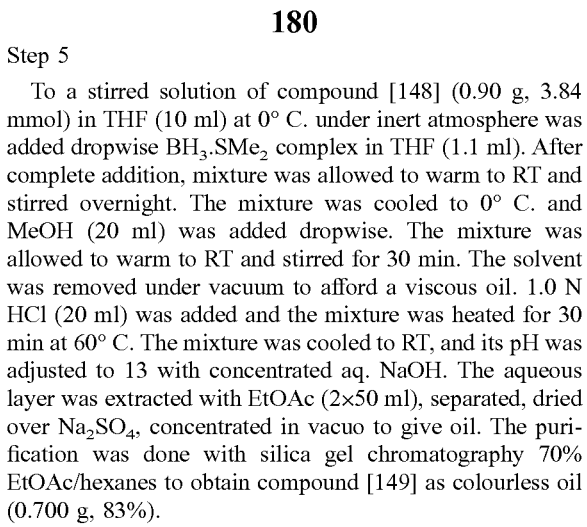

151

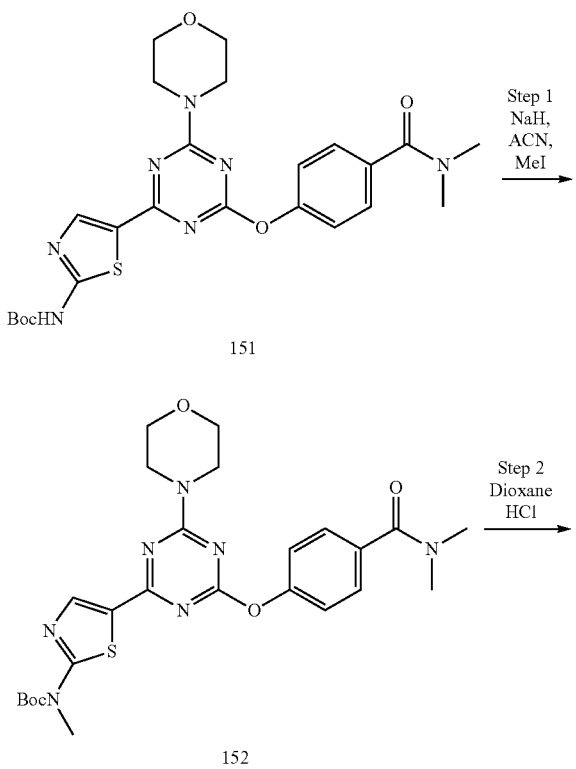

152

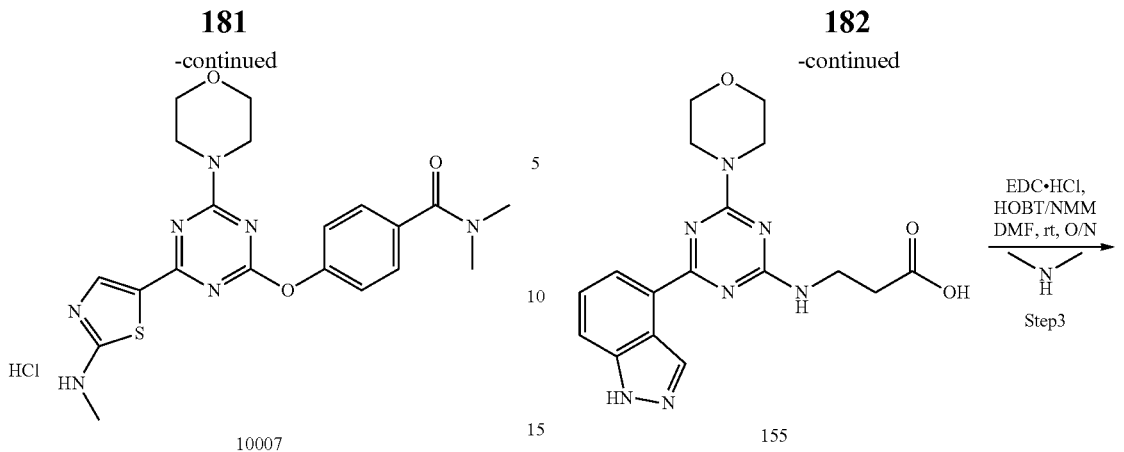

10007

Step 1

Under an inert atmosphere NaH (0.008 g, 0.195 mmol) was added to a solution of [151] (0.100 g, 0.184 mmol) at 0° C. in acetonitrile (10 ml). After stirring at 0° C. for 30 min, methyl iodide (0.012 ml, 0.195 mmol) was added. The resulting mixture was stirred at RT for 2 h followed by removal of the solvent under reduced pressure. Purification was done by silica gel column chromatography with 2% MeOH/DCM to give compound [152] as a white solid (0.90 g, 88%).

ESIMS: 542 (M$^+$+1)

Step 2

Compound [152] (0.090 g, 0.162 mmol) was dissolved in dioxane HCl (4 M, 10 ml) and the mixture was stirred for 24 h at RT. The solvent was evaporated and crude was purified by washing with DCM, ether and pentane to obtain compound [10007] (0.073 g, 89% yield) as a white solid.

ESIMS: 442 (M$^+$+1)

Scheme 28: Synthesis of 3-(4-(1H-indazol-4-yl)-6-morpholino-1,3,5-triazin-2-ylamino)-N,N dimethylpropanamide [10023]

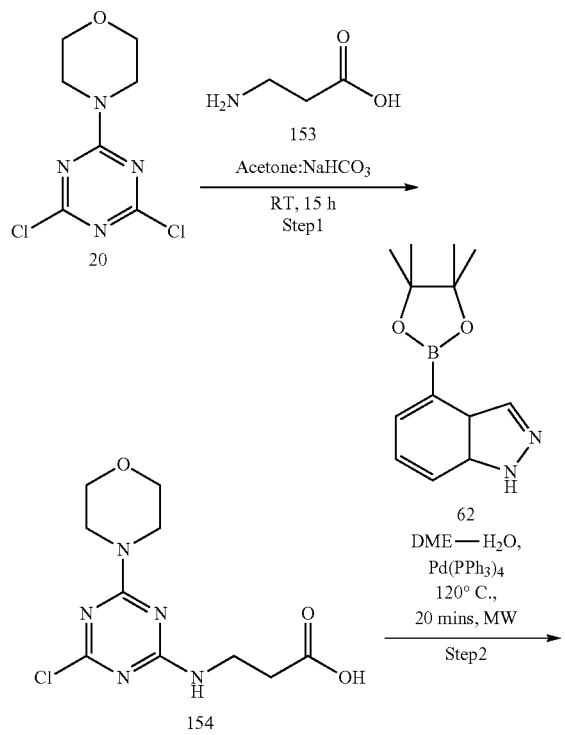

Step-1:

Compound [20] (2 g, 8.5 mmol, 1 eq) was added to a solution of acetone:NaHCO$_{3(aq)}$: 1:1 (30 ml). The reaction mass turned hazy and was stirred at RT until effervescence ceased. Compound [153] was then added (1.49 g, 6.83 mmol, 0.8 eq) and the reaction mixture was stirred at RT for 15 h. The excess acetone from the reaction mixture was removed in vacuo. Water (20 ml) was added to the reaction mixture and stirred followed by filtration through a Buchner funnel. The filtrate was washed with DCM. The DCM layer was discarded and the water layer was acidified to pH=4. A precipitate formed, was filtered, washed with water and dried to yield compound [154] (1.5 g, 60%) as white solid.

ESIMS: 288 (M$^+$+1)

Step-2:

To a solution of compound [154] (1.5 g, 5.2 mmol, 1 eq) in DME:H$_2$O: 1:1 (30 ml) was added successively compound [62] (1.91 g, 7.8 mmol, 1.5 eq.) and Na$_2$CO$_3$ (2.75 g, 26 mmol, 5 eq). Degassing was done for 15 min, and then Pd(PPh$_3$)$_4$ (0.3 g, 0.26 mmol, 0.05 eq) was added under inert atmosphere. The reaction mass was refluxed at 120° C. for 20 min in microwave. Excess solvent was removed under vacuum and the reaction mass was diluted with water and extracted with (2×30 ml) of DCM. The aqueous layer was acidified to pH=4 after which a solid formed, was filtered and dried under vacuum to get compound [155] (1.2 g, 62%) as pale white solid.

ESIMS: 370 (M$^+$+1)

Step-3

To a solution of compound [155] (0.13 g, 0.35 mmol, 1 eq) in DMF (2 ml) was added successively EDC hydrochloride (0.10 g, 0.53 mmol, 1.5 eq.) and HOBT (0.13 g, 0.53 mmol, 1.5 eq). NMM (0.12 ml, 1.07 mmol, 3 eq) was added next and the reaction mass was stirred for 10 min. Finally 2 M dimethyl amine in THF (0.5 ml, 3 eq) was added and the reaction mass was stirred overnight. The reaction mixture was diluted with water and extracted with (2×30 ml) of ethyl acetate. The ethyl acetate layers were combined and washed with brine, dried over anhydrous sodium sulphate, and then evaporated to obtain a viscous dark brown material. Purification of solid residue was done by column chromatography over silica gel (100:200 mesh) in a solvent system consisting of 2.5% MeOH in DCM to yield compound [10023] (20 mg, 14%) as an off white solid.

ESIMS: 397 (M⁺+1e).

Scheme 29: Synthesis of (S)-4-((4-(2-dimethylamino)thiazol-5-yl)-6-(3-methylmorpholino)-1,3,5-triazin-2-yl)-N,N-dimethlybenzamide

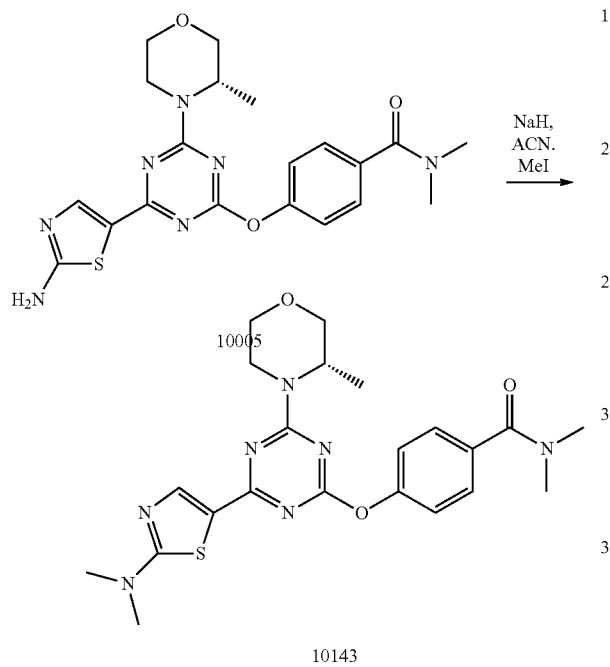

Under an inert atmosphere NaH (0.015 g, 0.625 mmol, 3 eq.) was added to a solution of [10005](0.100 g, 0.226 mmol) at 0° C. in acetonitrile (10 ml). After stirring at 0° C. for 30 min, methyl iodide (0.072 ml, 1.127 mmol, 5 eq.) was added. The resulting mixture was stirred at RT for 2 h followed by removal of the solvent under reduced pressure. Purification was done by silica gel column chromatography with 2% MeOH/DCM to give compound [10143] as a white solid (0.25 g, 24%).

ESIMS: 470 (M⁺+1)

Scheme 30: Synthesis of (S)-N-(5-(4-(4-(dimethylcarbomyl)phenoxy)-6-(3-methylmorpholino)-1,3,5-triazin-2-yl)thiazol-2-yl)nicotinamide

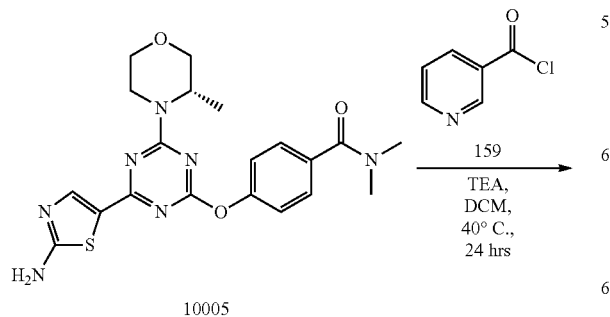

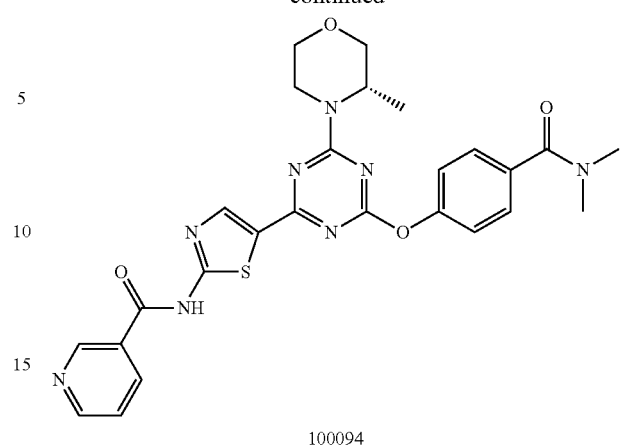

Compound [10005] (0.100 g, 0.226 mmol) was taken in DCM (100 ml). TEA (0.091 ml, 0.45 mmol) and compound [159] (0.040 g, 0.339 mmol) was added and mixture was stirred at 40° C. for 24 hrs. The mixture was cooled to RT, washed with aq NaHCO3. The organic layer was separated, dried over Na2SO4, concentrated under reduced pressure. Purification was done by silica gel column chromatography with 2% MeOH/DCM to give compound [10094] as a off-white solid (0.25 g, 20%).

ESIMS: 547 (M⁺+1)

Scheme 31: (S)-N,N-dimethyl-4-((4-(3-methylmorpholino-6-(2-(3-methylureido)thiazol-5-yl)-1,3,5-triazin-2-yl)oxy)benzamide

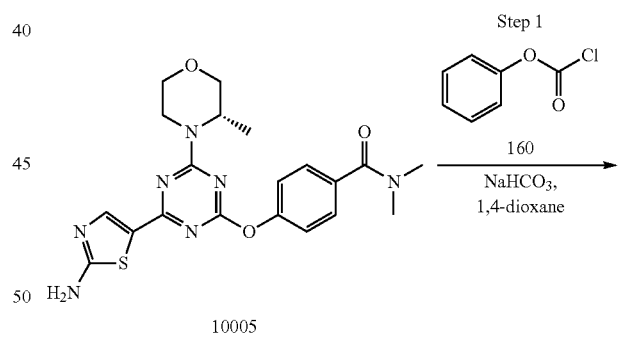

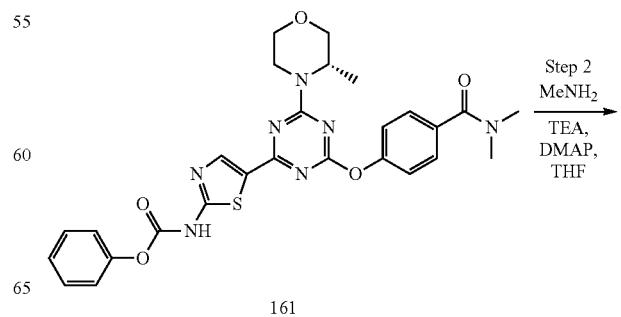

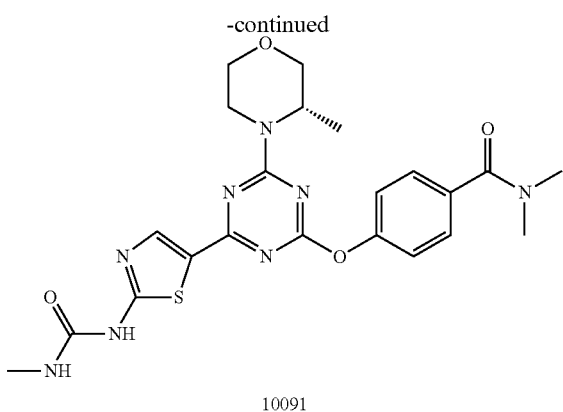

10091

Step-1:

Compound [10005] (0.300 g, 0.68 mmol, 1 eq) was taken in dioxane (100 ml) followed by addition of NaHCO₃ (0.180 g, 3.40 mmol, 5 eq.). Compound [160] was then added (0.126 ml, 1.02 mmol, 1.5 eq.) and the reaction mixture was stirred at RT for 3 h. Water (20 ml) was added to the reaction mixture and reaction mixture was extracted with ethyl acetate (3×100 ml The organic layer was separated, dried over Na₂SO₄ and concentrated under reduced pressure. The crude was purified by washing with diethyl ether to obtain compound [161] as white solid (0.350 g, 92%).

ESIMS: 562 (M⁺+1)

Step-2:

To a solution of compound [161] (0.100 g, 0.178 mmol, 1 eq) in THF (20 ml) was added successively TEA (0.037 ml, 0.267 mmol, 1.5 eq.), methyl amine (0.010 ml, 0.178 mmol, 1 eq.) and DMAP (0.005 g, catalytic). The reaction mass was stirred at 40° C. for 2 hrs. The solvent was evaporated under reduced pressure and crude was purified by silica gel column chromatography with 3% MeOH/DCM to give compound [10091] as a off-white solid (0.040 g, 46%).

ESIMS: 499 (M⁺+1)

Compound 10092, 10093, 10135, 10143 are synthesized by using same procedure for 10091

Scheme 32: Synthesis of 6-Chloro-N,N-dimethylnicotinamide [198]

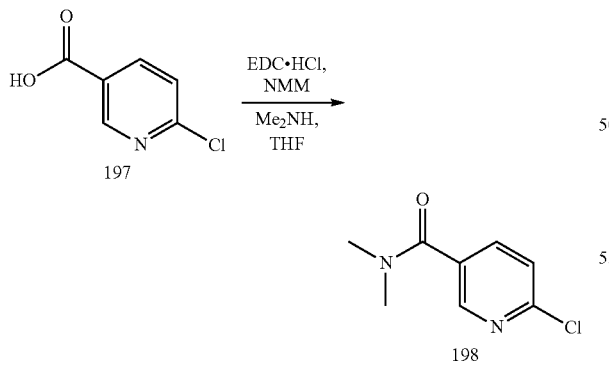

Compound [197] (3.0 g, 19.0 mmol) was dissolved in THF (100 ml) in a clean oven-dried two necked RB flask (250 ml) and degassed with nitrogen. To this clear solution, EDC.HCl (4.02 g, 20.9 mmol) was added, followed by NMM (2.3 ml, 20.9 mmol). The reaction mixture was stirred and heated at RT for 10 min, under nitrogen atmosphere. Me₂NH (13.06 ml, 2N, 28.5 mmol) was added dropwise and reaction mixture was stirred RT for 16 hrs. The reaction was monitored by TLC. The reaction mixture was quenched with aq. NaHCO₃, extracted with ethyl acetate (3×100 ml). The organic extracts were combined, washed with brine and dried using Na₂SO₄. The organic layer was evaporated to crude which was purified by column chromatography (100-200 mesh, 2% MeOH/DCM) to yield compound [198] (2.62 g, 75%) as white solid.

ESIMS: 185 (M⁺+1)

Scheme 33: Synthesis of N-cyanocarbamimidic chloride [202]

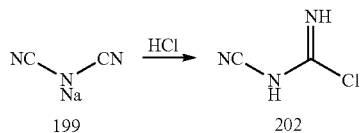

In two necked RBF, Con HCl (15 ml) was taken and cooled to −40° C. with dry ice-acetone bath. Compound [199] (3.0 g, 44.77 mmol) in water (3 ml) was added dropwise and reaction mixture was stirred at same temperature for 15 min. The mixture was then shifter to RT and stirred for 30 min. The reaction mixture was cooled to 0° C. for 15 min and precipitates formed were filtered under vacuum, washed with cold water (5 ml) and vacuum dried to yield compound [202] as white solid (2.5 g, 54% yield).

Scheme 34: (S)-4-((4-(6-Chloropyridin-3-yl)-6-(3-methylmorpholino)-1,3,5-triazin-2-yl)oxy-3-fluoro-N,N-dimethylbenzamide [210]

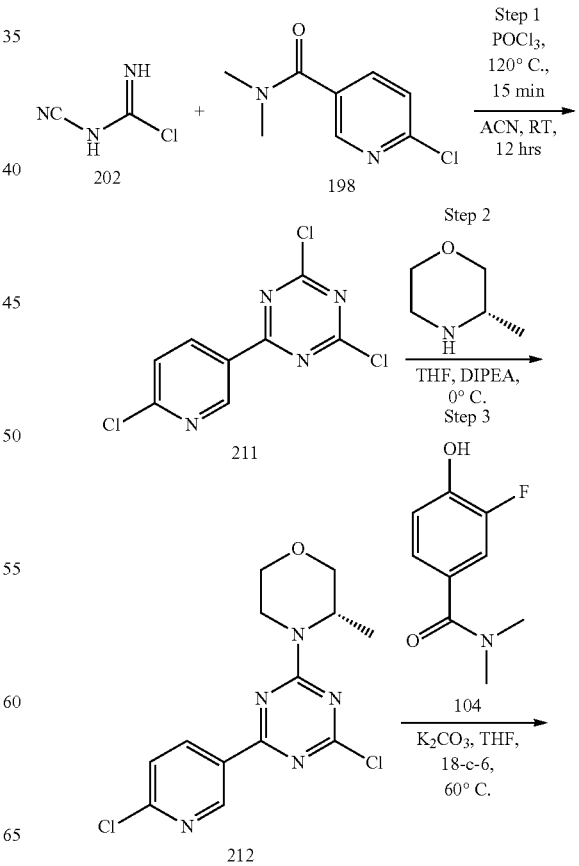

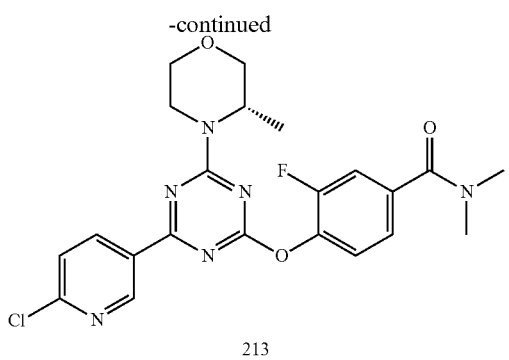

213

Step 1

In a sealed vessel, compound [198] (2.0 g, 10.86 mmol) was heated with POCl₃ (1.98 ml, 21.73 mmol) at 120° C. for 15 min. The mixture was cooled to RT. Compound [202] (0.335 g, 32.62 mmol) was added and mixture was stirred at RT for 12 hrs. The reaction Mixture was poured in ice. The precipitates formed were filtered, dried and crude was purified by column chromatography (silica 100-200 mesh, 5% ethyl acetate/cyclohexane) to obtain compound [211] (1.50 g, 53%) as white solid.

ESIMS: 261 (M⁺+1)

Step 2

To a solution of compound [211] (1.0 g, 3.84 mmol) in THF (100 ml) at 0° C. was added DIPEA (0.354 ml, 3.46 mmol) and (S)-3-methylmorpholine (0.233 g, 3.84 mmol). The resulting mixture was stirred at 0° C. for 4 hrs. TLC was used to monitor for consumption of starting material [211]. Once the starting material was consumed, solvent was removed under reduced pressure. Purification was done by silica gel column chromatography with 20% EtOAc/cyclohexane to give compound [212] as a white solid (0.42 g, 60%).

ESIMS: 324 (M⁺+1)

Step 3

To a solution of compound [212] (0.320 g, 0.98 mmol) in THF was added K₂CO₃ (0.27 g, 1.96 mmol) and compound [104] (0.180 g, 0.98 mmol) followed by catalytic amount of 18-crown-6. The mixture was heated at 60° C. for 2 hrs. TLC was used to monitor for consumption of starting material [212]. Once the starting material was consumed, reaction was cooled to RT, quenched with water (20 ml). The reaction mixture was extracted with ethyl acetate (3×50 ml). The organic layer was separated, dried over Na2SO₄, concentrated under reduced pressure to obtain compound [213] as a white solid (0.460 g, 99%).

ESIMS: 473 (M⁺+1)

Compound [213] ([206], G=Cl, Br, I) was converted to 10058 by amination. While compound ([206], G=NO₂) was converted to 10058 by Pd/C reduction.

BIOLOGICAL TESTINGS OF THE COMPOUNDS OF THE PRESENT INVENTION

Biological Example 1 mTOR Assay

Compounds were evaluated for mTOR activity using an in vitro kinase assay.

mTOR activity is measured in vitro by determining the level of phosphorylation of the protein substrate 4EBP-1. The phosphorylation of GFP-4E-BP1 at threonine residue is recognized by Ab Tb-Anti-p4EBP1, which results in time resolved fluorescence energy transfer (TR-FRET) between GFP and Terbium in the Ab-Protein complex.

Recombinant mTOR (FRAP1), Kinase reaction buffer, GFP-4E-BP1 and LanthaScreen Tb-anti-4E-BP1 (pThr46), TR FRET dilution buffer, Kinase Quench Buffer were obtained from Invitrogen.

Kinase reactions were performed in 10 µl volume in Corning white 384 well plates. Serially diluted compounds (10 µM-0.0005 µM) prepared in DMSO were incubated with mTOR (final concentration 150 ng/ml in the reaction) in the assay buffer for 15 minutes. The reaction was initiated by the addition of substrate (GFP-4E-BP1) and ATP at a final conc. of 400 nM and 8 µM ATP in the reaction respectively. The kinase reaction was allowed to proceed for 1 hour at room temperature before a 10 µL preparation of kinase quench buffer and Tb-labeled Antibody in TR-FRET dilution buffer was added. The final concentration of the antibody in the assay well is 2 nM and the final concentration of EDTA is 10 mM. The plate was incubated at room temperature for 1 h.

FRET signal was read in Envision Multilabel Reader with the following filters:

Excitation-330 nm and Emission 486 nm (donor) and 520 nm (acceptor).

TR FRET Ratio (Fluorescence 520 nm/Fluorescence 486 nm) was plotted against the concentration of inhibitor and data was fit to Non Linear Regression curve fit (sigmoidal dose response curve with variable slope-four parameters) using Graph Pad Prism 5.

In Vitro Kinase Activity:

PI3K TR-FRET Assay

Enzymatic activity of PI3K alpha was measured using Time resolved Fluorescence resonance energy transfer (TR-FRET) assay. This assay utilizes ADP detection as a means to screen inhibitor potency of compounds. The Transcreener ADP2 TR-FRET Red Assay is a competitive immunoassay for ADP with a far-red, TR-FRET readout and it has been used for this purpose. The assay can be used for any enzyme class that produces ADP (Kinases, ATPases). It consists of ADP HiLyte647 Tracer, ADP² Antibody-Tb conjugate (800 nM), stop & detect buffer, 5 mM ATP, 5 mM ADP. The ADP HiLyte647 Tracer is bound to an ADP² Antibody-Tb conjugate. The excitation of the terbium complex in the UV range results in energy transfer to the tracer and emission at a higher wavelength after a time delay ADP produced by the target enzyme displaces the tracer which causes decrease in TR-FRET.

The reaction buffer used for the assay was 50 mM HEPES, pH 7.4.3 mM MgCl2, 0.05% CHAPS, 50 mM NaCl, 2 mM DTT, 1 mM EGTA. PI3 Kinase alpha (p110 alpha/p85 alpha) and PIP2 Substrate (diC8,) were procured from Invitrogen and Echelon respectively.

Kinase reactions were performed in 10 µl volume in Corning white 384 well plates. Serially diluted compounds (10 µM-0.0005 µM) prepared in DMSO were incubated with PI3 Kinase (p110 alpha/p85 alpha) in the reaction buffer (final conc. 150 ng/ml in the reaction) for 15 minutes. Reaction was initiated by the addition of substrate (PIP2) and ATP at final conc. of 50 µM and 1 µM ATP in the reaction respectively. Kinase reactions were allowed to proceed for 1 hour at room temperature before a 10 µL preparation of Transcreener ADP detection mix was added. Plate was incubated at room temperature for 1 hr. ADP-ATP standard curves were also prepared.

FRET signal was read in Envision Multilabel Reader with the following filters:

Excitation-330 nm and Emission 615 nm (donor) and 665 nm (acceptor). TR FRET Ratio (Fluorescence 665 nm/Fluorescence 615 nm) was converted to amount of product formed using the standard curve generated. Percentage inhibition was calculated and plotted against the concentration of inhibitor and data was fit to Non Linear Regression curve fit (sigmoidal dose response curve with variable slope-four parameters) using Graph pad prism 5 and IC50 was calculated for the compound.

MTT Cell Viability Assay (A2780 Cell Line):

A2780 which is an ovarian cancer cell line was obtained from Sigma Aldrich. The cell line was maintained in DMEM (Sigma) and 10% fetal Bovine Serum. 10000 cells/well of A2780 cells were plated in 96 well tissue culture plate (Nunc). Cells were incubated for 48 hrs with serially diluted compound (final concentration from 20 μM-0.002 μM) for 48 hr along with the control containing only DMSO (1%). MTT ((3-(4,5-Dimethylthiazol-2-yl)-2,5-diphenyltetrazolium bromide) obtained from Sigma was added to the wells and plates were incubated at 37° C. in 5% $CO_2$ for 4 hrs. Plates were centrifuged at 1000 rpm for 10 minutes. Supernatant was removed from the plates. DMSO was added to the wells and plates were shaken for 30 minutes. Absorbance was read at 550 nm (Envision Multilabel Reader). Percentage inhibition was calculated and plotted against the concentration of inhibitor and data was fit to Non Linear Regression curve fit (sigmoidal dose response curve with variable slope-four parameters) using Graph pad prism 5 and 50% maximal effective concentration (EC50) was calculated for the compound.

The data of few representative compounds of the present invention tested as per the assay methods as enumerated herein are presented at Table 2.

As evident from the Table 2 the compounds of present invention exhibit inhibitory effect on the mTOR and PI3K. These compounds inhibit the phosphorylation of 4EBP-1 by mTOR at low concentrations, thus, these compounds can effectively inhibit the relay of signal transduction beyond the mTOR regulatory molecule.

TABLE 2

Biological activity of few representative compounds of the present invention.

| compound number | mTOR IC50 (uM) | PI3K IC50 (uM) | mTOR % Inhib@1 uM | PI3K % Inhib@1 uM |
|---|---|---|---|---|
| 10003 | <1 | <1 | >50 | NT |
| 10004 | <1 | >1 | <50 | NT |
| 10005 | <1 | <1 | >50 | NT |
| 10006 | NT | >1 | <50 | >50 |
| 10007 | <1 | >1 | >50 | NT |
| 10010 | <1 | <1 | >50 | >50 |
| 10011 | <1 | >1 | >50 | NT |
| 10015 | <1 | <1 | >50 | NT |
| 10017 | <1 | <1 | NT | NT |
| 10021 | <1 | <1 | >50 | NT |
| 10022 | <1 | <1 | >50 | NT |
| 10029 | <1 | >1 | >50 | <50 |
| 10046 | NT | NT | <50 | <50 |
| 10049 | <1 | <1 | >50 | NT |
| 10050 | <1 | >1 | >50 | NT |
| 10051 | <1 | >1 | >50 | NT |
| 10052 | <1 | <1 | NT | >50 |
| 10053 | <1 | >1 | NT | NT |
| 10057 | <1 | NT | NT | <50 |
| 10058 | <1 | <1 | NT | NT |
| 10063 | <1 | NT | NT | <50 |
| 10064 | <1 | NT | NT | <50 |
| 10065 | <1 | <1 | NT | NT |
| 10066 | <1 | <1 | NT | NT |
| 10067 | <1 | <1 | NT | NT |
| 10069 | <1 | >1 | NT | NT |
| 10070 | <1 | NT | NT | NT |
| 10071 | NT | NT | <50 | <50 |
| 10072 | NT | NT | <50 | <50 |
| 10073 | <1 | <1 | >50 | >50 |
| 10075 | <1 | >1 | >50 | <50 |
| 10076 | <1 | >1 | >50 | <50 |
| 10077 | <1 | <1 | NT | >50 |
| 10078 | <1 | <1 | >50 | >50 |
| 10079 | <1 | >1 | NT | <50 |
| 10081 | <1 | <1 | >50 | >50 |
| 10082 | NT | NT | <50 | <50 |
| 10083 | 1 | <1 | NT | NT |
| 10084 | <1 | NT | NT | NT |
| 10085 | <1 | 6 | NT | NT |
| 10086 | <1 | 1 | NT | NT |
| 10088 | NT | NT | <50 | NT |
| 10090 | NT | NT | NT | NT |
| 10091 | <1 | <1 | >50 | NT |
| 10092 | <1 | <1 | NT | <50 |
| 10093 | <1 | <1 | NT | >50 |
| 10094 | 1 | NT | NT | <50 |
| 10095 | <1 | >1 | NT | <50 |
| 10096 | <1 | <1 | >50 | NT |
| 10097 | <1 | <1 | NT | >50 |
| 10098 | <1 | <1 | NT | >50 |
| 10099 | <1 | <1 | NT | >50 |
| 10100 | <1 | <1 | >50 | NT |
| 10103 | <1 | <1 | NT | NT |
| 10104 | <1 | <1 | NT | NT |
| 10105 | <1 | >1 | NT | NT |
| 10115 | NT | <1 | >50 | NT |
| 10118 | >3.0 | >1 | >50 | NT |
| 10119 | NT | >10 | <50 | NT |
| 10122 | >1 | NT | >50 | <50 |
| 10123 | NT | NT | <50 | <50 |
| 10124 | 1 | NT | <50 | <50 |
| 10125 | NT | NT | <50 | <50 |
| 10126 | <1 | <1 | >50 | NT |
| 10127 | <1 | <1 | >50 | >50 |
| 10128 | <1 | <1 | >50 | >50 |
| 10131 | NT | NT | <50 | <50 |
| 10132 | <1 | <1 | >50 | <50 |
| 10135 | NT | NT | <50 | <50 |
| 10136 | <1 | >10 | >50 | <50 |
| 10137 | <1 | <1 | >50 | NT |
| 10138 | >1 | <1 | <50 | >50 |
| 10139 | <1 | <1 | >50 | NT |
| 10140 | <1 | >10 | >50 | NT |
| 10141 | <1 | >10 | NT | <50 |
| 10142 | <1 | >10 | NT | NT |
| 10143 | >1 | >1 | NT | <50 |
| 10145 | >1 | NT | NT | <50 |
| 10146 | <1 | <1 | NT | NT |
| 10147 | >1 | NT | NT | >50 |
| 10148 | <1 | NT | NT | <50 |
| 10150 | >10 | NT | NT | <50 |
| 10153 | <1 | <1 | NT | <50 |
| 10154 | <1 | >1 | NT | <50 |
| 10156 | <1 | 3 | NT | <50 |
| 10157 | <1 | <1 | NT | NT |
| 10158 | <1 | <1 | NT | NT |
| 10159 | <1 | <1 | NT | NT |
| 10161 | <1 | >10 | NT | NT |
| 10162 | >1 | >10 | NT | NT |
| 10174 | NT | >1 | <50 | NT |
| 10175 | NT | <1 | NT | NT |
| 10176 | NT | <1 | <50 | NT |

TABLE 2-continued

Biological activity of few representative compounds of the present invention.

| compound number | mTOR IC50 (uM) | PI3K IC50 (uM) | mTOR % Inhib@1 uM | PI3K % Inhib@1 uM |
|---|---|---|---|---|
| 10177 | NT | <1 | NT | NT |
| 10178 | NT | <1 | <50 | NT |
| 10179 | NT | <1 | NT | NT |
| 10180 | <1 | <1 | >50 | NT |
| 10181 | <1 | <1 | >50 | NT |
| 10182 | >1 | <1 | >50 | NT |
| 10183 | NT | <1 | NT | NT |
| 10184 | NT | <1 | NT | NT |
| 10185 | NT | <1 | <50 | NT |
| 10186 | NT | <1 | NT | NT |
| 10187 | NT | <1 | NT | NT |
| 10188 | NT | >1 | <50 | NT |
| 10189 | NT | <1 | <50 | NT |
| 10190 | NT | NT | NT | NT |
| 10191 | NT | >1 | <50 | NT |
| 10192 | >1 | >1 | <50 | NT |
| 10193 | NT | <1 | <50 | NT |
| 10194 | NT | <1 | <50 | NT |
| 10195 | NT | <1 | <50 | NT |
| 10196 | NT | <1 | <50 | NT |
| 10197 | NT | <1 | <50 | NT |
| 10198 | NT | <1 | NT | NT |
| 10199 | NT | <1 | <50 | NT |
| 10200 | NT | <1 | <50 | NT |
| 10201 | NT | <1 | <50 | NT |
| 10202 | >1 | >10 | NT | NT |
| 10203 | >3.0 | NT | NT | <50 |
| 10204 | <1 | <1 | NT | NT |
| 10205 | <1 | NT | NT | NT |
| 10206 | <1 | NT | NT | NT |
| 10207 | <1 | NT | NT | NT |

NT—not tested

The invention claimed is:

1. A compound

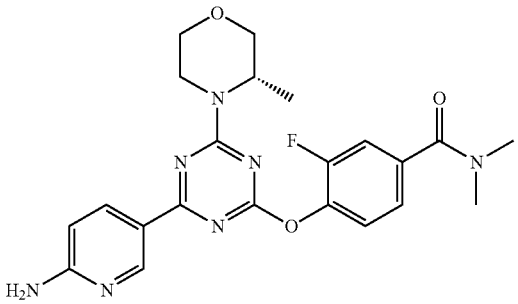 [SMILES: C[C@H]1COCCN1c1nc(Oc2ccc(C(=O)N(C)C)cc2F)nc(-c2ccc(N)nc2)n1]

and salts thereof.

2. A pharmaceutical composition comprising the compound of claim 1, and pharmaceutically acceptable excipients.

3. A process for synthesis of the compound of claim 1, comprising the steps of:
   i. reacting a 6-amino-N,N-dimethyl pyridinyl amide with a slight excess of phosphoryl chloride;
   ii. cyclization with N-cyanocarbamimidic chloride leading to the formation of 2-amino pyridinyl substituted 3,5-dichloro triazine core;
   iii. treating the 2-amino pyridinyl substituted 3,5-dichloro triazine core with methyl-morpholine in the presence of tertiary amine base to yield intermediate 1;
   iv. coupling the intermediate 1 with a 3-fluoro-4-hydroxyl-N,N-dimethyl benzamide in the presence of sodium bicarbonate or potassium bicarbonate to yield intermediate 2;
   v. optionally purifying intermediate 2;
   vi. hydrolysis;
   to yield the compound of claim 1.

4. A method of treating breast cancer or small-cell lung cancer comprising administering to a subject in need thereof a therapeutically effective amount of the compound of claim 1.

5. The compound of claim 1, as the hydrochloride salt.

* * * * *